United States Patent
Verdine et al.

(10) Patent No.: US 12,258,423 B2
(45) Date of Patent: Mar. 25, 2025

(54) STAPLED AND STITCHED POLYPEPTIDES AND USES THEREOF

(71) Applicant: President and Fellows of Harvard College, Cambridge, MA (US)

(72) Inventors: Gregory L. Verdine, Boston, MA (US); Gerard Hilinski, Somerville, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 816 days.

(21) Appl. No.: 16/950,540

(22) Filed: Nov. 17, 2020

(65) Prior Publication Data

US 2022/0372075 A1    Nov. 24, 2022

Related U.S. Application Data

(60) Continuation of application No. 16/140,113, filed on Sep. 24, 2018, now Pat. No. 11,332,496, which is a
(Continued)

(51) Int. Cl.
*C07K 7/08* (2006.01)
*A61P 1/00* (2006.01)
(Continued)

(52) U.S. Cl.
CPC .................... *C07K 7/08* (2013.01); *A61P 1/00* (2018.01); *C07D 205/04* (2013.01); *C07D 207/16* (2013.01); *C07K 1/04* (2013.01); *C07K 1/113* (2013.01); *C07K 7/06* (2013.01); *A61K 38/00* (2013.01)

(58) Field of Classification Search
CPC . C07K 7/08; C07K 1/04; C07K 1/113; C07K 7/06; C07D 205/04; C07D 207/04; C07D 203/08; C07D 207/16; C07D 211/04; A61P 1/00; C07C 69/74; C07C 69/743; C07C 69/75; A61K 31/196; A61K 31/396;
(Continued)

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,730,006 A | 3/1988 | Bohme et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,120,859 A | 6/1992 | Webb |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,364,851 A | 11/1994 | Joran |
| 5,383,851 A | 1/1995 | McKinnon et al. |
| 5,417,662 A | 5/1995 | Hjertman et al. |
| 5,446,128 A | 8/1995 | Kahn |
| 5,466,220 A | 11/1995 | Brenneman |

(Continued)

FOREIGN PATENT DOCUMENTS

DE    2610228    *   9/1976
EP    0160422 A1    11/1985
(Continued)

OTHER PUBLICATIONS

Nicole, et. al., Canadian Journal of Chemistry (1962), 40, 353-66. (Year: 1962).*
(Continued)

*Primary Examiner* — Kahsay Habte
(74) *Attorney, Agent, or Firm* — Hogan Lovells US LLP

(57) ABSTRACT

The present invention provides stapled polypeptides of the Formulae (I) and (VI):

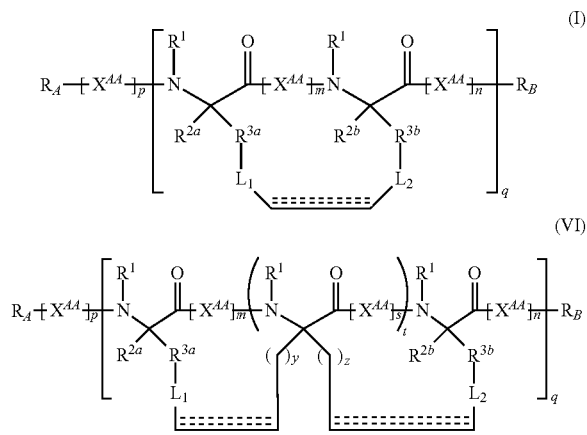

and salts thereof; wherein the groups ====; $R^{1a}$, $R^{1b}$, $R^{1c}$, $R^{2a}$, $R^{3a}$, $R^{2b}$, $R^{3b}$, $R^{4a}$, $R^{4b}$, $R_A$, $R_Z$, $L_{1a}$, $L_{1b}$, $L_2$, $L_3$, $X^{AA}$, v, w, p, m, s, n, t, and q are as defined herein. The present invention further provides methods of preparing the inventive stapled polypeptides from unstapled polypeptide precursors. The present invention further provides pharmaceutical compositions comprising a stapled polypeptide of Formula (I) or (VI), and methods of using the stapled peptides. The present invention also provides modifications of the staples post ring closing metathesis.

14 Claims, 25 Drawing Sheets

Specification includes a Sequence Listing.

Related U.S. Application Data division of application No. 14/775,315, filed as application No. PCT/US2014/025544 on Mar. 13, 2014, now Pat. No. 10,081,654.

(60) Provisional application No. 61/779,917, filed on Mar. 13, 2013.

(51) Int. Cl.
| | |
|---|---|
| *C07D 205/04* | (2006.01) |
| *C07D 207/16* | (2006.01) |
| *C07K 1/04* | (2006.01) |
| *C07K 1/113* | (2006.01) |
| *C07K 7/06* | (2006.01) |
| *A61K 38/00* | (2006.01) |

(58) Field of Classification Search
CPC ... A61K 31/397; A61K 31/40; A61K 31/4468
USPC ............ 546/244; 548/963, 965, 532; 514/210.17, 315, 423, 183, 529, 530, 531; 534/604
See application file for complete search history.

(56) References Cited

U.S. PATENT DOCUMENTS

| | | |
|---|---|---|
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,622,852 A | 4/1997 | Korsmeyer |
| 5,649,912 A | 7/1997 | Peterson |
| 5,663,316 A | 9/1997 | Xudong |
| 5,704,911 A | 1/1998 | Parsons |
| 5,708,136 A | 1/1998 | Burrell et al. |
| 5,750,767 A | 5/1998 | Carpino et al. |
| 5,811,515 A | 9/1998 | Grubbs et al. |
| 5,824,483 A | 10/1998 | Houston, Jr. et al. |
| 5,834,209 A | 11/1998 | Korsmeyer |
| 5,856,445 A | 1/1999 | Korsmeyer |
| 5,874,529 A | 2/1999 | Gilon et al. |
| 5,893,397 A | 4/1999 | Peterson et al. |
| 5,922,863 A | 7/1999 | Grubbs et al. |
| 5,955,593 A | 9/1999 | Korsmeyer |
| 5,965,703 A | 10/1999 | Horne et al. |
| 5,993,412 A | 11/1999 | Deily et al. |
| 5,998,583 A | 12/1999 | Korsmeyer |
| 6,051,554 A | 4/2000 | Hornik et al. |
| 6,153,391 A | 11/2000 | Picksley et al. |
| 6,184,344 B1 | 2/2001 | Kent et al. |
| 6,271,198 B1 | 8/2001 | Braisted et al. |
| 6,326,354 B1 | 12/2001 | Gross et al. |
| 6,348,558 B1 | 2/2002 | Harris et al. |
| 6,444,425 B1 | 9/2002 | Reed et al. |
| 6,610,657 B1 | 8/2003 | Goueli |
| 6,613,874 B1 | 9/2003 | Mazur et al. |
| 6,703,382 B2 | 3/2004 | Wang et al. |
| 6,713,280 B1 | 3/2004 | Huang et al. |
| 6,849,428 B1 | 2/2005 | Evans et al. |
| 6,875,594 B2 | 4/2005 | Muir et al. |
| 7,064,193 B1 | 6/2006 | Cory et al. |
| 7,083,983 B2 | 8/2006 | Lane et al. |
| 7,084,244 B2 | 8/2006 | Gilon et al. |
| 7,183,059 B2 | 2/2007 | Verdine et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,297,762 B2 | 11/2007 | Shrader et al. |
| 7,538,190 B2 | 5/2009 | Robinson et al. |
| 7,705,118 B2 | 4/2010 | Arora et al. |
| 7,723,469 B2 | 5/2010 | Walensky et al. |
| 7,745,573 B2 | 6/2010 | Robinson et al. |
| 7,786,072 B2 | 8/2010 | Verdine et al. |
| 8,324,428 B2 | 12/2012 | Verdine et al. |
| 8,592,377 B2 | 11/2013 | Verdine et al. |
| 8,895,699 B2 | 11/2014 | Verdine et al. |
| 8,957,026 B2 | 2/2015 | Verdine et al. |
| 9,163,330 B2 | 10/2015 | Verdine et al. |
| 9,617,309 B2 | 4/2017 | Verdine et al. |
| 10,081,654 B2 | 9/2018 | Verdine |
| 2004/0023887 A1 | 2/2004 | Pillutla et al. |
| 2004/0038901 A1 | 2/2004 | Basler et al. |
| 2004/0067503 A1 | 4/2004 | Tan et al. |
| 2004/0171809 A1 | 9/2004 | Korsmeyer et al. |
| 2005/0032800 A1 | 2/2005 | Bigot et al. |
| 2005/0250680 A1 | 11/2005 | Walensky et al. |
| 2006/0008848 A1 | 1/2006 | Verdine et al. |
| 2006/0014675 A1 | 1/2006 | Arora et al. |
| 2006/0148715 A1 | 7/2006 | Tweardy |
| 2008/0242598 A1 | 10/2008 | Fairlie et al. |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0326192 A1 | 12/2009 | Nash |
| 2010/0029552 A1 | 2/2010 | Watt et al. |
| 2010/0081611 A1 | 4/2010 | Bradner et al. |
| 2010/0152103 A1 | 6/2010 | Phadke et al. |
| 2010/0168388 A1 | 7/2010 | Bernal et al. |
| 2010/0184628 A1 | 7/2010 | Nash |
| 2010/0184645 A1 | 7/2010 | Verdine et al. |
| 2010/0216688 A1 | 8/2010 | Nash et al. |
| 2010/0234563 A1 | 9/2010 | Arora et al. |
| 2010/0298201 A1 | 11/2010 | Nash et al. |
| 2011/0028753 A1 | 2/2011 | Verdine et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0263815 A1 | 10/2011 | Nash |
| 2012/0082636 A1 | 4/2012 | Walensky et al. |
| 2012/0172402 A1 | 5/2012 | Schmalz et al. |
| 2012/0172311 A1 | 7/2012 | Nash et al. |
| 2012/0190818 A1 | 7/2012 | Nash |
| 2012/0270800 A1 | 10/2012 | Verdine et al. |
| 2013/0005943 A1 | 1/2013 | Arora et al. |
| 2013/0023646 A1 | 1/2013 | Nash et al. |
| 2013/0177979 A1 | 7/2013 | Turkson |
| 2013/0211046 A1 | 8/2013 | Verdine et al. |
| 2014/0005118 A1 | 1/2014 | Verdine et al. |
| 2014/0011979 A1 | 1/2014 | Verdine et al. |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0323701 A1 | 10/2014 | Nash et al. |
| 2015/0225471 A1 | 8/2015 | Liang |
| 2015/0239937 A1 | 8/2015 | Verdine et al. |
| 2015/0284437 A1 | 10/2015 | Verdine et al. |
| 2015/0376227 A1 | 12/2015 | Verdine et al. |
| 2016/0024153 A1 | 1/2016 | Verdine |

FOREIGN PATENT DOCUMENTS

| | | |
|---|---|---|
| JP | 2008501623 A | 1/2008 |
| JP | 2010510236 | 4/2010 |
| JP | 2010522769 A | 7/2010 |
| JP | 2012-532929 A | 12/2012 |
| KR | 1020090126308 B1 | 8/2009 |
| WO | 96/02642 A1 | 2/1996 |
| WO | 96/20951 A1 | 7/1996 |
| WO | 96/34878 A1 | 11/1996 |
| WO | 97/13537 A1 | 4/1997 |
| WO | 97/17092 A1 | 5/1997 |
| WO | 97/26002 A1 | 7/1997 |
| WO | 97/37705 A1 | 10/1997 |
| WO | 99/14259 A1 | 3/1999 |
| WO | 99/34833 A1 | 7/1999 |
| WO | 99/34850 A1 | 7/1999 |
| WO | 1999046367 A2 | 9/1999 |
| WO | 00/06187 A2 | 2/2000 |
| WO | 02/06479 A2 | 8/2002 |

(56) References Cited

FOREIGN PATENT DOCUMENTS

| | | | |
|---|---|---|---|
| WO | 2003053996 | A2 | 7/2003 |
| WO | 2003/106491 | A2 | 12/2003 |
| WO | 2003/106491 | A3 | 12/2003 |
| WO | 2004/041275 | A1 | 5/2004 |
| WO | 2004/058804 | A1 | 7/2004 |
| WO | 2004/093798 | A2 | 11/2004 |
| WO | 2005/040202 | A2 | 5/2005 |
| WO | 2005/040202 | A3 | 5/2005 |
| WO | 2005/044839 | A2 | 5/2005 |
| WO | 2005042531 | A1 | 5/2005 |
| WO | 2005/085457 | A2 | 9/2005 |
| WO | 2005/090388 | A1 | 9/2005 |
| WO | 2005/118620 | A2 | 12/2005 |
| WO | 2005/118620 | A3 | 12/2005 |
| WO | 2005/118634 | A2 | 12/2005 |
| WO | 2005/118634 | A3 | 12/2005 |
| WO | 2006/103666 | A2 | 10/2006 |
| WO | 2007013050 | A1 | 2/2007 |
| WO | 2007/141533 | A2 | 12/2007 |
| WO | 2008/061192 | A2 | 5/2008 |
| WO | 2008/061192 | A3 | 5/2008 |
| WO | 2008/095063 | A1 | 8/2008 |
| WO | 2008/121767 | A2 | 10/2008 |
| WO | WO2009005677 | * | 1/2009 |
| WO | 2009020477 | A1 | 2/2009 |
| WO | 2009/042237 | A2 | 4/2009 |
| WO | 2009046407 | A2 | 4/2009 |
| WO | 2009/126292 | A2 | 10/2009 |
| WO | 2010/011313 | A2 | 1/2010 |
| WO | 2010/034029 | A1 | 3/2010 |
| WO | 2010/068684 | A2 | 6/2010 |
| WO | 2011/008260 | A2 | 1/2011 |
| WO | 2011003626 | A1 | 1/2011 |
| WO | 2011082285 | A1 | 7/2011 |
| WO | 2011/146974 | A1 | 12/2011 |
| WO | 2011/156686 | A2 | 12/2011 |
| WO | 2012/040459 | A2 | 3/2012 |
| WO | 2012/065181 | A2 | 5/2012 |
| WO | 2012/174423 | A1 | 12/2012 |
| WO | 2014/052647 | A2 | 4/2014 |
| WO | 2014/055564 | A1 | 4/2014 |
| WO | 2014/110420 | A1 | 7/2014 |

OTHER PUBLICATIONS

Sliwinski, et. al., Comptes Rendus Chimie (2003), 6(1), 67-78. (Year: 2003).*
Notice of Preliminary Rejection issued in Korean Patent Application No. 10-2021-7018392, mailed Oct. 13, 2021.
Canadian Office Action for Canadian Patent Application No. 3,113,959, mailed Jun. 17, 2022.
Japanese Office Action for Japanese Patent Application No. 2019-62248, mailed Dec. 6, 2021.
European Extended Search Report for European Patent Application No. 21155269.0, mailed Jul. 27, 2021.
Chiba, et al., "Synthesis of hydrophobic phase-tagged prolyl peptides featuring rapid reaction/separation", Tetrahedron, 65, pp. 8014-8020, Jul. 24, 2009 (Jul. 24, 2009).
Bittermann, et al., "A Highly Practical RCM Approach towards a Molecular Building Kit of Spirocyclic Reverse Turn Mimics", Chemistry—A European Journal, vol. 12, No. 24, Aug. 16, 2006 (Aug. 16, 2006), pp. 6315-6322.
Wang, 4-Alkyl-2-trichloromethyloxazolidin-5-ones: Valuable Precursors to Enantiomerically Pure C- and N-Protected α-Alkyl Prolines. Synlett. 1999;1:33-36.
Kirira, et al: "Electrochemical Deallylation of [alpha]-Allyl Cyclic Amines and Synthesis of Optically Active Quaternary Cyclic Amino Acids", Chemistry—A European Journal, vol. 16, No. 13, Feb. 19, 2010 (Feb. 19, 2010), pp. 3970-3982.
Zhang, et al., "Efficient and stereoselective synthesis of novel cis-4-substituted proline analogues", Tetrahedron etters, 44, Jan. 30, 2003, pp. 1413-1415.

Einsiedel, et al., "Molecular Building Kit of Fused-Proline-Derived Peptide Mimetics Allowing Specific Adjustment of the Dihedral Angle," J. Org. Chem., 2007, 72, 9102-9113.
Kim, et al., "Anodic Modification of Proline Derivatives Using a Lithium Perchlorate/Nitromethane Electrolyte Solution," Organic Letters, 2002, vol. 4, No. 21, 3735-3737.
Banfi, et al., "A new convergent and stereoselective synthesis of 2,5-disubstituted N-acylpyrrolidines," Tetrahedron 62 (2006) 4331-4341.
Australian Examination Report issued in Australian Patent Application No. 2021200216, mailed Aug. 9, 2022.
Examination Report No. 1 for Australian Application No. 2014244232, dated Apr. 19, 2018 (16 pages).
Stafstrom et al., "Dormancy-associated gene expression in pea axillary buds. Cloning and expression of PsDRM1 and PsDRM2," Planta, 205 (4): 547-52 (1998).
Hilpert et al., "Peptide arrays on cellulose support: Spot synthesis, a time and cost efficient method for synthesis of large numbers of peptides in a parallel and addressable fashion," Nat Protoc., 2(6): 1333-1349 (2007).
Becker et al., "Three-dimensional structure of the Stat33 homodimer bound to DNA," Nature, 394, 145-151 (1998).
Zhao et al., "A cell-permeable Stat3 SH2 domain mimetic inhibits Stat3 activation and induces antitumor cell effects in vitro," J Biol Chem. 285(46):35855-65 (2010).
Robinson, "Beta-hairpin peptidomimetics: design, structures and biological activities," Ace Chem Res. 41(10):1278-88 (2008).
Oh et al., "A convergent synthesis of new beta-turn mimics by click chemistry," Chem Commun (Camb). (29):3069-71 (2006).
Holland-Nell et al., "Maintaining biological activity by using triazoles as disulfide bond mimetics," Angew Chem Int Ed Engl. 50(22):5204-6 (2011).
Search Report and Written Opinion for Singapore Patent Application No. 11201508431 V, dated Aug. 26, 2016 (17 pages).
International Preliminary Report on Patentability for PCT/US2014/058680, mailed Apr. 14, 2016.
[No Author Listed] Designing Custom Peptides from SIGMA Genosys, p. 1. Accessed Jul. 27, 2012.
[No Author Listed] Brain Tumors. Merck Manuals. Aug. 21, 2014. merckmanuals.com/home/brain_spinal_cord_and_nerve_disorders/tumors_of_the_nervous_system/brain tumors.html. 9 pages.
Lomar et al., Synthese symmetrischerf ketone unter verwendung von 2-Phenyl-2-oxazolin-5-on. Chemische Berichte. 1980;113(12): 3706-15.
Tsuji et al., Synthesis of gamma, delta-unsay urated ketones by the intramolecular decarboxylative allylation of allyl beta-reto carboxylates and alkenyl allyl carbonates catalyzed by molybdenum, nickel, and rhodium complexes. Chemistry Letters. 1984; 13(10):1721-1724.
Extended European Search Report for EP 10800148.8, mailed Oct. 16, 2013.
Invitation to Pay Additional Fees for PCT/US2010/001952, mailed Oct. 29, 2010.
International Search Report and Written Opinion for PCT/US2010/001952, mailed Feb. 2, 2011.
International Preliminary Report on Patentability for PCT/US2010/001952, mailed Jan. 26, 2012.
Extended European Search Report for EP 09800675.2, mailed Dec. 6, 2012.
Invitation to Pay Additional Fees for PCT/US2009/004260, mailed Mar. 19, 2010.
International Search Report and Written Opinion for PCT/US2009/004260, mailed Oct. 15, 2010.
International Preliminary Report on Patentability for PCT/US2009/004260, mailed Feb. 3, 2011.
Extended European Search Report for EP 12159110.1, mailed Jul. 20, 2012.
Extended European Search Report (Replacement Copy) for EP 12159110.1, mailed Sep. 27, 2012.
International Search Report and Written Opinion for PCT/US2008/058575, mailed Nov. 17, 2008.
International Preliminary Report on Patentability for PCT/US2008/058575, mailed Oct. 8, 2009.

(56) References Cited

OTHER PUBLICATIONS

Invitation to Pay Additional Fees for PCT/US2011/052755, mailed Feb. 16, 2012.
International Search Report and Written Opinion for PCT/US2011/052755, mailed Apr. 25, 2012.
International Preliminary Report on Patentability for PCT/US2011/052755, mailed Apr. 4, 2013.
International Search Report and Written Opinion for PCT/US2012/042738, mailed Oct. 18, 2012.
International Preliminary Report on Patentability for PCT/US2012/042738, mailed Jan. 3, 2014.
Invitation to Pay Additional Fees for PCT/US2013/062004, mailed Jan. 2, 2014.
International Search Report and Written Opinion for PCT/US2013/062004, mailed Apr. 23, 2014.
International Preliminary Report on Patentability for PCT/US2013/062004, mailed Apr. 9, 2015.
International Search Report and Written Opinion for PCT/US2013/062929, mailed Jan. 30, 2014.
International Preliminary Report on Patentability for PCT/US2013/062929, mailed Apr. 16, 2015.
Invitation to Pay Additional Fees for PCT/US2014/025544, mailed Jul. 22, 2014.
International Search Report and Written Opinion for PCT/US2014/025544, mailed Sep. 10, 2014.
International Preliminary Report on Patentability for PCT/US2014/025544, mailed Sep. 24, 2015.
International Search Report and Written Opinion for PCT/US2014/042329, mailed Nov. 24, 2014.
International Preliminary Report on Patentability for PCT/US2014/042329, mailed Dec. 23, 2015.
International Search Report and Written Opinion for PCT/US2014/041338, mailed Nov. 10, 2014.
International Preliminary Report on Patentability for PCT/US2014/041338, mailed Dec. 17, 2015.
International Search Report and Written Opinion for PCT/US2014/058680, mailed Apr. 23, 2015.
Extended European Search Report for EP 12800679.8, mailed Oct. 2, 2014.
International Search Report and Written Opinion for PCT/US2012/042719, mailed Nov. 1, 2012.
International Preliminary Report on Patentability for PCT/US2012/042719, mailed Jan. 3, 2014.
International Search Report and Written Opinion for PCT/US2008/052580, mailed May 16, 2008.
[No Author Listed] Overview of Leukemia. Merck Manuals. Aug. 20, 2014. merckmanuals.com/home/blood_disorders/leukemias/overview_of_leukemia.html?qt=Leukemia& alt=sh.
[No Author Listed] Colorectal Cancer. Merck Manuals. Aug. 21, 2014. merckmanuals.com/home/digestive_disorders/tumors_of_the_digestive_system/colorectal_cancer.html.
[No Author Listed] Prostate Cancer. Merck Manuals. Aug. 21, 2014. merckmanuals.com/home/kidney_and_urinary_tract_disorders/cancers_of_the_kidney_and_genito urinary_tract/prostate_cancer.html?qt=prostatecancer&alt=sh.
[No Author Listed] Breast Cancer. Merck Manuals. Aug. 21, 2014. merckmanuals.com/home/womens_health_issues/breast_disorders/breast_cancer.html.
[No Author Listed] Bladder Cancer. Merck Manuals. Aug. 21, 2014. merckmanuals.com/home/kidney_and_urinary_tract_disorders/cancers_of_the_kidney_and_genito urinary_tract/bladder_cancer.html.
[No Author Listed] Wikipedia Entry, "Willgerodt Rearrangement." Oct. 7, 2012. http://en.wikipedia.org/wiki/Willgerodt_rearrangement. [Last accessed Feb. 12, 2013].
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011, 80(4): 305-318.
Altschul et al., Basic local alignment search tool. J Mol Biol. Oct. 5, 1990;215(3):403-10.
Aman et al., cDNA cloning and characterization of the human interleukin 13 receptor alpha chain. J Biol Chem. Nov. 15, 1996;271(46):29265-70.
Andrews et al., Forming Stable Helical Peptides Using Natural and Artificial Amino Acids. Tetrahedron. 1999;55:11711-43.
Andrews et al., Kinetic analysis of the interleukin-13 receptor complex. J Biol Chem. Nov. 29, 2002;277(48):46073-8. Epub Sep. 26, 2002.
Armstrong et al., X=Y-ZH Systems as potential 1,3-dipoles. 5. Intramolecular cycloadditions of imines of a-amino acid esters. Tetrahedron. 1985;41(17):3547-58.
Artavanis-Tsakonas et al., Notch signaling: cell fate control and signal integration in development. Science. Apr. 30, 1999;284(5415):770-6.
Attisano et al., TGFbeta and Wnt pathway cross-talk. Cancer Metastasis Rev. Jan.-Jun. 2004;23(1-2):53-61.
Babcock, Proteins, radicals, isotopes, and mutants in photosynthetic oxygen evolution. Proc Natl Acad Sci USA Dec. 1, 1993;90(23):10893-5.
Babine et al., Molecular Recognition of Proteinminus signLigand Complexes: Applications to Drug Design. Chem Rev. Aug. 5, 1997;97(5):1359-1472.
Balthaser et al., Remodelling of the natural product fumagillol employing a reaction discovery approach. Nat Chem. Dec. 2011;3(12):969-73.
Banerjee et al., Structure of a DNA glycosylase searching for lesions. Science. Feb. 24, 2006;311(5764): 1153-7.
Banerjee et al., Structure of a repair enzyme interrogating undamaged DNA elucidates recognition of damaged DNA Nature. Mar. 31, 2005;434(7033):612-8.
Bang et al., Total chemical synthesis of crambin. J Am Chem Soc. Feb. 11, 2004;126(5):1377-83.
Barandon et al., Reduction of infarct size and prevention of cardiac rupture in transgenic mice overexpressing FrzA. Circulation. Nov. 4, 2003;108(18):2282-9. Epub Oct. 27, 2003.
Barker et al., Mining the Wnt pathway for cancer therapeutics. Nat Rev Drug Discov. Dec. 2006;5(12):997-1014.
Beloken et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (S)-2-[N-(N'-benzyl-prolyl)amino]benzophenone (BPB) and Ni(II) complexes of Schiffs bases derived from BPB and amino acids. Tetrahedron: Asymmetry. 1998;9:4249-52.
Bennett et al., Regulation of osteoblastogenesis and bone mass by Wnt1Ob. Proc Natl Acad Sci USA. Mar. 1, 2005;102(9):3324-9. Epub Feb. 22, 2005.
Berendsen et al., A glimpse of the Holy Grail? Science. Oct. 23, 1998;282(5389):642-3.
Berge et al., Pharmaceutical salts. J Pharm Sci. Jan. 1977;66(1):1-19.
Bernal et al., Reactivation of the p53 tumor suppressor pathway by a stapled p53 peptide. J Am Chem Soc. Mar. 7, 2007;129(9):2456-7. Epub Feb. 7, 2007.
Biagini et al., Cross-metathesis of Unsaturated a-amino Acid Derivatives. J Chem Soc Perkin Trans. 1998;1:2485-99.
Bierzynski et al., A salt bridge stabilizes the helix formed by isolated C-peptide of Rnase A Proc Natl Acad Sci US A. Apr. 1982;79(8):2470-4.
Blackwell et al., Highly Efficient Synthesis of Covalently Cross-Linked Peptide Helices by Ring-Closing Metathesis. Angew Chem Int Ed. 1998;37(23):3281-84.
Blackwell et al., Ring-closing metathesis of olefinic peptides: design, synthesis, and structural characterization of macrocyclic helical peptides. J Org Chem. Aug. 10, 2001;66(16):5291-302.
Blangetti et al., Suzuki-miyaura cross-coupling in acylation reactions, scope and recent developments. Molecules. Jan. 17, 2013;18(1):1188-213. doi:10.3390/molecules18011188.
Blundell et al., Atomic positions in rhombohedral 2-zinc insulin crystals. Nature. Jun. 25, 1971;231(5304):506-11.

(56) References Cited

OTHER PUBLICATIONS

Bode et al., Chemoselective amide ligations by decarboxylative condensations of N-alkylhydroxylamines and alpha-ketoacids. Angew Chem Int Ed Engl. Feb. 13, 2006;45(8):1248-52.

Boyden et al., High bone density due to a mutation in LDL-receptor-related protein 5. N Engl J Med. May 16, 2002;346(20):1513-21.

Bracken et al., Synthesis and Nuclear Magnetic Resonance Structure Determination of an a-Helical, Bicyclic, Lactam-Bridged Hexapeptide. J Am Chem Soc. 1994;116:6431-32.

Bradley et al., Limits of cooperativity in a structurally modular protein: response of the Notch ankyrin domain to analogous alanine substitutions in each repeat. J Mol Biol. Nov. 22, 2002;324(2):373-86.

Brandt et al., Dimeric fragment of the insulin receptor alpha-subunit binds insulin with full holoreceptor affinity. J Biol Chem. Apr. 13, 2001;276(15):12378-84. Epub Jan. 12, 2001.

Bray, Notch signalling: a simple pathway becomes complex. Nat Rev Mol Cell Biol. Sep. 2006;7(9):678-89.

Brou et al., A novel proteolytic cleavage involved in Notch signaling: the role of the disintegrin-metalloprotease TACE. Mol Cell. Feb. 2000;5(2):207-16.

Brubaker et al., Solution structure of the interacting domains of the Mad-Sin3 complex: implications for recruitment of a chromatin-modifying complex. Cell. Nov. 10, 2000;103(4):655-65.

Brusselle et al., Allergen-induced airway inflammation and bronchial responsiveness in wild-type and interleukin-4-deficient mice. Am J Respir Cell Mol Biol. Mar. 1995;I2(3):254-9.

Burger et al., Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.

Caricasole et al., The Wnt pathway, cell-cycle activation and beta-amyloid: novel therapeutic strategies in Alzheimer's disease? Trends Pharmacol Sci. May 2003;24(5):233-8.

Carillo et al., The Multiple Sequence Alignment Problem in Biology. SIAM J Applied Math. 1988;48:1073-82.

Carlson et al., Specificity landscapes of DNA binding molecules elucidate biological function. Proc Natl Acad Sci US A. Mar. 9, 2010;107(10):4544-9. doi: 10.1073/pnas.0914023107. Epub Feb. 22, 2010.

Chang et al., Insulin signaling and the regulation of glucose transport. Mol Med. Jul.-Dec. 2004;10(7-12):65 71.

Chen et al., Determination of the helix and beta form of proteins in aqueous solution by circular dichroism. Biochemistry. Jul. 30, 1974;13(16):3350-9.

Chen et al., Small molecule-mediated disruption of Wnt-dependent signaling in tissue regeneration and cancer. Nat Chem Biol. Feb. 2009;5(2):100-7. Epub Jan. 4, 2009.

Cheng et al., Emerging role of RAB GTPases in cancer and human disease. Cancer Res. Apr. 1, 2005;65(7):2516-9.

Furstner et al., Nozaki-Hiyama-Kishi Reactions Catalytic in Chromium. J Am Chem Soc. 1996:118:12349-57.

Fustero et al., Asymmetric synthesis of new beta, beta-difluorinated cyclic quaternary alpha- amino acid derivatives. Org Lett. Aug. 31, 2006;8(18):4129-32.

Gallivan et al., A neutral, water-soluble olefin metathesis catalyst based on an N-heterocyclic carbene ligand. Tetrahedron Letters. 2005;46:2577-80.

Gante, Peptidomimetics-Tailored Enzyme Inhibitors. J Angew Chem Int Ed Engl. 1994;33:1699-1720.

Garg et al., Mutations in NotchI cause aortic valve disease. Nature. Sep. 8, 2005;437(7056):270-4. Epub Jul. 17, 2005.

Gat et al., De Novo hair follicle morphogenesis and hair tumors in mice expressing a truncated beta-catenin in skin. Cell. Nov. 25, 1998;95(5):605-14.

Gav Athiotis et al., BAX activation is initiated at a novel interaction site. Nature. Oct. 23, 2008;455(7216): 1076-81.

Gentle et al., Direct production of proteins with N-terminal cysteine for site-specific conjugation. Bioconjug Chem. May-Jun. 2004;I5(3):658-63.

Gerber-Lemaire et al., Glycosylation pathways as drug targets for cancer: glycosidase inhibitors. Mini Rev Med Chem. Sep. 2006;6(9):1043-52.

Giannis et al., Peptidomimetics for Receptor Ligands-Discovery, Development, and Medical Perspectives. Angew Chem Int Ed Engl. 1993;32:1244-67.

Gong et al., LDL receptor-related protein 5 (LRP5) affects bone accrual and eye development. Cell. Nov. 16, 2001;107(4):513-23.

Goodson et al., Potential Growth Antagonists. I. Hydantoins and Disubstituted Glycines. J Org Chem. 1960;25:1920-24.

Gorlich et al., Transport between the cell nucleus and the cytoplasm. Annu Rev Cell Dev Biol. 1999;15:607-60.

Goun et al., Molecular transporters: synthesis of oligoguanidinium transporters and their application to drug delivery and real-time imaging. Chembiochem. Oct. 2006;7(10):1497-515.

Greenfield et al., Computed circular dichroism spectra for the evaluation of protein conformation. Biochemistry. Oct. 1969;8(10):4108-16.

Greenlee et al., A General Synthesis of a-vinyl-a-amino acids. Tetrahedron Letters. 1978;42:3999-4002.

Grossmann et al., Inhibition of oncogenic Wnt signaling through direct targeting of -catenin. Proc Natl Acad Sci US A. Oct. 30, 2012;109(44):17942-7. doi: 10.1073/pnas.1208396109. Epub Oct. 15, 2012.

Grubbs et al., Ring-Closing Metathesis and Related Processes in Organic Synthesis. Ace Chem Res. 1995;28:446-52.

Grunig et al., Requirement for IL-13 independently of IL-4 in experimental asthma. Science. Dec. 18, 1998;282(5397):2261-3.

Guinn et al., Synthesis and characterization of polyamides containing unnatural amino acids. Biopolymers. May 1995;35(5):503-12.

Guo et al., Probing the alpha-helical structural stability of stapled p53 peptides: molecular dynamics simulations and analysis. Chem Biol Drug Des. Apr. 2010;75(4):348-59. doi: 10.1111/j.1747-0285.2010.00951.x.

Gupta et al., Long-term effects of tumor necrosis factor-alpha treatment on insulin signaling pathway in HepG2 cells and HepG2 cells overexpressing constitutively active Akt/PKB. J Cell Biochem. Feb. 15, 2007;100(3):593-607.

Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.

Harris et al., Synthesis of praline-modified analogues of the neuroprotective agent glycyl-1-prolyl-glutamic acid (GPE). Tetrahedron. 2005;61:10018-35.

Hartmann et al., Dual roles of Wnt signaling during chondrogenesis in the chicken limb. Development. Jul. 2000;127(14):3141-59.

Hartmann, A Wnt canon orchestrating osteoblastogenesis. Trends Cell Biol. Mar. 2006;16(3):151-8. Epub Feb. 7, 2006.

Hellman et al., Electrophoretic mobility shift assay (EMSA) for detecting protein-nucleic acid interactions. Nat Protoc. 2007;2(8):1849-61.

Henchey et al., Contemporary strategies for the stabilization of peptides in the a-helical conformation. Curr Opin Chem Biol. 2008;12:692-97.

Hilton et al., Notch signaling maintains bone marrow mesenchymal progenitors by suppressing osteoblast differentiation. Nat Med. Mar. 2008;14(3):306-14. doi: 10.1038/nml 716. Epub Feb. 24, 2008.

Hipfner et al., Connecting proliferation and apoptosis in development and disease. Nat Rev Mol Cell Biol. Oct. 2004;5(10):805-15.

Hoang et al., Dickkopf 3 inhibits invasion and motility of Saos-2 osteosarcoma cells by modulating the Wnt-beta-catenin pathway. Cancer Res. Apr. 15, 2004;64(8):2734-9.

Holford et al., Adding 'splice' to protein engineering. Structure. Aug. 15, 1998;6(8):951-6.

Huang et al., How insulin binds: the B-chain alpha-helix contacts the L1 beta-helix of the insulin receptor. J Mol Biol. Aug. 6, 2004;341(2):529-50.

Huang et al., Tankyrase inhibition stabilizes axin and antagonizes Wnt signalling. Nature. Oct. 1, 2009;461(7264):614-20. Epub Sep. 16, 2009.

Jackson et al., General Approach to the Synthesis of Short a-Helical Peptides. J Am Chem Soc. 1991;113:9391-92.

(56) References Cited

OTHER PUBLICATIONS

Jamieson et al., Granulocyte-macrophage progenitors as candidate leukemic stem cells in blast-crisis CML. N Engl J Med. Aug. 12, 2004;351(7):657-67.
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Jordan et al., Wnt4 overexpression disrupts normal testicular vasculature and inhibits testosterone synthesis by repressing steroidogenic factor 1/beta-catenin synergy. Proc Natl Acad Sci US A. Sep. 16, 2003;100(19):10866-71. Epub Aug. 29, 2003.
Joutel et al., Notch3 mutations in Cadasil, a hereditary adult-onset condition causing stroke and dementia. Nature. Oct. 24, 1996;383(6602):707-10.
Junutula et al., Molecular characterization of Rab11 interactions with members of the family of Rab1-interacting proteins. J Biol Chem. Aug. 6, 2004;279(32):33430-7. Epub Jun. 1, 2004.
Karle et al., Structural characteristics of alpha-helical peptide molecules containing Aib residues. Biochemistry. Jul. 24, 1990;29(29):6747-56.
Karwoski et al., Lysinonorleucine cross-link formation in alpha amino heptenoic acid-substituted peptide derivatives. Biopolymers. 1978;17(5):1119-27.
Katoh et al., Cross-talk of WNT and FGF signaling pathways at GSK3beta to regulate beta-catenin and Snail signaling cascades. Cancer Biol Ther. Sep. 2006;5(9):1059-64. Epub Sep. 4, 2006.
Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.
Kaul et al., Stereochemical control of peptide folding. Bioorg Med Chem. Jan. 1999;7(1):105-17.
Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.
Kazmaier, Sythesis of Quaternary Amino Acids Containing , γ- as well as γ,δ-Unsaturated Side Chains via Chelate-Enolate Claisen Rearrangement. Tetrahedron Letters. 1996;37(30):5351-4.
Kelly-Welch et al., Interleukin-4 and Interleukin-13 Signaling Connections Maps. Science. 2003;300:1527-28.
Khalil et al., An efficient and high yield method for the N-tert-butoxycarbonyl protection of sterically hindered amino acids. Tetrahedron Lett. 1996;37(20):3441-44.
Kim et al., Introduction of all-hydrocarbon i,i+3 staples into alpha-helices via ring-closing olefin metathesis. Org Lett. Jul. 2, 2010;12(13):3046-9. doi: 10.1021/ol1010449.
Bird, et al, "Chemical Synthesis of Hydrocarbon-Stapled Peptides for Protein Interaction Research and Therapeutic Targeting", Curr Protoc Chem Biol. (2011) 3(3): 99-117.
Goudreau, et. al., "Potent Inhibitors of the Hepatitis C Virus NS3 Protease: Design and Synthesis of Macrocyclic Substrate-Based â-Strand Mimics", The Journal of Organic Chemistry, vol. 69, No. 19, Sep. 17, 2004, pp. 6185-6201.
CAS Registry No. 933687-70-8; 3-(dimethylamino)-a-(2-propen-1-yl)-3-pyrrolidinecarboxylic acid; Apr. 30, 2007.
CAS Registry No. 933687-66-2; 3-(methylamino)-1-(2-propen-1-yl)-3-pyrrolidinecarboxylic acid; Apr. 30, 2007.
Kowalczyk, R. et al., "How to blast osteoblasts? Novel dicarba analogues of amylin-(1-8) to treat osteoporosis," Bioorganic & Medicinal Chemistry, 2012, vol. 20, Issue 20, pp. 6011-6018.
Fujimoto, K. et al., "Development of a series of cross-linking agents that effectively stabilize alpha-helical structures in various short peptides," Chemistry, 2008, vol. 14, Issue 3, pp. 857-863.
Kim et al., Stereochemical effects of all-hydrocarbon tethers in i,i+4 stapled peptides. Bioorg Med Chem Lett. May 1, 2009;19(9):2533-6. Epub Mar. 13, 2009.
Kim et al., Synthesis of all-hydrocarbon stapled a-helical peptides by ring-closing olefin metathesis. Nat Protoc. Jun. 2011;6(6):761-71. doi: 10.1038/nprot.2011.324. Epub May 12, 2011.
Kimmerlin et al., '100 years of peptide synthesis': ligation methods for peptide and protein synthesis with applications to beta-peptide assemblies. J Pept Res. Feb. 2005;65(2):229-60.
Kinage et al., Highly regio-selective synthesis of beta-amino alcohol by reaction with aniline and propylene carbonate In self solvent systems over large pore zeolite catalyst. Green and Sustainable Chem. Aug. 2011;I: 76-84.
Kinzler et al., Identification of FAP locus genes from chromosome 5q21. Science. Aug. 9, 1991;253(5020):661-5.
Kinzler et al., Lessons from hereditary colorectal cancer. Cell. Oct. 18, 1996;87(2):159-70.
Knackmuss et al., Specific inhibition of interleukin-13 activity by a recombinant human single-chain immunoglobulin domain directed against the IL-13 receptor alpha1 chain. Biol Chem. Mar. 2007;388(3):325-30.
Kohler et al., DNA specificity enhanced by sequential binding of protein monomers. Proc Natl Acad Sci US A. Oct. 12, 1999;96(21):11735-9.
Kolb et al., Click Chemistry: Diverse Chemical Function from a Few Good Reactions. Angew Chem Int Ed Engl. Jun. 1, 2001;40(11):2004-2021.
Kondo et al., Frizzled 4 gene (FZD4) mutations in patients with familial exudative vitreoretinopathy with variable expressivity. Br J Ophthalmol. Oct. 2003;87(10):1291-5.
Konishi et al., Gamma-secretase inhibitor prevents Notch3 activation and reduces proliferation in human lung cancers. Cancer Res. Sep. 1, 2007;67(17):8051-7.
Korcsmaros et al., Uniformly curated signaling pathways reveal tissue-specific cross-talks and support drug target discovery. Bioinformatics. Aug. 15, 2010;26(16):2042-50. Epub Jun. 11, 2010.
Korinek et al., Depletion of epithelial stem-cell compartments in the small intestine of mice lacking Tcf-4. Nat Genet. Aug. 1998;I9(4):379-83.
Kotha et al., Modification of constrained peptides by ring-closing metathesis reaction. Bioorg Med Chem Lett. Jun. 4, 2001;11(11):1421-3.
Kouzarides, Acetylation: a regulatory modification to rival phosphorylation? EMBO J. Mar. 15, 2000;19(6):1176-9.
Koy All et al., Crystal structure of the nuclear effector of Notch signaling, CSL, bound to DNA. EMBO J. Sep. 1, 2004;23(17):3441-51. Epub Aug. 5, 2004.
Kozlovsky et al., GSK-3 and the neurodevelopmental hypothesis of schizophrenia. Eur Neuropsychopharmacol. Feb. 2002;12(1):13-25.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.
Kussie et al., Structure of the MDM2 oncoprotein bound to the p53 tumor suppressor transactivation domain. Science. Nov. 8, 1996;274(5289):948-53.
Kutchukian et al., All-atom model for stabilization of alpha-helical structure in peptides by hydrocarbon staples. J Am Chem Soc. Apr. 8, 2009;131(13):4622-7.
Lacombe et al., Reduction of Olefins on Solid Support Using Diimide. Tetrahderon Lett. 1998;39:6785-86.
Lammi et al., Mutations in AXIN2 cause familial tooth agenesis and predispose to colorectal cancer. Am J Hum Genet. May 2004;74(5):1043-50. Epub Mar. 23, 2004.
Laporte et al., Molecular and structural basis of cytokine receptor pleiotropy in the interleukin-4/13 system. Cell. Jan. 25, 2008;132(2):259-72.

(56) References Cited

OTHER PUBLICATIONS

Le Guezennec et al., Molecular characterization of Sin3 PAH-domain interactor specificity and identification of PAH partners. Nucleic Acids Res. 2006;34(14):3929-37. Epub Aug. 12, 2006.

Le Guezennec et al., Molecular determinants of the interaction of Mad with the PAH2 domain of mSin3. J Biol Chem. Jun. 11, 2004;279(24):25823-9. Epub Mar. 26, 2004.

Leduc et al., Helix-stabilized cyclic peptides as selective inhibitors of steroid receptor-coactivator interactions. Proc Natl Acad Sci USA. 2003;100(20):11273-78.

Lewis et al., Apoptosis in T cell acute lymphoblastic leukemia cells after cell cycle arrest induced by pharmacological inhibition of notch signaling. Chem Biol. Feb. 2007;14(2):209-19.

Li et al., Alagille syndrome is caused by mutations in human Jagged1, which encodes a ligand for NotchI. Nat Genet. Jul. 1997;I6(3):243-51.

Li et al., Modulation of Notch signaling by antibodies specific for the extracellular negative regulatory region of Notch3. J Biol Chem. Mar. 21, 2008;283(12):8046-54. doi: 10.1074/jbc.M800170200. Epub Jan. 8, 2008.

Li et al., Notch3 signaling promotes the development of pulmonary arterial hypertension. Nat Med. Nov. 2009;I5(11):1289-97. doi: 10.1038/nm.2021. Epub Oct. 25, 2009.

Liang et al., Wnt5a inhibits B cell proliferation and functions as a tumor suppressor in hematopoietic tissue. Cancer Cell. Nov. 2003;4(5):349-60.

Lindsay et al., Rab coupling protein (RCP), a novel Rab4 and Rab1 effector protein. J Biol Chem. Apr. 5, 2002;277(14):12190-9. Epub Jan. 10, 2002.

Liskamp, Conformationally restricted amino acids and dipeptides, (non)peptidomimetics and secondary structure mimetics. Reel Travl Chim Pays-Bas. 1994;113:1-19.

Little et al., A Mutation in the LDL Receptor-Related Protein 5 Gene Results in the Autosomal Dominant High-Bone-Mass Trait. Am J Hum Genet. 2002;70:11-19.

Liu et al., Chemical Ligation Approach to Form a Peptide Bond between Unprotected Peptide Segments. Concept and Model Study. J Am Chem Soc. 1994;116(10):4149-53.

Liu et al., Targeted degradation of beta-catenin by chimeric F-box fusion proteins. Biochem Biophys Res Commun. Jan. 23, 2004;313(4):1023-9.

Lo et al., Phosphorylation by the beta-catenin/MAPK complex promotes 14-3-3-mediated nuclear export of TCF/POP-1 in signal-responsive cells in C.elegans. Cell. Apr. 2, 2004;117(1):95-106.

Logan et al., The Wnt signaling pathway in development and disease. Annu Rev Cell Dev Biol. 2004;20:781-810.

Losey et al., Crystal structure of *Staphylococcus aureus* tRNA adenosine deaminase TadA in complex with RNA Nat Struct Mol Biol. Feb. 2006;I3(2):153-9. Epub Jan. 15, 2006.

Lou et al., The first three domains of the insulin receptor differ structurally from the insulin-like growth factor 1 receptor in the regions governing ligand specificity. Proc Natl Acad Sci USA. Aug. 15, 2006;103(33):12429-34. Epub Aug. 7, 2006.

Loughlin et al., Functional variants within the secreted frizzled-related protein 3 gene are associated with hip osteoarthritis in females. Proc Natl Acad Sci US A Jun. 29, 2004;101(26):9757-62. Epub Jun. 21, 2004.

Lu et al., Both Pbxl and E2A-Pbxl bind the DNA motif ATCAATCAA cooperatively with the products of multiple murine Hox genes, some of which are themselves oncogenes. Mol Cell Biol. Jul. 1995;I5(7):3786-95.

Lu et al., Structural determinants within Pbxl that mediate cooperative DNA binding with pentapeptide-containing Hox proteins: proposal for a model of a Pbxl-Hox-DNA complex. Mol Cell Biol. Apr. 1996;I6(4):1632-40.

Lubman et al., Quantitative dissection of the Notch:CSL interaction: insights into the Notch-mediated transcriptional switch. J Mol Biol. Jan. 19, 2007;365(3):577-89. Epub Oct. 3, 2006.

Luo et al., Wnt signaling and human diseases: what are the therapeutic implications? Lab Invest. Feb. 2007;87(2):97-103. Epub Jan. 8, 2007.

Luscher et al., The basic region/helix-loop-helix/leucine zipper domain of Myc proto-oncoproteins: function and regulation. Oncogene. May 13, 1999;18(19):2955-66.

Luu et al., Wnt/beta-catenin signaling pathway as a novel cancer drug target. Curr Cancer Drug Targets. Dec. 2004;4(8):653-71.

MacMillan, Evolving strategies for protein synthesis converge on native chemical ligation. Angew Chem Int Ed Engl. Nov. 27, 2006;45(46):7668-72.

Yang YL et al., "Synthesis and analgesic activity of 1-subsituted derivatives of 4-methoxycarbonyl-4-N-propionylanilinopiperidine", Yao Hsueh Hsueh Pao—Acta Pharmaceutica Sinica, Yaoxue Xuebao, vol. 25, No. 4, 1990, pp. 253-259.

Christopher L Wysong et al., "Novel [alpha], [alpha]-disubsituted amino acids for peptide secondary structure control", Peptides: Frontiers of Peptide Science; Proceedings of the Fifteenth American Peptide Symposium, Jun. 14-19, 1997, Nashville, Tennessee, USA; 15th APS, Kluwer Academic, pp. 116-117.

Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.

Ye et al., Neurogenic phenotypes and altered Notch processing in *Drosophila presenilin* mutants. Nature. Apr. 8, 1999;398(6727):525-9.

Yu et al., The role of Axin2 in calvarial morphogenesis and craniosynostosis. Development. Apr. 2005;132(8):1995-2005.

Zhang et al., A cell-penetrating helical peptide as a potential HIV-1 inhibitor. J Mol Biol. May 2, 2008;378(3):565-80. doi: 10.1016/j.jmb.2008.02.066. Epub Mar. 6, 2008.

Zhang et al., A triazole-templated ring-closing metathesis for constructing novel fused and bridged triazoles. Chem Commun (Camb). Jun. 21, 2007;(23):2420-2.

Zhou et al., Identification of Ubiquitin Target Proteins Using Cell-Based Arrays. J Proteome Res. 2007;6:4397-4406.

Zhou et al., Lymphoid enhancer factor 1 directs hair follicle patterning and epithelial cell fate. Genes Dev. Mar. 15, 1995;9(6):700-13.

Zhou et al., Tyrosine kinase inhibitor STI-571/Gleevec down-regulates the beta-catenin signaling activity. Cancer Lett. Apr. 25, 2003;193(2):161-70.

Zimm et al., Theory of the Phase Transition between Helix and Random Coil in Polypeptide Chains. J Chem Phys. 1959;31:526-35.

Zor et al., Solution structure of the KIX domain of CBP bound to the transactivation domain of c-Myb. J Mol Biol. Mar. 26, 2004;337(3):521-34.

Polakis, The oncogenic activation of beta-catenin. Curr Opin Genet Dev. Feb. 1999;9(1):15-21.

Qiu et al., Convenient, Large-Scale Asymmetric Synthesis of Enantiomerically Pure trans-Cinnamylglycine and -a-Alanine. Tetrahedron. 2000;56:2577-82.

Rao et al., Inhibition of Notch signaling by gamma secretase inhibitor engages the RB pathway and elicits cell cycle exit in T-cell acute lymphoblastic leukemia cells. Cancer Res. Apr. 1, 2009;69(7):3060-8. doi: 10.1158/0008-5472.CAN-08-4295. Epub Mar. 24, 2009.

Rawlinson et al., CRMI-mediated nuclear export of dengue virus RNA polymerase NS5 modulates interleukin-8 Induction and virus production. J Biol Chem. Jun. 5, 2009;284(23):15589-97. Epub Mar. 18, 2009.

Reya et al., Wnt signalling in stem cells and cancer. Nature. Apr. 14, 2005;434(7035):843-50.

Rich et al., Synthesis of the cytostatic cyclic tetrapeptide, chlamydocin. Tetrahderon Letts. 1983;24(48):5305-08.

Ridgway et al., Inhibition of Dll4 signalling inhibits tumour growth by deregulating angiogenesis. Nature. Dec. 21, 2006;444(7122):1083-7.

Robert, A hierarchical "nesting" approach to describe the stability of alpha helices with side-chain interactions. Biopolymers. 1990;30(3-4):335-47.

(56) References Cited

OTHER PUBLICATIONS

Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-I promoter is a target of the beta-catenin/T-cell factor pathway. J Biol Chem. Aug. 16, 2002;277(33):29577-83. Epub Jun. 4, 2002.
Roos et al., Synthesis of a-Substituted a-Amino Acids via Cationic Intermediates. J Org Chem. 1993;58:3259-68.
Ross et al., Inhibition of adipogenesis by Wnt signaling. Science. Aug. 11, 2000;289(5481):950-3.
Rudinger, Characteristics of the amino acids as components of a peptide hormone sequence. In: Peptide Hormones. J. A. Parsons, ed. University Park Press. Jun. 1976:1-7.
Sadot et al., Down-regulation of beta-catenin by activated p53. Mol Cell Biol. Oct. 2001;21(20):6768-81.
Sali et al., Stabilization of protein structure by interaction of alpha-helix dipole with a charged side chain. Nature. Oct. 20, 1988;335(6192):740-3.
Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Sattler et al., Structure of Bcl-xL-Bak peptide complex: recognition between regulators of apoptosis. Science. Feb. 14, 1997;275(5302):983-6.
Saxon et al., Cell surface engineering by a modified Staudinger reaction. Science. Mar. 17, 2000;287(5460):2007-10.
Schaffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schaffer et al., Assembly of high-affinity insulin receptor agonists and antagonists from peptide building blocks. Proc Natl Acad Sci US A Apr. 15, 2003;100(8):4435-9. Epub Apr. 8, 2003.
Schafmiester et al., An All-Hydrocarbon Cross-Linking System for Enhancing the Helicity and Metabolic Stability of Peptides. J Am Chem Soc. 2000;122:5891-92.
Scheffzek et al., The Ras-RasGAP complex: structural basis for GTPase activation and its loss in oncogenic Ras mutants. Science. Jul. 18, 1997;277(5324):333-8.
Schinzel et al., The phosphate recognition site of Escherichia coli maltodextrin phosphorylase. FEES Lett. Jul. 29, 1991;286(1-2):125-8.
Schmiedeberg et al., Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Schwarzer et al., Protein semisynthesis and expressed protein ligation: chasing a protein's tail. Curr Opin Chem Biol. Dec. 2005;9(6):561-9. Epub Oct. 13, 2005.
Scott et al., Evidence of insulin-stimulated phosphorylation and activation of the mammalian target of rapamycin mediated by a protein kinase B signaling pathway. Proc Natl Acad Sci USA Jun. 23, 1998;95(13):7772-7.
Seabra et al., Rab GTPases, intracellular traffic and disease. Trends Mol Med. Jan. 2002;8(1):23-30.
Seiffert et al., Presenilin-1 and -2 are molecular targets for gamma-secretase inhibitors. J Biol Chem. Nov. 3, 2000;275(44):34086-91.
Shair, A closer view of an oncoprotein-tumor suppressor interaction. Chem Biol. Nov. 1997;4(11):791-4.
Shiba et al., Structural basis for Rabl I-dependent membrane recruitment of a family of Rabl 1-interacting protein 3 (FIP3)/Arfophilin-1. Proc Natl Acad Sci US A Oct. 17, 2006;103(42):15416-21. Epub Oct. 9, 2006.
Si et al., CCN1/Cyr61 is regulated by the canonical Wnt signal and plays an important role in Wnt3A-induced osteoblast differentiation of mesenchymal stem cells. Mol Cell Biol. Apr. 2006,26(8):2955-64.
Siddle et al., Specificity in ligand binding and intracellular signalling by insulin and insulin-like growth factor receptors. Biochem Soc Trans. Aug. 2001;29(Pt 4):513-25.
Singh et al., Iridium(I)-catalyzed regio- and enantioselective allylic amidation. Tet. Lett. 2007;48 (40): 7094-7098.
Skinner et al., Basic helix-loop-helix transcription factor gene family phylogenetics and nomenclature. Differentiation. Jul. 2010;80(1):I-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci USA Apr. 13, 2010;107(15):6771-6. doi: 10.1073/pnas.1001813107. Epub Mar. 26, 2010.
Soucek et al., Modelling Myc inhibition as a cancer therapy. Nature. Oct. 2, 2008;455(7213):679-83. Epub Aug. 17, 2008.
Sparey et al., Cyclic sulfamide gamma-secretase inhibitors. Bioorg Med Chem Lett. Oct. 1, 2005;15(19):4212-6.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Still et al., Semianalytical Treatment of Salvation for Molecular Mechanics and Dynamics. J Am Chem Soc. 1990;112:6127-29.
Struhl et al., Presenilin is required for activity and nuclear access of Notch in *Drosophila*. Nature. Apr. 8, 1999;398(6727):522-5.
Stueanaes et al., Beta-adrenoceptor stimulation potentiates insulin-stimulated PKB phosphorylation in rat cardiomyocytes via CAMP and PKA. Br J Pharmacol. May 2010;160(1):116-29. doi: 10.1111/j.1476-5381.2010.00677.
Su et al., Eradication of pathogenic beta-catenin by Skpl/Cullin/F box ubiquitination machinery. Proc Natl Acad Sci US A. Oct. 28, 2003;100(22):12729-34. Epub Oct. 16, 2003.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Takeda et al., Human sebaceous tumors harbor inactivating mutations in LEFI. Nat Med. Apr. 2006;I2(4):395-7. Epub Mar. 26, 2006.
Tanaka, Design and synthesis of non-proteinogenic amino acids and secondary structures of their peptides. Yakugaku Zasshi. Oct. 2006:126(10):931-44. Japanese (Abstract Only).
Thompson et al., Mutants of interleukin 13 with altered reactivity toward interleukin 13 receptors. J Biol Chem. Oct. 15, 1999;274(42):29944-50.
Marshall et al., Back to the future: ribonuclease A Biopolymers. 2008;90(3):259-77.
McKern et al., Structure of the insulin receptor ectodomain reveals a folded-over conformation. Nature. Sep. 14, 2006;443(7108):218-21. Epub Sep. 6, 2006.
McNamara et al., Peptides constrained by an aliphatic linkage between two C(alpha) sites: design, synthesis, and unexpected conformational properties of an i, (i+4)-linked peptide. J Org Chem. Jun. 29, 2001;66(13):4585-94.
Mellegaardw Aetzig et al., Allylic amination via decarboxylative C—N bond formation Synlett. 2005;18:182759-2762.
Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.
Meyers et al., Formation of mutually exclusive Rabl 1 complexes with members of the family of Rabl1-interacting proteins regulates Rab11 endocytic targeting and function. J Biol Chem. Dec. 13, 2002;277(50):49003-10. Epub Oct. 9, 2002.
Miller et al., Application of Ring-Closing Metathesis to the Synthesis of Rigidified Amino Acids and Peptides. J Am Chem Soc. 1996;118(40):9606-9614.

(56) References Cited

OTHER PUBLICATIONS

Miller et al., Synthesis of Conformationally Restricted Amino Acids and Peptides Employing Olefin Metathesis. J Am Chem Soc. 1995;117(21):5855-5856.
Miloux et al., Cloning of the human IL-13R alpha1 chain and reconstitution with the IL4R alpha of a functional IL-4/IL-13 receptor complex. FEES Lett. Jan. 20, 1997;401(2-3):163-6.
Miyaoka et al., Increased expression of Wnt-1 in schizophrenic brains. Schizophr Res. Jul. 27, 1999;38(1):1-6.
Moellering et al., Computational modeling and molecular optimization of stabilized alpha-helical peptides targeting Notch-CSL transcriptional complexes. European Journal of Cancer Supplements Nov. 2010;8(7):30. DOI: 10.1016/S1359-6349(10)71774-2. Abstract 69.
Moellering et al., Direct inhibition of the Notch transcription factor complex. Nature. Nov. 12, 2009;462(7270):182-8.
Moon et al., WNT and beta-catenin signalling: diseases and therapies. Nat Rev Genet. Sep. 2004;5(9):689-99.
Morin, beta-catenin signaling and cancer. Bioessays. Dec. 1999;21(12):1021-30.
Moses et al., The growing applications of click chemistry. Chem Soc Rev. Aug. 2007;36(8):1249-62.
Moy et al., Solution structure of human IL-13 and implication for receptor binding. J Mol Biol. Jun. 29, 2001;310(1):219-30.
Mudher et al., Alzheimer's disease-do tauists and baptists finally shake hands? Trends Neurosci. Jan. 2002;25(1):22-6.
Muir et al., Expressed protein ligation: a general method for protein engineering. Proc Natl Acad Sci US A. Jun. 9, 1998;95(12):6705-10.
Muir, Semisynthesis of proteins by expressed protein ligation. Annu Rev Biochem. 2003;72:249-89. Epub Feb. 27, 2003.
Muppidi et al., Conjugation of spermine enhances cellular uptake of the stapled peptide-based inhibitors of p53-Mdm2 interaction. Bioorg Med Chem Lett. Dec. 15, 2011;21(24):7412-5. doi:10.1016/j.bmcl.2011.10.009. Epub Oct. 12, 2011.
Mynarcik et al., Alanine-scanning mutagenesis of a C-terminal ligand binding domain of the insulin receptor alpha subunit. J Biol Chem. Feb. 2, 1996;271(5):2439-42.
Mynarcik et al., Identification of common ligand binding determinants of the insulin and insulin-like growth factor 1 receptors. Insights into mechanisms of ligand binding. J Biol Chem. Jul. 25, 1997;272(30):18650-5.
Myung et al., The ubiquitin-proteasome pathway and proteasome inhibitors. Med Res Rev. Jul. 2001;21(4):245-73.
Nair et al., X-ray structures of Myc-Max and Mad-Max recognizing DNA Molecular bases of regulation by proto-oncogenic transcription factors. Cell. Jan. 24, 2003;112(2):193-205.
Nakashima et al., Cross-talk between Wnt and bone morphogenetic protein 2 (BMP-2) signaling in differentiation bathway of C2C12 myoblasts. J Biol Chem. Nov. 11, 2005;280(45):37660-8. Epub Sep. 2, 2005.
Nam et al., Structural basis for cooperativity in recruitment of MAML coactivators to Notch transcription complexes. Cell. Mar. 10, 2006;124(5):973-83.
Nam et al., Structural requirements for assembly of the CSL. intracellular Notch1 .Mastermind-like 1 transcriptional activation complex. J Biol Chem. Jun. 6, 2003;278(23):21232-9. Epub Mar. 18, 2003.
Nefedov A et al., Involvement of Notch-1 signaling in bone marrow stroma-mediated de novo drug resistance of myeloma and other malignant lymphoid cell lines. Blood. May 1, 2004;103(9):3503-10. Epub Dec. 11, 2003.
Ngo et al., Computational complexity, protein structure prediction, and the levinthal paradox. In: The Protein Folding Problem and Tertiary Structure Prediction. K. Mem, Jr., et al. Eds. 1994:433-506.
Niemann et al., Homozygous WNT3 mutation causes tetra-amelia in a large consanguineous family. Am J Hum Genet. Mar. 2004;74(3):558-63. Epub Feb. 5, 2004.
Nilsson et al., Staudinger ligation: a peptide from a thioester and azide. Org Lett. Jun. 29, 2000;2(13):1939-41.
Niranjan et al., The Notch pathway in podocytes plays a role in the development of glomerular disease. Nat Med. Mar. 2008;14(3):290-8. doi: 10.1038/nml 731. Epub Mar. 2, 2008.
Nishisho et al., Mutations of chromosome 5q21 genes in FAP and colorectal cancer patients. Science. Aug. 9, 1991;253(5020):665-9.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Noguera-Troise et al., Blockade of Dll4 inhibits tumour growth by promoting non-productive angiogenesis. Nature. Dec. 21, 2006;444(7122):1032-7.
Okamura et al., Redundant regulation of T cell differentiation and TCRalpha gene expression by the transcription factors LEF-1 and TCF-1. Immunity. Jan. 1998;8(1):I 1-20.
Olson et al., Sizing up the heart: development redux in disease. Genes Dev. Aug. 15, 2003;17(16):1937-56. Epub Jul. 31, 2003.
O'Neil et al., FBW7 mutations in leukemic cells mediate Notch pathway activation and resistance to gamma-secretase inhibitors. J Exp Med. Aug. 6, 2007;204(8):1813-24. Epub Jul. 23, 2007.
Oswald et al., RBP-Jkappa/Sharp recruits CtIP/CtBP corepressors to silence Notch target genes. Mol Cell Biol. Dec. 2005;25(23):10379-90.
Pakotiprapha et al., Crystal structure of Bacillus stearothermophilus UvrA provides insight into ATP-modulated dimerization, UvrB interaction, and DNA binding. Mol Cell. Jan. 18, 2008;29(1):122-33. Epub Dec. 27, 2007.
Palchaudhuri et al., Differentiation induction in acute myeloid leukemia using site-specific DNA-targeting. 55th ASH Annual Meeting and Exposition. Dec. 9, 2013. Accessed at https://ash.confex.com/ash/2013/webprogram/Paper60843.html.
Palomero et al., Mutational loss of PTEN induces resistance to Notch1 inhibition in T-cell leukemia. Nat Med. Oct. 2007;13(10):1203-10. Epub Sep. 16, 2007.
Park et al., Notch3 gene amplification in ovarian cancer. Cancer Res. Jun. 15, 2006;66(12):6312-8.
Parrish et al., Perspectives on alkyl carbonates in organic synthesis. Tetrahedron, 2000; 56(42):8207-8237.
Pellois et al., Semisynthetic proteins in mechanistic studies: using chemistry to go where nature can't. Curr Opin Chem Biol. Oct. 2006;10(5):487-91. Epub Aug. 28, 2006.
Perantoni, Renal development: perspectives on a Wnt-dependent process. Semin Cell Dev Biol. Aug. 2003;14(4):201-8.
Phelan et al., A General Method for Constraining Short Peptides to an a-Helical Conformation. J Am Chem Soc. 1997;119(3):455-60.
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Pinnix et al., Active Notch1 confers a transformed phenotype to primary human melanocytes. Cancer Res. Jul. 1, 2009;69(13):5312-20. doi: 10.1158/0008-5472.CAN-08-3767. Epub Jun. 23, 2009.
Thundimadathil, New Reactions with Click Chemistry. An R&D Magazine Webcast. Oct. 10, 2012. www.rdmag.com/articles/2012/10/new-reactions-click-chemistry.
Tian et al., Linear non-competitive inhibition of solubilized human gamma-secretase by pepstatin A methylester, L685458, sulfonamides, and benzodiazepines. J Biol Chem. Aug. 30, 2002;277(35):31499-505. Epub Jun. 18, 2002.
Tian et al., The role of the Wnt-signaling antagonist DKKI in the development of osteolytic lesions in multiple myeloma. N Engl J Med. Dec. 25, 2003;349(26):2483-94.
Tolbert et al., New methods for proteomic research: preparation of proteins with N-terminal cysteines for labeling and conjugation. Angew Chem Int Ed Engl. Jun. 17, 2002;41(12):2171-4.
Toniolo, Conformationally restricted peptides through short-range cyclizations. Int J Pept Protein Res. Apr. 1990;35(4):287-300.
Toomes et al., Mutations in LRP5 or FZD4 underlie the common familial exudative vitreoretinopathy locus on chromosome 1 lq. Am J Hum Genet. Apr. 2004;74(4):721-30. Epub Mar. 11, 2004.

(56) References Cited

OTHER PUBLICATIONS

Tornoe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Torrance et al., Combinatorial chemoprevention of intestinal neoplasia. Nat Med. Sep. 2000;6(9):1024-8.
Tsuji et al., Antiproliferative activity of REIC/Dkk-3 and its significant down-regulation in non-small-cell lung carcinomas. Biochem Biophys Res Commun. Nov. 23, 2001;289(1):257-63.
Tsuji et al., Synthesis of y, 8-unsay urated ketones by the intramolecular decarboxylative allylation of allyl-reto carboxylates and alkenyl allyl carbonates catalyzed by molybdenum, nickel, and rhodium complexes. Chemistry Letters. 1984; 13(10):1721-1724.
Tsuruzoe et al., Insulin receptor substrate 3 (IRS-3) and IRS-4 impair IRS-1- and IRS-2-mediated signaling. Mol Cell Biol. Jan. 2001;21(1):26-38.
Ueki et al., Increased insulin sensitivity in mice lacking p85beta subunit of phosphoinositide 3-kinase. Proc Natl Acad Sci US A Jan. 8, 2002;99(1):419-24. Epub Dec. 18, 2001.
Ueki et al., Positive and negative regulation of phosphoinositide 3-kinase-dependent signaling pathways by three different gene products of the p85alpha regulatory subunit. Mol Cell Biol. Nov. 2000;20(21):8035-46.
Uesugi et al., The alpha-helical FXXPhiPhi motif in p53: TAF interaction and discrimination by MDM2. Proc Natl Acad Sci US A. Dec. 21, 1999;96(26):14801-6.
Ullman et al., Luminescent oxygen channeling immunoassay: measurement of particle binding kinetics by chemiluminescence. Proc Natl Acad Sci US A Jun. 7, 1994;91(12):5426-30.
Vaickus et al., Immune markers in hematologic malignancies. Crit Rev Oncal Hematol. Dec. 1991;I 1(4):267-97.
Van Genderen et al., Development of several organs that require inductive epithelial-mesenchymal interactions is Impaired in LEF-1-deficient mice. Genes Dev. Nov. 15, 1994;8(22):2691-703.
Van Gun et al., The wnt-frizzled cascade in cardiovascular disease. Cardiovasc Res. Jul. 2002;55(1):16-24.
Varallo et al., Beta-catenin expression in Dupuytren's disease: potential role for cell-matrix interactions in modulating beta-catenin levels in vivo and in vitro. Oncogene. Jun. 12, 2003;22(24):3680-4.
Vartak et al., Allosteric Modulation of the Dopamine Receptor by Conformationally Constrained Type VI-Turn Peptidomimetics of Pro-Leu-Gly-NH2. J Med Chem. 2007;50(26):6725-6729.
Venancio et al., Reconstructing the ubiquitin network: cross-talk with other systems and identification of novel functions. Genome Biol. 2009;10(3):R33. Epub Mar. 30, 2009.
Verdine et al., Stapled peptides for intracellular drug targets. Methods Enzymol. 2012;503:3-33. doi: 10.1016/B978-0-12-396962-0.00001-X.
Verdine et al., The challenge of drugging undruggable targets in cancer: lessons learned from targeting BCL-2 family members. Clin Cancer Res. Dec. 15, 2007;13(24):7264-70.
Verma et al., Small interfering RNAs directed against beta-catenin inhibit the in vitro and in vivo growth of colon cancer cells. Clin Cancer Res. Apr. 2003;9(4):1291-300.
Voet et al., Biochemistry. Second Edition. John Wiley & Sons, Inc. 1995:235-241.
Walensky et al., A stapled BID BH3 helix directly binds and activates BAX. Mol Cell. Oct. 20, 2006;24(2):199-210.
Walensky et al., Activation of apoptosis in vivo by a hydrocarbon-stapled BH3 helix. Science. Sep. 3, 2004;305(5689):1466-70.
Walter et al., Critical role for IL-13 in the development of allergen-induced airway hyperreactivity. J Immunol. Oct. 15, 2001;167(8):4668-75.
Wang et al., Inhibition of p53 degradation by Mdm2 acetylation. FEES Lett. Mar. 12, 2004;561(1-3):195-201.
Wang, 4-Alkyl-2-trichloromethyloxazolidin-5-ones: Valuable Precursors to Enantiomerically Pure C- and N-Protected a-Alkyl Pralines. Synlett. 1999;1:33-36.

Weaver et al., Transition metal-catalyzed decarboxylative allylation and benzylation reactions.Chemical Rev. Mar. 9, 2011;111(3):1846-913.
Wei et al., Disorder and structure in the Rab11 binding domain of Rab11 family interacting protein 2. Biochemistry. Jan. 27, 2009;48(3):549-57. doi: 10.1021/bi8020197.
Weng et al., Activating mutations of NotchI in human T cell acute lymphoblastic leukemia. Science. Oct. 8, 2004;306(5694):269-71.
Weng et al., Growth suppression of pre-T acute lymphoblastic leukemia cells by inhibition of notch signaling. Mol Cell Biol. Jan. 2003;23(2):655-64.
Westhoff et al., Alterations of the Notch pathway in lung cancer. Proc Natl Acad Sci USA. Dec. 29, 2009;106(52):22293-8. doi: 10.1073/pnas.0907781106. Epub Dec. 10, 2009.
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Williams et al., Asymmetric synthesis of 2,6-diamino-6-(hydroxymethyl)pimelic acid:assignment of stereochemistry. J Am Chem Soc. 1991;113(18):6976-6981.
Williams et al., Asymmetric Synthesis of Monosubstituted and a,a-Disubstituted a-Amino Acids via Diastereoselective Glycine Enolate Alkylations. J Am Chem Soc. 1991;113:9276-86.
Wills-Karp et al., Interleukin-13: central mediator of allergic asthma. Science. Dec. 18, 1998;282(5397):2258-61.
Wills-Karp, Interleukin-13 in asthma pathogenesis. Immunol Rev. Dec. 2004;202:175-90.
Wills-Karp, The gene encoding interleukin-13: a susceptibility locus for asthma and related traits. Respir Res. 2000;1(1):19-23. Epub Jul. 17, 2000.
Wilson et al., Crystal structure of the CSL-Notch-Mastermind ternary complex bound to DNA. Cell. Mar. 10, 2006;124(5):985-96.
Wilson et al., The FIP3-Rab11 protein complex regulates recycling endosome targeting to the cleavage furrow during ate cytokinesis. Mol Biol Cell. Feb. 2005;16(2):849-60. Epub Dec. 15, 2004.
Woon et al., Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.
Wu et al., MAMLI, a human homologue of *Drosophila* mastermind, is a transcriptional co-activator for Notch receptors. Nat Genet. Dec. 2000;26(4):484-9.
Wu et al., Therapeutic antibody targeting of individual Notch receptors. Nature. Apr. 15, 2010;464(7291):1052-7. doi: 10.1038/nature08878.
Xi et al., Use of DNA and peptide nucleic acid molecular beacons for detection and quantification of rRNA in solution and in whole cells. Appl Environ Microbiol. Sep. 2003;69(9):5673-8.
Xing et al., Crystal structure of a beta-catenin/axin complex suggests a mechanism for the beta-catenin destruction complex. Genes Dev. Nov. 15, 2003;17(22):2753-64. Epub Nov. 4, 2003.
Yang et al., Synthesis and helical structure of lactam bridged BH3 peptides derived from pro-apoptotic Bcl-2 family proteins. Bioorg Med Chem Lett. 2004;14:1403-06.
Cheng et al., The RAB25 small GTPase determines aggressiveness of ovarian and breast cancers. Nat Med. Nov. 2004;IO(I 1):1251-6. Epub Oct. 24, 2004.
Cheon et al., beta-Catenin stabilization dysregulates mesenchymal cell proliferation, motility, and invasiveness and causes aggressive fibromatosis and hyperplastic cutaneous wounds. Proc Natl Acad Sci US A. May 14, 2002;99(10):6973-8. Epub Apr. 30, 2002.
Chia et al., Emerging roles for Rab family GTPases in human cancer. Biochim Biophys Acta. Apr. 2009;1795(2):110-6.
Chiaramonte et al., Studies of murine schistosomiasis reveal interleukin-13 blockade as a treatment for established and progressive liver fibrosis. Hepatology. Aug. 2001;34(2):273-82.
Christodoulides et al., WNTIOB mutations in human obesity. Diabetologia. Apr. 2006;49(4):678-84. Epub Feb. 14, 2006.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.

(56) References Cited

OTHER PUBLICATIONS

Clevers, Wnt/beta-catenin signaling in development and disease. Cell. Nov. 3, 2006;127(3):469-80.
Cohn et al., Cutting Edge: IL-4-independent induction of airway hyperresponsiveness by Th2, but not Thl, cells. J Immunol. Oct. 15, 1998;161(8):3813-6.
Colaluca et al., Numb controls p53 tumour suppressor activity. Nature. Jan. 3, 2008;451(7174):76-80. doi: 10.1038/nature06412.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Cossu et al., Wnt signaling and the activation of myogenesis in mammals. EMBO J. Dec. 15, 1999;18(24):6867-72.
Cox et al., Insulin receptor expression by human prostate cancers. Prostate. Jan. 1, 2009;69(1):33-40. doi: 10.1002/pros.20852.
Cusack et al., 2,4,6-Tri-isopropylbenzenesulphonyl Hydrazide: A Convenient Source of Di-imide. Tetrahedron. 1976;32:2157-62.
Danial et al., Dual role of proapoptotic BAD in insulin secretion and beta cell survival. Nat Med. Feb. 2008;14(2):144-53. doi: 10.1038/nml 717. Epub Jan. 27, 2008.
Darnell, Transcription factors as targets for cancer therapy. Nat Rev Cancer. Oct. 2002;2(10):740-9.
Dayid et al., Expressed protein ligation. Method and applications. Eur J Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
De Lao et al., Notch and Kras reprogram pancreatic acinar cells to ductal intraepithelial neoplasia. Proc Natl Acad Sci US A. Dec. 2, 2008;105(48):18907-12. doi: 10.1073/pnas.0810111105. Epub Nov. 21, 2008.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
De Strooper et al., A presenilin-1-dependent gamma-secretase-like protease mediates release of Notch Intracellular domain. Nature. Apr. 8, 1999;398(6727):518-22.
Debinski et al., Retargeting interleukin 13 for radioimmunodetection and radioimmunotherapy of human high-grade gliomas. Clin Cancer Res. Oct. 1999;5(10 Suppl):3143s-3147s.
Del Bianco et al., Mutational and energetic studies of Notch 1 transcription complexes. J Mol Biol. Feb. 8, 2008;376(1):131-40. Epub Nov. 28, 2007.
Denmark et al., Cyclopropanation with Diazomethane and Bis(oxazoline)palladium(II) Complexes. J Org Chem. May 16, 1997;62(10):3375-3389.
Devereux et al., A comprehensive set of sequence analysis programs for the VAX. Nucleic Acids Res. Jan. 11, 1984;12(1 Pt 1):387-95.
Dombroski et al., Isolation of an active human transposable element. Science. Dec. 20, 1991;254(5039): 1805-8.
Doron et al., Probiotics: their role in the treatment and prevention of disease. Expert Rev Anti Infect Ther. 2006;4:261-75.
Dovey et al., Functional gamma-secretase inhibitors reduce beta-amyloid peptide levels in brain. J Neurochem. Jan. 2001;76(1):173-81.
Duronio, Insulin receptor is phosphorylated in response to treatment of HepG2 cells with insulin-like growth factor I. Biochem J. Aug. 15, 1990;270(1):27-32.
Eglen et al., The use of AlphaScreen technology in HTS: current status. Curr Chem Genomics. Feb. 25, 2008;1:2-10. doi: 10.2174/1875397300801010002.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Ellisen et al., TAN-1, the human homolog of the Drosophila notch gene, is broken by chromosomal translocations in T lymphoblastic neoplasms. Cell. Aug. 23, 1991;66(4):649-61.
Erlanson et al., The leucine zipper domain controls the orientation of AP-1 in the NFAT.AP-I.DNA complex. Chem Biol. Dec. 1996;3(12):981-91.
Evans et al., The Rise of Azide-Alkyne 1,3-Dipolar 'Click' Cycloaddition and its Application to Polymer Science and Surface Modification. Australian Journal of Chemistry. 2007;60:384-95.
Favrin et al., Two-state folding over a weak free-energy barrier. Biophys J. Sep. 2003;85(3):1457-65.
Fischbach et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Fisher et al., Myc/Max and other helix-loop-helix/leucine zipper proteins bend DNA toward the minor groove. Proc Natl Acad Sci US A. Dec. 15, 1992;89(24):11779-83.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Friedman-Einat et al., Target gene identification: target specific transcriptional activation by three murine homeodomain/VP16 hybrid proteins in *Saccharomyces cerevisiae*. J Exp Zool. Feb. 15, 1996;274(3):145-56.
Friedmann et al., RAM-induced allostery facilitates assembly of a notch pathway active transcription complex. J Biol Chem. May 23, 2008;283(21):14781-91. doi: 10.1074/jbc.M709501200. Epub Apr. 1, 2008.
Fromme et al., Structural basis for removal of adenine mispaired with 8-oxoguanine by MutY adenine DNA glycosylase. Nature. Feb. 12, 2004;427(6975):652-6.
Fryer et al., Mastermind mediates chromatin-specific transcription and turnover of the Notch enhancer complex. Genes Dev. Jun. 1, 2002;16(11):1397-411.
Fuchs et al., Socializing with the neighbors: stem cells and their niche. Cell. Mar. 19, 2004;116(6):769-78.
Fung et al., Delta-like 4 induces notch signaling in macrophages: implications for inflammation. Circulation. Jun. 12, 2007;115(23):2948-56. Epub May 28, 2007.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner et al., Mo[N(t-Bu)(AR)]3 Complexes As Catalyst Precursors: In Situ Activation and Application to Metathesis Reactions of Alkynes and Diynes. J Am Chem Soc. 1999;121:9453-54.

\* cited by examiner (A)

(B)

(A)

(B)

(C)

(D)

(A)

(B)

(C)

(D)

(E)

(F)

(G)

(H)

(I)

(J)

SEQUENCE LISTING

<160> NUMBER OF SEQ ID NOS: 14

<210> SEQ ID NO 1
<211> LENGTH: 16

```
<212> TYPE: PRT
<213> ORGANISM: Artificial Sequence
<220> FEATURE:
<223> OTHER INFORMATION: Synthetic Polypeptide

<400> SEQUENCE: 1

Gln Ser Gln Gln Thr Phe Ser Asn Leu Trp Arg Leu Leu Pro Gln Asn
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is R5
<220> FEATURE:
<221> NAME/KEY: misc_feature
<222> LOCATION: (14)..(14)
<223> OTHER INFORMATION: Xaa  is S8

<400> SEQUENCE: 2

Gln Ser Gln Gln Thr Phe Xaa Asn Leu Trp Arg Leu Leu Xaa Gln Asn
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is PyrR
<220> FEATURE:
<221> NAME/KEY: misc_feature
<222> LOCATION: (14)..(14)
<223> OTHER INFORMATION: Xaa is S8

<400> SEQUENCE: 3

Gln Ser Gln Gln Thr Phe Xaa Asn Leu Trp Arg Leu Leu Xaa Gln Asn
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa is PyrR

<400> SEQUENCE: 4

Gln Ser Gln Gln Thr Phe Xaa Asn Leu Trp Arg
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
```

```
<223> OTHER INFORMATION: Xaa is S8

<400> SEQUENCE: 5

Leu Leu Xaa Gln Asn
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 6

Glu Trp Ala Glu Thr Ala Ala Ala Lys Phe Leu Ala Ala His Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be S5, PyrR or PyrS
<220> FEATURE:
<221> NAME/KEY: misc_feature
<222> LOCATION: (8)..(8)
<223> OTHER INFORMATION: Xaa can be S5, PyrR or PyrS

<400> SEQUENCE: 7

Glu Trp Ala Xaa Thr Ala Ala Xaa Lys Phe Leu Ala Ala His Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be S5 or Az
<220> FEATURE:
<221> NAME/KEY: misc_feature
<222> LOCATION: (8)..(8)
<223> OTHER INFORMATION: Xaa can be S5 or Az

<400> SEQUENCE: 8

Glu Trp Ala Xaa Thr Ala Ala Xaa Lys Phe Leu Ala Ala His Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be S5, Az, PyrR or PyrS
<220> FEATURE:
<221> NAME/KEY: misc_feature
<222> LOCATION: (8)..(8)
<223> OTHER INFORMATION: Xaa can be S5, Az, PyrR or PyrS

<400> SEQUENCE: 9
```

Glu Trp Ala Xaa Thr Ala Ala Xaa Lys Phe Leu Ala Ala His Ala
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 10

Leu Ser Gln Glu Thr Phe Ser Asp Leu Trp Lys Leu Leu Pro Glu Asn
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be PyrR or R8
<220> FEATURE:
<221> NAME/KEY: misc_feature
<222> LOCATION: (14)..(14)
<223> OTHER INFORMATION: Xaa can be S8 or PyrS

<400> SEQUENCE: 11

Leu Ser Gln Glu Thr Phe Xaa Asp Leu Trp Lys Leu Leu Xaa Glu Asn
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be PyrR, R8, Az, RDN or REN
<220> FEATURE:
<221> NAME/KEY: misc_feature
<222> LOCATION: (14)..(14)
<223> OTHER INFORMATION: Xaa can be S8, PyrS, Az, SGN, SDN or SEN

<400> SEQUENCE: 12

Gln Ser Gln Gln Thr Phe Xaa Asn Leu Trp Arg Leu Leu Xaa Gln Asn
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 13

Thr Ser Phe Ala Glu Tyr Trp Ala Leu Leu Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: misc_feature
<222> LOCATION: (4)..(4)
<223> OTHER INFORMATION: Xaa can be PyrR or R8
<220> FEATURE:
<221> NAME/KEY: misc_feature
<222> LOCATION: (11)..(11)
<223> OTHER INFORMATION: Xaa can be S8, PyrS or SGN

<400> SEQUENCE: 14

Thr Ser Phe Xaa Glu Tyr Trp Ala Leu Leu Xaa
1               5                   10
```

STAPLED AND STITCHED POLYPEPTIDES AND USES THEREOF

RELATED APPLICATIONS

This application is a U.S. Continuation Application of Ser. No. 16/140,113, filed on Sep. 24, 2018, which is a Divisional Application of Ser. No. 14/775,315, filed on Sep. 11, 2015, which is a 371 National Phase Application of International Patent Application No. PCT/US2014/25544, filed on Mar. 13, 2014, which claims the benefit of U.S. Provisional Patent Application No. 61/779,917, filed on Mar. 13, 2013. The entire teachings of the above applications are incorporated herein by reference.

SEQUENCE LISTING

The instant application contains a Sequence Listing, which has been submitted electronically in ASCII format and is hereby incorporated by reference in its entirety. Said ASCII copy, created on Oct. 2, 2014 is named H0824.70132W000.txt and is 4.93 KB bytes in size.

BACKGROUND OF THE INVENTION

The important biological roles that peptides and polypeptides play as hormones, enzyme inhibitors and substrates, neurotransmitters, and neuromediators has led to the widespread use of peptides or peptide mimetics as therapeutic agents. A peptide's bioactive conformation, combining structural elements such as alpha-helices, beta-sheets, turns, and loops, is important as it allows for selective biological recognition of receptors or enzymes, thereby influencing cell-cell communication and/or controlling vital cell functions, such as metabolism, immune defense, and reproduction (Babine et al., *Chem. Rev.* (1997) 97:1359). The alpha-helix is one of the major structural components of peptides. However, alpha-helical peptides have a propensity for unraveling and forming random coils, which are, in most cases, biologically less active, or even inactive, and are highly susceptible to proteolytic degradation.

Many research groups have developed strategies for the design and synthesis of more robust peptides as therapeutics. For example, one strategy has been to incorporate more robust functionalities into the peptide chain while still maintaining the peptide's unique conformation and secondary structure (see, for example, Gante et al., *Angew. Chem. Int. Ed. Engl.* (1994) 33:1699-1720; Liskamp et al., *Recl. Trav. Chim. Pays-Bas* (1994) 113:1; Giannis et al., *Angew. Chem. Int. Ed. Engl.* (1993) 32:1244; P. D. Bailey, Peptide Chemistry, Wiley, New York, 1990, p. 182; and references cited therein). Another approach has been to stabilize the peptide via covalent cross-links (see, for example, Phelan et al., *J. Am. Chem. Soc.* (1997) 119:455; Leuc et al., *Proc. Nat'l. Acad. Sci. USA* (2003) 100:11273; Bracken et al., *J. Am. Chem. Soc.* (1994) 116:6432; and Yan et al., *Bioorg. Med. Chem.* (2004) 14:1403). Crosslinking a polypeptide predisposed to having an alpha-helical secondary structure can constrain the polypeptide to its native alpha-helical conformation. The constrained secondary structure may increase the peptide's resistance to proteolytic cleavage, increase the peptide's hydrophobicity, allow for better penetration of the peptide into the target cell's membrane (e.g., through an energy-dependent transport mechanism such as pinocytosis), and/or lead to an improvement in the peptide's biological activity relative to the corresponding uncrosslinked peptide.

One such technique for crosslinking peptides is "peptide stapling." "Peptide stapling" is a term coined to describe a synthetic methodology wherein two olefin-containing sidechains present in a polypeptide are covalently joined ("stapled") using a ring-closing metathesis (RCM) reaction to form a crosslink (see, the cover art for *J. Org. Chem.* (2001) vol. 66, issue 16 describing metathesis-based crosslinking of alpha-helical peptides; Blackwell et al.; *Angew Chem. Int. Ed.* (1994) 37:3281; and U.S. Pat. No. 7,192,713). "Peptide stitching" involves multiple "stapling" events in a single polypeptide chain to provide a multiply stapled (also known as "stitched") polypeptide (see WO 2008/121767 and WO 2011/008260). Stapling of a peptide using all-hydrocarbon crosslinks has been shown to help maintain its native conformation and/or secondary structure, particularly under physiologically relevant disorders (see Schafmiester et al., *J. Am. Chem. Soc.* (2000) 122:5891-5892; Walensky et al., *Science* (2004) 305:1466-1470). This stapling technology has been applied to the apoptosis-inducing BID-BH3 alpha-helix, resulting in a higher suppression of malignant growth of leukemia in an animal model compared to the unstapled polypeptide. See Walensky et al., *Science* (2004) 305:1466-1470; U.S. Patent Application Publication No. 2005/02506890; and U.S. Patent Application Publication No. 2006/0008848. However, there remains a need and interest in the development of new techniques for stapling and stitching polypeptides which may be useful as therapeutics or research tools.

SUMMARY OF THE INVENTION

"Peptide stapling" refers to cross-linking sidechains of a polypeptide chain by covalently joining olefin moieties (i.e., "stapled together") using a ring-closing metathesis (RCM) reaction. "Peptide stitching" encompasses multiple "staples" in a single polypeptide chain to provide a multiply stapled (also known as "stitched") polypeptide (see International PCT Publications WO2008/121767 and WO2011/008260). Peptide stapling and stitching stabilizes the alpha-helical conformation of a polypeptide. The present invention provides stapled and stitched polypeptides with heteroaliphatic or ring-containing crosslinks that connect the alpha-carbons of two amino acids in an alpha-helix. The present invention further provides pharmaceutical compositions of the stapled or stitched polypeptides, methods of preparing the inventive polypeptides, as well as methods of using the inventive polypeptides. The present invention also provides post ring-closing metathesis (RCM) modifications of the staples such as —C(=O)O-extrusion, reduction of the resulting olefin, or addition of a targeting moiety.

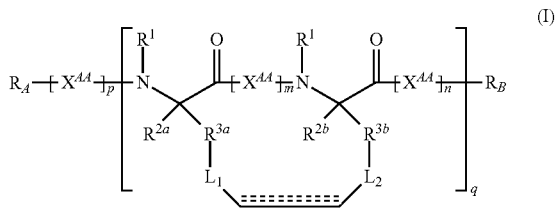

(I)

or a pharmaceutically acceptable salt thereof, wherein $R_A$, $R_B$, $R^1$, $R^{2a}$, $R^{3a}$, $R^{2b}$, $R^{3b}$, $L_1$, $L_2$, $X^{AA}$, p, m, n, and q are as defined herein.

In another aspect, the present invention provides stitched polypeptides (i.e., multiply stapled polypeptides) of Formula (VI):

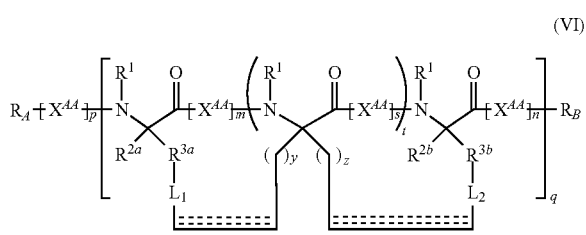

(VI)

or a pharmaceutically acceptable salt thereof, wherein $R_A$, $R_B$, $R^1$, $R^{2a}$, $R^{3a}$, $R^{2b}$, $R^{3b}$, $L_1$, $L_2$, $X^{AA}$, p, m, s, t, y, z, n, and q are as defined herein.

In another aspect, the present invention provides methods of making stapled polypeptides of Formula (I). Such method comprises treating Formula (i):

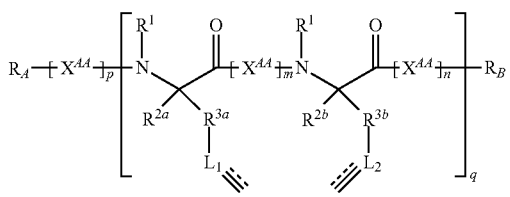

(i)

or a salt thereof, with a ring-closing metathesis (RCM) catalyst.

In another aspect, the present invention provides methods of making stitched polypeptides of Formula (VI). Such method comprises treating Formula (ii):

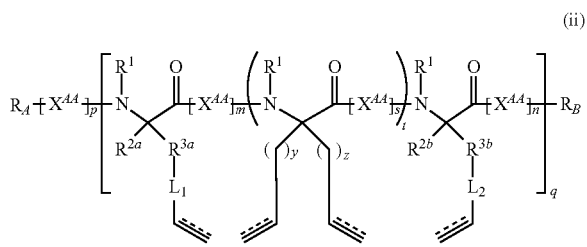

(ii)

or a salt thereof, with a ring-closing metathesis (RCM) catalyst.

In another aspect, the present invention provides pharmaceutical compositions comprising a compound of Formula (I) or (VI), or a pharmaceutically acceptable salt, and optionally a pharmaceutically acceptable carrier. In certain embodiments, the pharmaceutical compositions described herein include a therapeutically effective amount of a compound of Formula (I) or (VI), or a pharmaceutically acceptable salt thereof.

In another aspect, the present invention provides kits comprising a compound of Formulae (I) or (VI), or a pharmaceutically acceptable salt, or a pharmaceutical composition thereof. In certain embodiments, the kits further include instructions for administering the compound of Formulae (I) or (VI), or the pharmaceutically acceptable salt, or the pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

In another aspect, the present invention provides methods of treating a disorder in vivo or in vitro comprising administering to a subject a therapeutically effective amount of a compound of Formula (I) or (VI). Exemplary disorders are proliferative disorders, neurological disorders, immunological disorders, endocrinologic disorders, cardiovascular disorders, hematologic disorders, inflammatory disorders, and disorders characterized by premature or unwanted cell death.

This application refers to various issued patent, published patent applications, journal articles, and other publications, all of which are incorporated herein by reference.

The details of various embodiments of the invention are set forth herein. Other features, objects, and advantages of the invention will be apparent from the Description, Figures, Examples, and Claims.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds, amino acids, and polypeptides described herein can comprise one or more asymmetric centers, and thus can exist in various isomeric forms, e.g., enantiomers and/or diastereomers. For example, the compounds, amino acids, and polypeptides described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds, amino acids, and polypeptides described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, substituent names which end in the suffix "-ene" refer to a biradical derived from the removal of an additional hydrogen atom from monoradical group as defined herein. Thus, for example, the monoradical alkyl, as defined herein, is the biradical alkylene upon removal of an additional hydrogen atom. Likewise, alkenyl is alkenylene; alkynyl is alkynylene; heteroalkyl is heteroalkylene; heteroalkenyl is heteroalkenylene; heteroalkynyl is heteroalkynylene; carbocyclyl is carbocyclylene; heterocyclyl is heterocyclylene; aryl is arylene; and heteroaryl is heteroarylene.

The term "aliphatic," as used herein, includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups. As will be appreciated by one of ordinary skill in the art, "aliphatic" is intended herein to include alkyl, alkenyl, alkynyl, cycloalkyl, and cycloalkenyl moieties.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_{xa}$; —$OCO_2R_{xa}$; —$OCON(R_{xa})_2$; —$N(R_{xa})_2$; —$S(O)_2R_{xa}$; —$NR_{xa}(CO)R_{xa}$, wherein each occurrence of $R_{xa}$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

As used herein, "alkyl" refers to a radical of a straight-chain or branched saturated hydrocarbon group having from 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to a radical of a straight-chain or branched saturated hydrocarbon group having from 1 to 30 carbon atoms, and which further comprises 1-10 heteroatoms independently selected from oxygen, nitrogen, and sulfur included within the parent chain ("$C_{1-30}$ heteroalkyl"). In some embodiments, a heteroalkyl group has 1 to 20 carbon atoms and 1-10 heteroatoms, inclusive ("$C_{1-20}$ heteroalkyl"). In some embodiments, a heteroalkyl group has 1 to 20 carbon atoms and 1-10 heteroatoms, inclusive ("$C_{1-10}$ heteroalkyl"). In some embodiments, a heteroalkyl group has 1 to 9 carbon atoms and 1-6 heteroatoms, inclusive ("$C_{1-9}$ heteroalkyl"). In some embodiments, a heteroalkyl group has 1 to 8 carbon atoms and 1-5 heteroatoms, inclusive ("$C_{1-8}$ heteroalkyl"). In some embodiments, a heteroalkyl group has 1 to 7 carbon atoms, and 1-4 heteroatoms, inclusive ("$C_{1-7}$ heteroalkyl"). In some embodiments, a heteroalkyl group has 1 to 6 carbon atoms and 1-3 heteroatoms, inclusive ("$C_{1-6}$ heteroalkyl"). In some embodiments, a heteroalkyl group has 1 to 5 carbon atoms and 1-2 heteroatoms, inclusive ("$C_{1-5}$ heteroalkyl"). In some embodiments, a heteroalkyl group has 1 to 4 carbon atoms and 1-2 heteroatoms, inclusive ("$C_{1-4}$ heteroalkyl"). In some embodiments, a heteroalkyl group has 1 to 3 carbon atoms and 1-2 heteroatoms, inclusive ("$C_{1-3}$ heteroalkyl"). In some embodiments, a heteroalkyl group has 1 to 2 carbon atoms and 1 heteroatom, inclusive ("$C_{1-2}$ heteroalkyl"). In some embodiments, a heteroalkyl group has 1 carbon atom and 1 heteroatom, inclusive ("$C_1$ heteroalkyl"). In some embodiments, a heteroalkyl group has 2 to 6 carbon atoms and 1-3 heteroatoms, inclusive ("$C_{2-6}$ heteroalkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted $C_{1-10}$ alkyl. In certain embodiments, the heteroalkyl group is a substituted $C_{1-10}$ heteroalkyl.

As used herein, "alkenyl" refers to a radical of a straight-chain or branched hydrocarbon group having from 2 to 30 carbon atoms, one or more carbon-carbon double bonds, and no triple bonds ("$C_{2-30}$ alkenyl"). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to a radical of a straight-chain or branched hydrocarbon group having from 2 to 30 carbon atoms, one or more carbon-carbon double bonds, no triple bonds, and which further comprises 1-10 heteroatoms independently selected from oxygen, nitrogen, and sulfur included within the parent chain ("$C_{2-30}$ heteroalkenyl"). In some embodiments, a heteroalkenyl group has 2 to 20 carbon atoms and 1-10 heteroatoms, inclusive ("$C_{2-20}$ heteroalkenyl"). In some embodiments, a heteroalkenyl group has 2 to 10 carbon atoms and 1-10 heteroatoms, inclusive ("$C_{2-10}$ heteroalkenyl"). In some embodiments, a heteroalkenyl group has 2 to 9 carbon atoms and 1-6 heteroatoms, inclusive ("$C_{2-9}$ heteroalkenyl"). In some embodiments, a heteroalkenyl group has 2 to 8 carbon atoms and 1-5 heteroatoms, inclusive ("$C_{2-8}$ heteroalkenyl"). In some embodiments, a heteroalkenyl group has 2 to 7 carbon atoms, and 1-4 heteroatoms, inclusive ("$C_{2-7}$ heteroalkenyl"). In some embodiments, a heteroalkenyl group has 2 to 6 carbon atoms and 1-3 heteroatoms, inclusive ("$C_{2-6}$ heteroalkenyl"). In some embodiments, a heteroalkenyl group has 2 to 5 carbon atoms and 1-2 heteroatoms, inclusive ("$C_{2-5}$ heteroalkenyl"). In some embodiments, a heteroalkenyl group has 2 to 4 carbon atoms and 1-2 heteroatoms, inclusive ("$C_{2-4}$ heteroalkenyl"). In some embodiments, a heteroalkenyl group has 2 to 3 carbon atoms and 1-2 heteroatoms, inclusive ("$C_{2-3}$ heteroalkenyl"). In some embodiments, a heteroalkenyl group has 2 carbon atoms and 1 heteroatom, inclusive ("$C_2$ heteroalkenyl"). In some embodiments, a heteroalkenyl group has 2 to 6 carbon atoms and 1-3 heteroatoms, inclusive ("$C_{2-6}$ heteroalkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted $C_{2-10}$ heteroalkenyl. In certain embodiments, the heteroalkenyl group is a substituted $C_{2-10}$ heteroalkenyl.

As used herein, "alkynyl" refers to a radical of a straight-chain or branched hydrocarbon group having from 2 to 30 carbon atoms, one or more carbon-carbon triple bonds, and optionally one or more double bonds ("$C_{2-30}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to a radical of a straight-chain or branched hydrocarbon group having from 2 to 30 carbon atoms, one or more carbon-carbon triple bonds, optionally one or more double bonds, and which further comprises 1-10 heteroatoms independently selected from oxygen, nitrogen, and sulfur included within the parent chain ("$C_{2-30}$ heteroalkynyl"). In some embodiments, a heteroalkynyl group has 2 to 20 carbon atoms and 1-10 heteroatoms, inclusive ("$C_{2-20}$ heteroalkynyl"). In some embodiments, a heteroalkenyl group has 2 to 10 carbon atoms and 1-10 heteroatoms, inclusive ("$C_{2-10}$ heteroalkynyl"). In some embodiments, a heteroalkynyl group has 2 to 9 carbon atoms and 1-6 heteroatoms, inclusive ("$C_{2-9}$ heteroalkynyl"). In some embodiments, a heteroalkynyl group has 2 to 8 carbon atoms and 1-5 heteroatoms, inclusive ("$C_{2-8}$ heteroalkynyl"). In some embodiments, a heteroalkynyl group has 2 to 7 carbon atoms, and 1-4 heteroatoms, inclusive ("$C_{2-7}$ heteroalkynyl"). In some embodiments, a heteroalkynyl group has 2 to 6 carbon atoms and 1-3 heteroatoms, inclusive ("$C_{2-6}$ heteroalkynyl"). In some embodiments, a heteroalkynyl group has 2 to 5 carbon atoms and 1-2 heteroatoms, inclusive ("$C_{2-5}$ heteroalkynyl"). In some embodiments, a heteroalkynyl group has 2 to 4 carbon atoms and 1-2 heteroatoms, inclusive ("$C_{2-4}$ heteroalkynyl"). In some embodiments, a heteroalkynyl group has 2 to 3 carbon atoms and 1-2 heteroatoms, inclusive ("$C_{2-3}$ heteroalkynyl"). In some embodiments, a heteroalkynyl group has 2 carbon atoms and 1 heteroatom, inclusive ("$C_2$ heteroalkynyl"). In some embodiments, a heteroalkynyl group has 2 to 6 carbon atoms and 1-3 heteroatoms, inclusive ("$C_{2-6}$ heteroalkynyl"). Unless otherwise specified, each instance of a heteroalkynyl group is independently unsubstituted (an "unsubstituted heteroalkynyl") or substituted (a "substituted heteroalkynyl") with one or more substituents.

In certain embodiments, the heteroalkynyl group is an unsubstituted $C_{2-10}$ heteroalkynyl. In certain embodiments, the heteroalkynyl group is a substituted $C_{2-10}$ heteroalkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-9}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-9}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiorenyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl, and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl, and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl group. In certain embodiments, the aryl group is a substituted $C_{6-14}$ aryl group.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a group that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$—OP(=O)(R$^{aa}$), —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$), —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$), —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$), —OP(=O)(R$^{ee}$), —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$), —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$, and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$, and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$ wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" or a "quaternary amino salt" or a "quaternary salt" refers to a nitrogen atom covalently attached to four groups such that the nitrogen is cationic, wherein the cationic nitrogen atom is further complexed with an anionic counterion, e.g., such as groups of the Formula —N(R$^{bb}$)$_3^+$X$^-$ and —N(R$^{bb}$)$_2$—$^+$X$^-$, wherein R$^{bb}$ and X$^-$ are as defined herein.

As used herein, a "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "acyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$), thioesters (—C(=O)SR$^{aa}$, —C(=S)SR$^{aa}$), amides (—C(=O)N(R$^{bb}$)$_2$, —C(=O)NR$^{bb}$SO$_2$R$^{aa}$) thioamides (—C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

As used herein, the term "azido" refers to a group of the formula: —N$_3$.

As used herein, the term "cyano" refers to a group of the formula: —CN.

As used herein, the term "isocyano" refers to a group of the formula: —NC.

As used herein, the term "nitro" refers to a group of the formula: —NO$_2$.

As used herein, the term "halo" or "halogen" refers to fluorine (fluoro, —F), chlorine (chloro, —Cl), bromine (bromo, —Br), or iodine (iodo, —I).

As used herein, the term "oxo" refers to a group of the formula: =O.

As used herein, the term "thiooxo" refers to a group of the formula: =S.

As used herein, the term "imino" refers to a group of the formula: =N(R$^b$).

As used herein, the term "silyl" refers to the group —Si($R^{aa}$)$_3$, wherein $R^{aa}$ is as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an amino protecting group (also referred to herein as a "nitrogen protecting group"). Amino protecting groups include, but are not limited to, —OH, —$OR^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(=O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1, 3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyl-eneamine, N-benzylideneamine, N-p-methoxybenzylideneamine, N-diphenylmethyleneamine, N-[(2-pyridyl)mesityl]methyleneamine, N—(N',N' dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is a hydroxyl protecting group (also referred to herein as an "oxygen protecting group"). Hydroxyl protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilyl-ethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "thiol protecting group" is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of ester groups include formates, acetates, proprionates, pentanoates, crotonates, and benzoates. Specific examples of ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6- trimethylbenzoate. Examples of carbonates include 9-fluorenylmethyl, ethyl, 2,2,2-trichloroethyl, 2-(trimethylsilyl) ethyl, 2-(phenylsulfonyl)ethyl, vinyl, allyl, and p-nitrobenzyl carbonate. Examples of silyl groups include trimethylsilyl, triethylsilyl, t-butyldimethylsilyl, t-butyldiphenylsilyl, triisopropylsilyl ether, and other trialkylsilyl ethers. Examples of alkyl groups include methyl, benzyl, p-methoxybenzyl, 3,4-dimethoxybenzyl, trityl, t-butyl, and allyl ether, or derivatives thereof. Examples of arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "amino acid" refers to a molecule containing both an amino group and a carboxyl group. Amino acids include alpha-amino acids and beta-amino acids, the structures of which are depicted below. In certain embodiments, the amino acid is an alpha-amino acid. In certain embodiments, the amino acid is an unnatural amino acid. In certain embodiments, the amino acid is a natural amino acid. In certain embodiments, the amino acid is an unnatural amino acid.

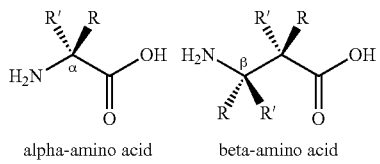

alpha-amino acid     beta-amino acid

Exemplary amino acids include, without limitation, natural alpha-amino acids such as D- and L-isomers of the 20 common naturally occurring alpha amino acids found in peptides, unnatural alpha-amino acids, natural beta-amino acids (e.g., beta-alanine), and unnnatural beta-amino acids. Amino acids used in the construction of peptides of the present invention may be prepared by organic synthesis, or obtained by other routes, such as, for example, degradation of or isolation from a natural source. Amino acids may be commercially available or may be synthesized.

A "peptide" or "polypeptide" comprises a polymer of amino acid residues linked together by peptide (amide) bonds. The term(s), as used herein, refers to proteins, polypeptides, and peptide of any size, structure, or function. The term(s), as used herein, include stapled, unstapled, stitched, and unstitched polypeptides. Typically, a peptide or polypeptide will be at least three amino acids long. A peptide or polypeptide may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. One or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof.

As used herein, the term "salt" or "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds, amino acids, and polypeptides of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary amino salts, e.g., trisubstituted amino groups defined herein.

These and other exemplary functional groups are described in more detail in the Detailed Description, Examples, and claims. The invention is not intended to be limited in any manner by the above exemplary listing of substituents.

DETAILED DESCRIPTION OF FIGURES

Figure 3:
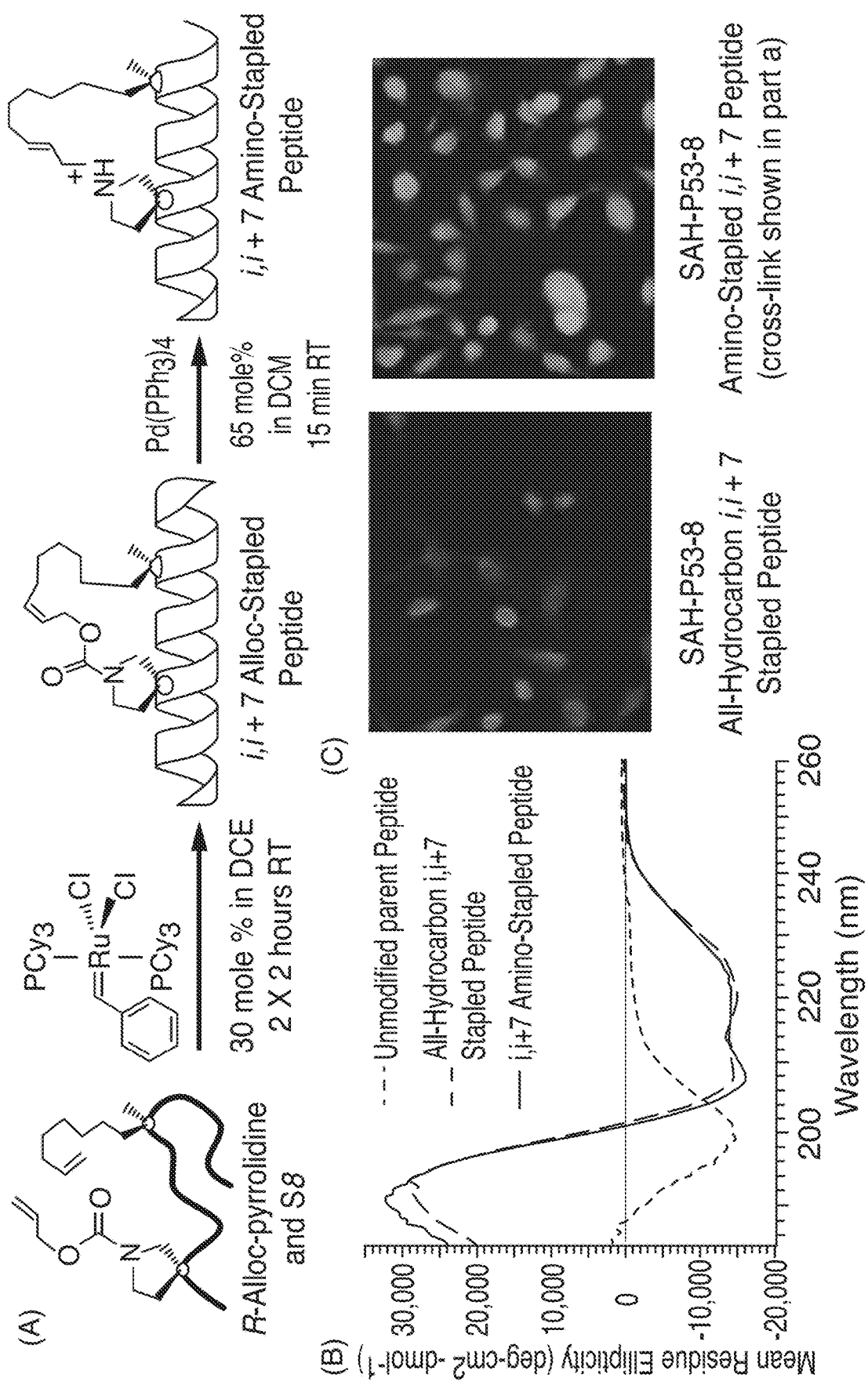

FIG. 3 shows preliminary characterization of an amino-stapled i, i+7 peptide. (a) General scheme of preparing amino stapled stapled i, i+7 peptide. The (R)-Alloc-pyrrolidine amino acid was incorporated at the i position and the $S_8$ amino acid at the i+7 position in the SAH-p53-8 peptide sequence. After RCM, nearly complete conversion to the Alloc-stapled intermediate was obtained. This intermediate was then subjected to Pd-mediated $CO_2$ extrusion, which gave nearly complete conversion to the indicated i, i+7 amino-stapled peptide. The double bond in the amino-staple can be either E or Z conformation. (b) Circular Dichroism (CD) spectrum showing comparable levels of helix induction by the first-generation staple in the SAH-p53-8 peptide (dashed long lines; FITC-β-ala-p53-8 $R_5/S_8$ hydrocarbon-stapled) and the amino-stapled version (solid line; FITC-β- ala-p53-8 Pyr$_R$/S$_8$ amino-stapled). The unmodified parent peptide is also shown (dashed short lines). The sequence comparison of the unmodified peptide, all-hydrocarbon stapled peptide, and amino-stapled peptide is shown in Table (i)

TABLE i

| | | | | | | | | | | | | | | | |
|---|---|---|---|---|---|---|---|---|---|---|---|---|---|---|---|
| Parent Unmodified Peptide | Q | S | Q | Q | T | F | S | N | L | W | R | L | L | P | Q | N |
| SAH-p53-8 (i, i + 7 All-Hydrocarbon Stapled Peptide) | Q | S | Q | Q | T | F | R$_5$ | N | L | W | R | L | L | S$_8$ | Q | N |
| SAH-p53-8 (i, i + 7 Amino-Stapled Peptide) | Q | S | Q | Q | T | F | Pyr$_R$ | N | L | W | R | L | L | S$_8$ | Q | N |

α-Helical peptides display a CD spectrum with characteristic dual minima at 208 nm and 222 nm.

(c) The amino-stapled version of SAH-p53-8 shows more robust cell-penetration than the original hydrocarbon-stapled version. HeLa cells were treated with 10 μM peptide labeled N-terminally with Fluorescein isothiocyanate, separated from the peptide by a P-alanine linker, at 37° C. for 4 hours in media containing 10% fetal bovine serum. The cells were washed, fixed with paraformaldehyde, then imaged using an Olympus FV300 fluoview confocal fluorescence microscope. The amino-stapled peptide exhibits higher intracellular accumulation at these conditions, as evidenced by a more robust fluorescein signal. Instrument settings were identical for acquisition of each image shown.

Figure 4A:
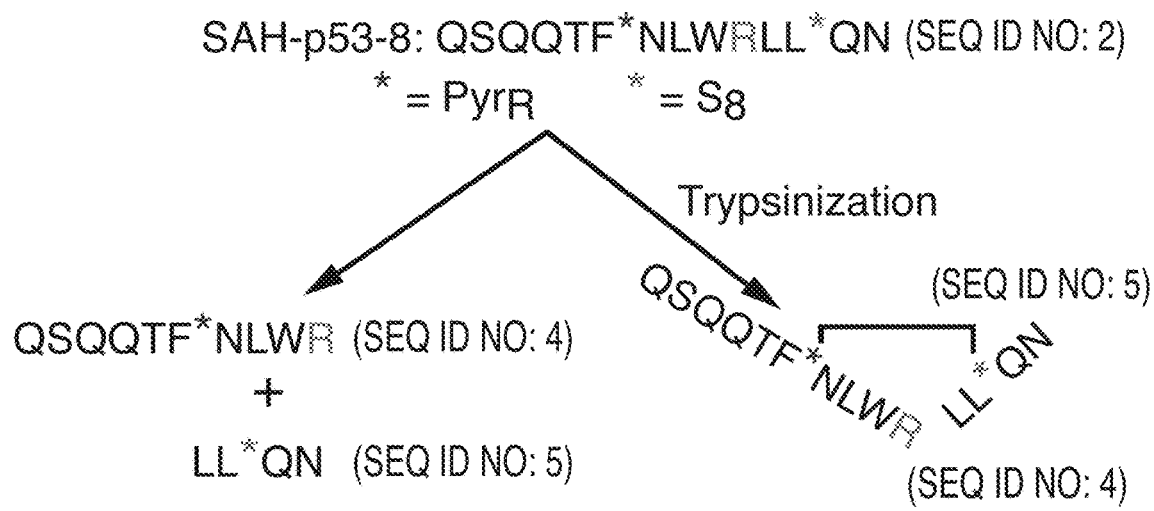

FIG. 4A shows trypsinization scheme of amino-stapled polypeptide and unstapled polypeptide. The amino acid located at the first asterisk is Pyr$_R$ and the amino acid located at the second asterisk is S$_8$. Trypsin cleaves peptides on the C-terminal side of K and R of the polypeptide. Trypsin proteolysis of unstapled peptide will result in two fragments. Proteolysis of an amino-stapled peptide with a covalent cross-link will yield a single fragment after proteolysis with trypsin.

Figure 4B:
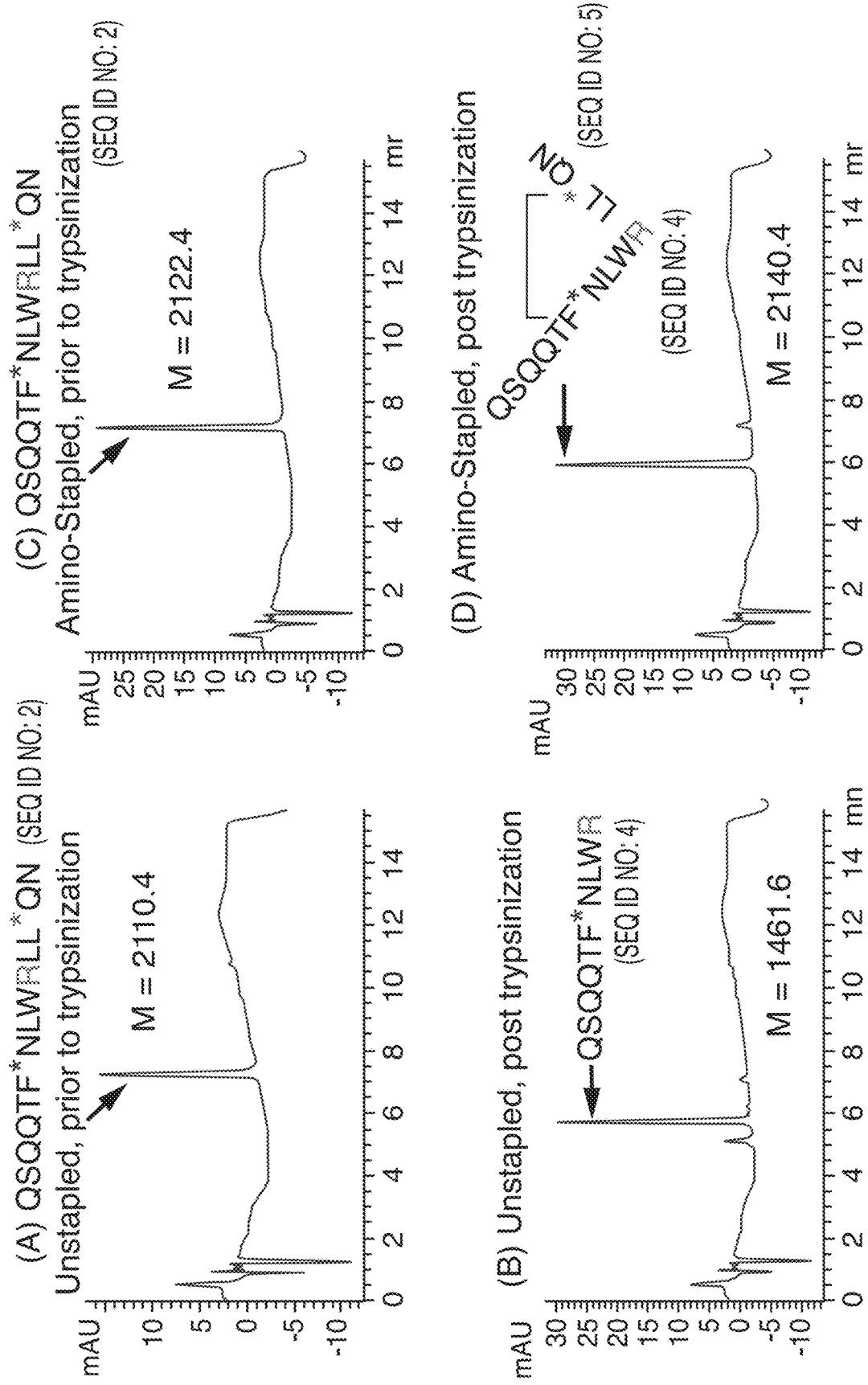

FIG. 4B shows LC/MS spectra of pre-trypsinization and post-trypsinization of unstapled polypeptide and amino-stapled polypeptide. The trypsinization experiment, analyzed by LC/MS, confirms that RCM of the Alloc group of the Pyr$_R$ amino acid and the olefin of Sg, followed by Pd(PPh$_3$)$_4$-catalyzed CO$_2$ extrusion, produces an amino-stapled peptide with a covalent cross-link. (A) shows LC/MS spectrum of unstapled polypeptide prior to trypsinization. (B) shows LC/MS spectrum of unstapled polypeptide after trypsinization. (C) shows LC/MS spectrum of amino-stapled polypeptide prior to trypsinization. (D) shows LC/MS spectrum of amino-stapled polypeptide after trypsinization.

Figure 5:
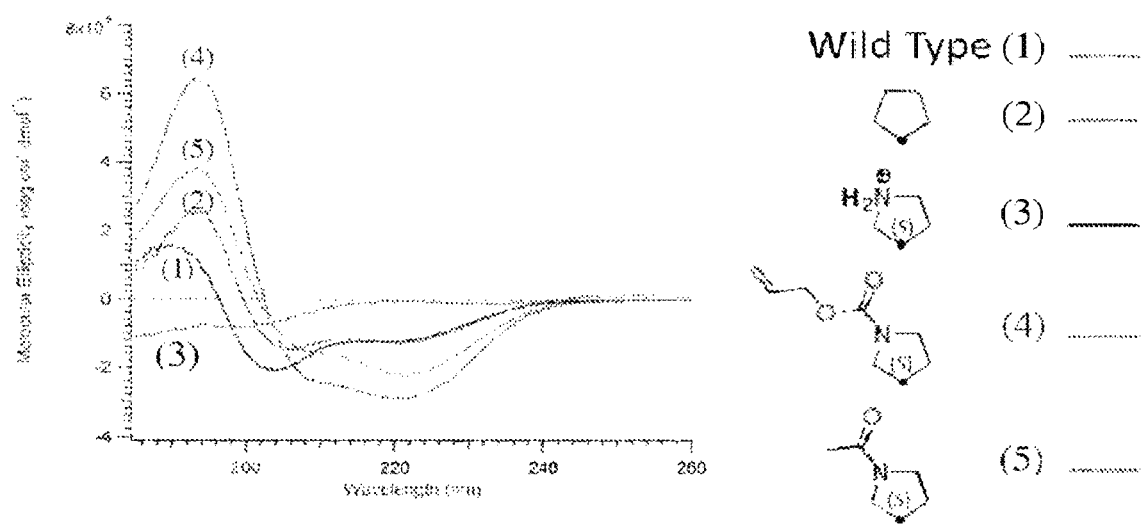

FIG. 5 shows CD spectra of unstapled peptides with different pyrrolidine side chains (numbered 2-5). The base peptide used is RNAse A wild type peptide sequence: EWAETAAAKFLAAHA (SEQ ID NO: 6). The underlined residues were replaced with the amino acids as shown in the legend. Pyrrolidine amino acids bearing an acetyl cap or Alloc protecting group on the side chain nitrogen induced a-helicity more than a cyclopentane amino acid, suggesting they are useful in inducing a-helicity even in the absence of cross-linking. The pyrrolidine amino acids containing secondary amines appeared to decrease helicity in the absence of a cross-link.

Figure 6:
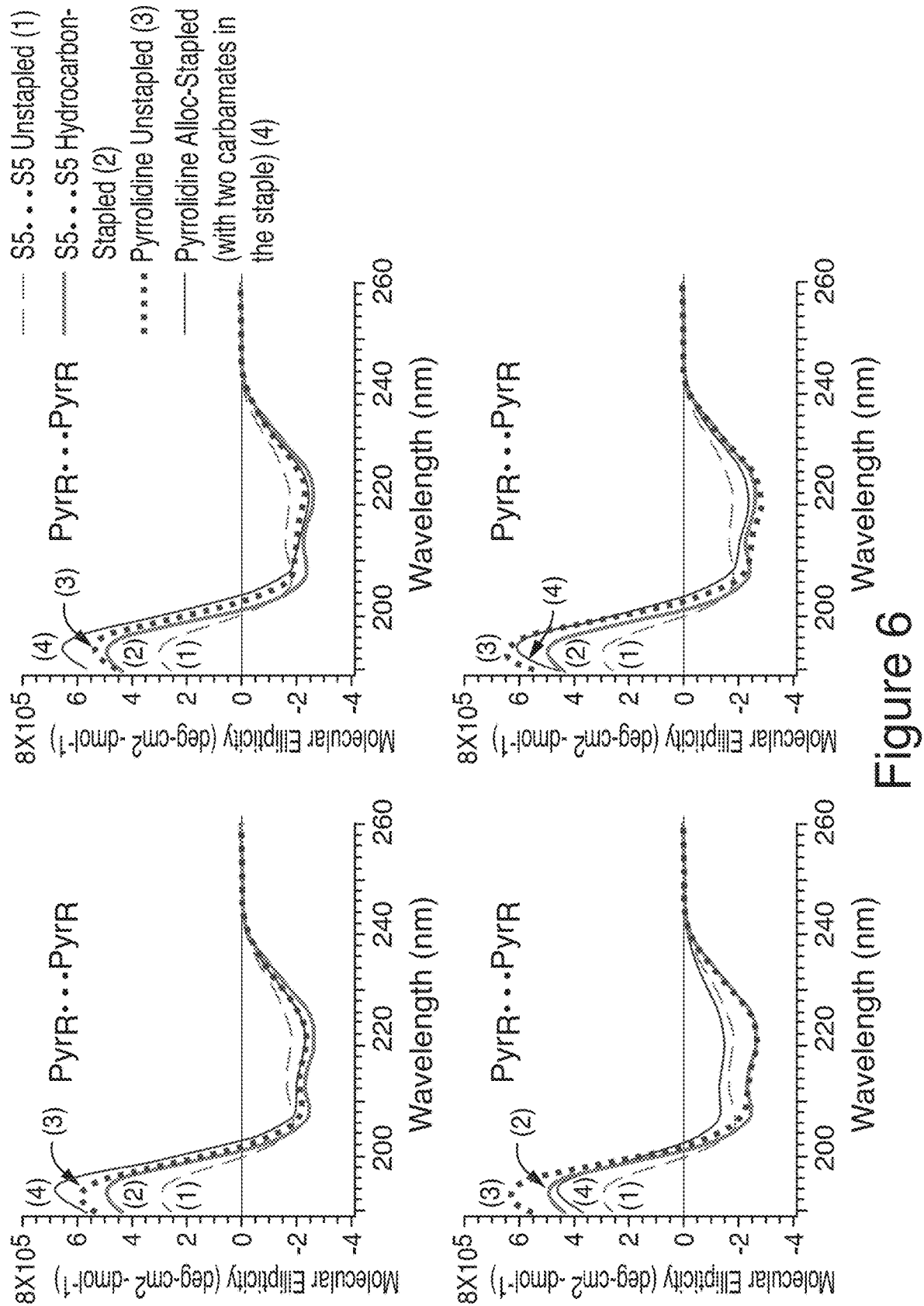

FIG. 6 shows CD spectra of Alloc-stapled i, i+4 pyrrolidine peptides with different sterochemistries at the alpha-carbon. The corresponding sequence is EWA*TAA*KFLAAHA (SEQ ID NO: 7). The asterisks correspond to either the S5 amino acid or the pyrrolidine amino acids with the indicated stereochemistries. Multiple combinations of the pyrrolidine amino acids yield Alloc-stapled peptides with significant helical stabilization.

Figure 7:
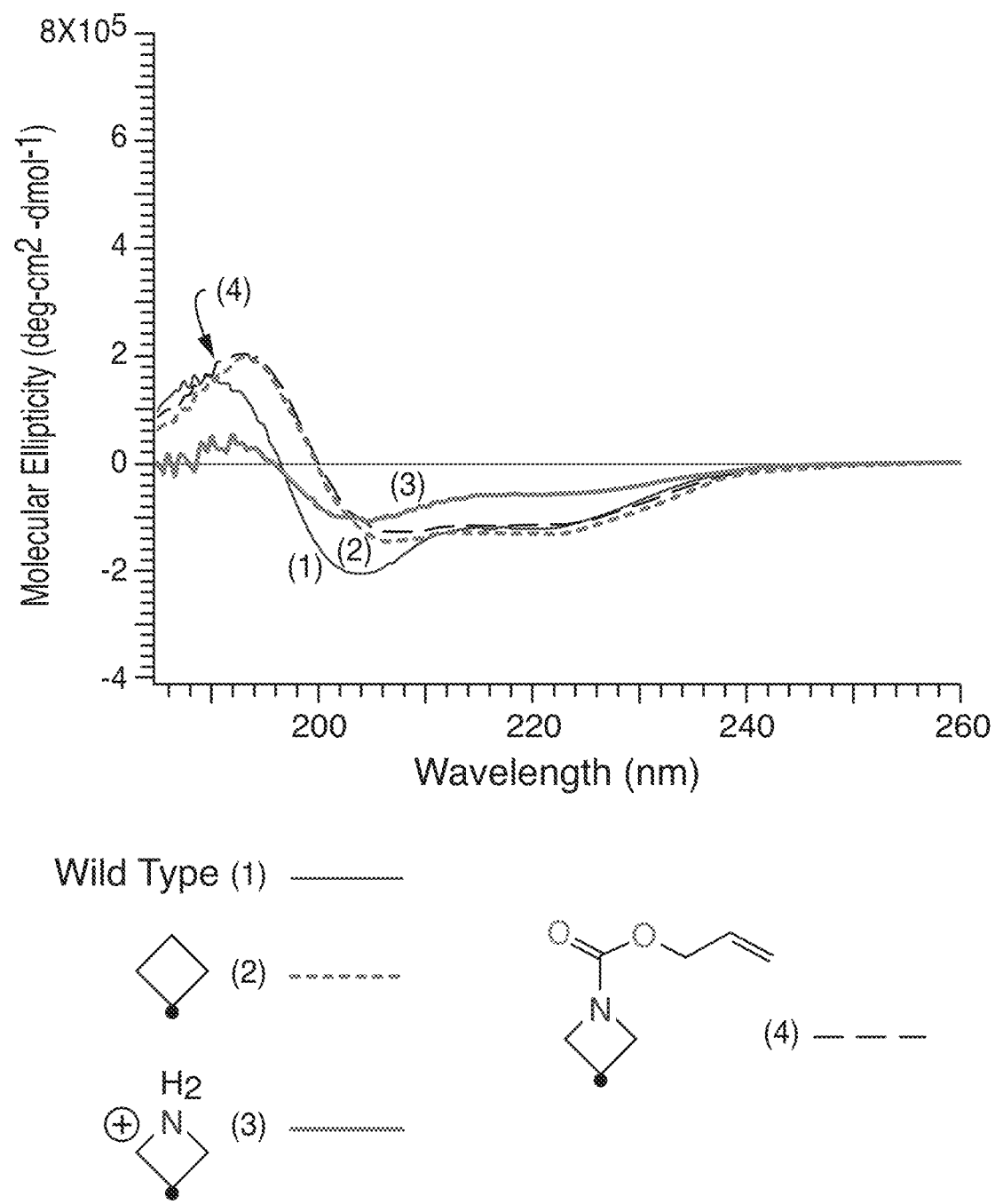

FIG. 7 shows CD spectra of unstapled peptides with different azetidine (Az) side chains. The base peptide used is RNAse A Wild Type Peptide Sequence: EWAETAAAKFLAAHA (SEQ ID NO: 6). The underlined residues were replaced with the amino acids (numbered 2-4) as shown in the legend. The azetidine amino acid bearing an Alloc protecting group on the side chain nitrogen induced a-helicity as well as a cyclobutane amino acid, suggesting it is useful in inducing a-helicity even in the absence of cross-linking. The azetidine amino acid containing a secondary amine appeared to decrease helicity in the absence of a cross-link.

Figure 8:
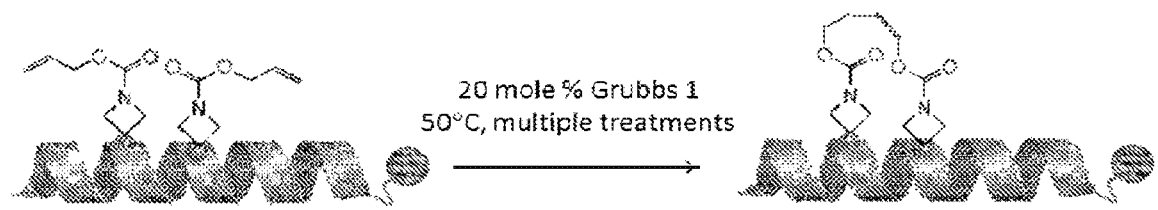
Figure 8:
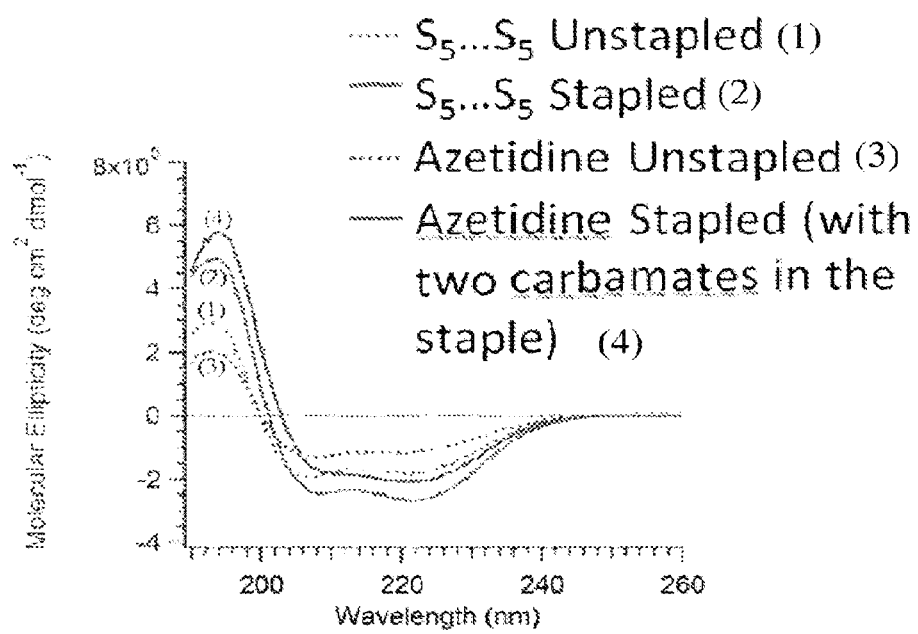

FIG. 8 shows an Alloc-stapled i, i+4 azetidine peptide. The base sequence is EWA*TAA*KFLAAHA (SEQ ID NO: 8). The asterisks correspond to either the S5 amino acid or the azetidine amino acid. FIG. 8 shows Alloc-stapling increases the α-helicity of the azetidine peptide.

Figure 9:
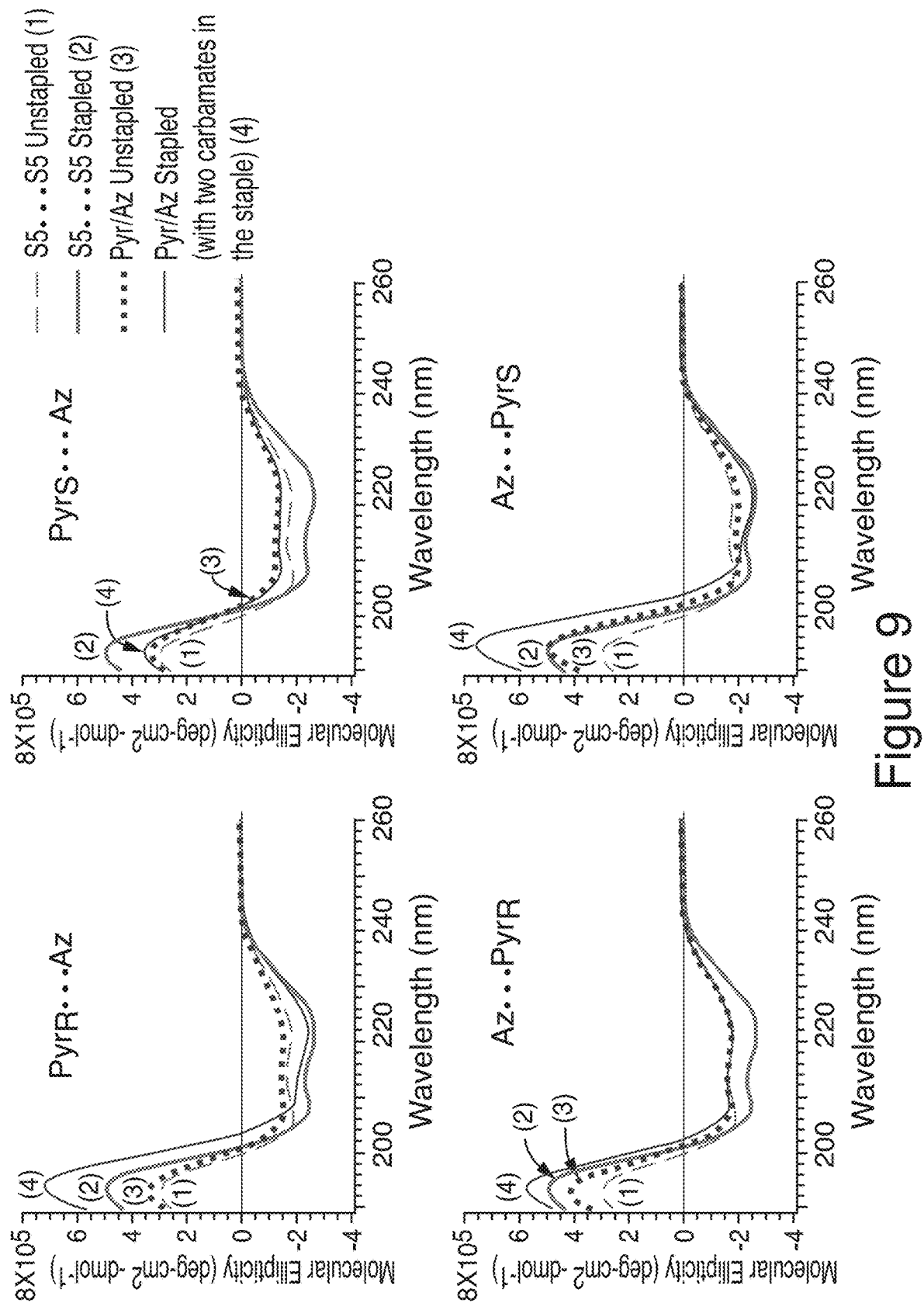

FIG. 9 shows Alloc-stapled hybrid i, i+4 pyrrolidine/azetidine peptides. The base sequence is EWA*TAA*KFLAAHA (SEQ ID NO: 9). The asterisks correspond to either the S$_5$ amino acid, the azetidine amino acid, or the pyrrolidine amino acid with the indicated stereochemistry. The Pyr$_R$ . . . Az and Az . . . Pyr$_S$ Alloc-stapled peptides yield helical stabilization comparable to the all-hydrocarbon stapled peptide.

Figure 10:
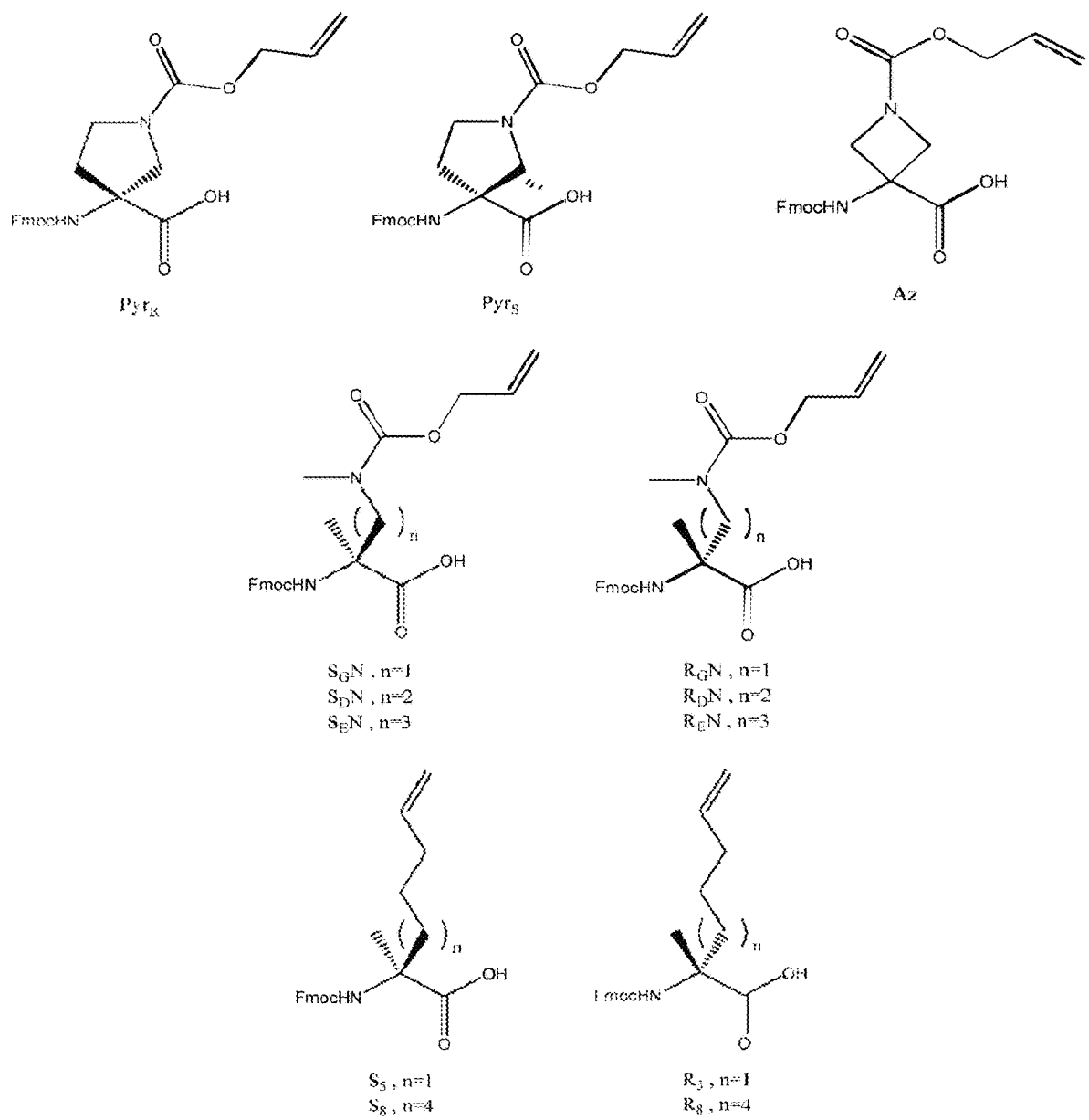

FIG. 10 shows the structure of Fmoc-protected amino acids (and their abbreviations) used to form the exemplary amino-stapled and alloc-stapled peptides described herein. Amino-stapled peptides contain either one or two tertiary amines in the staple, and alloc-stapled peptides contain either one or two carbamates in the staple.

FIGS. 11A to 11D show the circular dichroism (CD) spectra for exemplary amino-stapled and alloc-stapled peptides. The CD spectra are compared to the wild-type peptide and/or the hydrocarbon stapled peptide. Ac is an abbreviation for an acetyl cap. b-ala is an abbreviation for P-alanine.

FIGS. 12A to 12K show fluorescence polarization (FP) binding assay data. FAM is an abbreviation for 5-carboxyfluorescein. FITC is an abbreviation for fluorescein isothiocyanate isomer 1.

Figure 13A:
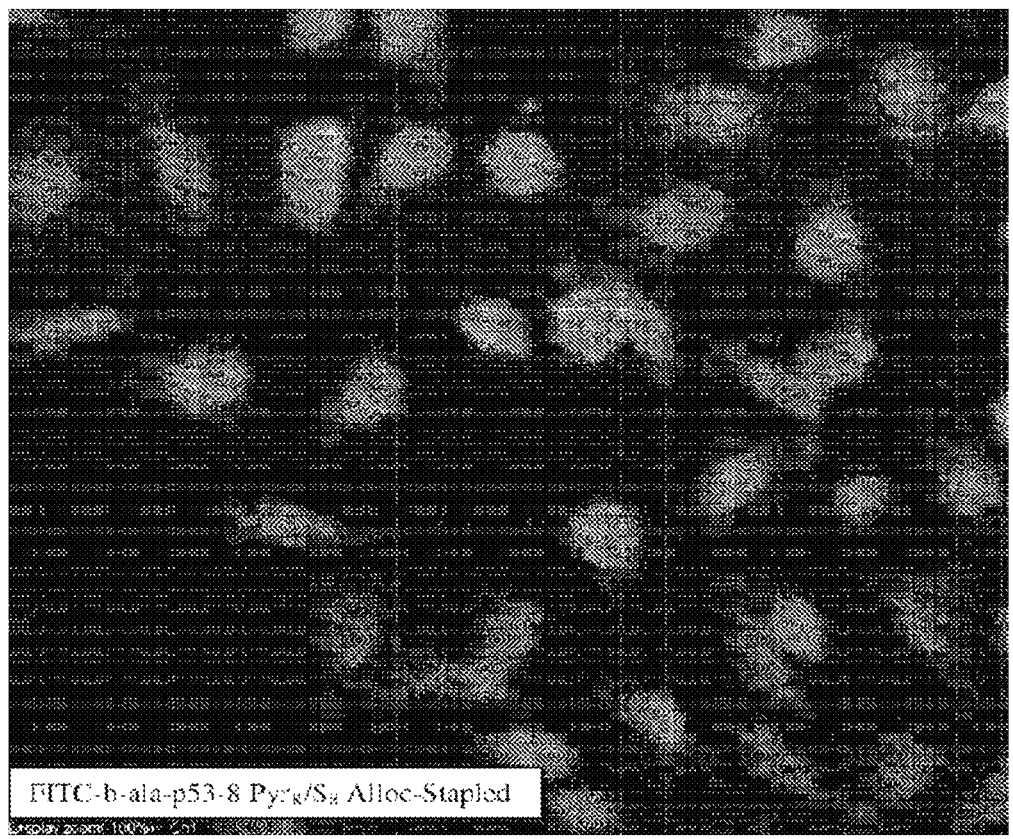
Figure 13B:
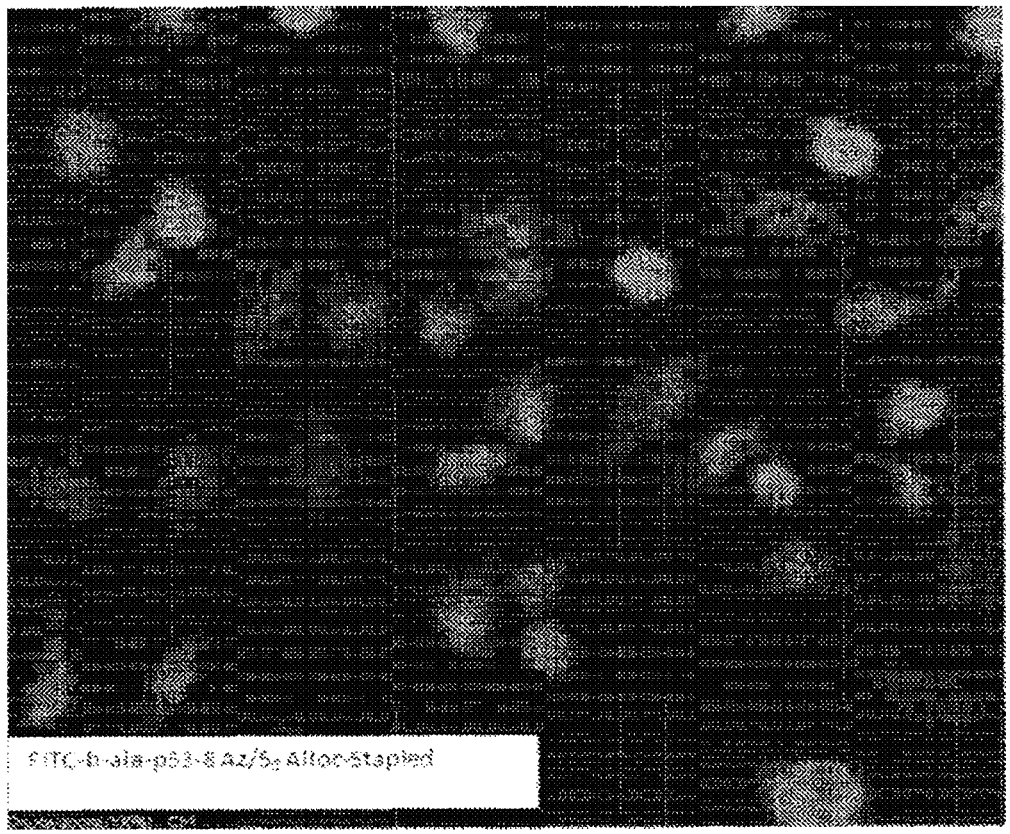
Figure 13C:
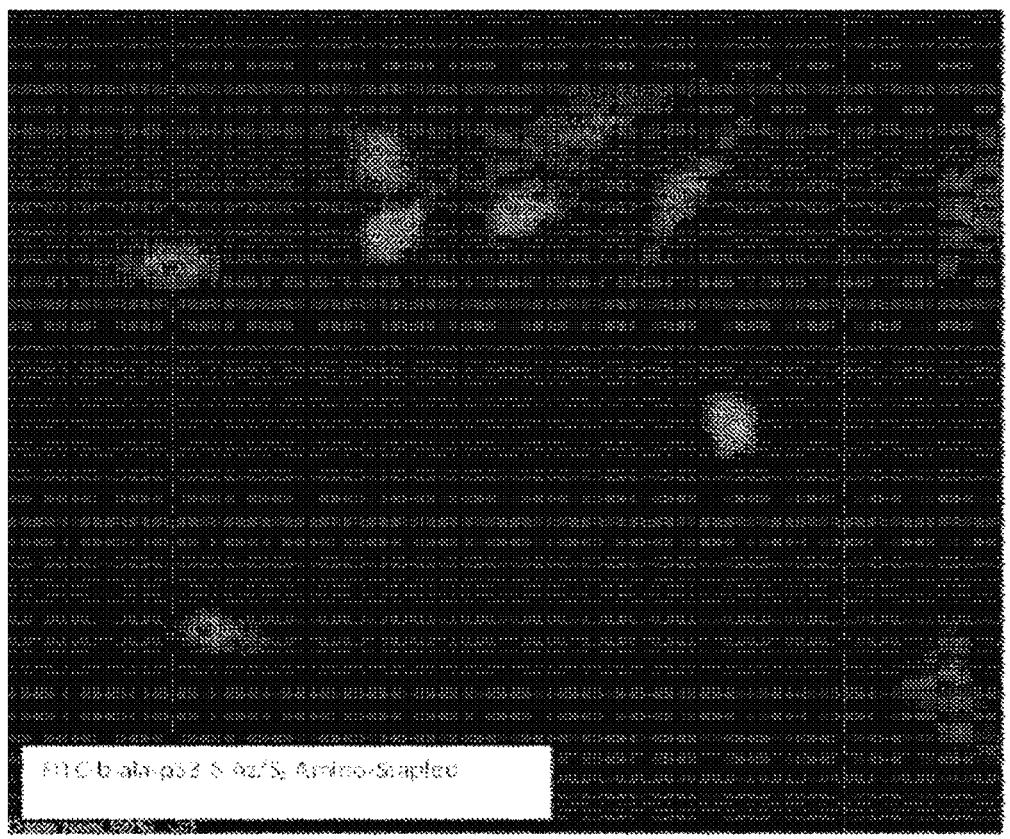

FIGS. 13A to 13C show the cell penetration assay data for exemplary labeled peptides using confocal microscopy.

Figure 14A:
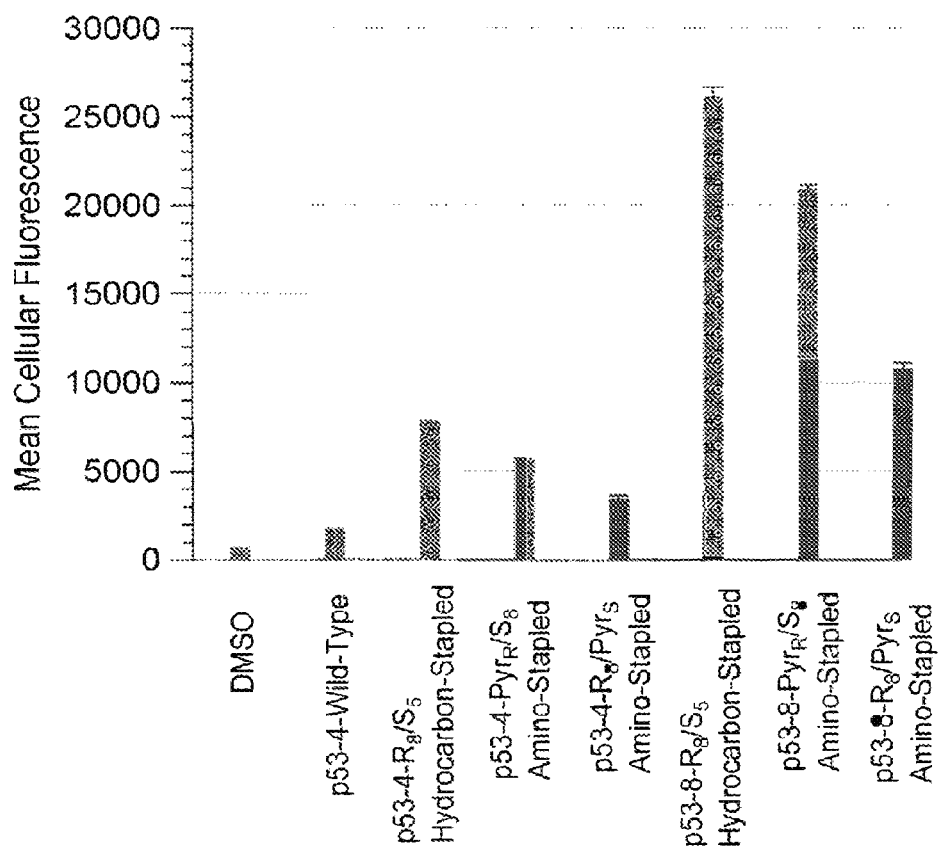
Figure 14B:
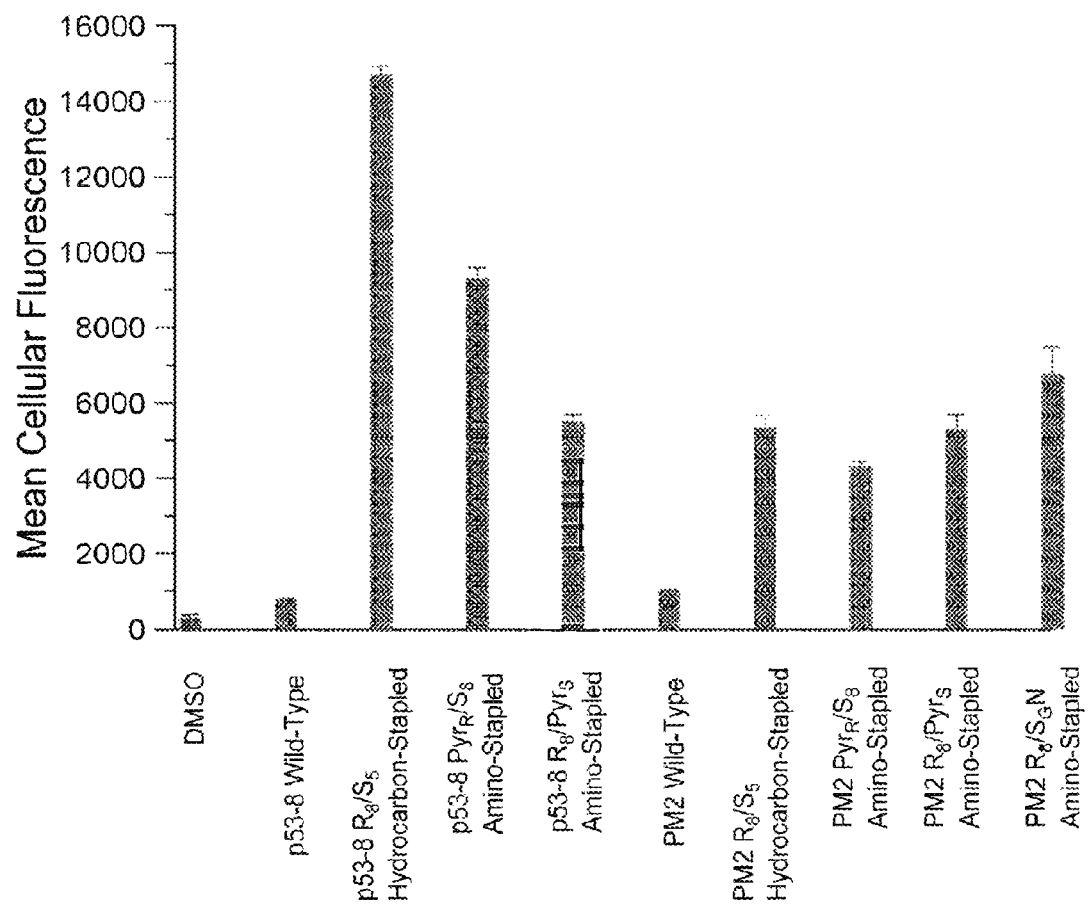

FIGS. 14A and 14B show the cell penetration assay data for exemplary labeled peptides using flow cytometry.

DETAILED DESCRIPTION OF CERTAIN EMBODIMENTS OF THE INVENTION

Figure 1:
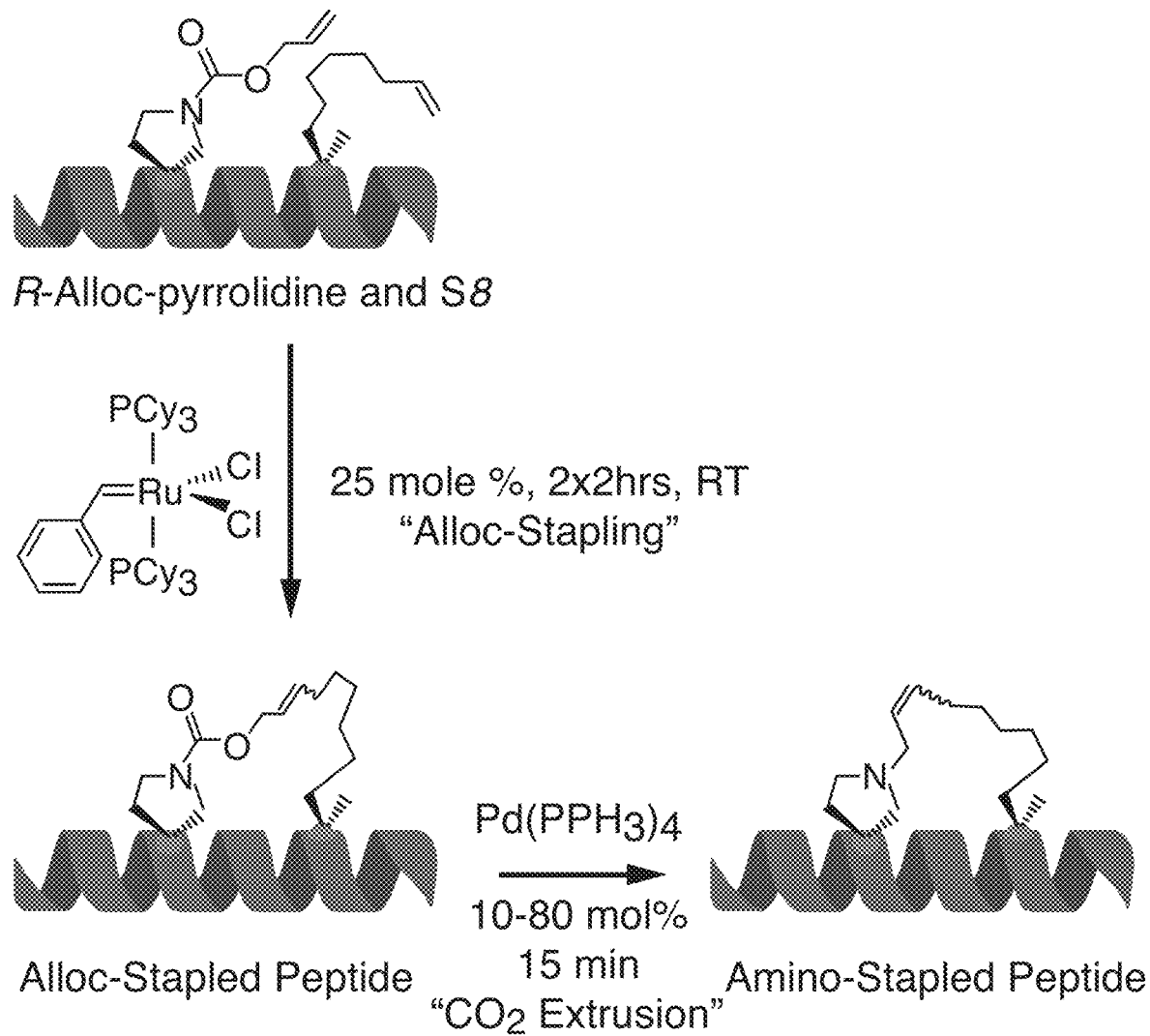
FIG. 1 shows formation of exemplary staples from the Alloc moiety from the pyrrolidine side chain and subsequent $CO_2$ extrusion.

The present invention provides inventive polypeptides containing one or more staples, provided that at least one of the staples comprises a heteroaliphatic group or a cyclic group. The presence of the heteroaliphatic moiety or a cyclic moiety in the staple helps to stabilize the alpha helical structure of the polypeptide. The present invention also provides pharmaceutical compositions comprising an inventive stapled or stitched polypeptide, and methods of preparing and using the inventive polypeptides. The present invention provides for the staples to contain one or two carbamate moieties ("Alloc-stapled peptides") or one or two tertiary amine moieties ("amino-stapled peptides"). The present invention also provides post ring-closing metathesis (RCM) modifications of the staples such as —C(=O)O-extrusion. For example, treating a stapled polypeptide containing an Alloc moiety on the pyrrolidine side chain with a palladium catalyst provides a reduced sized staple in the polypeptide with $CO_2$ removed (FIG. 1).

The inventive stapled and stitched polypeptides, as described herein, may be useful wherever such stabilized secondary structural motifs are advantageous, for example, as therapeutic agents, biological probes, or drug delivery agents. The inventive stapled or stitched polypeptides may function as modulators of protein-protein, protein-ligand, cell-cell, or protein-receptor binding interactions. In certain embodiments, these stapled polypeptides are useful in the treatment of a disorder in a subject, e.g., a disorder selected from the group consisting of proliferative disorders, neurological disorders, immunological disorders, endocrinologic disorders, cardiovascular disorders, hematologic disorders, inflammatory disorders, and disorders characterized by premature or unwanted cell death. The present invention also contemplates use of the inventive stapled and stitched polypeptides as research tools, e.g., in cellular or biochemical studies.

Polypeptides

The present invention provides stapled or stitched polypeptides with heteroaliphatic moiety or cyclic moiety in at least one staple. In one aspect, the present invention provides a polypeptide of Formula (I):

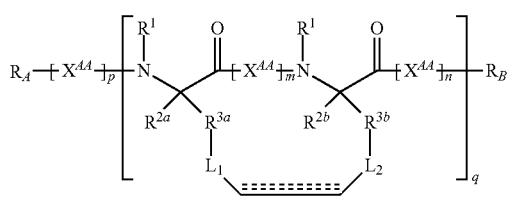

(I)

or a pharmaceutically acceptable salt thereof;
wherein:

each instance of ========== independently represents a single bond, a double bond, or a triple bond;

each instance of $R^1$ is, independently, hydrogen, acyl, substituted or unsubstituted $C_{1-6}$ alkyl, or an amino protecting group;

each of $R^{2a}$ and $R^{2b}$ is, independently, substituted or unsubstituted alkyl; substituted or unsubstituted alkenyl; substituted or unsubstituted alkynyl; substituted or unsubstituted heteroalkyl; substituted or unsubstituted carbocyclyl; or substituted or unsubstituted heterocyclyl;

each of $R^{3a}$ and $R^{3b}$ is, independently, substituted or unsubstituted alkylene; unsubstituted heteroalkylene; substituted or unsubstituted carbocyclylene; or substituted or unsubstituted heterocyclylene; or optionally $R^{2a}$, $R^{3a}$, and the carbon to which $R^{2a}$ and $R^{3a}$ are attached are joined to form a ring; or optionally $R^{2b}$, $R^{3b}$, and the carbon to which $R^{2b}$ and $R^{3b}$ are attached are joined to form a ring;

$L_1$ is independently, a bond, substituted or unsubstituted $C_{1-10}$ alkylene, or —C(=O)O$R^{L1}$;

$L_2$ is independently, a bond, substituted or unsubstituted $C_{1-10}$ alkylene, or —C(=O)O$R^{L2}$—; provided that when neither $R^{2a}$ and $R^{3a}$ nor $R^{2b}$ and $R^{3b}$ forms a ring, $L_1$ is —C(=O)O$R^{L1}$— or $L_2$ is —C(=O)O$R^{L1}$—;

each of $R^{L1}$ and $R^{L2}$ is independently optionally substituted $C_{1-10}$ alkylene;

$R_A$ is, independently, —$R_C$, —O$R_C$, —N($R_C$)$_2$, or —S$R_C$, wherein each instance of $R_C$ is, independently, hydrogen; cyclic or acyclic, branched or unbranched aliphatic; cyclic or acyclic, branched or unbranched heteroaliphatic; aryl; heteroaryl; acyl; a resin; a hydroxyl, amino, or thiol protecting group; or two $R_C$ groups together form a 5- to 6-membered heterocyclic or heteroaromatic ring;

$R_B$ is, independently, hydrogen; cyclic or acyclic, branched or unbranched aliphatic; cyclic or acyclic, branched or unbranched heteroaliphatic; aryl; heteroaryl; acyl; a resin; an amino protecting group; a label optionally joined by a linker, wherein the linker is selected from cyclic or acyclic, branched or unbranched alkylene; cyclic or acyclic, branched or unbranched alkenylene; cyclic or acyclic, branched or unbranched, alkynylene; cyclic or acyclic, branched or unbranched heteroalkylene; cyclic or acyclic, branched or unbranched heteroalkenylene; cyclic or acyclic, branched or unbranched heteroalkynylene; arylene; heteroarylene; or acylene; or $R_A$ and $R_B$ together form a 5- to 6-membered heterocyclic or heteroaromatic ring;

each instance of $X_{AA}$ is, independently, an amino acid;

m is independently, an integer between 2 and 6, inclusive;

each instance of p and n is, independently, 0, or an integer between 1 and 100, inclusive; and q is an integer between 1 and 10, inclusive.

In another aspect, the present invention provides a polypeptide of Formula (VI):

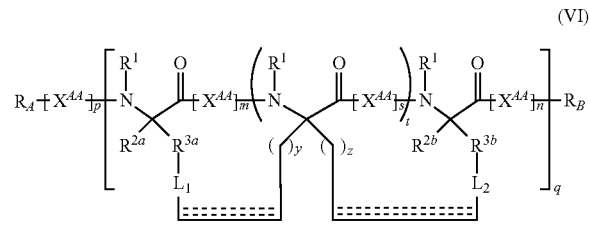

(VI)

or a pharmaceutically acceptable salt thereof,
wherein:

each instance of ========== independently represents a single bond, a double bond, or a triple bond;

each instance of $R^1$ is, independently, hydrogen, acyl, substituted or unsubstituted $C_{1-6}$ alkyl, or an amino protecting group;

each of $R^{2a}$ and $R^{2b}$ is, independently, substituted or unsubstituted alkyl; substituted or unsubstituted alkenyl; substituted or unsubstituted alkynyl; substituted or unsubstituted heteroalkyl; substituted or unsubstituted carbocyclyl; substituted or unsubstituted heterocyclyl;

each of $R^{3a}$ and $R^{3b}$ is, independently, substituted or unsubstituted alkylene; unsubstituted heteroalkylene; substituted or unsubstituted carbocyclylene; or substituted or unsubstituted heterocyclylene; or optionally $R^{2a}$, $R^{3a}$ and the carbon to which $R^{2a}$ and $R^{3a}$ are attached are joined to form a ring; or optionally $R^{2b}$, $R^{3b}$ and the carbon to which $R^{2b}$ and $R^{3b}$ are attached are joined to form a ring;

$L_1$ is independently, a bond, substituted or unsubstituted $C_{1-10}$ alkylene, or $-C(=O)OR^{L1}-$;

$L_2$ is independently, a bond, substituted or unsubstituted $C_{1-10}$ alkylene, or $-C(=O)OR^{L2}-$; provided that when neither $R^{2a}$ and $R^{3a}$ nor $R^{2b}$ and $R^{3b}$ forms a ring, $L_1$ is $-C(=O)OR^{L1}-$ or $L_2$ is $-C(=O)OR^{L1}-$;

each of $R^{L1}$ and $R^{L2}$ is independently optionally substituted $C_{1-10}$ alkylene;

$R_A$ is, independently, $-R_C$, $-OR_C$, $-N(R_C)_2$, or $-SR_C$, wherein each instance of $R_C$ is, independently, hydrogen; cyclic or acyclic, branched or unbranched aliphatic; cyclic or acyclic, branched or unbranched heteroaliphatic; aryl; heteroaryl; acyl; a resin; a hydroxyl, amino, or thiol protecting group; or two $R_C$ groups together form a 5- to 6-membered heterocyclic or heteroaromatic ring;

$R_B$ is, independently, hydrogen; cyclic or acyclic, branched or unbranched aliphatic; cyclic or acyclic, branched or unbranched heteroaliphatic; aryl; heteroaryl; acyl; a resin; an amino protecting group; a label optionally joined by a linker, wherein the linker is selected from cyclic or acyclic, branched or unbranched alkylene; cyclic or acyclic, branched or unbranched alkenylene; cyclic or acyclic, branched or unbranched alkynylene; cyclic or acyclic, branched or unbranched heteroalkylene; cyclic or acyclic, branched or unbranched heteroalkenylene; cyclic or acyclic, branched or unbranched heteroalkynylene; arylene; heteroarylene; or acylene; or $R_A$ and $R_B$ together form a 5- to 6-membered heterocyclic or heteroaromatic ring;

each instance of $X_{AA}$ is, independently, an amino acid;

each instance of p and n is, independently, 0 or an integer between 1 and 100, inclusive;

each of m and s is independently, an integer between 2 and 6, inclusive; and each of q, t, s, y, and z is independently an integer between 1 and 10, inclusive.

As generally described above for Formula (I) and (VI), $R^{3a}$ is independently substituted or unsubstituted alkylene; substituted or unsubstituted heteroalkylene; substituted or unsubstituted carbocyclylene; or substituted or unsubstituted heterocyclylene; or optionally $R^{2a}$, $R^{3a}$ and the carbon to which $R^{2a}$ and $R^{3a}$ are attached are joined to form a ring. In certain embodiments, $R^{3a}$ is substituted or unsubstituted alkylene. In certain embodiments, $R^{3a}$ is substituted or unsubstituted $C_{1-10}$ alkylene. In certain embodiments, $R^{3a}$ is substituted $C_{1-10}$ alkylene. In certain embodiments, $R^{3a}$ is unsubstituted $C_{1-10}$ alkylene. In certain embodiments, $R^{3a}$ is substituted or unsubstituted heteroalkylene. In certain embodiments, $R^{3a}$ is substituted heteroalkylene. In certain embodiments, $R^{3a}$ is unsubstituted heteroalkylene. In certain embodiments, $R^{3a}$ is substituted or unsubstituted heteroalkylene containing at least one nitrogen. In certain embodiments, $R^{3a}$ is $-(CH_2)_j-X_1-$, wherein j is independently an integer between 0 and 10, inclusive; and $X_1$ is independently a bond, $-CR^5R^6-$ or $-NR^1-$, wherein each of $R^5$ and $R^6$ is independently hydrogen, halogen, or $C_{1-6}$ alkyl. In certain embodiments, $R^{3a}$ is $-(CH_2)_j-$. In certain embodiments, $R^{3a}$ is $-(CH_2)_j-NR^1-$. In certain embodiments, $R^{3a}$ is $-(CH_2)_j-NH-$. In certain embodiments, $R^{3a}$ is $-(CH_2)_{j+1}-$. In certain embodiments, j is 0. In certain embodiments, j is 1. In certain embodiments, j is 2. In certain embodiments, j is 3. In certain embodiments, j is 4. In certain embodiments, j is 5. In certain embodiments, j is 6. In certain embodiments, j is 7. In certain embodiments, j is 8. In certain embodiments, j is 9. In certain embodiments, j is 10.

As generally described above for Formula (I) and (VI), $R^{2a}$ is, independently, substituted or unsubstituted alkyl; substituted or unsubstituted alkenyl; substituted or unsubstituted alkynyl; substituted or unsubstituted heteroalkyl; substituted or unsubstituted carbocyclyl; substituted or unsubstituted heterocyclyl. In certain embodiments, $R^{2a}$ is substituted or unsubstituted $C_{1-10}$ alkyl. In certain embodiments, $R^{2a}$ is substituted methyl. In certain embodiments, $R^{2a}$ is unsubstituted methyl. In certain embodiments, $R^{2a}$ is substituted ethyl. In certain embodiments, $R^{2a}$ is unsubstituted ethyl. In certain embodiments, $R^{2a}$ is substituted n-propyl. In certain embodiments, $R^{2a}$ is unsubstituted n-propyl. In certain embodiments, $R^{2a}$ is substituted iso-propyl. In certain embodiments, $R^{2a}$ is unsubstituted iso-propyl. In certain embodiments, $R^{2a}$ is substituted or unsubstituted heteroalkyl. In certain embodiments, $R^{2a}$ is substituted or unsubstituted heteroalkyl with at least one nitrogen. In certain embodiments, $R^{2a}$ is unsubstituted heteroalkyl containing at least one nitrogen. In certain embodiments, $R^{2a}$ is substituted heteroalkyl containing at least one nitrogen.

In certain embodiments, at least one instance of $R^{2a}$ and $R^{3a}$ together with the carbon atom to which they are attached, are joined to form a ring. In this instance, in certain embodiments, the ring formed by $R^{2a}$ and $R^{3a}$ together with the carbon atom to which they are attached is substituted or unsubstituted $C_{3-6}$ carbocyclyl or heterocyclyl. In certain embodiments, the ring formed by $R^{2a}$ and $R^{3a}$ together with the carbon atom to which they are attached is substituted or unsubstituted $C_{3-6}$ carbocyclyl. In certain embodiments, the ring formed by $R^{2a}$ and $R^{3a}$ together with the carbon atom to which they are attached is substituted or unsubstituted $C_{3-6}$ heterocyclyl. In certain embodiments, the ring formed by $R^{2a}$ and $R^{3a}$ together with the carbon atom to which they are attached is substituted or unsubstituted $C_{3-6}$ heterocyclyl containing at least one O, N, or S atom. In certain embodiments, the ring formed by $R^{2a}$ and $R^{3a}$ together with the carbon atom to which they are attached is substituted or unsubstituted $C_{3-6}$ heterocyclyl containing at least one nitrogen atom. In certain embodiments, the ring formed by $R^{2a}$ and $R^{3a}$ together with the carbon atom to which they are attached is substituted or unsubstituted $C_{3-6}$ heterocyclyl containing one nitrogen atom. In certain embodiments, the ring formed by $R^{2a}$ and $R^{3a}$ together with the carbon atom to which they are attached is unsubstituted $C_{3-6}$ heterocyclyl containing one nitrogen atom.

In certain embodiments, $R^{2a}$, $R^{3a}$, and the carbon to which $R^{2a}$ and $R^{3a}$ are attached are joined to form a ring. In certain embodiments, the ring formed by $R^{2a}$, $R^{3a}$, and the carbon to which $R^{2a}$ and $R^{3a}$ are attached is of the formula:

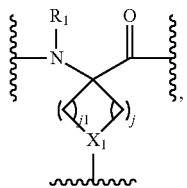

wherein $X_1$ is independently —$CR^5$— or —N—, and j1 is independently 0, 1, 2, 3, 4, 5, or 6. In certain embodiments, j1 is zero, and the ring formed by $R^{2a}$, $R^{3a}$ and the carbon to which $R^{2a}$ and $R^{3a}$ are attached is of the formula:

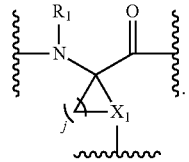

In certain embodiments, j is 0 and $X_1$ is directly linked to the alpha-carbon of the amino acid. In certain embodiments, j is 1. In certain embodiments, j is 2. In certain embodiments, j is 3. In certain embodiments, j is 4. In certain embodiments, j is 5. In certain embodiments, j is 6. In certain embodiments, j is 7. In certain embodiments, j is 8. In certain embodiments, j is 9. In certain embodiments, j is 10. In certain embodiments, the ring formed by $R^{2a}$, $R^{3a}$ and the carbon to which $R^{2a}$ and $R^{3a}$ are attached is of the formula:

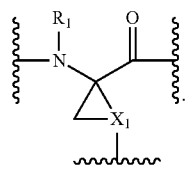

In certain embodiments, the ring formed by $R^{2a}$, $R^{3a}$ and the carbon to which $R^{2a}$ and $R^{3a}$ are attached is of the formula:

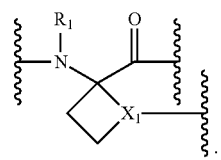

In certain embodiments, the ring formed by $R^{2a}$, $R^{3a}$ and the carbon to which $R^{2a}$ and $R^{3a}$ are attached is of the formula:

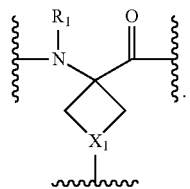

In certain embodiments, the ring formed by $R^{2a}$, $R^{3a}$ and the carbon to which $R^{2a}$ and $R^{3a}$ are attached is of the formula:

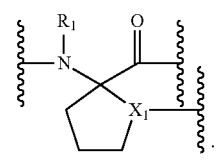

In certain embodiments, the ring formed by $R^{1a}$, $R^{3a}$ and the carbon to which $R^{2a}$ and $R^{3a}$ are attached is of the formula:

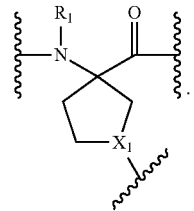

In certain embodiments, the ring formed by $R^{2a}$, $R^{3a}$ and the carbon to which $R^{2a}$ and $R^{3a}$ are attached is of the formula:

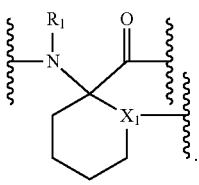

In certain embodiments, the ring formed by $R^{2a}$, $R^{3a}$ and the carbon to which $R^{2a}$ and $R^{3a}$ are attached is of the formula:

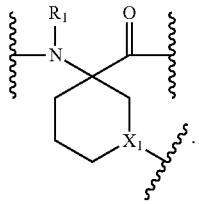

In certain embodiments, the ring formed by $R^{2a}$, $R^{3a}$ and the carbon to which $R^{2a}$ and $R^{3a}$ are attached is of the formula:

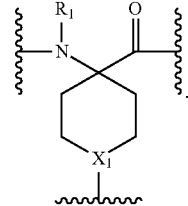

In certain embodiments, the ring formed by $R^{2a}$, $R^{3a}$ and the carbon to which $R^{2a}$ and $R^{3a}$ are attached is of the formula

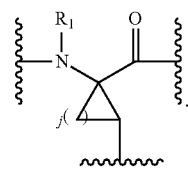

In certain embodiments, the ring formed by $R^{2a}$, $R^{3a}$ and the carbon to which $R^{2a}$ and $R^{3a}$ are attached is of the formula

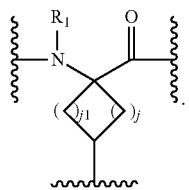

In certain embodiments, the ring formed by $R^{2a}$, $R^{3a}$ and the carbon to which $R^{2a}$ and $R^{3a}$ are attached is of the formula

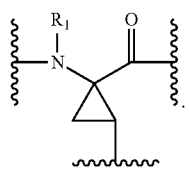

In certain embodiments, the ring formed by $R^{2a}$, $R^{3a}$ and the carbon to which $R^{2a}$ and $R^{3a}$ are attached is of the formula

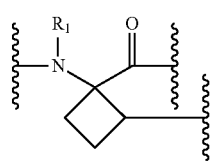

In certain embodiments, the ring formed by $R^{2a}$, $R^{3a}$ and the carbon to which $R^{2a}$ and $R^{3a}$ are attached is of the formula

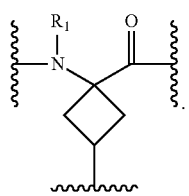

In certain embodiments, the ring formed by $R^{2a}$, $R^{3a}$ and the carbon to which $R^{2a}$ and $R^{3a}$ are attached is of the formula

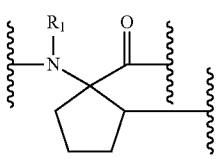

In certain embodiments, the ring formed by $R^{2a}$, $R^{3a}$ and the carbon to which $R^{2a}$ and $R^{3a}$ are attached is of the formula

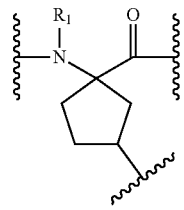

In certain embodiments, the ring formed by $R^{2a}$, $R^{3a}$ and the carbon to which $R^{2a}$ and $R^{3a}$ are attached is of the formula

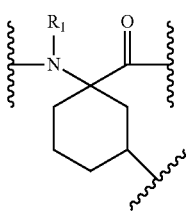

In certain embodiments, the ring formed by $R^{2a}$, $R^{3a}$ and the carbon to which $R^{2a}$ and $R^{3a}$ are attached is of the formula

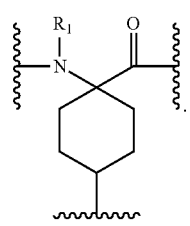

In certain embodiments, the ring formed by $R^{2a}$, $R^{3a}$ and the carbon to which $R^{2a}$ and $R^{3a}$ are attached is of the formula

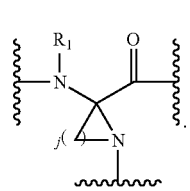

In certain embodiments, the ring formed by $R^{2a}$, $R^{3a}$ and the carbon to which $R^{2a}$ and $R^{3a}$ are attached is of the formula

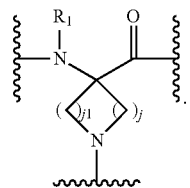

In certain embodiments, the ring formed by $R^{2a}$, $R^{3a}$ and the carbon to which $R^{2a}$ and $R^{3a}$ are of the formula:

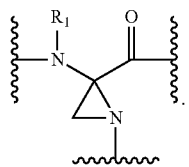

In certain embodiments, the ring formed by $R^{2a}$, $R^{3a}$ and the carbon to which $R^{2a}$ and $R^{3a}$ are attached is of the formula:

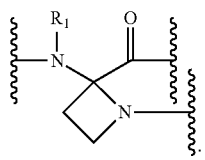

In certain embodiments, the ring formed by $R^{2a}$, $R^{3a}$ and the carbon to which $R^{2a}$ and $R^{3a}$ are attached to is of the formula:

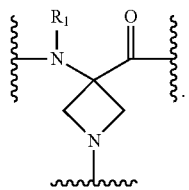

In certain embodiments, the ring formed by $R^{2a}$, $R^{3a}$ and the carbon to which $R^{2a}$ and $R^{3a}$ are attached is of the formula:

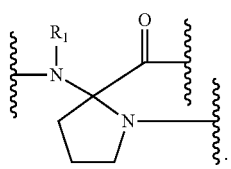

In certain embodiments, the ring formed by $R^{2a}$, $R^{3a}$ and the carbon to which $R^{2a}$ and $R^{3a}$ are attached is of the formula:

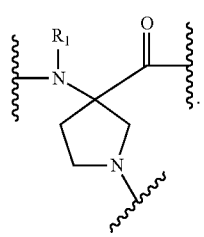

In certain embodiments, the ring formed by $R^{2a}$, $R^{3a}$ and the carbon to which $R^{2a}$ and $R^{3a}$ are attached is of the formula:

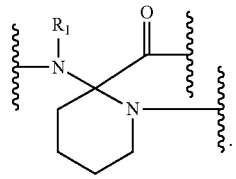

In certain embodiments, the ing formed by $R^{2a}$, $R^{3a}$ and the carbon to which $R^{2a}$ and $R^{3a}$ are attached is of the formula:

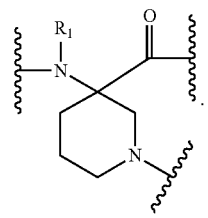

In certain embodiments, the ring formed by $R^{2a}$, $R^{3a}$ and the carbon to which $R^{2a}$ and $R^{3a}$ are attached is of the formula:

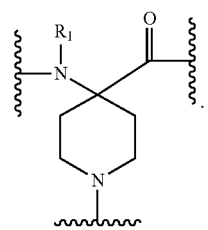

As used herein, each of j and j1 is independently an integer between 1 and 10, inclusive. In certain embodiments, j is 1. In certain embodiments, j is 2. In certain embodiments, j is 3. In certain embodiments, j is 4. In certain embodiments, j is 5. In certain embodiments, j is 6. In certain embodiments, j is 7. In certain embodiments, j is 8. In certain embodiments, j is 9. In certain embodiments, j is 10. In certain embodiments, j1 is 1. In certain embodiments, j1 is 2. In certain embodiments, j1 is 3. In certain embodiments, j1 is 4. In certain embodiments, j1 is 5. In certain embodiments, j1 is 6. In certain embodiments, j1 is 7. In certain embodiments, j1 is 8. In certain embodiments, j1 is 9. In certain embodiments, j1 is 10.

In certain embodiments, $R^{2a}$, $R^{3a}$ and the carbon to which $R^{2a}$ and $R^{3a}$ are attached are not joined to form a ring. In this instance, $R^{3a}$ is independently substituted or unsubstituted alkylene, substituted or unsubstituted alkenylene, substituted or unsubstituted alkynylene, substituted or unsubstituted heteroalkylene, or substituted or unsubstituted heterocyclylene. In certain embodiments, $R^{3a}$ is independently substituted or unsubstituted $C_{1-10}$ alkylene. In certain embodiments, $R^{3a}$ is substituted $C_{1-10}$ alkylene. In certain embodiments, $R^{3a}$ is independently —$(CH_2)_j$—, wherein j is an integer between 0 and 10, inclusive.

In certain embodiments, $R^{2a}$, $R^{3a}$ and the carbon to which $R^{2a}$ and $R^{3a}$ are attached are not joined to form a ring. In this instance, $R^{2a}$ is independently substituted or unsubstituted alkyl, substituted or unsubstituted alkenyl, substituted or unsubstituted alkynyl, substituted or unsubstituted heteroalkyl, or substituted or unsubstituted heterocyclyl. In certain embodiments, $R^{2a}$ is independently substituted or unsubstituted $C_{1-10}$ alkyl. In certain embodiments, $R^{2a}$ is independently substituted methyl. In certain embodiments, $R^{2a}$ is independently unsubstituted methyl. In certain embodiments, $R^{2a}$ is independently substituted ethyl. In certain embodiments, $R^{2a}$ is independently unsubstituted ethyl. In certain embodiments, $R^{2a}$ is independently substituted or unsubstituted $C_{2-6}$ alkyl.

As generally described above, $R^{3b}$ is independently substituted or unsubstituted alkylene; substituted or unsubstituted heteroalkylene; substituted or unsubstituted carbocyclylene; or substituted or unsubstituted heterocyclylene; or optionally $R^{2b}$, $R^{3b}$ and the carbon to which $R^{2b}$ and $R^{3b}$ are attached are joined to form a ring. In certain embodiments, $R^{3b}$ is substituted or unsubstituted $C_{1-10}$ alkylene. In certain embodiments, $R^{3b}$ is substituted $C_{1-10}$ alkylene. In certain embodiments, $R^{3b}$ is unsubstituted $C_{1-10}$ alkylene. In certain embodiments, $R^{3b}$ is substituted or unsubstituted heteroalkylene. In certain embodiments, $R^{3b}$ is substituted heteroalkylene. In certain embodiments, $R^{3b}$ is unsubstituted heteroalkylene. In certain embodiments, $R^{3b}$ is substituted or unsubstituted heteroalkylene with at least one nitrogen. In certain embodiments, $R^{3b}$ is $-(CH_2)_k-X_2-$, wherein k is independently an integer between 0 and 10, inclusive, and $X_2$ is independently a bond, $-CR^5R^6-$, or $-NR^1-$, wherein each of $R^5$ and $R^6$ is independently hydrogen, halogen, or $C_{1-6}$ alkyl. In certain embodiments, $R^{3b}$ is $-(CH_2)_k-$. In certain embodiments, $R^{3b}$ is $-(CH_2)_k-NR^1-$. In certain embodiments, $R^{3b}$ is $-(CH_2)_k-NH-$. In certain embodiments, $R^{3b}$ is $-(CH_2)_{k+1}-$. In certain embodiments, k is 0. In certain embodiments, k is 1. In certain embodiments, k is 2. In certain embodiments, k is 3. In certain embodiments, k is 4. In certain embodiments, k is 5. In certain embodiments, k is 6. In certain embodiments, k is 7. In certain embodiments, k is 8. In certain embodiments, k is 9. In certain embodiments, k is 10.

As generally described above, $R^{2b}$ is, independently, substituted or unsubstituted alkyl; substituted or unsubstituted alkenyl; substituted or unsubstituted alkynyl; substituted or unsubstituted heteroalkyl; substituted or unsubstituted carbocyclyl; or substituted or unsubstituted heterocyclyl. In certain embodiments, $R^{2b}$ is substituted or unsubstituted $C_{1-10}$ alkyl. In certain embodiments, $R^{2b}$ is substituted or unsubstituted heteroalkyl. In certain embodiments, $R^{2b}$ is substituted or unsubstituted heteroalkyl with at least one nitrogen atom. In certain embodiments, $R^{2b}$ is unsubstituted heteroalkyl with at least one nitrogen atom. In certain embodiments, $R^{2b}$ is substituted heteroalkyl with at least one nitrogen atom.

In certain embodiments, for at least one instance, $R^{2b}$, $R^{3b}$ and the carbon to which $R^{2b}$ and $R^{3b}$ are attached are joined to form a ring. In this instance, in certain embodiments, the ring formed by $R^{2b}$ and $R^{3b}$ together with the carbon atom to which they are attached is substituted or unsubstituted $C_{3-6}$ carbocyclyl or heterocyclyl. In certain embodiments, the ring formed by $R^{2b}$ and $R^{3b}$ together with the carbon atom to which they are attached is substituted or unsubstituted $C_{3-6}$ carbocyclyl. In certain embodiments, the ring formed by $R^{2b}$ and $R^{3b}$ together with the carbon atom to which they are attached is substituted or unsubstituted $C_{3-6}$ heterocyclyl. In certain embodiments, the ring formed by $R^{2b}$ and $R^{3b}$ together with the carbon atom to which they are attached is substituted or unsubstituted $C_{3-6}$ heterocyclyl with at least one O, N, or S atom. In certain embodiments, the ring formed by $R^{2b}$ and $R^{3b}$ together with the carbon atom to which they are attached is substituted or unsubstituted $C_{3-6}$ heterocyclyl with at least one N. In certain embodiments, the ring formed by $R^{2b}$ and $R^{3b}$ together with the carbon atom to which they are attached is substituted or unsubstituted $C_{3-6}$ heterocyclyl with one N. In certain embodiments, the ring formed by $R^{2b}$ and $R^{3b}$ together with the carbon atom to which they are attached is unsubstituted $C_{3-6}$ heterocyclyl with one N.

In certain embodiments, the ring formed by $R^{2b}$, $R^{3b}$ and the carbon to which $R^{2b}$ and $R^{3b}$ are attached is of the formula

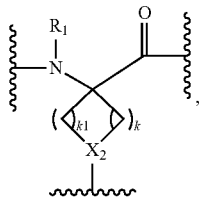

wherein k is as defined herein, $X_2$ is independently $-CR^5-$ or $-N-$, and k1 is independently 0, 1, 2, 3, 4, 5, or 6. In certain embodiments, k1 is zero, and the ring formed by $R^{2b}$, $R^{3b}$ and the carbon to which $R^{2b}$ and $R^{3b}$ are attached is of the formula

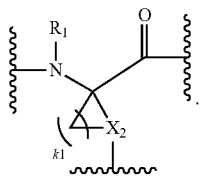

In certain embodiments, k1 is 1. In certain embodiments, k1 is 2. In certain embodiments, k1 is 3. In certain embodiments, k1 is 4. In certain embodiments, k1 is 5. In certain embodiments, k1 is 6. In certain embodiments, the ring formed by $R^{2b}$, $R^{3b}$ and the carbon to which $R^{2b}$ and $R^{3b}$ are attached is of the formula

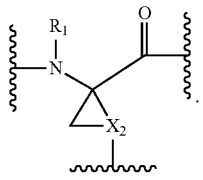

In certain embodiments, the ring formed by $R^{2b}$, $R^{3b}$ and the carbon to which $R^{2b}$ and $R^{3b}$ are attached is of the formula

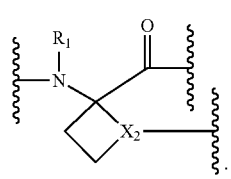

In certain embodiments, the ring formed by $R^{2b}$, $R^{3b}$ and the carbon to which $R^{2b}$ and $R^{3b}$ are attached is of the formula

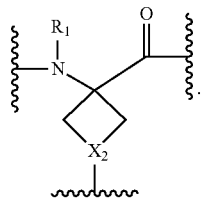

In certain embodiments, the ring formed by $R^{2b}$, $R^{3b}$ and the carbon to which $R^{2b}$ and $R^{3b}$ are attached is of the formula

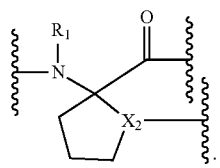

In certain embodiments, the ring formed by $R^{2b}$, $R^{3b}$ and the carbon to which $R^{2b}$ and $R^{3b}$ are attached is of the formula

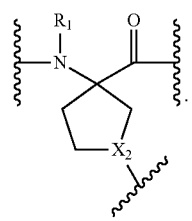

In certain embodiments, the ring formed by $R^{2b}$, $R^{3b}$ and the carbon to which $R^{2b}$ and $R^{3b}$ are attached is of the formula

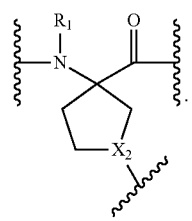

In certain embodiments, the ring formed by $R^{2b}$, $R^{3b}$ and the carbon to which $R^{2b}$ and $R^{3b}$ are attached is of the formula

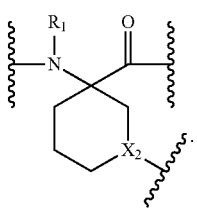

In certain embodiments, the ring formed by $R^{2b}$, $R^{3b}$ and the carbon to which $R^{2b}$ and $R^{3b}$ are attached is of the formula

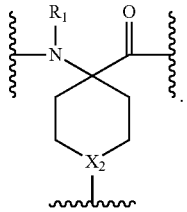

In certain embodiments, the ring formed by $R^{2b}$, $R^{3b}$ and the carbon to which $R^{2b}$ and $R^{3b}$ are attached is of the formula

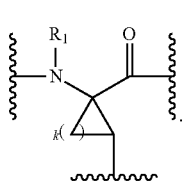

In certain embodiments, the ring formed by $R^{2b}$, $R^{3b}$ and the carbon to which $R^{2b}$ and $R^{3b}$ are attached is of the formula

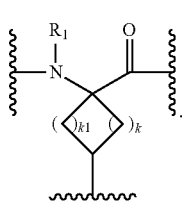

In certain embodiments, the ring formed by $R^{2b}$, $R^{3b}$ and the carbon to which $R^{2b}$ and $R^{3b}$ are attached is of the formula

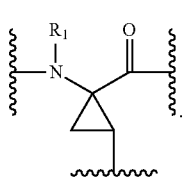

In certain embodiments, the ring formed by $R^{2b}$, $R^{3b}$ and the carbon to which $R^{2b}$ and $R^{3b}$ are attached is of the formula

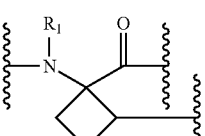

In certain embodiments, the ring formed by $R^{2b}$, $R^{3b}$ and the carbon to which $R^{2b}$ and $R^{3b}$ are attached is of the formula

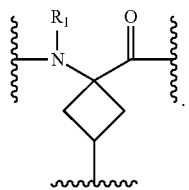

In certain embodiments, the ring formed by $R^{2b}$, $R^{3b}$ and the carbon to which $R^{2b}$ and $R^{3b}$ are attached is of the formula

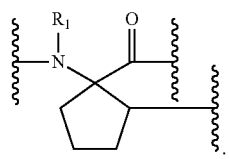

In certain embodiments, the ring formed by $R^{2b}$, $R^{3b}$ and the carbon to which $R^{2b}$ and $R^{3b}$ are attached is of the formula

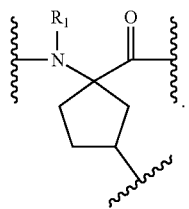

In certain embodiments, the ring formed by $R^{2b}$, $R^{3b}$ and the carbon to which $R^{2b}$ and $R^{3b}$ are attached s of the formula

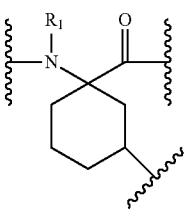

In certain embodiments, the ring formed by $R^{2b}$, $R^{3b}$ and the carbon to which $R^{2b}$ and $R^{3b}$ are attached is of the formula

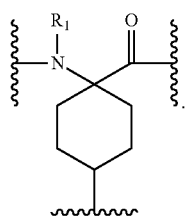

In certain embodiments, the ring formed by $R^{2b}$, $R^{3b}$ and the carbon to which $R^{2b}$ and $R^{3b}$ are attached is of the formula

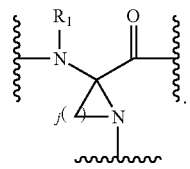

In certain embodiments, the ring formed by $R^{2b}$, $R^{3b}$ and the carbon to which $R^{2b}$ and $R^{3b}$ are attached is of the formula

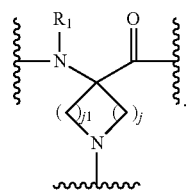

In certain embodiments, the ring formed by $R^{2b}$, $R^{3b}$ and the carbon to which $R^{2b}$ and $R^{3b}$ are attached is of the formula

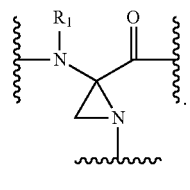

In certain embodiments, the ring formed by $R^{2b}$, $R^{3b}$ and the carbon to which $R^{2b}$ and $R^{3b}$ are attached is of the formula

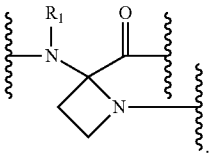

In certain embodiments, the ring formed by $R^{2b}$, $R^{3b}$ and the carbon to which $R^{2b}$ and $R^{3b}$ are attached is of the formula

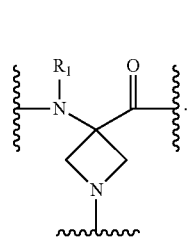

In certain embodiments, the ring formed by $R^{2b}$, $R^{3b}$ and the carbon to which $R^{2b}$ and $R^{3b}$ are attached is of the formula

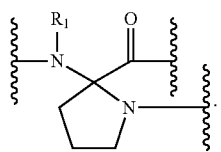

In certain embodiments, the ring formed by $R^{2b}$, $R^{3b}$ and the carbon to which $R^{2b}$ and $R^{3b}$ are attached is of the formula

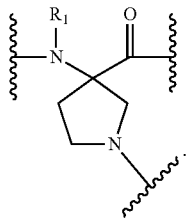

In certain embodiments, the ring formed by $R^{2b}$, $R^{3b}$ and the carbon to which $R^{2b}$ and $R^{3b}$ are attached is of the formula

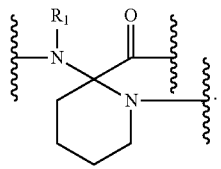

In certain embodiments, the ring formed by $R^{2b}$, $R^{3b}$ and the carbon to which $R^{2b}$ and $R^{3b}$ are attached is of the formula

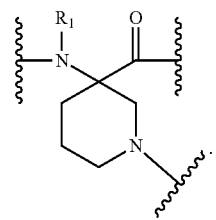

In certain embodiments, the ring formed by $R^{2b}$, $R^{3b}$ and the carbon to which $R^{2b}$ and $R^{3b}$ are attached is of the formula

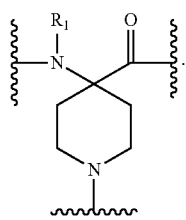

As used herein, k is an integer between 0 and 10, inclusive; and k1 is independently an integer between 1 and 10, inclusive. In certain embodiments, k is 0. In certain embodiments, k is 1. In certain embodiments, k is 2. In certain embodiments, k is 3. In certain embodiments, k is 4. In certain embodiments, k is 5. In certain embodiments, k is 6. In certain embodiments, k is 7. In certain embodiments, k is 8. In certain embodiments, k is 9. In certain embodiments, k is 10. In certain embodiments, k1 is 1. In certain embodiments, k1 is 2. In certain embodiments, k1 is 3. In certain embodiments, k1 is 4. In certain embodiments, k1 is 5. In certain embodiments, k1 is 6. In certain embodiments, k1 is 7. In certain embodiments, k1 is 8. In certain embodiments, k1 is 9. In certain embodiments, k1 is 10.

In certain embodiments, $R^{2b}$, $R^{3b}$ and the carbon to which $R^{2b}$ and $R^{3b}$ are attached are not joined to form a ring. In this instance, $R^{3b}$ is independently substituted or unsubstituted alkylene, substituted or unsubstituted alkenylene, substituted or unsubstituted alkynylene, substituted or unsubstituted heteroalkylene, or substituted or unsubstituted heterocyclylene. In certain embodiments, $R^{3b}$ is independently substituted or unsubstituted $C_{1-10}$ alkylene. In certain embodiments, $R^{3b}$ is substituted $C_{1-10}$ alkylene. In certain embodiments, $R^{3b}$ is independently —$(CH_2)_k$—, wherein k is as defined above.

In certain embodiments, $R^{2b}$, $R^{3b}$ and the carbon to which $R^{2b}$ and $R^{3b}$ are attached are not joined to form a ring. In this instance, in certain embodiments, $R^{2b}$ is independently substituted or unsubstituted $C_{1-10}$ alkyl, substituted or unsubstituted alkenyl, substituted or unsubstituted alkynyl, substituted or unsubstituted heteroalkyl, or substituted or unsubstituted heterocyclyl. In certain embodiments, $R^{2b}$ is independently substituted or unsubstituted $C_{1-10}$ alkyl. In certain embodiments, $R^{2b}$ is independently substituted methyl. In certain embodiments, $R^{2b}$ is independently unsubstituted methyl. In certain embodiments, $R^{2b}$ is independently ethyl. In certain embodiments, $R^{2b}$ is independently unsubstituted ethyl. In certain embodiments, $R^{2b}$ is independently substituted or unsubstituted $C_{2-6}$ alkyl.

In certain embodiments, for at least one instance, $R^{2a}$, $R^{3a}$, and the carbon to which $R^{2a}$ and $R^{3a}$ are attached are not joined to form a ring, and $R^{2b}$, $R^{3b}$, and the carbon to which $R^{2b}$ and $R^{3b}$ are attached are not joined form a ring. In certain embodiments, $R^{2a}$, $R^{3a}$ and the carbon to which $R^{2a}$ and $R^{3a}$ are attached are not joined to form a ring, and $R^{2b}$, $R^{3b}$ and the carbon to which $R^{2b}$ and $R^{3b}$ are attached are joined form a ring. In certain embodiments, $R^{2a}$, $R^{3a}$ and the carbon to which $R^{2a}$ and $R^{3a}$ are attached are joined to form a ring, and $R^{2b}$, $R^{3b}$ and the carbon to which $R^{2b}$ and $R^{3b}$ are attached are not joined form a ring. In certain embodiments, for at least one instance, $R^{2a}$, $R^{3a}$ and the carbon to which $R^{2a}$ and $R^{3a}$ are attached are joined to form a ring, and $R^{2b}$, $R^{3b}$ and the carbon to which $R^{2b}$ and $R^{3b}$ are attached are joined form a ring.

As generally described above, $L_1$ is independently, a bond, substituted or unsubstituted $C_{1-10}$ alkylene, or —C(=O)O$R^{L1}$—, wherein $R^{L1}$ is optionally substituted $C_{1-10}$ alkylene. In some embodiments, $L_1$ is substituted or unsubstituted $C_{1-10}$ alkylene. In some embodiments, $L_1$ is substituted $C_{1-10}$ alkylene. In some embodiments, $L_1$ is —$(CH_2)_g$—, wherein g is 0 or an integer between 1 and 10. In some embodiments, g is 0, and $L_1$ is a bond. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10. In certain embodiments, RY is substituted $C_{1-10}$ alkylene. In certain embodiments, $R^{L1}$ is —$(CH_2)_{g1}$—, wherein g1 is an integer between 1 and 10 inclusive. In some embodiments, g1 is 1. In some embodiments, g1 is 2. In some embodiments, g1 is 3. In some embodiments, g1 is 4. In some embodiments, g1 is 5. In some embodiments, g1 is 6. In some embodiments, g1 is 7. In some embodiments, g1 is 8. In some embodiments, g1 is 9. In some embodiments, g1 is 10.

As generally described above, $L_2$ is independently, a bond, substituted or unsubstituted $C_{1-10}$ alkylene, or —C(=O)OR$^{L2}$—, wherein R$^{L2}$ is optionally substituted $C_{1-10}$ alkylene. In some embodiments, $L_2$ is substituted or unsubstituted $C_{1-10}$ alkylene. In some embodiments, $L_2$ is substituted $C_{1-10}$ alkylene. In some embodiments, $L_2$ is —(CH$_2$)$_h$—, wherein h is 0 or an integer between 1 and 10 inclusive. In some embodiments, h is 0, and $L_2$ is a bond. In some embodiments, h is 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10. In certain embodiments, R$^{L2}$ is substituted $C_{1-10}$ alkylene. In certain embodiments, R$^{L2}$ is —(CH$_2$)$_{h1}$—, wherein h1 is an integer between 1 and 10 inclusive. In some embodiments, h1 is 1. In some embodiments, h1 is 2. In some embodiments, h1 is 3. In some embodiments, h1 is 4. In some embodiments, h1 is 5. In some embodiments, h1 is 6. In some embodiments, h1 is 7. In some embodiments, h1 is 8. In some embodiments, h1 is 9. In some embodiments, h1 is 10.

In certain embodiments, for at least one instance of a staple, neither R$^{2a}$ and R$^{3a}$ nor R$^{2b}$ and R$^{3b}$ of the same staple are joined to form a ring. In this instance, $L_1$ is —C(=O)OR$^{L1}$—, or $L_2$ is —C(=O)OR$^{L2}$—, wherein each of R$^{L1}$ and R$^{L2}$ is optionally substituted $C_{1-10}$ alkylene. In this instance, in certain embodiments, R$^{L1}$ is substituted $C_{1-10}$ alkylene. In this instance, in certain embodiments, R$^{L1}$ is —(CH$_2$)$_{g1}$—, wherein g1 is as defined above. In this instance, in certain embodiments, R$^{L2}$ is substituted $C_{1-10}$ alkylene. In this instance, in certain embodiments, R$^{L2}$ is —(CH$_2$)$_{h1}$—, wherein h1 is as defined above.

In certain embodiments, q is 0. In certain embodiments, q is 1. In certain embodiments, q is 2. In certain embodiments, q is 3. In certain embodiments, q is 4. In certain embodiments, q is 5. In certain embodiments, q is 6. In certain embodiments, q is 7. In certain embodiments, q is 8. In certain embodiments, q is 9. In certain embodiments, q is 10.

In certain embodiments, —[X$_{AA}$]— corresponds to the formula:

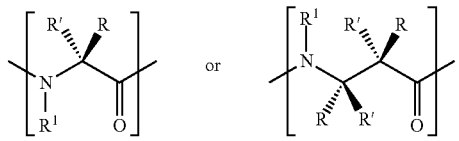

wherein each instance of R and R' are, independently, hydrogen or a suitable amino acid side chain as defined herein, and R$^1$ is as defined herein. Suitable amino acid side chains include, but are not limited to, both natural and unnatural amino acid side chains as provided in Tables 1 to 3, and as described herein. In certain embodiments, each instance of X$_{AA}$ is an alpha-amino acid. In certain embodiments, each instance of X$_{AA}$ is a natural L-amino acid, as provided in Table 1. In certain embodiments, each instance of X$_{AA}$ is, independently, a natural L-amino acid as provided in Table 1, or an unnatural D-amino acid as provided in Table 2.

In certain embodiments, each instance of X$_{AA}$ is a natural amino acid. In certain embodiments, each instance of X$_{AA}$ is an alpha-amino acid. In certain embodiments, each instance of X$_{AA}$ is a natural L-amino acid, as provided in Table 1. In certain embodiments, each instance of X$_{AA}$ is, independently, a natural L-amino acid as provided in Table 1, or an unnatural amino acid as provided in Tables 2, 3, 4, and/or 5.

TABLE 1

| Exemplary natural alpha-amino acids | R | R' |
|---|---|---|
| L-Alanine (A) | —CH$_3$ | —H |
| L-Arginine (R) | —CH$_2$CH$_2$CH$_2$—NHC(=NH)NH$_2$ | —H |
| L-Asparagine (N) | —CH$_2$C(=O)NH$_2$ | —H |
| L-Aspartic acid (D) | —CH$_2$CO$_2$H | —H |
| L-Cysteine (C) | —CH$_2$SH | —H |
| L-Glutamic acid (E) | —CH$_2$CH$_2$CO$_2$H | —H |
| L-Glutamine (Q) | —CH$_2$C(=O)NH$_2$ | —H |
| Glycine (G) | —H | —H |
| L-Histidine (H) | —CH$_2$-2-(1H-imidazole) | —H |
| L-Isoleucine (I) | -sec-butyl | —H |
| L-Leucine (L) | -iso-butyl | —H |
| L-Lysine (K) | —CH$_2$CH$_2$CH$_2$CH$_2$NH$_2$ | —H |
| L-Methionine (M) | —CH$_2$CH$_2$SCH$_3$ | —H |
| L-Phenylalanine (F) | —CH$_2$Ph | —H |
| L-Proline (P) | -2-(pyrrolidine) | —H |
| L-Serine (S) | —CH$_2$OH | —H |
| L-Threonine (T) | —CH$_2$CH(OH)(CH$_3$) | —H |
| L-Tryptophan (W) | —CH$_2$-3-(1H-indole) | —H |
| L-Tyrosine (Y) | —CH$_2$-(p-hydroxyphenyl) | —H |
| L-Valine (V) | -isopropyl | —H |

TABLE 2

| Exemplary unnatural alpha-amino acids | R | R' |
|---|---|---|
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |
| Di-vinyl | —CH=CH$_2$ | —CH=CH$_2$ |

TABLE 3

| Exemplary unnatural alpha-amino acids | R and R' are equal to: | |
|---|---|---|
| α-methyl-Alanine (Aib, 2-amino-2-methylpropanoic acid) | —CH$_3$ | —CH$_3$ |
| α-methyl-Arginine | —CH$_3$ | —CH$_2$CH$_2$CH$_2$—NHC(=NH)NH$_2$ |
| α-methyl-Asparagine | —CH$_3$ | —CH$_2$C(=O)NH$_2$ |

TABLE 3-continued

| Exemplary unnatural alpha-amino acids | | R and R' are equal to: |
|---|---|---|
| α-methyl-Aspartic acid | —$CH_3$ | —$CH_2CO_2H$ |
| α-methyl-Cysteine | —$CH_3$ | —$CH_2SH$ |
| α-methyl-Glutamic acid | —$CH_3$ | —$CH_2CH_2CO_2H$ |
| α-methyl-Glutamine | —$CH_3$ | —$CH_2CH_2C(=O)NH_2$ |
| α-methyl-Histidine | —$CH_3$ | —$CH_2$-2-(1H-imidazole) |
| α-methyl-Isoleucine | —$CH_3$ | -sec-butyl |
| α-methyl-Leucine | —$CH_3$ | -iso-butyl |
| α-methyl-Lysine | —$CH_3$ | —$CH_2CH_2CH_2CH_2NH_2$ |
| α-methyl-Methionine | —$CH_3$ | —$CH_2CH_2SCH_3$ |
| α-methyl-Phenylalanine | —$CH_3$ | —$CH_2Ph$ |
| α-methyl-Proline | —$CH_3$ | -2-(pyrrolidine) |
| α-methyl-Serine | —$CH_3$ | —$CH_2OH$ |
| α-methyl-Threonine | —$CH_3$ | —$CH_2CH(OH)(CH_3)$ |
| α-methyl-Tryptophan | —$CH_3$ | —$CH_2$-3-(1H-indole) |
| α-methyl-Tyrosine | —$CH_3$ | —$CH_2$-(p-hydroxyphenyl) |
| α-methyl-Valine | —$CH_3$ | -isopropyl |
| Di-vinyl | —$CH=CH_2$ | —$CH=CH_2$ |
| Norleucine | —H | —$CH_2CH_2CH_2CH_3$ |

TABLE 4

| Exemplary unnatural alpha-amino acids | R and R' is independently equal to hydrogen or —$CH_3$, and the group: |
|---|---|
| Terminally unsaturated alpha-amino acids and bis alpha-amino acids (e.g., modified cysteine, modified lysine, modified tryptophan, modified serine, modified threonine, modified proline, modified histidine, modified alanine, and the like). | —$(CH_2)_g$—S—$(CH_2)_g CH=CH_2$, <br> —$(CH_2)_g$—O—$(CH_2)_g CH=CH_2$, <br> —$(CH_2)_g$—NH—$(CH_2)_g CH=CH_2$, <br> —$(CH_2)_g$—(C=O)—S—$(CH_2)_g CH=CH_2$, <br> —$(CH_2)_g$—(C=O)—O—$(CH_2)_g CH=CH_2$, <br> —$(CH_2)_g$—(C=O)—NH—$(CH_2)_g CH=CH_2$, <br> —$CH_2CH_2CH_2CH_2$—NH—$(CH_2)_g CH=CH_2$, <br> —$(C_6H_5)p$—O—$(CH_2)_g CH=CH_2$, <br> —$CH(CH_3)$—O—$(CH_2)_g CH=CH_2$, <br> —$CH_2CH(-O-CH=CH_2)(CH_3)$, <br> -histidine-N$((CH_2)_g CH=CH_2)$, <br> -tryptophan-N$((CH_2)_g CH=CH_2)$, and <br> —$(CH_2)_g(CH=CH_2)$, <br> wherein: <br> each instance of g is, independently, 0 to 10. |

TABLE 5

| Other unnatural alpha-amino acids | R and R' are equal to: | |
|---|---|---|
| 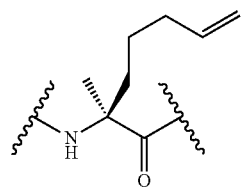 [SMILES: *N[C@@](C)(CCCC=C)C(*)=O]<br>$R_5$-(R)-2-amino-2-methylhept-6-enoic acid | -$CH_3$ | -$(CH_2)_3CH=CH_2$ |
| $S_5$-(S)-2-amino-2-methylhept-6-enoic acid | | |

TABLE 5-continued

| Other unnatural alpha-amino acids | R and R' are equal to: |
|---|---|
| $R_8$-(R)-2-amino-2-methyldec-9-enoic acid | -$CH_3$    -$(CH_2)_6CH=CH_2$ |
| $S_8$-(S)-2-amino-2-methyldec-9-enoic acid | |
| $B_5$-2-amino-2-(pent-4-enyl)hept-6-enoic acid | -$(CH_2)_3CH=CH_2$    -$(CH_2)_3CH=CH_2$ |

There are many known unnatural amino acids any of which may be included in the peptides of the present invention. See, for example, S. Hunt, *The Non-Protein Amino Acids: In Chemistry and Biochemistry of the Amino Acids*, edited by G. C. Barrett, Chapman and Hall, 1985. Some additional examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine. Furthermore, the amino acids for use in the present invention may be derivatized to include amino acid residues that are hydroxylated, phosphorylated, sulfonated, acylated, alkylated, farnesylated, geryanylated, and/or glycosylated.

The group $R_A$ corresponds to the N-terminus of the polypeptide. For example, if —[$X_{AA}$]— corresponds to an alpha-amino acid of formula:

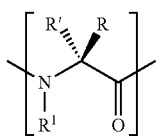

it follows that, in certain embodiments, $R_A$—[$X_{AA}$]$_p$— corresponds to the formula:

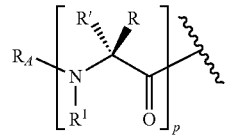

wherein p, R, and R' are as defined herein; and $R_A$ is hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a linker, wherein the linker is cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R_A$ and $R^1$ together form a substituted or unsubstituted heterocyclic or heteroaromatic ring.

In certain embodiments, $R_A$ is hydrogen. In certain embodiments, $R_A$ is $C_{1-6}$ alkyl. In certain embodiments, $R_A$ is —CH$_3$. In certain embodiments, $R_A$ is an amino protecting group. In certain embodiments, $R_A$ is -Boc. In certain embodiments, $R_A$ is -Fmoc. In certain embodiments, $R_A$ is acyl. In certain embodiments, $R_A$ is —(C=O)CH$_3$. In certain embodiments, $R^A$ is a label. In certain embodiments, $R^A$ is a resin. In certain embodiments, $R^A$ is a solid support.

In certain embodiments, $R_A$ is a label optionally joined by a linker, wherein the linker is cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

As generally described above, the group $R_B$ corresponds to the C-terminus of the peptide chain, and corresponds to the variables —$R_C$, —$OR_C$, —$N(R_C)_2$, or —$SR_C$, wherein $R_C$ is as defined herein. For example, if —[$X_{AA}$]— corresponds to an alpha-amino acid of the

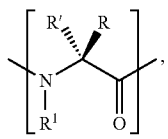

it follows that, in certain embodiments, —[$X_{AA}$]$_n$—$R_B$ corresponds to the formula:

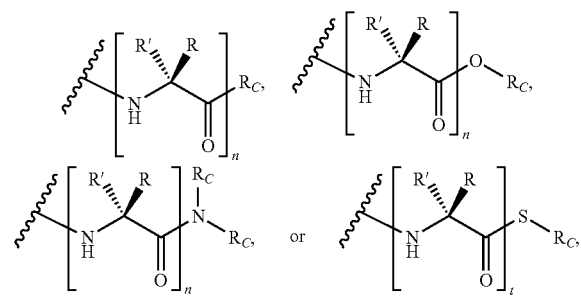

wherein each instance of $R_C$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a suitable hydroxyl, amino, or thiol protecting group; and two $R_C$ groups taken together may optionally form a substituted or unsubstituted heterocyclic or heteroaromatic ring.

In certain embodiments, $R_B$ is —$OR_C$, wherein $R_C$ is hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a suitable hydroxyl protecting group.

In certain embodiments, $R_B$ is —$SR_C$, wherein $R_C$ is hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; or a suitable thiol protecting group.

In certain embodiments, $R_B$ is —$N(R_C)_2$, wherein each instance of $R_C$ is, independently, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; or two $R_C$ groups together form a substituted or unsubstituted heterocyclic or heteroaromatic ring.

As used herein, a "label" refers to a moiety that has at least one element, isotope, or functional group incorporated into the moiety which enables detection of the inventive polypeptide to which the label is attached. Labels encompass moieties that are directly attached (i.e., via a bond) to the polypeptide or such moieties that attached to the polypeptide by a linking group. It will be appreciated that the label may be attached to the polypeptide at any position that does not interfere with the biological activity or characteristic of the inventive polypeptide that is being detected. In general, a label can fall into any one (or more) of five classes: a) a label which contains isotopic moieties, which may be radioactive or heavy isotopes, including, but not limited to, $^2$H, $^3$H, $^{13}$C, $^{14}$C, $^{15}$N, $^{18}$F, $^{31}$P, $^{32}$P, $^{35}$S, $^{67}$Ga, $^{99m}$Tc (Tc-99m), $^{111}$In, $^{123}$I, $^{125}$I, $^{169}$Yb and $^{186}$Re; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP). Any of these types of labels as described above may also be referred to as "diagnostic agents" as defined herein. Exemplary labels include, but are not limited to, FITC, 5-carboxyfluorescein (FAM) and biotin:

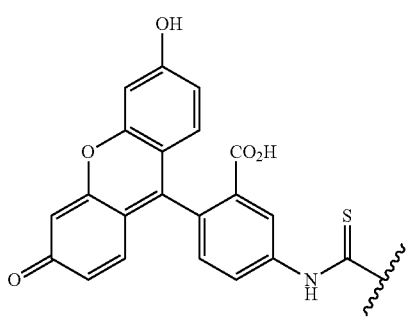

FITC

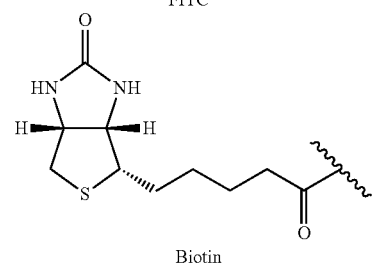

Biotin

In certain embodiments, the label is directly attached to the inventive polypeptide (i.e., through a bond). In certain embodiments, the label is indirectly attached to the inventive polypeptide (i.e., through a linker). In certain embodiments, the linker is a cyclic or acyclic, branched or unbranched, substituted or unsubstituted alkylene. In certain embodiments, the linker is a cyclic or acyclic, branched or unbranched, substituted or unsubstituted alkenylene. In certain embodiments, the linker is a cyclic or acyclic, branched or unbranched, substituted or unsubstituted alkynylene. In certain embodiments, the linker is a cyclic or acyclic, branched or unbranched, substituted or unsubstituted heteroalkylene. In certain embodiments, the linker is a cyclic or acyclic, branched or unbranched, substituted or unsubstituted heteroalkenylene. In certain embodiments, the linker is a cyclic or acyclic, branched or unbranched, substituted or unsubstituted heteroalkynylene. In certain embodiments, the linker is a substituted or unsubstituted arylene. In certain embodiments, the linker is a substituted or unsubstituted heteroarylene. In certain embodiments, the linker is a substituted or unsubstituted acylene. In certain embodiments, the linked is a P-alanine (P-ala) linker.

As used herein, a "diagnostic agent" refers to imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); and contrast agents.

In certain embodiments, such as in the identification of a biological target, the label comprises a radioactive isotope, preferably an isotope which emits detectable particles, such as β particles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid. In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

As used herein, a "solid support" includes, but is not limited to, solid insoluble surface to which the polypeptide is attached. Solid supports include, but are not limited to, glass slides, glass beads, resins, and the like.

As used herein, a "resin" refers to a material useful in solid phase synthesis, wherein the polypeptide is attached thereto. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis*, 2nd edition, Pierce Chemical Company, Rockford, 1984, the entire contents of each of which are hereby incorporated herein by reference. Exemplary resins which may be employed by the present invention include, but are not limited to, alkenyl resins, amine functionalized resins, benzhydrylamine (BHA) resins, Br-functionalized resins, Chloromethyl resins, CHO-functionalized resins, Cl-functionalized resins, $CO_2H$ functionalized resins, Hypo-Gel resins, I-functionalized resins, MBHA resins, OH-functionalized resins, oxime resins, PEG resins, Boc-Blz peptide synthesis resins, Fmoc-tBu peptide synthesis resins, thiol-functionalized resins, and Wang resins.

Exemplary alkenyl resins include, but are not limited to, REM resin, vinyl sulfone polymer-bound resin, and vinyl-polystyrene resin.

Exemplary amine functionalized resins include, but are not limited to, amidine resin, N-(4-benzyloxybenzyl)hydroxylamine polymer bound, (aminomethyl)polystyrene, polymer bound (R)-(+)-α-methylbenzylamine, 2-chlorotrityl Knorr resin, 2-N-Fmoc-amino-dibenzocyclohepta-1,4-diene, polymer-bound resin, 4-[4-(1-Fmoc-aminoethyl)-2-methoxy-5-nitrophenoxy]butyramidomethyl-polystyrene resin, 4-benzyloxybenzylamine, polymer-bound, 4-Carboxybenzenesulfonamide, polymer-bound, bis(tert-butoxycarbonyl)thiopseudourea, polymer-bound, dimethylaminomethyl-polystyrene, Fmoc-3-amino-3-(2-nitrophenyl) propionic acid, polymer-bound, N-methyl aminomethylated polystyrene, PAL resin, Sieber amide resin, tert-butyl N-(2-mercaptoethyl)carbamate, polymer-bound, and triphenylchloromethane-4-carboxamide polymer bound resin.

Exemplary benzhydrylamine (BHA) resins include, but are not limited to, 2-chlorobenzhydryl chloride, polymer-bound, HMPB-benzhydrylamine polymer bound, 4-m, polymer-bound, benzhydryl chloride, polymer-bound, and benzhydrylamine polymer-bound resin.

Exemplary PEG resins include but are not limited to ethylene glycol polymer bound resin.

The variable m indicates how many amino acids, defined by the variable $X_{AA}$, there are between amino acids containing the terminally unsaturated side chains in the polypeptides of Formulae (I)-(V). As depicted below for a polypeptide of Formula (I)-(V), variable m provides information as to the position of the amino acid containing a terminally unsaturated side chain on the C-terminal side of i, such as the positions i+3, i+4, i+5, i+6, and i+7. Table 6 correlates the specific positions of terminally unsaturated side chains present in Formulae (I).

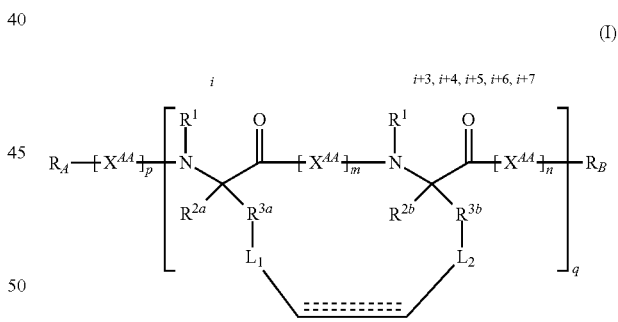

(I)

TABLE 6

| | i + 3 | i + 4 | i + 5 | i + 6 | i + 7 |
|---|---|---|---|---|---|
| m | 2 | 3 | 4 | 5 | 6 |

The variables m and s indicate how many amino acids, defined by the variable $X_{AA}$, there are between amino acids containing the terminally unsaturated side chains in the bis-polypeptides of Formulae (VI)-(IX). In certain embodiments, m is 2. In certain embodiments, m is 3. In certain embodiments, m is 4. In certain embodiments, m is 5. In certain embodiments, m is 6. For example, as depicted below for a polypeptide of Formula (VI), wherein variables $R_A$, $R_B$, $R^1$, $R^{2a}$, $R^{2b}$, $R^{3a}$, $R^{3b}$, $L_1$, $L_2$, p, m, s, t, n, and q are as defined above, i represents one site of an alpha, alpha-disubstituted (terminally unsaturated amino acid side chain) amino acid, variable m provides information as to the position of the amino acid containing a terminally unsaturated side chain on the N-terminal side of i, such as the positions i-3, i-4, i-5, i-6, and i-7, and s provides information as to the position of the amino acid containing a terminally unsaturated side chain on the C-terminal side of i, such as the positions i+3, i+4, i+5, i+6, and i+7. Table 3 correlates these specific locations of i relative to the variables m and s for Formulae (VI)-(IX).

amino acid, excluding the alpha carbons of each amino acid and the polypeptide chain of which they are a part.

In certain embodiments, wherein two amino acids in staple are related by (i, i+3) or (i, i-3), there comprise less than 10 consecutively bound atoms, inclusive, from alpha carbon to alpha carbon of the staple provided in the polypeptide of the Formula (I) or (VI).

In certain embodiments, wherein two amino acids in a staple are related by (i, i+4) or (i, i-4) there comprise between 8 and 15 consecutively bound atoms, inclusive, from alpha carbon to alpha carbon of the staple provided in the polypeptide of the Formula (I) or (VI)

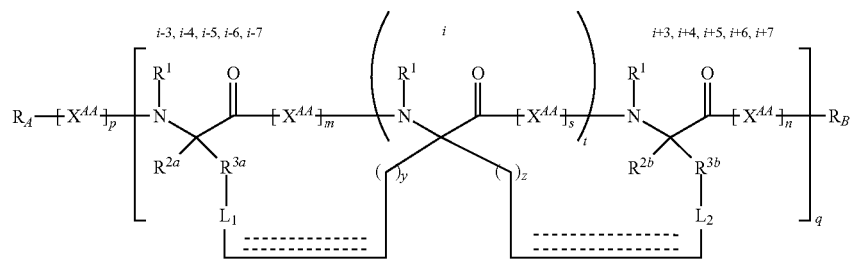

TABLE 7

| | i−7 | i−6 | i−5 | i−4 | i−3 | I | i+3 | i+4 | i+5 | i+6 | i+7 |
|---|---|---|---|---|---|---|---|---|---|---|---|
| m | 6 | 5 | 4 | 3 | 2 | | | | | | |
| s | | | | | | | 2 | 3 | 4 | 5 | 6 |

In certain embodiments, each instance of m is independently, an integer of between 2 and 6, inclusive. In certain embodiments, m is 2. In certain embodiments, m is 3. In certain embodiments, m is 4. In certain embodiments, m is 5. In certain embodiments, m is 6.

In certain embodiments, each instance of s is independently, an integer of between 2 and 6, inclusive. In certain embodiments, s is 2. In certain embodiments, s is 3. In certain embodiments, s is 4. In certain embodiments, s is 5. In certain embodiments, s is 6.

In certain embodiments, m is 2, and s is 2. In certain embodiments, m is 2, and s is 3. In certain embodiments, m is 2, and s is 4. In certain embodiments, m is 2, and s is 5. In certain embodiments, m is 2, and s is 6.

In certain embodiments, m is 3, and s is 2. In certain embodiments, m is 3 and s is 3. In certain embodiments, m is 3 and s is 4. In certain embodiments, m is 3 and s is 5. In certain embodiments, m is 3 and s is 6.

In certain embodiments, m is 4 and s is 2. In certain embodiments, m is 4 and s is 3. In certain embodiments, m is 4 and s is 4. In certain embodiments, m is 4 and s is 5. In certain embodiments, m is 4 and s is 6.

In certain embodiments, m is 5 and s is 2. In certain embodiments, m is 5 and s is 3. In certain embodiments, m is 5, and s is 4. In certain embodiments, m is 5 and s is 5. In certain embodiments, m is 5 and s is 6.

In certain embodiments, m is 6, and s is 2. In certain embodiments, m is 6, and s is 3. In certain embodiments, m is 6 and s is 4. In certain embodiments, m is 6, and s is 5. In certain embodiments, m is 6, and s is 6.

As used herein, a "staple" encompasses the entire cross-link attaching one alpha-amino acid to the second alpha- In certain embodiments, wherein two amino acids in a staple are related by (i, i+7) or (i, i-7), there comprise between 11 and 20 consecutively bound atoms, inclusive, from alpha carbon to alpha carbon of the staple provided in the polypeptide of the Formula (I) or (VI).

As generally defined above, each instance of p and n is, independently, 0 or an integer between 1 and 100, inclusive.

In certain embodiments, p is 0 or an integer between 1 and 100, inclusive. In certain embodiments, p is 0. In certain embodiments, p is an integer between 1 and 100, inclusive. In certain embodiments, p is an integer between 75 and 100, inclusive. In certain embodiments, p is an integer between 50 and 100, inclusive. In certain embodiments, p is an integer between 25 and 100, inclusive. In certain embodiments, p is an integer between 15 and 100, inclusive. In certain embodiments, p is an integer between 10 and 100, inclusive. In certain embodiments, p is an integer between 5 and 100, inclusive. In certain embodiments, p is an integer between 10 and 75, inclusive. In certain embodiments, p is an integer between 25 and 50, inclusive. In certain embodiments, p is an integer between 1 and 10, inclusive. In certain embodiments, p is an integer between 3 and 6, inclusive.

In certain embodiments, n is 0 or an integer between 1 and 100, inclusive. In certain embodiments, n is 0. In certain embodiments, n is an integer between 1 and 100, inclusive. In certain embodiments, n is an integer between 75 and 100, inclusive. In certain embodiments, n is an integer between 50 and 100, inclusive. In certain embodiments, n is an integer between 25 and 100, inclusive. In certain embodiments, n is an integer between 15 and 100, inclusive. In certain embodiments, n is an integer between 10 and 100, inclusive. In certain embodiments, n is an integer between 5 and 100, inclusive. In certain embodiments, n is an integer between 10 and 75, inclusive. In certain embodiments, n is an integer between 25 and 50, inclusive. In certain embodiments, n is an integer between 1 and 10, inclusive. In certain embodiments, n is an integer between 1 and 5, inclusive.

As generally defined above, q is an integer between 1 and 10, inclusive. In certain embodiments, q is an integer between 1 and 9, inclusive. In certain embodiments, q is an integer between 1 and 8, inclusive. In certain embodiments, q is an integer between 1 and 7, inclusive. In certain embodiments, q is an integer between 1 and 6, inclusive. In certain embodiments, q is an integer between 1 and 5, inclusive. In certain embodiments, q is an integer between 1 and 4, inclusive. In certain embodiments, q is an integer between 1 and 3, inclusive. In certain embodiments, q is an integer between 1 and 2, inclusive. In certain embodiments, q is 10. In certain embodiments, q is 9. In certain embodiments, q is 8. In certain embodiments, q is 7. In certain embodiments, q is 6. In certain embodiments, q is 5. In certain embodiments, q is 4. In certain embodiments, q is 3. In certain embodiments, q is 2. In certain embodiments, q is 1.

In certain embodiments, m is 6, p is 3 or 6, n is 0 or 2, and q is 1. In certain embodiments, m is 6, p is 6, n is 2, and q is 1. In certain embodiments, m is 6, p is 3, n is 0, and q is 1. In certain embodiments, the polypeptide has a staple with one tertiary amine. In certain embodiments, the polypeptide has a staple with two tertiary amines. In certain embodiments, the polypeptide has a staple with one carbamate. In certain embodiments, the polypeptide has a staple with two carbamates. In certain embodiments, the polypeptides comprises both staples with the E and Z configurations. In certain embodiments, the staple has a double bond with an E configuration. In certain embodiments, the staple has a double bond with a Z configuration.

As generally defined above, y is an integer between 1 and 10. In certain embodiments, y is 10. In certain embodiments, y is 9. In certain embodiments, y is 8. In certain embodiments, y is 7. In certain embodiments, y is 6. In certain embodiments, y is 5. In certain embodiments, y is 4. In certain embodiments, y is 3. In certain embodiments, y is 2. In certain embodiments, y is 1.

As generally defined above, z is an integer between 1 and 10. In certain embodiments, z is 10. In certain embodiments, z is 9. In certain embodiments, z is 8. In certain embodiments, z is 7. In certain embodiments, z is 6. In certain embodiments, z is 5. In certain embodiments, z is 4. In certain embodiments, z is 3. In certain embodiments, z is 2. In certain embodiments, z is 1.

In certain embodiments, y is 1 and z is 1. In certain embodiments, y is 1 and z is 2. In certain embodiments, y is 1 and z is 3. In certain embodiments, y is 1 and z is 4. In certain embodiments, y is 1 and z is 5. In certain embodiments, y is 1 and z is 6. In certain embodiments, y is 2 and z is 1. In certain embodiments, y is 2 and z is 2. In certain embodiments, y is 2 and z is 3. In certain embodiments, y is 2 and z is 4. In certain embodiments, y is 2 and z is 5. In certain embodiments, y is 2 and z is 6. In certain embodiments, y is 3 and z is 6. In certain embodiments, y is 3 and z is 1. In certain embodiments, y is 3 and z is 2. In certain embodiments, y is 3 and z is 3. In certain embodiments, y is 3 and z is 4. In certain embodiments, y is 3 and z is 5. In certain embodiments, y is 3 and z is 6. In certain embodiments, y is 4 and z is 6. In certain embodiments, y is 4 and z is 1. In certain embodiments, y is 4 and z is 2. In certain embodiments, y is 4 and z is 3. In certain embodiments, y is 4 and z is 4. In certain embodiments, y is 4 and z is 5. In certain embodiments, y is 4 and z is 6. In certain embodiments, y is 5 and z is 6. In certain embodiments, y is 5 and z is 1. In certain embodiments, y is 5 and z is 2. In certain embodiments, y is 5 and z is 3. In certain embodiments, y is 5 and z is 4. In certain embodiments, y is 5 and z is 5. In certain embodiments, y is 5 and z is 6. In certain embodiments, y is 6 and z is 6. In certain embodiments, y is 6 and z is 1. In certain embodiments, y is 6 and z is 2. In certain embodiments, y is 6 and z is 3. In certain embodiments, y is 6 and z is 4. In certain embodiments, y is 6 and z is 5. In certain embodiments, y is 6 and z is 6.

Exemplary secondary structural motifs of polypeptides and proteins include, but are not limited to, an alpha-helix, alpha-L, $3_{10}$ helix, $\pi$ helix, and type II helices (e.g., left-handed helices). In certain embodiments, the predominant secondary structural motif of the inventive polypeptide is an alpha-helix.

In certain embodiments, the polypeptide of the above Formulae (I)-(X), or subset thereof, is an alpha-helical polypeptide. In certain embodiments, the polypeptide of the above Formulae (I)-(X), or subset thereof, is a substantially alpha-helical polypeptide. As used herein, the phrase "substantially alpha-helical" refers to a polypeptide comprising: (I) backbone ($\varphi$, $\psi$) dihedral angles, on average, in a range from about (−90°, −15°) to about (−35°, −70°); and/or (ii) dihedral angles such that the $\psi$ dihedral angle of one residue and the $\varphi$ dihedral angle of the next residue sums, on average, about −80° to about −125°; and/or (iii) having at least 50%, 60%, 70%, 80%, 90%, or 95% of the amino acids provided in the polypeptide chain adopting an alpha-helical conformation.

In certain embodiments, the inventive polypeptide adopts dihedral angles such that the $\psi$ dihedral angle of one residue and the $\varphi$ dihedral angle of the next residue sums, on average, about −100° to about −110°. In certain embodiments, the inventive polypeptide adopts dihedral angles such that the $\omega$ dihedral angle of one residue and the $\varphi$ dihedral angle of the next residue sums, on average, about −105°. Confirmation of a polypeptide's alpha-helical secondary structure may be ascertained by well-known analytical techniques, such as x-ray crystallography, electron crystallography, fiber diffraction, fluorescence anisotropy, circular dichrosim (CD), and nuclear magnetic resonance spectroscopy.

In certain embodiments, the inventive polypeptide is homologous to a known alpha helical peptide. In certain embodiments, the inventive polypeptide is at least 80%, 85%, 90%, or 95% homologous to a known alpha helical peptide.

In certain embodiments, the present invention also provides intermediates and starting materials used in the synthesis of the inventive polypeptides. For example, the present invention provides amino acids of Formula (D):

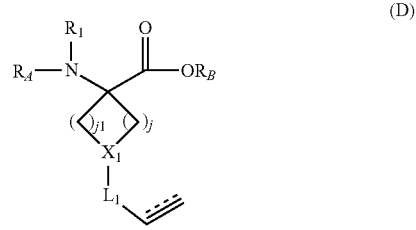

wherein $R_A$, $R_B$, $R_1$, $L_1$, $X_1$, $j_1$, and j are defined herein.

In certain embodiments, the present invention also provides intermediates used in the synthesis of inventive polypeptides. For example, the present invention provides amino acids of any one of the following structures:
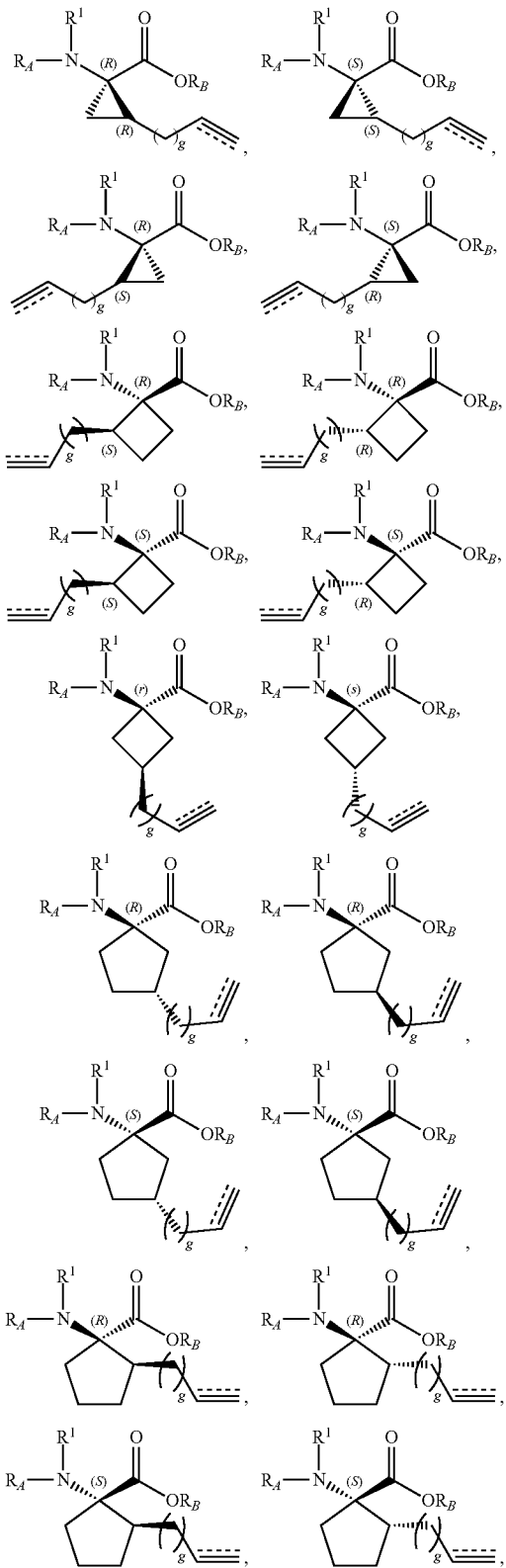
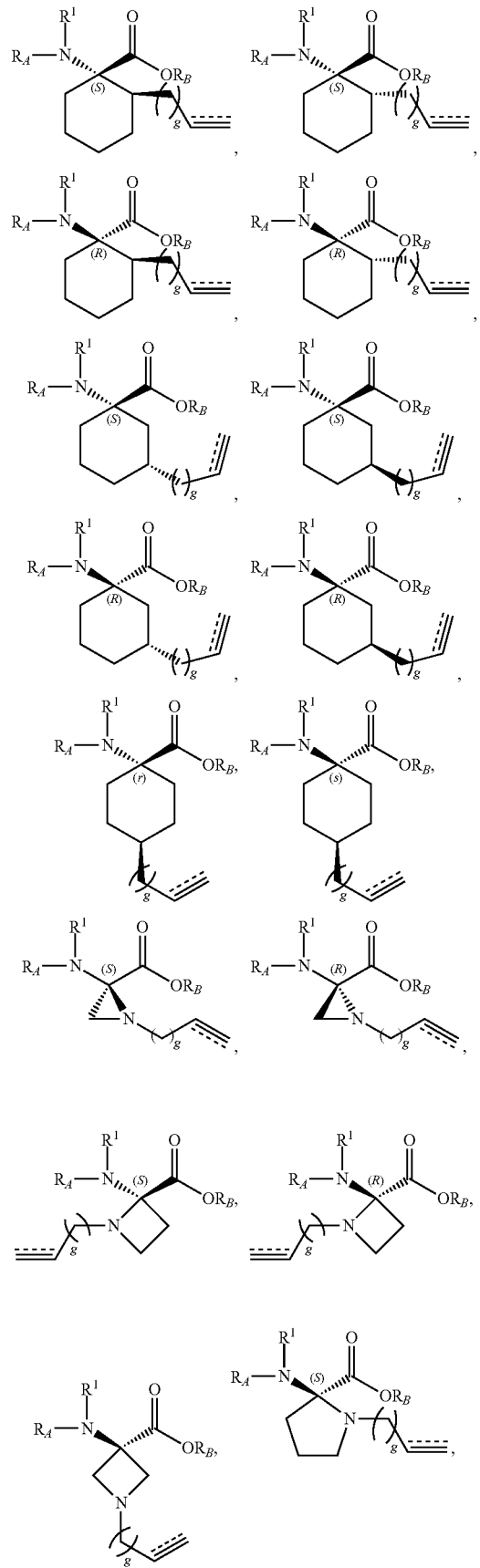

-continued
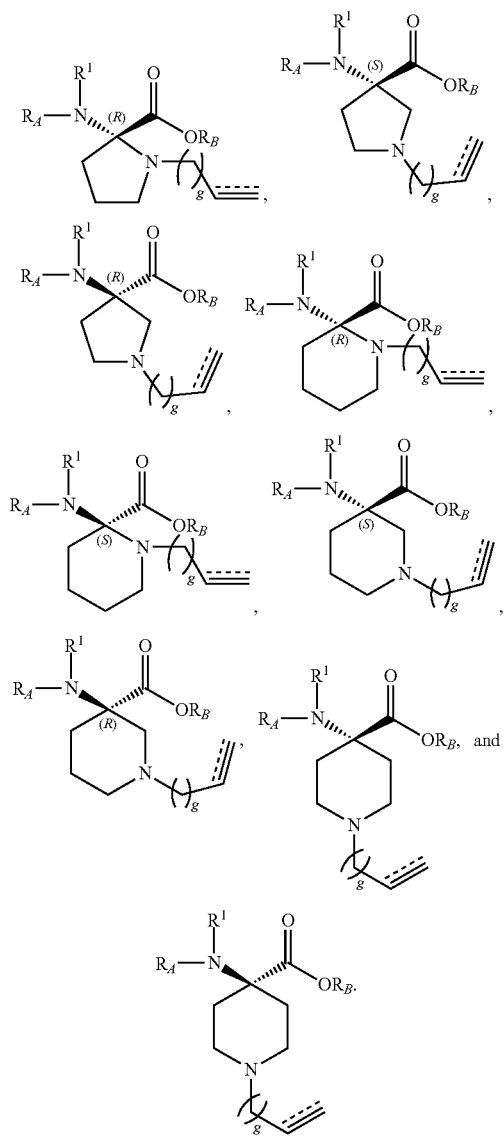
and salts thereof, wherein g is 0 or an integer of between 1 and 10, inclusive.
In certain embodiments, amino acids provided herein are selected from any one of the following structures:
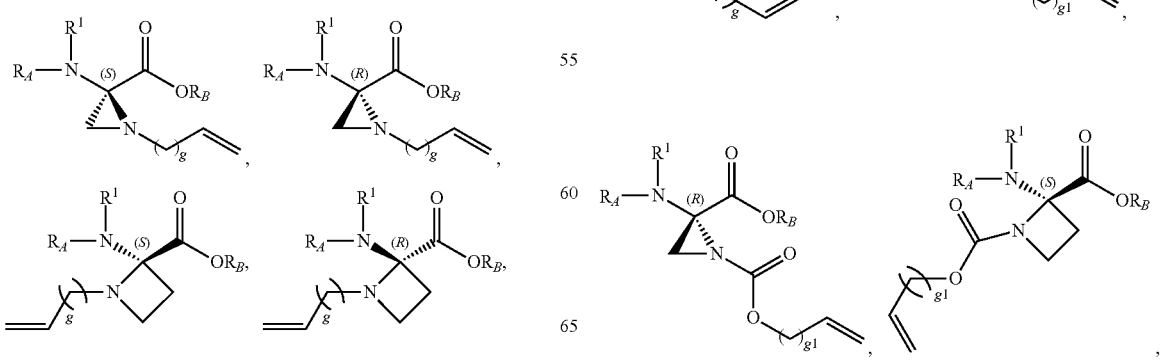

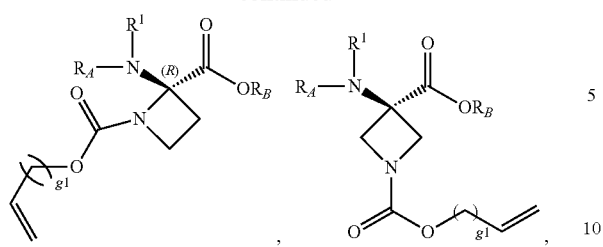

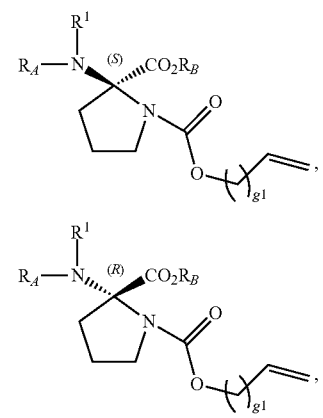

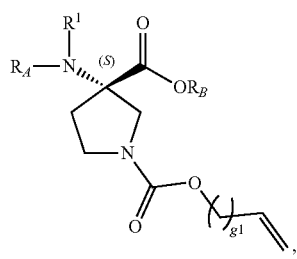

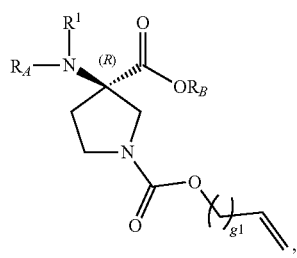

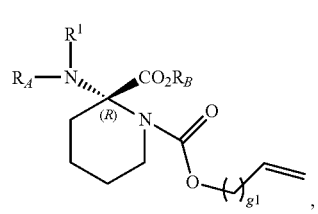

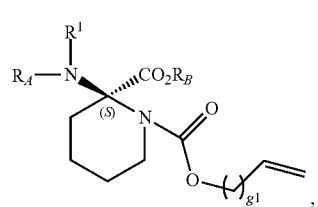

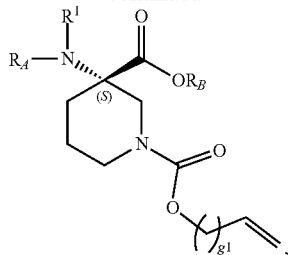

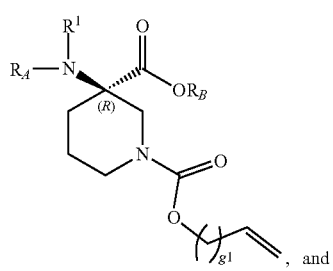

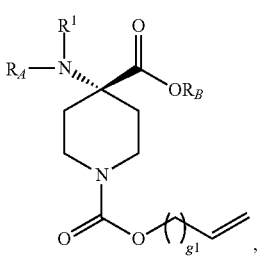

and salts thereof, wherein g is 0 or an integer of between 1 and 10, inclusive.

In certain embodiments, g is 0. In certain embodiments, g is 1. In certain embodiments, g is 2. In certain embodiments, g is 3. In certain embodiments, g is 4. In certain embodiments, g is 5. In certain embodiments, g is 6. In certain embodiments, g is 7. In certain embodiments, g is 8. In certain embodiments, g is 9. In certain embodiments, g is 10.

In certain embodiments, provided is a polypeptide of Formula (I):

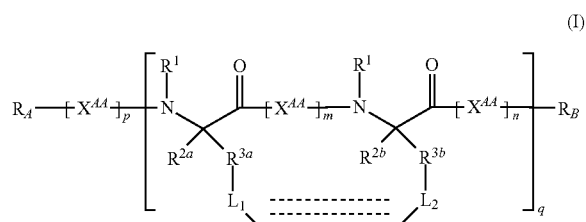

or a pharmaceutically acceptable salt thereof.

In certain embodiments, provided is a polypeptide of Formula (II):

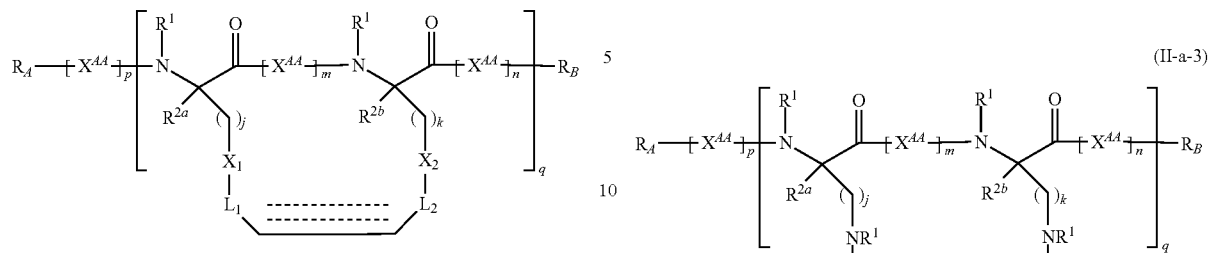

or a pharmaceutically acceptable salt thereof.

In certain embodiments, provided is a polypeptide of Formula (II-a):

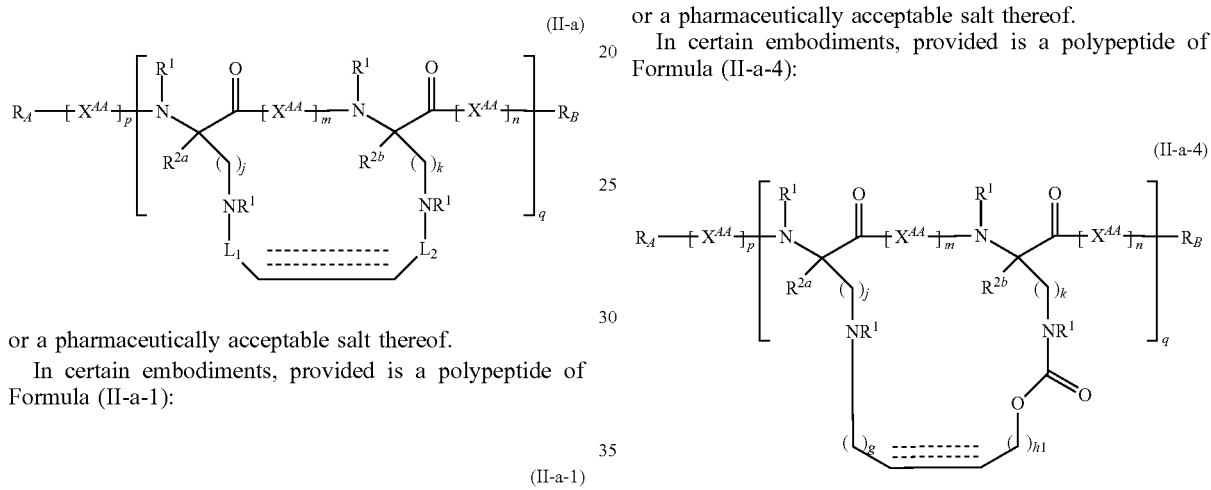

or a pharmaceutically acceptable salt thereof.

In certain embodiments, provided is a polypeptide of Formula (II-a-2):

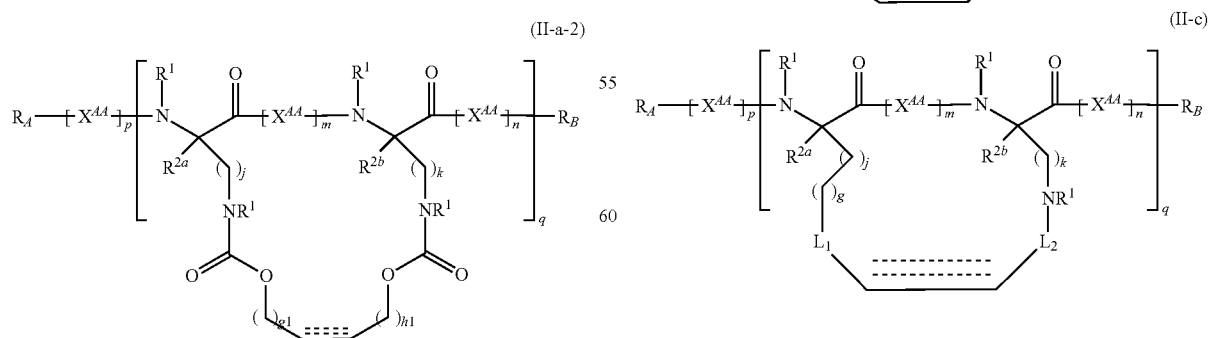

or a pharmaceutically acceptable salt thereof.

In certain embodiments, provided is a polypeptide of Formula (II-a-3):

or a pharmaceutically acceptable salt thereof.

In certain embodiments, provided is a polypeptide of Formula (II-a-4):

or a pharmaceutically acceptable salt thereof.

In certain embodiments, provided is a polypeptide of Formula (II-b) or (II-c):

or a pharmaceutically acceptable salt thereof.

In certain embodiments, provided is a polypeptide of Formula (II-b-1):

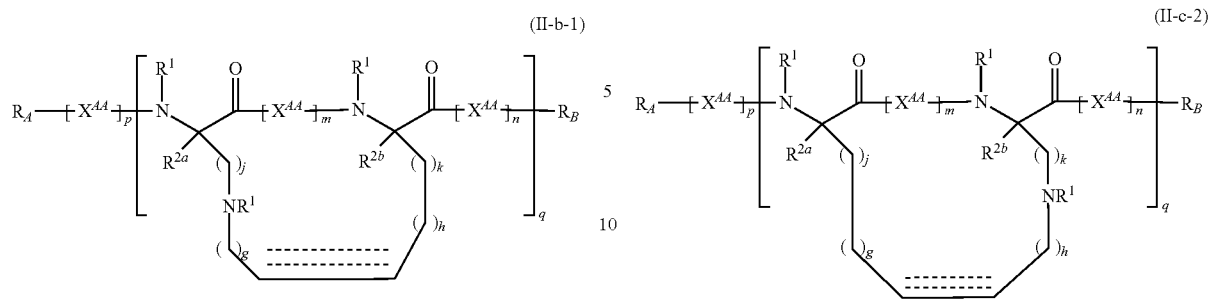

(II-b-1)

or a pharmaceutically acceptable salt thereof.

In certain embodiments, provided is a polypeptide of Formula (II-b-2):

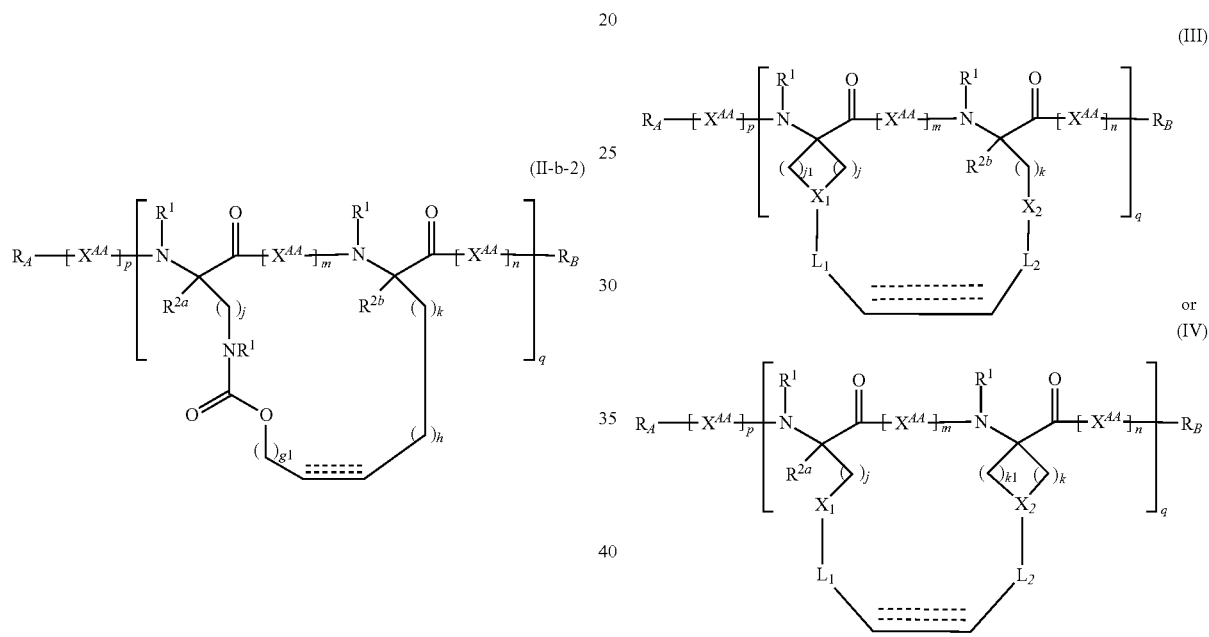

(II-b-2)

or a pharmaceutically acceptable salt thereof.

In certain embodiments, provided is a polypeptide of Formula (II-c-1):

(II-c-1)

or a pharmaceutically acceptable salt thereof.

The polypeptide of claim 8, wherein the polypeptide is of Formula (II-c-2):

(II-c-2)

or a pharmaceutically acceptable salt thereof.

In certain embodiments, provided is a polypeptide of Formula (III) or Formula (IV):

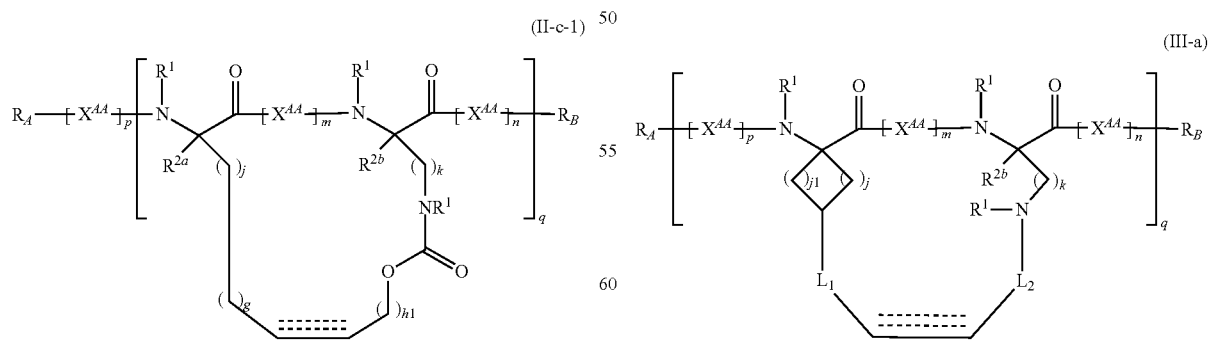

(III)

or (IV)

or a pharmaceutically acceptable salt thereof.

In certain embodiments, provided is a polypeptide of Formula (III-a):

(III-a)

or a pharmaceutically acceptable salt thereof.

In certain embodiments, provided is a polypeptide of Formula (III-a-1):

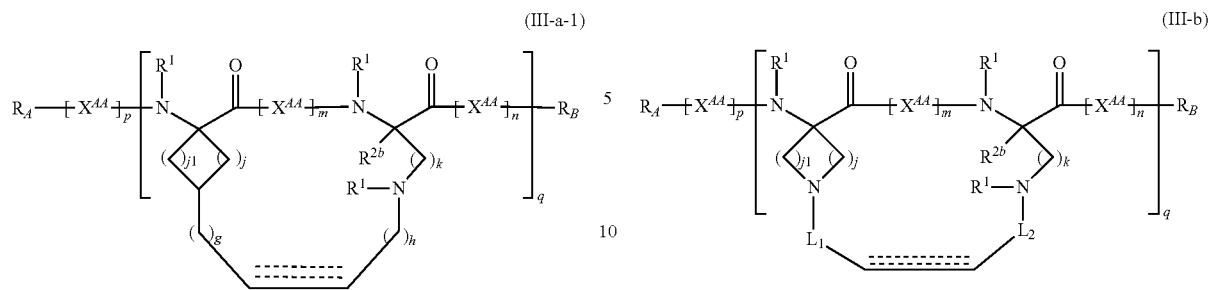

or a pharmaceutically acceptable salt thereof.

In certain embodiments, provided is a polypeptide of Formula (III-a-2):

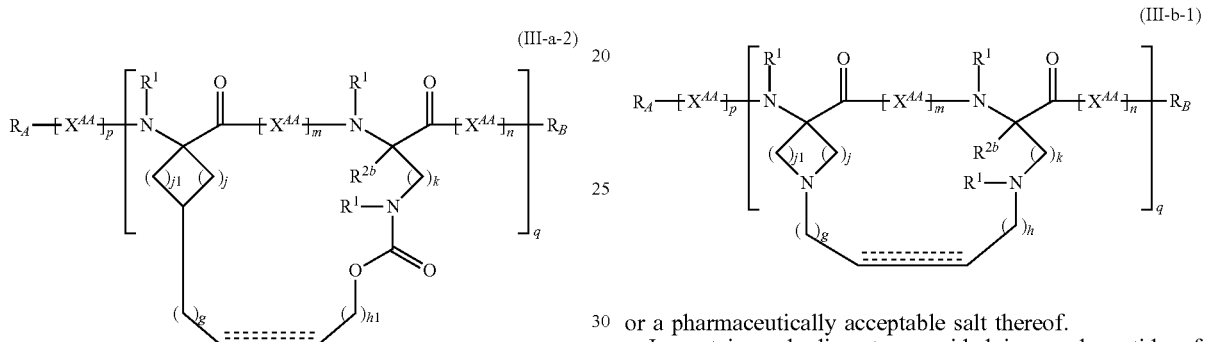

or a pharmaceutically acceptable salt thereof

In certain embodiments, provided is a polypeptide of Formula (III-a-3):

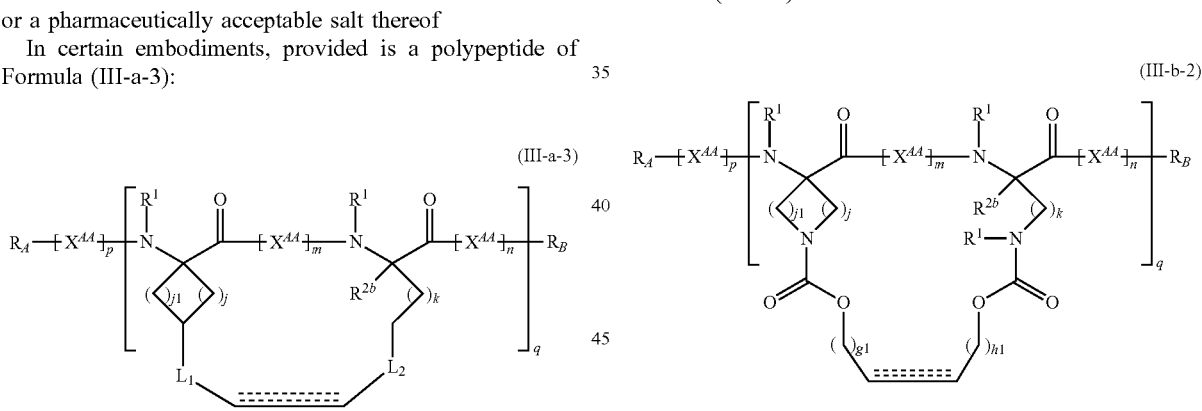

or a pharmaceutically acceptable salt thereof.

In certain embodiments, provided is a polypeptide of Formula (III-a-4):

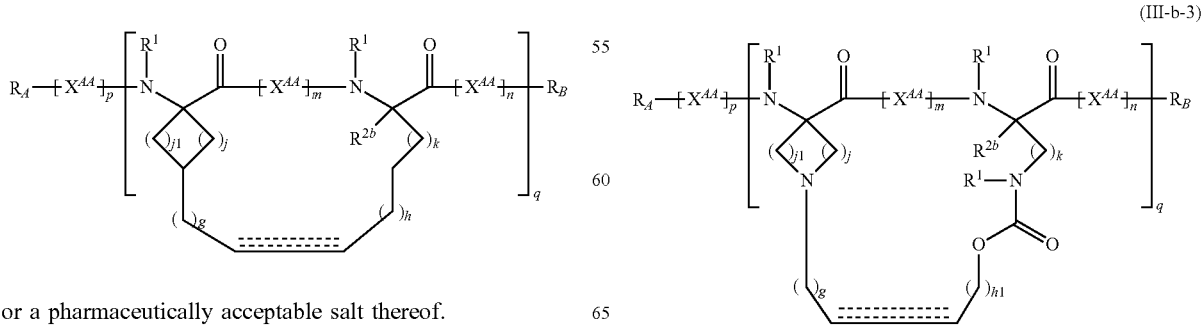

or a pharmaceutically acceptable salt thereof.

In certain embodiments, provided is a polypeptide of Formula (III-b):

or a pharmaceutically acceptable salt thereof.

In certain embodiments, provided is a polypeptide of Formula (III-b-1):

or a pharmaceutically acceptable salt thereof.

In certain embodiments, provided is a polypeptide of Formula (III-b-2):

or a pharmaceutically acceptable salt thereof.

In certain embodiments, provided is a polypeptide of Formula (III-b-3):

or a pharmaceutically acceptable salt thereof.

In certain embodiments, provided is a polypeptide of Formula (III-b-4):

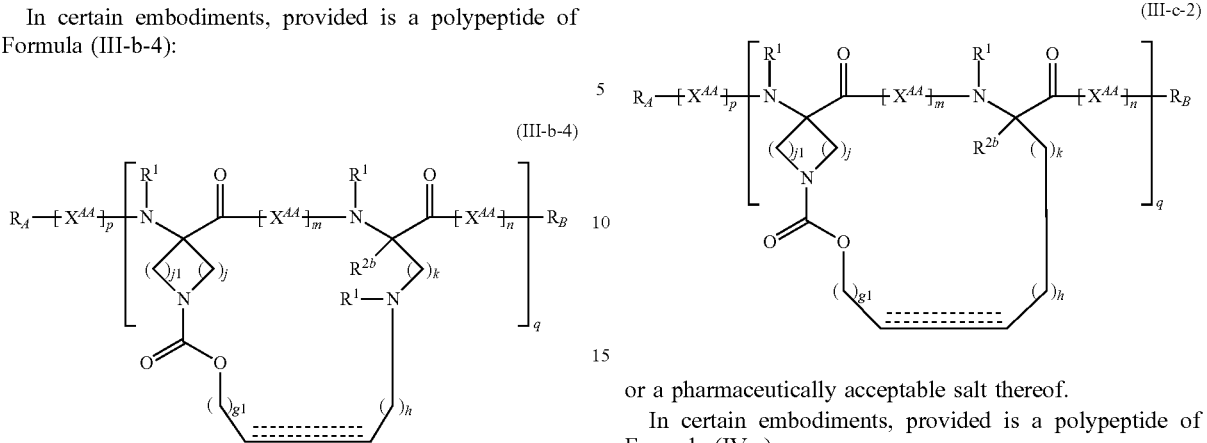

(III-b-4)

or a pharmaceutically acceptable salt thereof.

In certain embodiments, provided is a polypeptide of Formula (III-c):

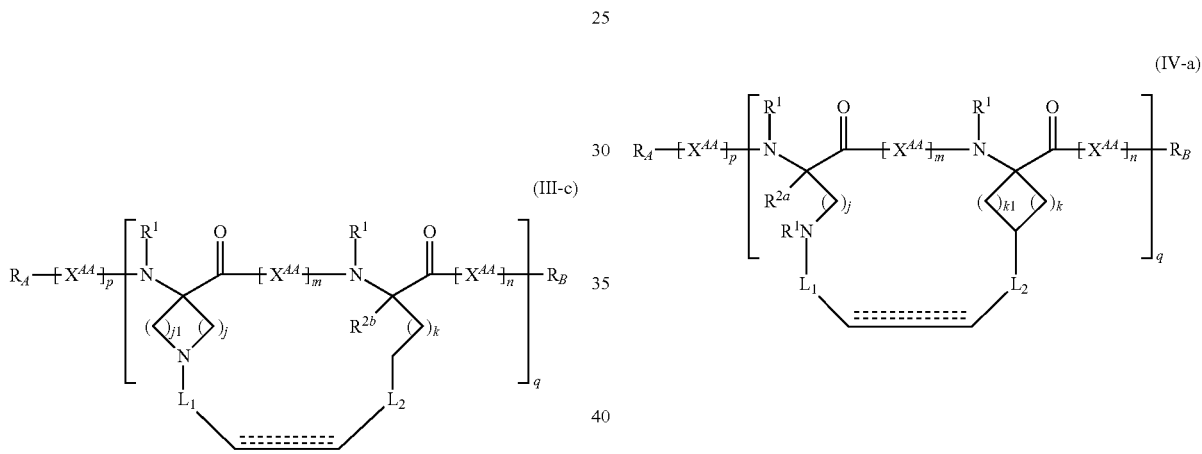

(III-c)

or a pharmaceutically acceptable salt thereof.

In certain embodiments, provided is a polypeptide of Formula (III-c-1):

(III-c-1)

or a pharmaceutically acceptable salt thereof.

In certain embodiments, provided is a polypeptide of Formula (III-c-2):

(III-c-2)

or a pharmaceutically acceptable salt thereof.

In certain embodiments, provided is a polypeptide of Formula (IV-a):

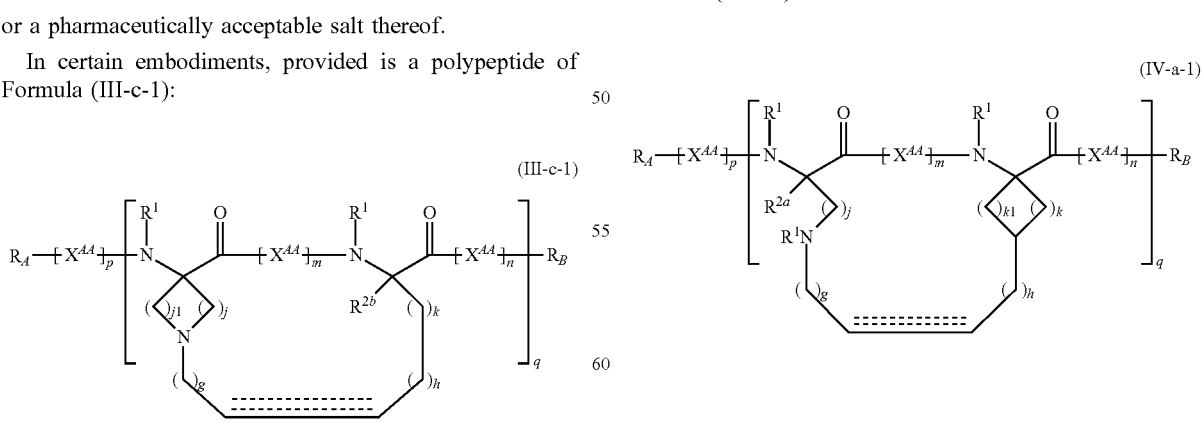

(IV-a)

or a pharmaceutically acceptable salt thereof.

In certain embodiments, provided is a polypeptide of Formula (IV-a-1):

(IV-a-1)

or a pharmaceutically acceptable salt thereof.

In certain embodiments, provided is a polypeptide of Formula (IV-a-2):

(IV-a-2)

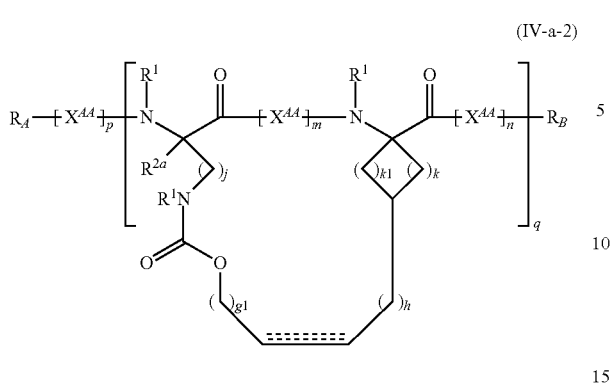

or a pharmaceutically acceptable salt thereof.

In certain embodiments, provided is a polypeptide of Formula (IV-a-3):

(IV-a-3)

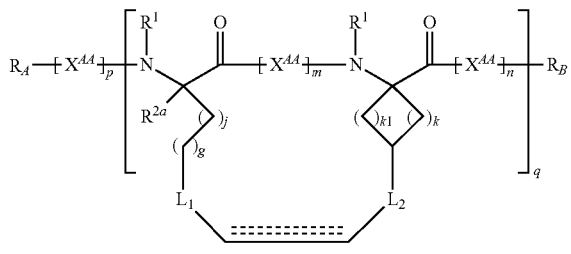

or a pharmaceutically acceptable salt thereof.

In certain embodiments, provided is a polypeptide of Formula (IV-a-4):

(IV-a-4)

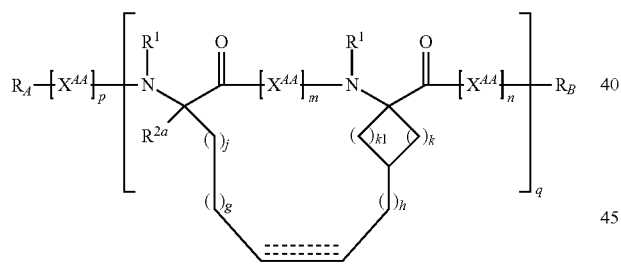

or a pharmaceutically acceptable salt thereof.

In certain embodiments, provided is a polypeptide of Formula (IV-b):

(IV-b)

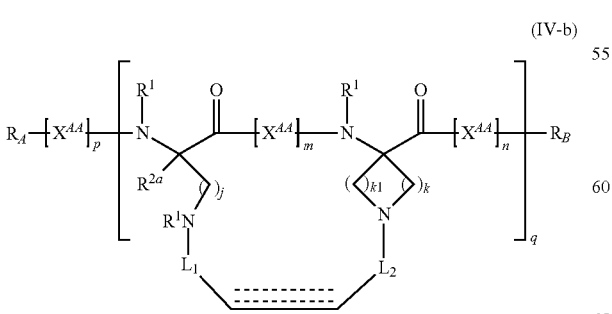

or a pharmaceutically acceptable salt thereof.

In certain embodiments, provided is a polypeptide of Formula (IV-b-1):

(IV-b-1)

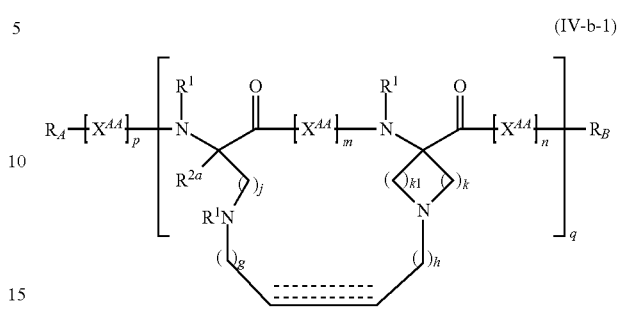

or a pharmaceutically acceptable salt thereof.

In certain embodiments, provided is a polypeptide of Formula (IV-b-2):

(IV-b-2)

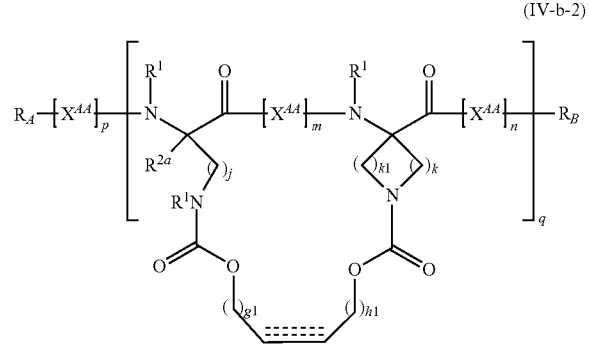

or a pharmaceutically acceptable salt thereof.

In certain embodiments, provided is a polypeptide of Formula (IV-b-3):

(IV-b-3)

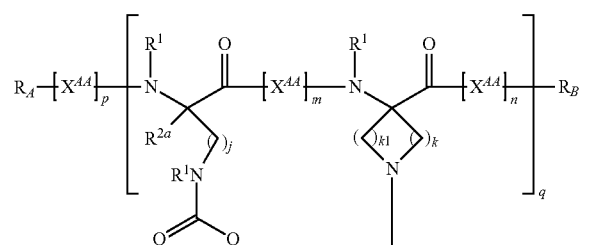

or a pharmaceutically acceptable salt thereof.

In certain embodiments, provided is a polypeptide of Formula (IV-b-4):

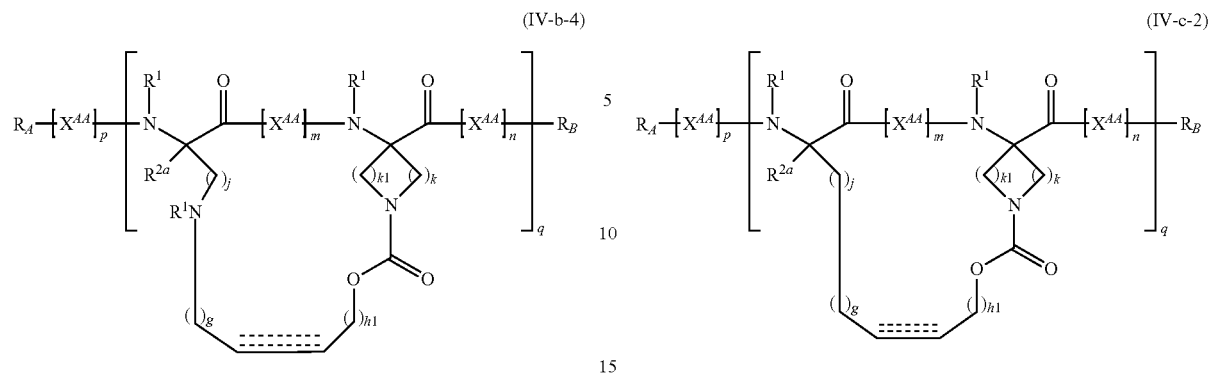

(IV-b-4)

(IV-c-2)

or a pharmaceutically acceptable salt thereof.

In certain embodiments, provided is a polypeptide of Formula (IV-c):

or a pharmaceutically acceptable salt thereof.

In certain embodiments, provided is a polypeptide of Formula (V):

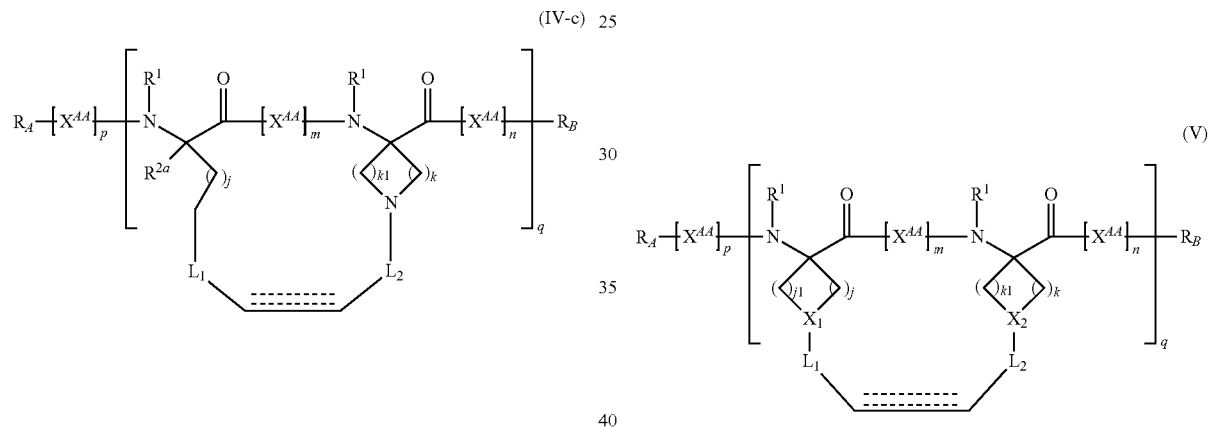

(IV-c)

(V)

or a pharmaceutically acceptable salt thereof.

In certain embodiments, provided is a polypeptide of Formula (IV-c-1):

or a pharmaceutically acceptable salt thereof.

In certain embodiments, provided is a polypeptide of Formula (V-a):

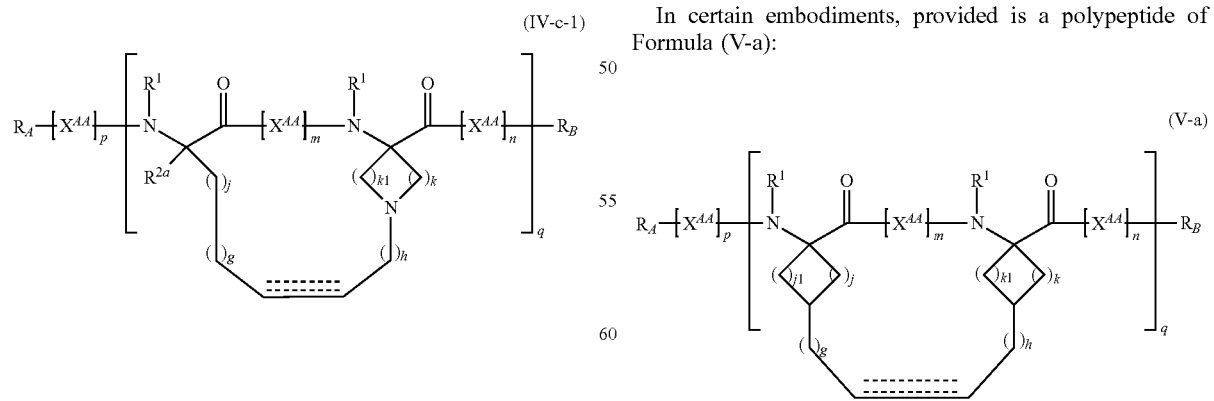

(IV-c-1)

(V-a)

or a pharmaceutically acceptable salt thereof.

In certain embodiments, provided is a polypeptide of Formula (IV-c-2):

or a pharmaceutically acceptable salt thereof.

In certain embodiments, provided is a polypeptide of Formula (V-b):

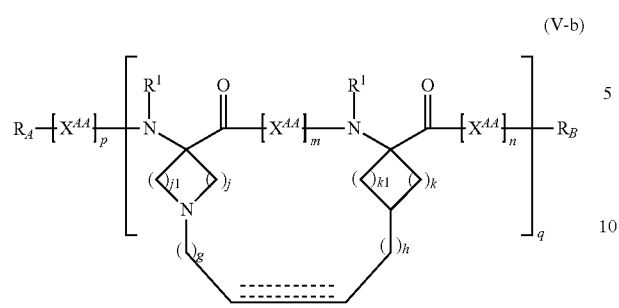

(V-b)

or a pharmaceutically acceptable salt thereof.

In certain embodiments, provided is a polypeptide of Formula (V-b-1):

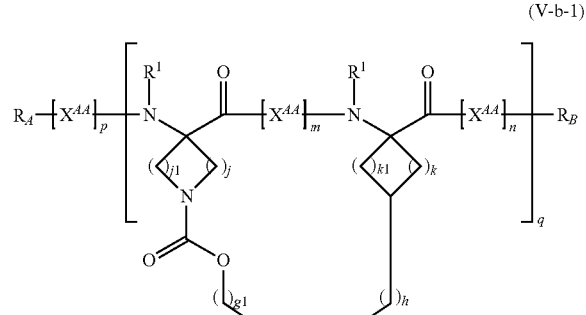

(V-b-1)

or a pharmaceutically acceptable salt thereof.

In certain embodiments, provided is a polypeptide of Formula (V-c):

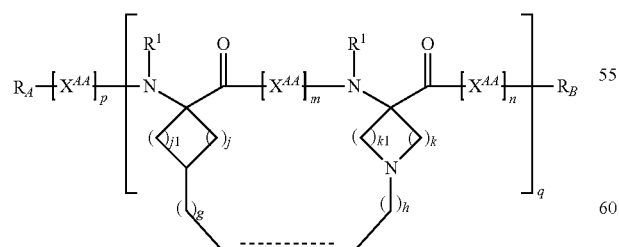

(V-c)

or a pharmaceutically acceptable salt thereof.

In certain embodiments, provided is a polypeptide of Formula (V-c-1):

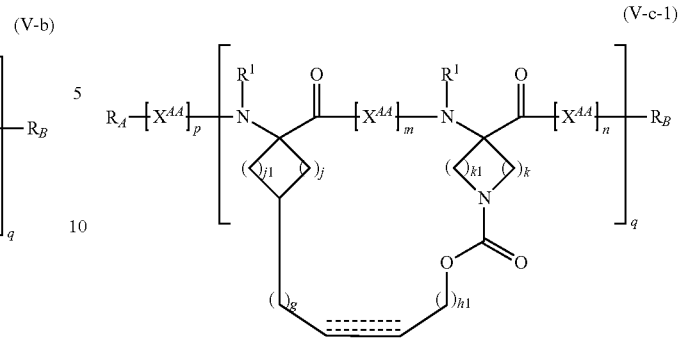

(V-c-1)

or a pharmaceutically acceptable salt thereof.

In certain embodiments, provided is a polypeptide of Formula (V-d)

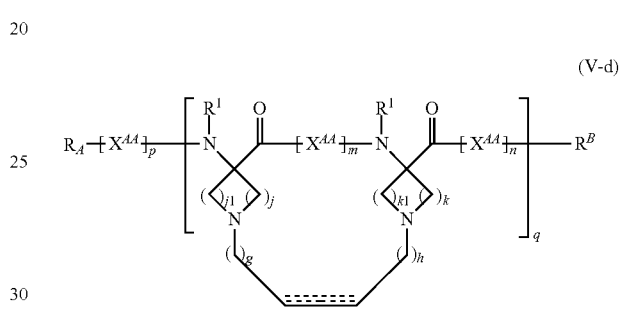

(V-d)

or a pharmaceutically acceptable salt thereof.

In certain embodiments, provided is a polypeptide of Formula (V-d-1):

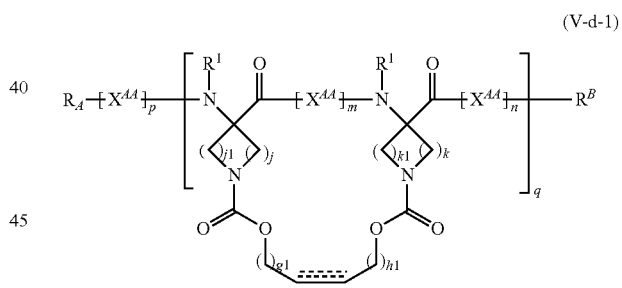

(V-d-1)

or a pharmaceutically acceptable salt thereof.

In certain embodiments, provided is a polypeptide of Formula (V-d-2):

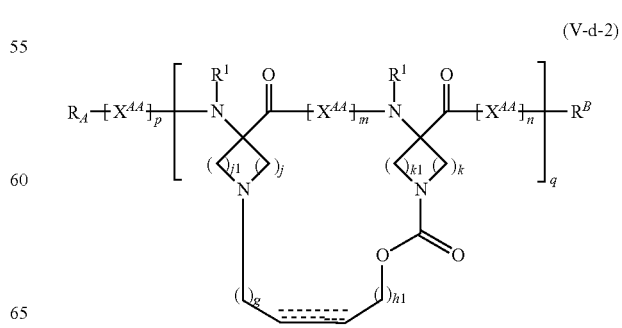

(V-d-2)

or a pharmaceutically acceptable salt thereof.

In certain embodiments, provided is a polypeptide of Formula (V-d-3):

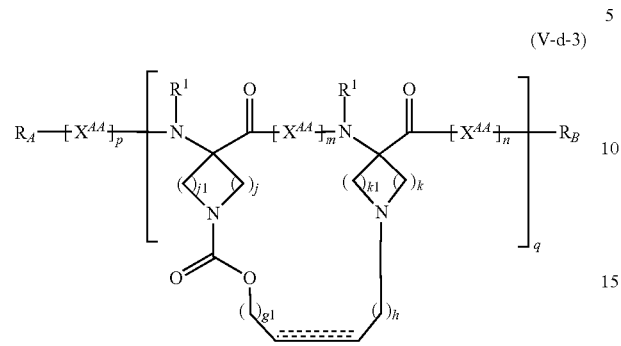

(V-d-3)

or a pharmaceutically acceptable salt thereof.

In certain embodiments, provided is a polypeptide of the Formula (VI):

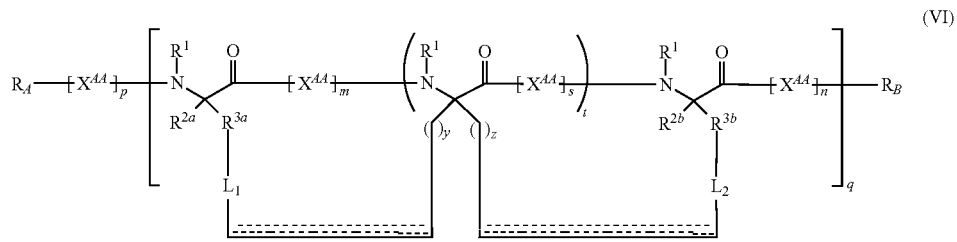

(VI)

In certain embodiments, provided is a polypeptide of Formula (VII):

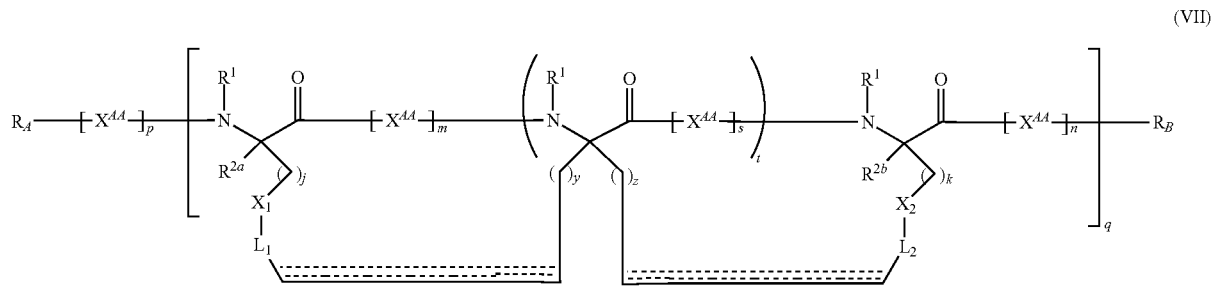

(VII)

or a pharmaceutically acceptable salt thereof.

In certain embodiments, provided is a polypeptide of Formula (VIII):

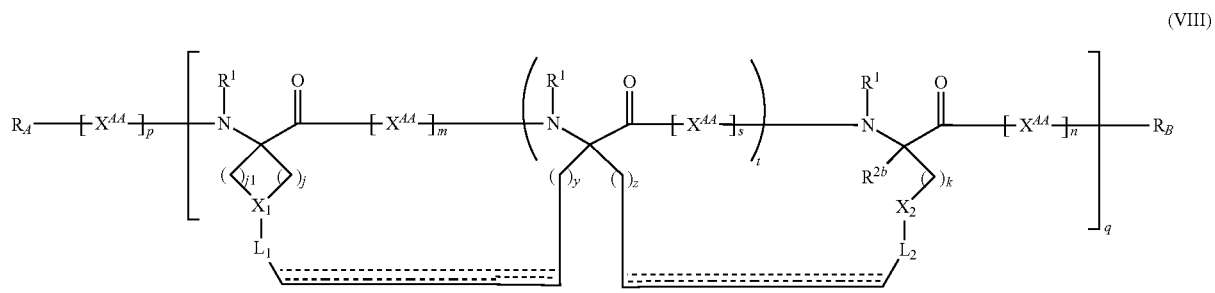

(VIII)

or a pharmaceutically acceptable salt thereof.

In certain embodiments, provided is a polypeptide of Formula (IX):

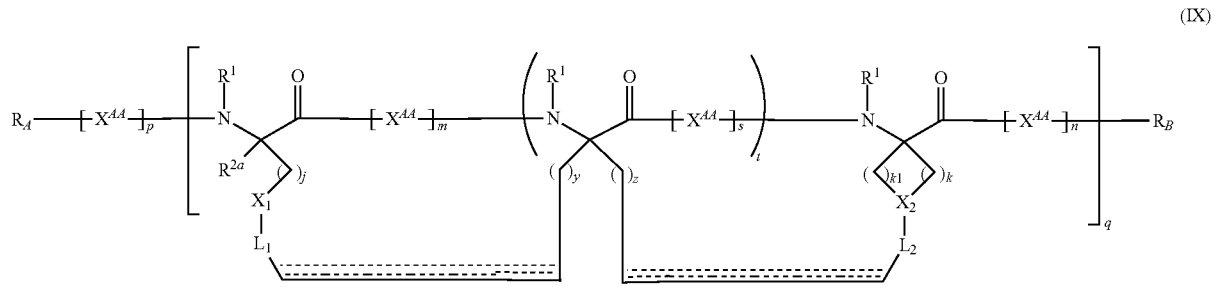

(IX)

or a pharmaceutically acceptable salt thereof.

In certain embodiments, provided is a polypeptide of Formula (X):

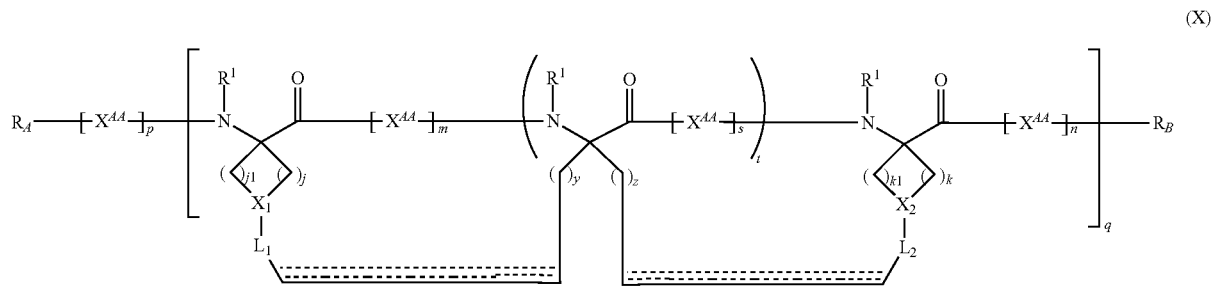

(X)

or a pharmaceutically acceptable salt thereof.

In certain embodiments, the staple is prepared using two amino acids each comprising a carbamate moiety. In certain embodiments, the staple is prepared using an amino acid selected from one without a carbamate moiety and another amino acid is selected from one with a carbamate moiety. In certain embodiments, the staple is prepared using two amino acids selected from $Pyr_R$, $Pyr_S$, Az, $S_GN$, $S_DN$, $S_EN$, $R_GN$, $R_DN$, $R_EN$, $S_5$, $S_8$, $R_5$, and $R_8$. In certain embodiments, the amino acid used is an analog of one of the exemplary amino acids shown in FIG. 10. For example, analogs of $S_5$, $S_8$, $R_5$, or $R_8$ containing additional methylene units (e.g., $S_{10}$ or $R_{10}$) can be used. In certain embodiments, the staple is prepared using an amino acid selected from either $R_5$, $R_8$, $S_5$, $S_8$ or an analog thereof and another amino acid selected from either $Pyr_R$, $Pyr_S$, Az, $S_GN$, $S_DN$, $S_EN$, $R_GN$, $R_DN$, or $R_EN$. In certain embodiments, the staple is prepared using an amino acid selected from either $R_8$ or $S_8$ and another amino acid selected from either $Pyr_R$, $Pyr_S$, Az, $S_GN$, $S_DN$, $S_EN$, $R_GN$, $R_DN$, or $R_EN$. In certain embodiments, the staple is prepared from $Pyr_R$ and $S_8$. In certain embodiments, the staple is using $R_8$ and $Pyr_S$. In certain embodiments, the staple is prepared using Az and $S_8$. In certain embodiments, the staple is prepared using $R_8$ and Az. In certain embodiments, the staple is prepared using $R_8$ and $S_GN$. In certain embodiments, the staple is prepared using $R_8$ and $S_DN$. In certain embodiments, the staple is prepared using $R_8$ and $S_EN$. In certain embodiments, the staple is prepared using $S_{10}$ and $S_EN$. In certain embodiments, the staple is prepared using $R_DN$ and $S_8$. In certain embodiments, the staple is prepared using $R_DN$ and $S_EN$. In certain embodiments, the staple is an Alloc-staple comprising one or two carbamate moieties. In certain embodiments, the staple is an Alloc-staple comprising two carbamate moieties. In certain embodiments, the staple is an Alloc-staple with one carbamate moiety. In certain embodiments, the staple is an amino-staple comprising one or two amino moieties. In certain embodiments, the staple is an amino-staple comprising two amino moieties. In certain embodiments, the staple is an amino-staple with one amino moiety. In certain embodiments, the cross-linking amino acids are located at positions i and i+7. In certain embodiments, the stapled peptide is prepared from a peptide segment of p53. In certain embodiments, the stapled peptide is prepared from a p53-4 parent peptide. In certain embodiments, the stapled peptide is prepared from a p53-8 parent peptide. In certain embodiments, the stapled peptide is prepared from a PM2 parent peptide.

Examples of inventive peptides are listed in Table 8.

TABLE 8

| Peptide | Sequence (asterisk denotes the i, i + 7 positions of the cross-link amino acid incorporation) | Position i (first asterisk) | Position i + 7 (second asterisk) | Type of staple |
|---|---|---|---|---|
| p53-4: wild-type | LSQETFSDLWKLLP EN (SEQ ID NO: 10) | — | — | n/a |

TABLE 8-continued

| Peptide | Sequence (asterisk denotes the i, i + 7 positions of the cross-link amino acid incorporation) | Position i (first asterisk) | Position i + 7 (second asterisk) | Type of staple |
|---|---|---|---|---|
| p53-4: modified; i, i + 7 | LSQETF*DLWKLL* EN (SEQ ID NO: 11) | $Pyr_R$<br>$R_8$ | $S_8$<br>$Pyr_S$ | Amino-stapled<br>Amino-stapled |
| p53-8: wild-type | QSQQTFSNLWRLLP QN (SEQ ID NO: 1) | — | — | n/a |
| p53-8: modified; i, i + 7 | QSQQTF*NLWRLL* QN (SEQ ID NO: 2) | $Pyr_R$<br>$Pyr_R$<br>$R_8$<br>$Az$<br>$Az$<br>$R_8$<br>$R_8$<br>$R_8$<br>$R_8$<br>$R_DN$<br>$R_EN$ | $S_8$<br>$S_8$<br>$Pyr_S$<br>$S_8$<br>$S_8$<br>$Az$<br>$S_GN$<br>$S_DN$<br>$S_EN$<br>$S_8$<br>$S_EN$ | Amino-stapled<br>Alloc-stapled<br>Amino-stapled<br>Amino-stapled<br>Alloc-stapled<br>Amino-stapled<br>Amino-stapled<br>Amino-stapled<br>Amino-stapled<br>Amino-stapled<br>Amino-stapled |
| PM2: wild-type | TSFAEWALLS (SEQ ID NO: 13) | — | — | n/a |
| PM2: modified; i, i + 7 | TSF*EYWALL* (SEQ ID NO: 14) | $Pyr_R$<br>$R_8$<br>$R_8$<br>$Pyr_R$<br>$Pyr_R$<br>$Pyr_R$ | $S_8$<br>$Pyr_S$<br>$S_GN$<br>$S_8$<br>$Pyr_S$<br>$Pyr_S$ | Amino-stapled<br>Amino-stapled<br>Amino-stapled<br>Alloc-stapled<br>Alloc-stapled; isomer A<br>Alloc-stapled; isomer B |

Methods of Preparing Stapled and Stitched Polypeptides

The present invention is also directed to methods of preparing polypeptides of the Formulae (I)-(X), and salts thereof. The invention also provides intermediates in the synthesis of the inventive polypetides. The synthesis typically involves preparing unstapled polypeptide precursors of Formula (i) or (ii), or salts thereof, unstapled polypeptide precursor is treated with a ring-closing metathesis catalyst to provide an inventive stapled polypeptide of Formula (I) or (VI).

The synthesis of an inventive unstapled polypeptide first involves the selection of a desired sequence and number of amino acids and amino acid analogues. As one of ordinary skill in the art will realize, the number, stereochemistry, and

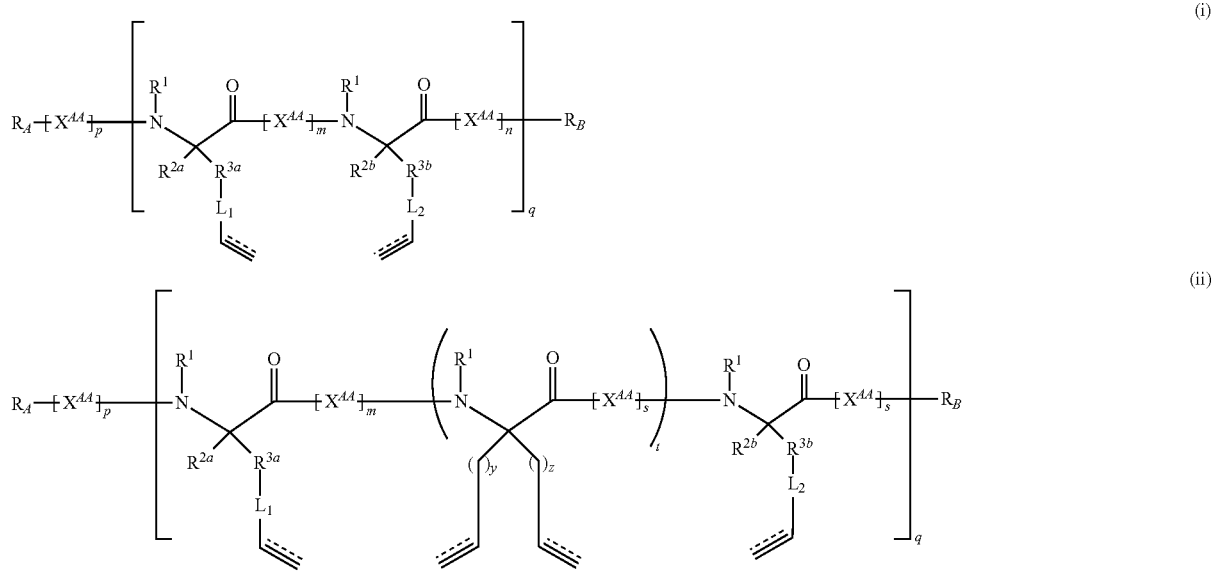

wherein $R_A$, $R_B$, $R^1$, $R^{2a}$, $R^{3a}$, $L_1$, $L_2$, p, m, n, q, s, t, y, z, and $X^{AA}$ are as defined in Formula (I) and (VI). Then the type of amino acid structures (natural or non-natural) selected will depend upon the size of the polypeptide to be prepared, the ability of the particular amino acids to generate a desired structural motif (e.g., an alpha-helix), and any particular peptide sequences that are desirable to mimic (for example, a p53 donor helical peptide).

Once the amino acids are selected, synthesis of the inventive unstapled polypeptide can be achieved using standard deprotection and coupling reactions. Formation of peptide bonds and polypeptide synthesis are techniques well-known to one skilled in the art, and encompass both solid phase and solution phase methods; see generally, Bodanszky and Bodanszky, *The Practice of Peptide Synthesis*, Springer-Verlag, Berlin, 1984; Atherton and Sheppard, *Solid Phase Peptide Synthesis: A Practical Approach*, IRL Press at Oxford University Press Oxford, England, 1989, and Stewart and Young, *Solid phase Peptide Synthesis*, 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, Hecht, *Bioorganic chemistry: Peptides and Proteins*, Oxford University Press, New York: 1998, the entire contents of which are incorporated herein by reference.

In certain embodiments, the methods comprises associating the inventive stapled peptides by ligating it to another polypeptide or a protein following the strategies as described in International Application No. PCT/US2010/001952, which is also incorporated herein by reference.

In certain embodiments, the method comprises a solution phase synthesis of an unstapled polypeptide precursor of Formula (i) or (ii). Solution phase synthesis, as mentioned above, is a well-known technique for the construction of polypeptides. An exemplary solution phase synthesis comprises the steps of: (1) providing an amino acid protected at the N-terminus with an amino protecting group; (2) providing an amino acid protected at the C-terminus with an oxygen protecting group; (3) coupling the N-protected amino acid to the C-protected amino acid; (4) deprotecting the product of the coupling reaction either at the N-terminus or C-terminus; and (5) repeating steps (3) to (4) until a desired polypeptide is obtained, wherein at least two of the amino acids coupled at any of the above steps each comprise at least one terminally unsaturated amino acid sidechain, and, optionally, an amino acid comprising two terminally unsaturated amino acid side chains. During the course of the above synthesis, various parameters can be varied, including, but not limited to, placement of amino acids with terminally unsaturated side chains, stereochemistry of amino acids, terminally unsaturated side chain length and functionality, and amino acid residues utilized.

In certain embodiments, the method comprises a solid phase synthesis of an unstapled polypeptide precursor of the Formula (i) or (ii). Solid phase synthesis, as mentioned above, is a well-known technique for the construction of polypeptides. An exemplary solid phase synthesis includes the steps of: (1) providing a resin-bound amino acid; (2) deprotecting the resin bound amino acid; (3) coupling an amino acid to the deprotected resin-bound amino acid; (4) repeating steps (3) until a desired peptide is obtained, wherein at least two of the amino acids coupled at any of the above steps each comprise at least one terminally unsaturated amino acid sidechain, and, optionally, an amino acid comprising two terminally unsaturated amino acid side chains. During the course of the above synthesis, various parameters can be varied, including, but not limited to placement of amino acids with terminally unsaturated side chains, stereochemistry of amino acids, terminally unsaturated side chain length and functionality, and amino acid residues utilized.

After a desired polypeptide is synthesized, the polypeptide of Formula (i) or (ii) is contacted with a specific catalyst to promote the stapling, or multiple stapling, to provide a polypeptide of Formula (I) or (VI). For example, the resin-bound polypeptide may be contacted with a catalyst to promote stapling or may first be cleaved from the resin, and then contacted with a catalyst to promote stapling. The amino acids comprising one to two terminally unsaturated amino acid sidechains are so incorporated into the polypeptide chain in order to provide proximal terminally unsaturated sidechains. These proximal terminally unsaturated sidechains may be in the same plane as, or same side of the polypeptide chain as each other in any given conformation of the polypeptide. Upon treatment with a catalyst, these proximal side chains react with each other via stapling to provide a conformationally stabilized polypeptide. In certain embodiments, the proximal terminally unsaturated sidechains are arranged such that the resulting staple does not interfere with the biological/therapeutic activity of the inventive stapled polypeptide.

After stapling of an inventive polypeptide, the method may further comprise additional synthetic modification(s). Any chemical or biological modification to the stapled or stitched polypeptide may be made. In certain embodiments, the modifications are carried out on the Alloc moiety of a polypeptide. In certain embodiments, the modifications extrude $CO_2$ from the Alloc moiety of the stapled peptides. In certain embodiments, the $CO_2$ extrusion is carried out in the presence of a palladium catalyst. In certain embodiments, the $CO_2$ extrusion is carried out in the presence of $Pd(PPh_3)_4$. In certain embodiments, about 10-80 mole % of a palladium catalyst is used for the $CO_2$ extrusion. In certain embodiments, about 20-40 mole % of a palladium catalyst is used for the $CO_2$ extrusion.

In certain embodiments, additional modifications of the stapled or stitched peptides include reduction, oxidation, and nucleophilic or electrophilic additions to the double bond provided from a metathesis reaction to provide a synthetically modified polypeptide. Other modifications may include conjugation of a stapled polypeptide, or a synthetically modifying the stapled polypeptide with a therapeutically active agent, label, or diagnostic agent anywhere on the stapled polypeptide scaffold, e.g., such as at the N-terminus of the stapled polypeptide, the C-terminus of the stapled polypeptide, on an amino acid side chain of the stapled polypeptide, or at one or more modified or unmodified stapled sites (i.e., to a staple). Such modification may be useful in delivery of the peptide or therapeutically active agent to a cell, tissue, or organ. Such modifications may, in certain embodiments, allow for targeting to a particular type of cell or tissue.

In one aspect, provided is a method of making a polypeptide of Formula (I), or a salt thereof, comprising the steps of:

(i) providing an amino acid of Formula (A)

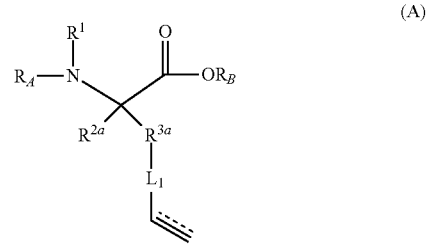

(A)

or a salt thereof;

(ii) providing an amino acid of Formula (B):

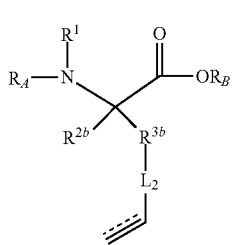
(B)

or a salt thereof;
(iii) providing at least one additional amino acid; and
(iv) coupling the amino acids of Formulae (A) and (B), and optionally step (iii) to provide a polypeptide of Formula (i):

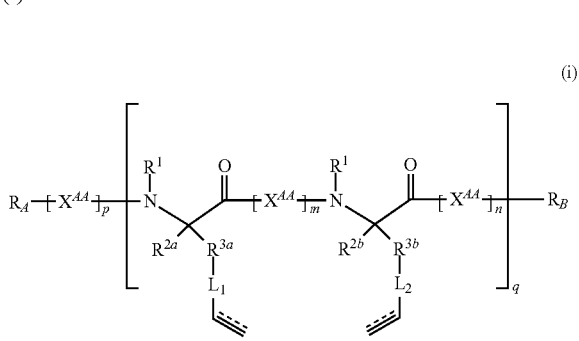
(i)

or a salt thereof.

In another aspect, provided is a method of making a polypeptide of Formula (VI), or a salt thereof, comprising the steps of:
(I) providing an amino acid of Formula (A)

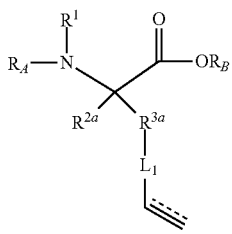
(A)

or a salt thereof;

(ii) providing an amino acid of Formula (B):

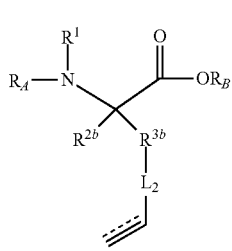
(B)

or a salt thereof;
(iii) providing an amino acid of Formula (C):

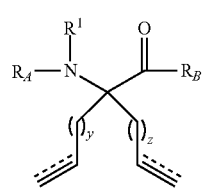
(C)

or a salt thereof;
(iv) providing at least one amino acid; and
(v) coupling the amino acids of (A), (B), and (C), and optionally step (iv) to provide a polypeptide of Formula (ii):

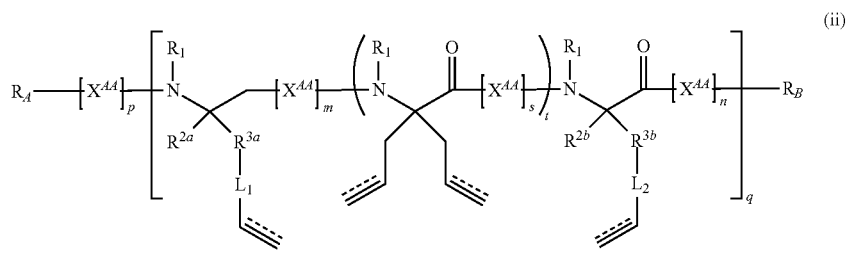
(ii)

or a salt thereof.

In certain embodiments, the amino acid of Formula (A) is of Formula (A-1):

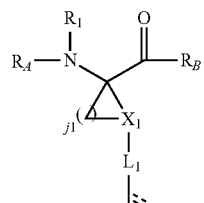
(A-1)

or a salt thereof.

In certain embodiments, the amino acid of Formula (A) is of Formula (A-2):

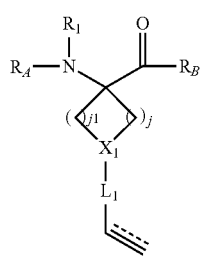
(A-2)

or a salt thereof.

In certain embodiments, the amino acid of Formula (A) is of Formula (A-3):

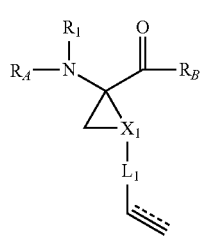
(A-3)

or a salt thereof.

In certain embodiments, the amino acid of Formula (A) is of Formula (A-4):

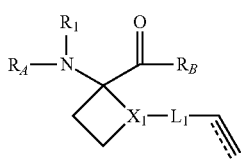
(A-4)

or a salt thereof.

In certain embodiments, the amino acid of Formula (A) is of Formula (A-5):

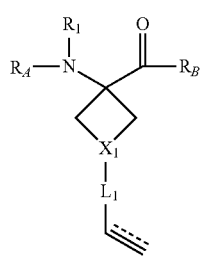
(A-5)

or a salt thereof.

In certain embodiments, the amino acid of Formula (A) is of Formula (A-6):

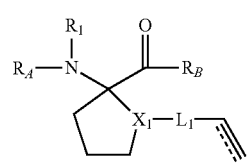
(A-6)

or a salt thereof.

In certain embodiments, the amino acid of Formula (A) is of Formula (A-7):

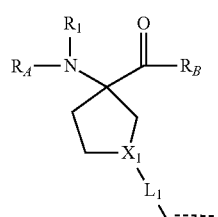
(A-7)

or a salt thereof.

In certain embodiments, the amino acid of Formula (A) is of Formula (A-8):

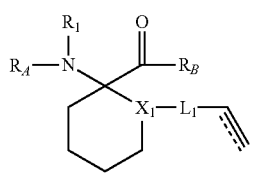
(A-8)

or a salt thereof.

In certain embodiments, the amino acid of Formula (A) is of Formula (A-9):

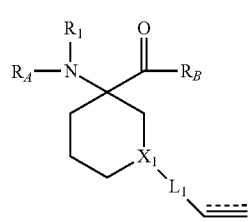
(A-9)

or a salt thereof.

In certain embodiments, the amino acid of Formula (A) is of Formula (A-10):

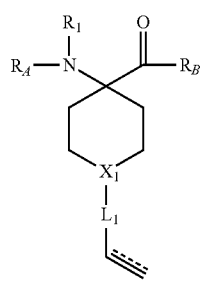
(A-10)

or a salt thereof.

In certain embodiments, the amino acid of Formula (A) is of Formula (A-11):

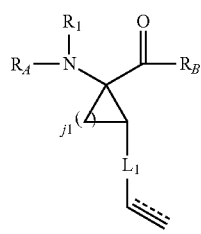
(A-11)

or a salt thereof.

In certain embodiments, the amino acid of Formula (A) is of Formula (A-12):

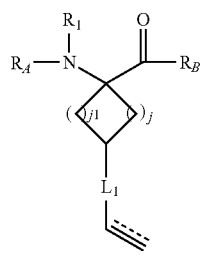
(A-12)

or a salt thereof.

In certain embodiments the amino acid of Formula (A) is of Formula (A-13):

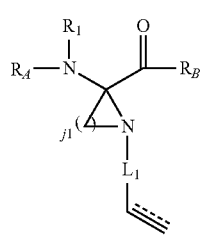
(A-13)

or a salt thereof.

In certain embodiments, the amino acid of Formula (A) is of Formula (A-14):

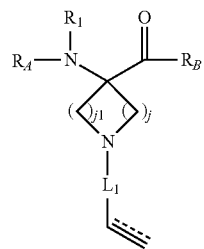
(A-14)

or a salt thereof.

In certain embodiments, the amino acid of Formula (A) is of Formula (A-15):

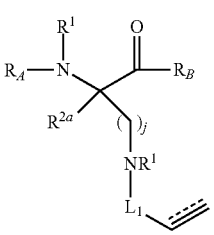
(A-15)

or a salt thereof.

In certain embodiments, the amino acid of Formula (A) is of Formula (A-16):

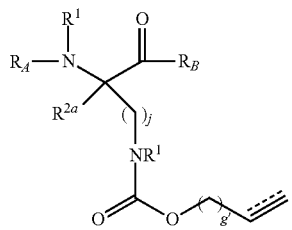
(A-16)

or a salt thereof.

In certain embodiments, the amino acid of Formula (A) is of Formula (A-17):

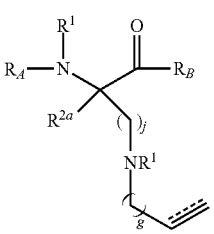
(A-17)

or a salt thereof.

In certain embodiments, the amino acid of Formula (A) is of Formula (A-18):

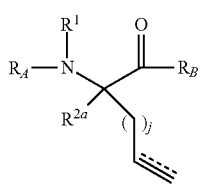
(A-18)
or a salt thereof.
In certain embodiments, the amino acid of Formula (A) is selected from the group consisting of:
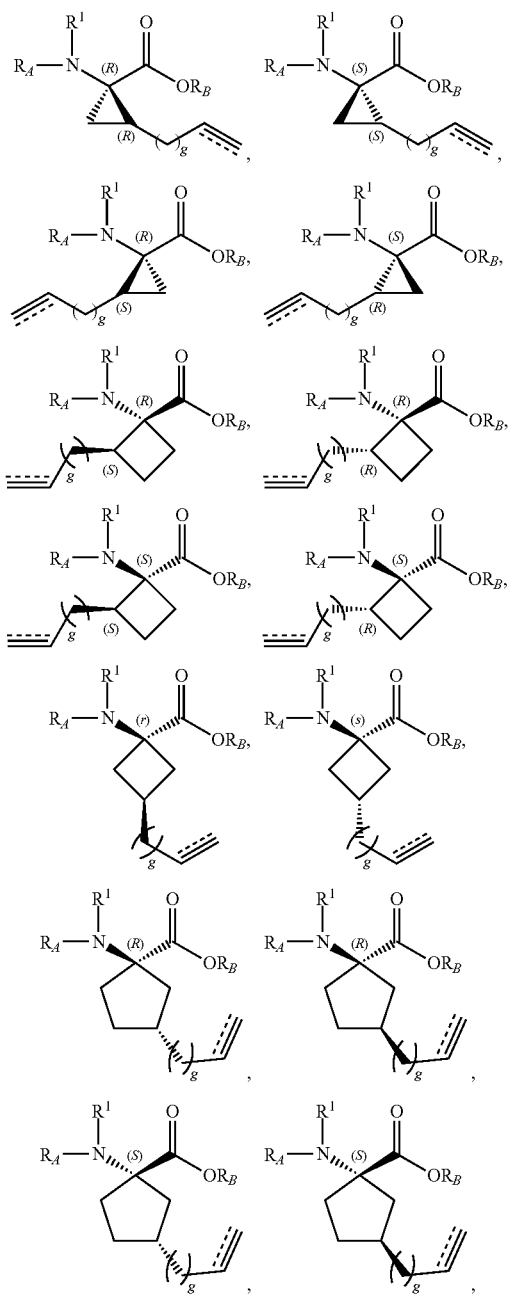
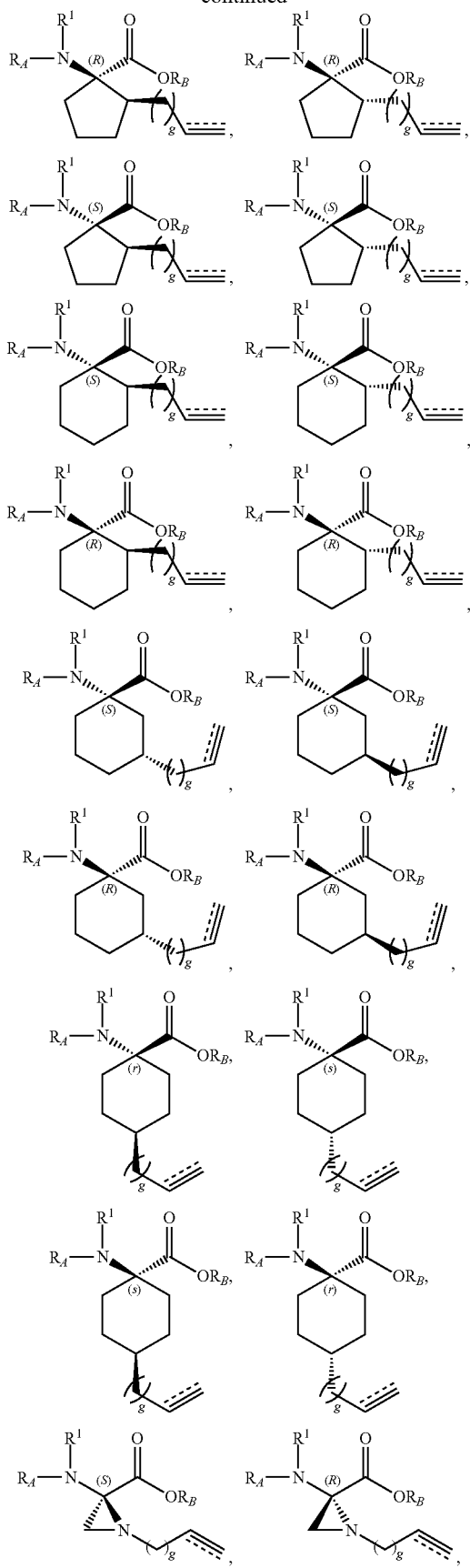

93
-continued
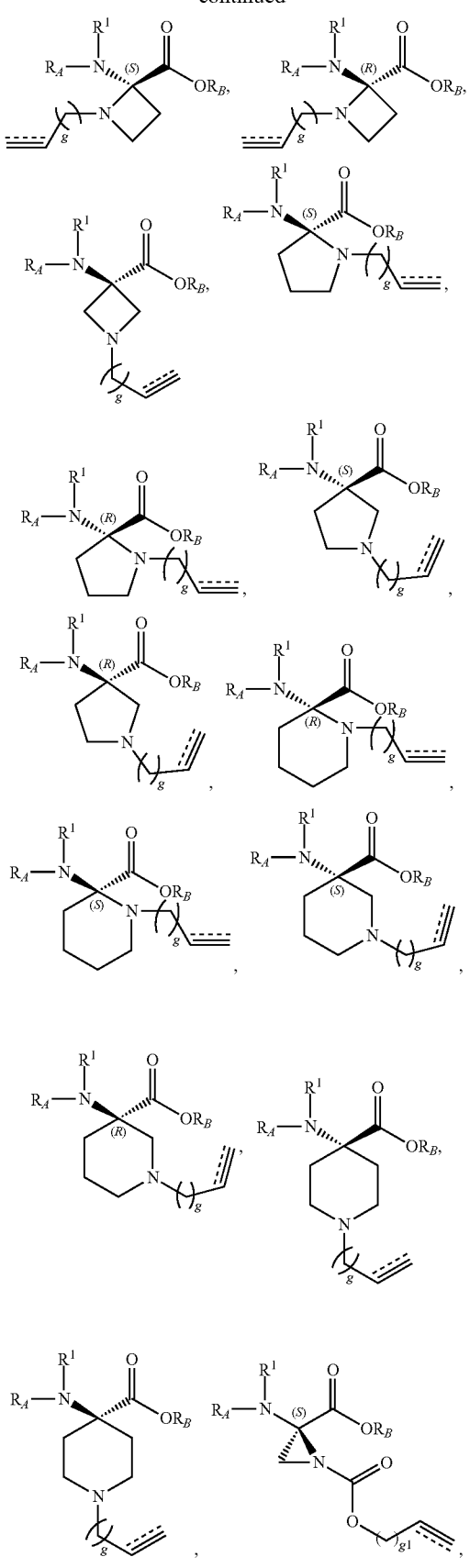
94
-continued
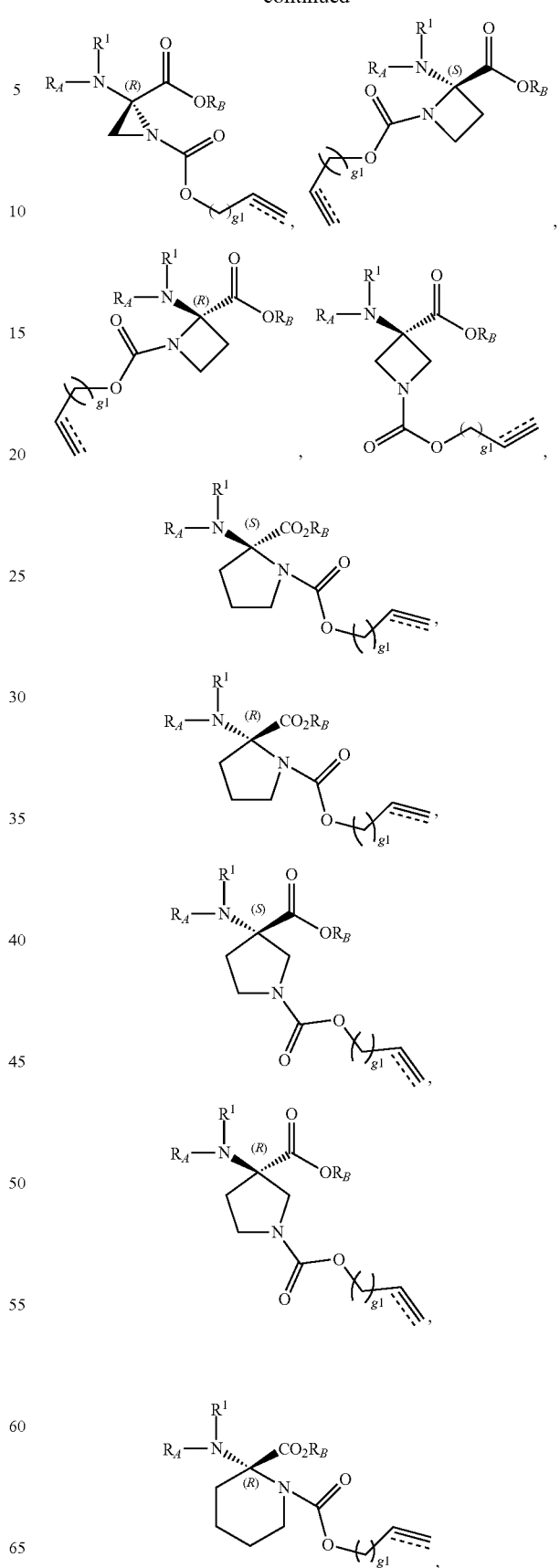

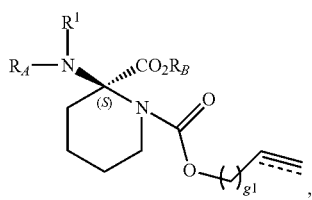

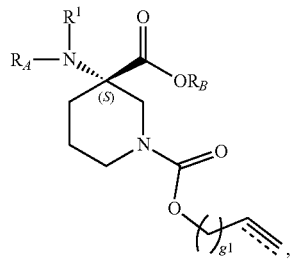

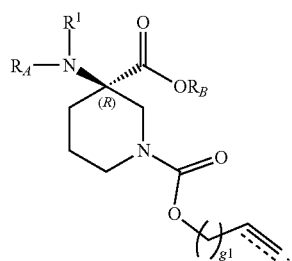

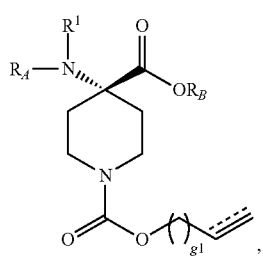

or a salt thereof, wherein each of g and g1 are as defined herein.

In certain embodiments, the amino acid of Formula (A) is of the formula:

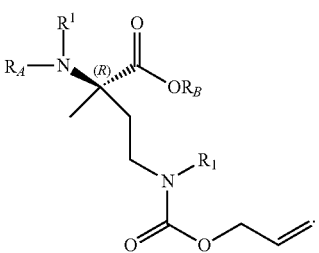

In certain embodiments, the amino acid of Formula (A) is of the formula:

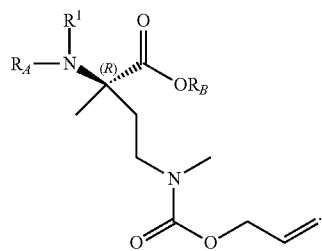

In certain embodiments, the amino acid of Formula (A) is of the formula:

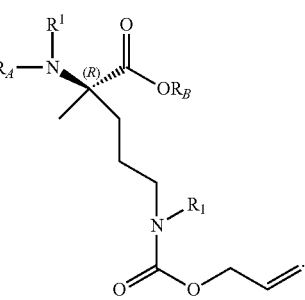

In certain embodiments, the amino acid of Formula (A) is of the formula:

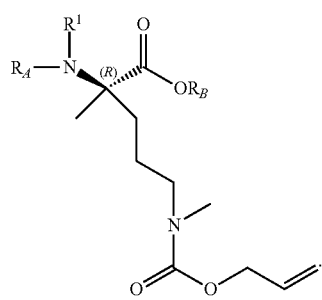

In certain embodiments, the amino acid of Formula (A) is of the formula:

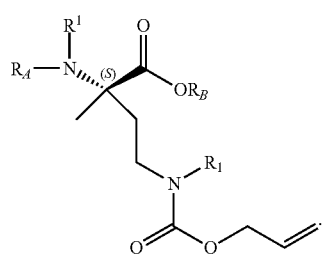

In certain embodiments, the amino acid of Formula (A) is of the formula:

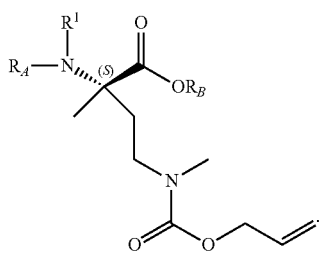

In certain embodiments, the amino acid of Formula (A) is of the formula:

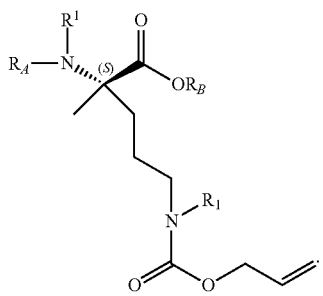

In certain embodiments, the amino acid of Formula (A) is of the formula:

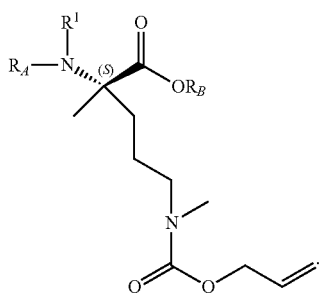

In certain embodiments, the amino acid of Formula (A) is of the formula:

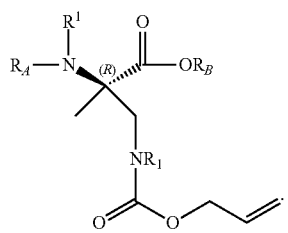

In certain embodiments, the amino acid of Formula (A) is of the formula:

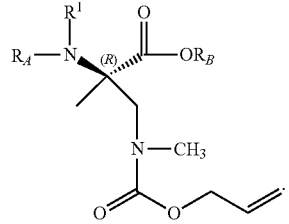

In certain embodiments, the amino acid of Formula (A) is of the formula:

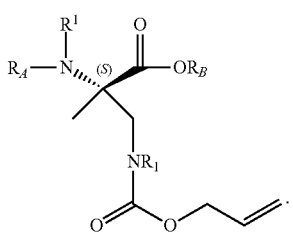

In certain embodiments, the amino acid of Formula (A) is of the formula:

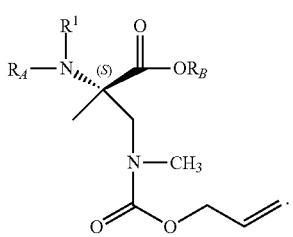

In certain embodiments, the amino acid of Formula (A) is of the formula:

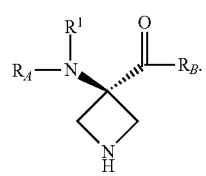

In certain embodiments, the amino acid of Formula (A) is of the formula:

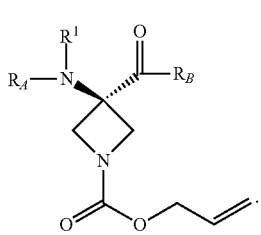

In certain embodiments, the amino acid of Formula (A) is of the formula:

In certain embodiments, the amino acid of Formula (A) is of the formula:

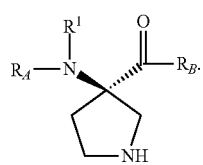

In certain embodiments, the amino acid of Formula (A) is of the formula:

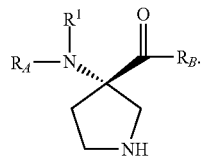

In certain embodiments, the amino acid of Formula (A) is of the formula:

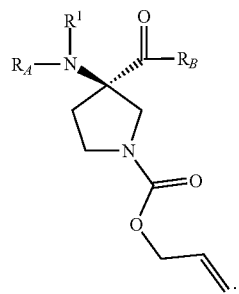

In certain embodiments, the amino acid of Formula (A) is of the formula:

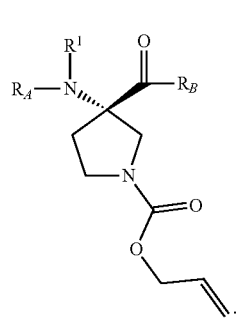

In certain embodiments, the amino acid of Formula (A) is of the formula:

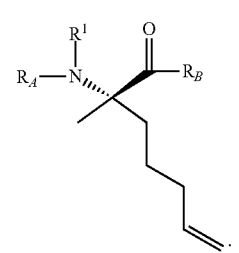

In certain embodiments, the amino acid of Formula (A) is of the formula:

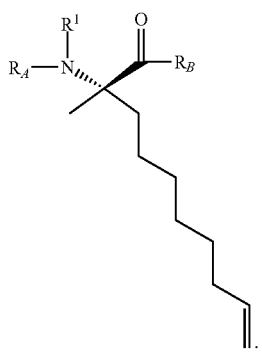

In certain embodiments, the amino acid of Formula (A) is of the formula:

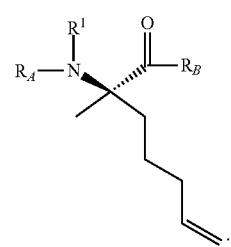

In certain embodiments, the amino acid of Formula (A) is of the formula:

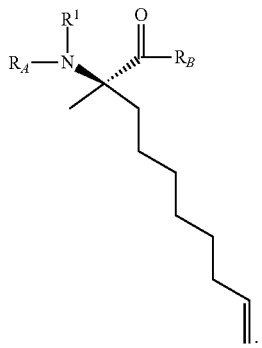

In certain embodiments, Formula (A) is of the formula

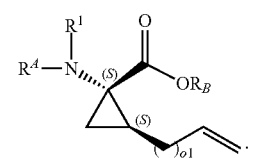

In certain embodiments, Formula (A) is of the formula

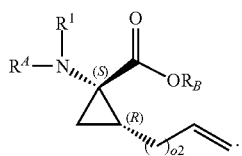

In certain embodiments, Formula (A) is of the formula

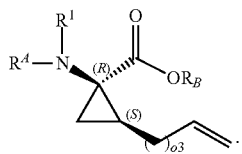

In certain embodiments, Formula (A) is of the formula

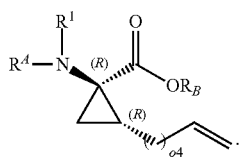

As generally used above, o1, o2, o3, o4 are as defined herein.
In certain embodiments, the amino acid of Formula (A) is of the formula:

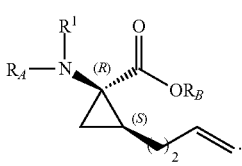

In certain embodiments, the amino acid of Formula (A) is of the formula:

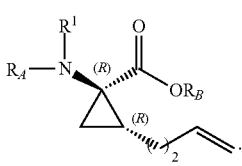

In certain embodiments, the amino acid of Formula (A) is of the formula:

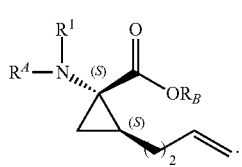

In certain embodiments, the amino acid of Formula (A) is of the formula:

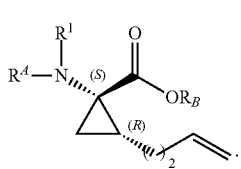

In certain embodiments, the amino acid of Formula (B) is of Formula (B-1):

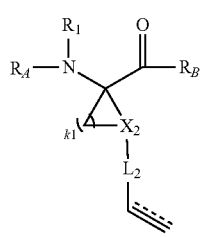

(B-1)

or a salt thereof.

In certain embodiments, the amino acid of Formula (B) is of Formula (B-2):

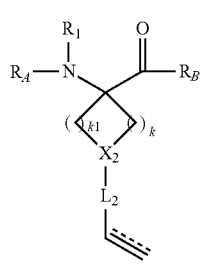

(B-2)

or a salt thereof.

In certain embodiments, the amino acid of Formula (B) is of Formula (B-3):

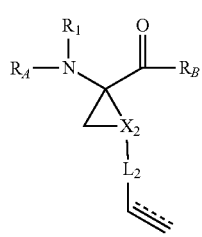

or a salt thereof.

In certain embodiments, the amino acid of Formula (B) is of Formula (B-4):

(B-4)

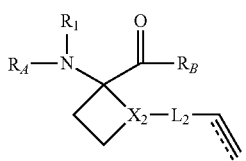

or a salt thereof.

In certain embodiments, the amino acid of Formula (B) is of Formula (B-5):

(B-5)

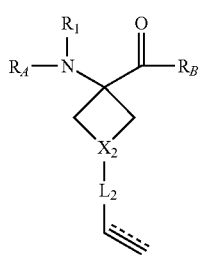

or a salt thereof.

In certain embodiments, the amino acid of Formula (B) is of Formula (B-6):

(B-6)

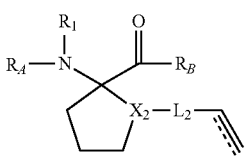

or a salt thereof.

In certain embodiments, the amino acid of Formula (B) is of Formula (B-7):

(B-7)

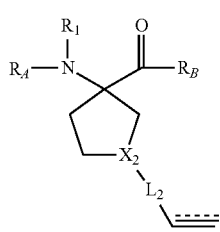

or a salt thereof.

In certain embodiments, the amino acid of Formula (B) is of Formula (B-8):

(B-8)

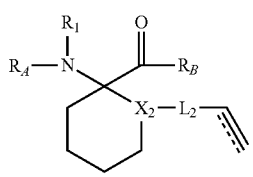

or a salt thereof.

In certain embodiments, the amino acid of Formula (B) is of Formula (B-9):

(B-9)

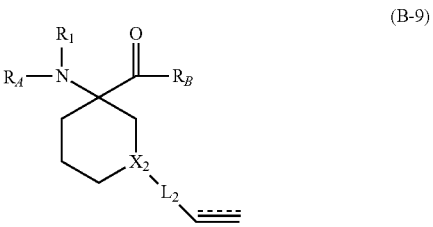

or a salt thereof.

In certain embodiments, the amino acid of Formula (B) is of Formula (B-10):

(B-10)

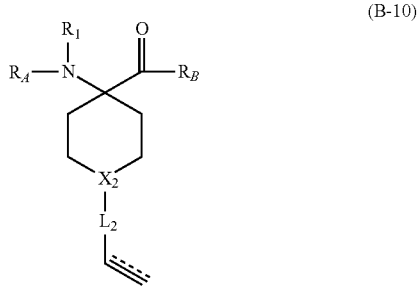

or a salt thereof.

In certain embodiments, the amino acid of Formula (B) is of Formula (B-11):

(B-11)

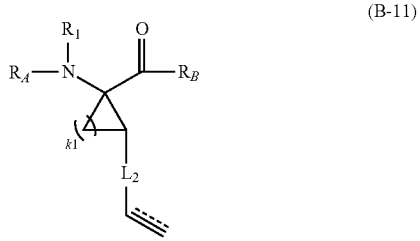

or a salt thereof.

In certain embodiments, the amino acid of Formula (B) is of Formula (B-12):

(B-12)

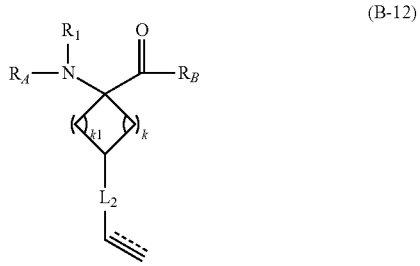

or a salt thereof.

In certain embodiments, the amino acid of Formula (B) is of Formula (B-13):

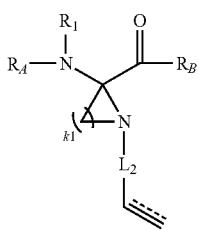
(B-13)

or a salt thereof.

In certain embodiments, the amino acid of Formula (B) is of Formula (B-14):

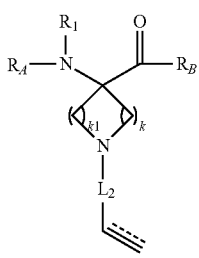
(B-14)

or a salt thereof.

In certain embodiments, the amino acid of Formula (B) is of Formula (B-15):

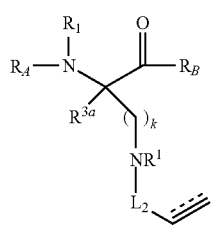
(B-15)

or a salt thereof.

In certain embodiments, the amino acid of Formula (B) is of Formula (B-16):

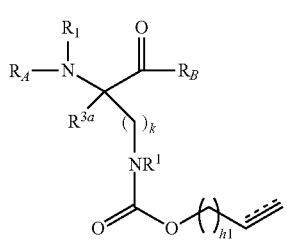
(B-16)

or a salt thereof.

In certain embodiments, the amino acid of Formula B is of Formula (B-17):

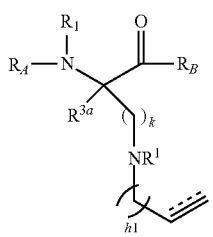
(B-17)

or a salt thereof.

In certain embodiments, the amino acid of Formula (B) is of Formula (B-18):

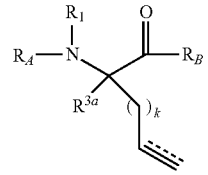
(B-18)

or a salt thereof.

In certain embodiments, the amino acid of Formula (B) is one of the following structures:

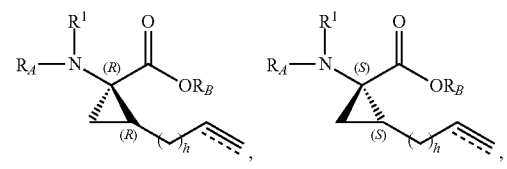

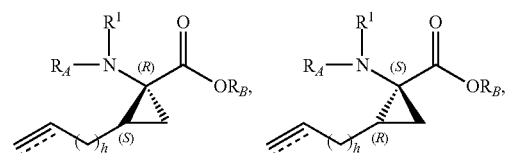

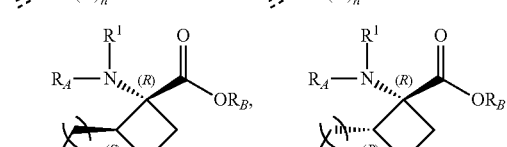

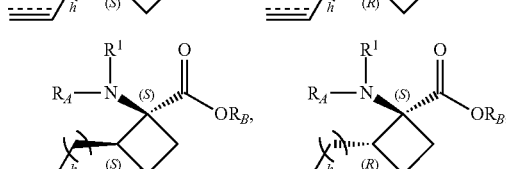

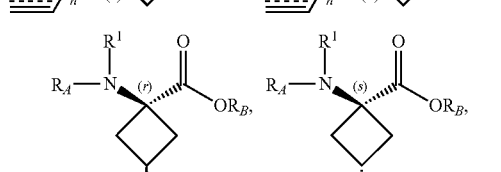

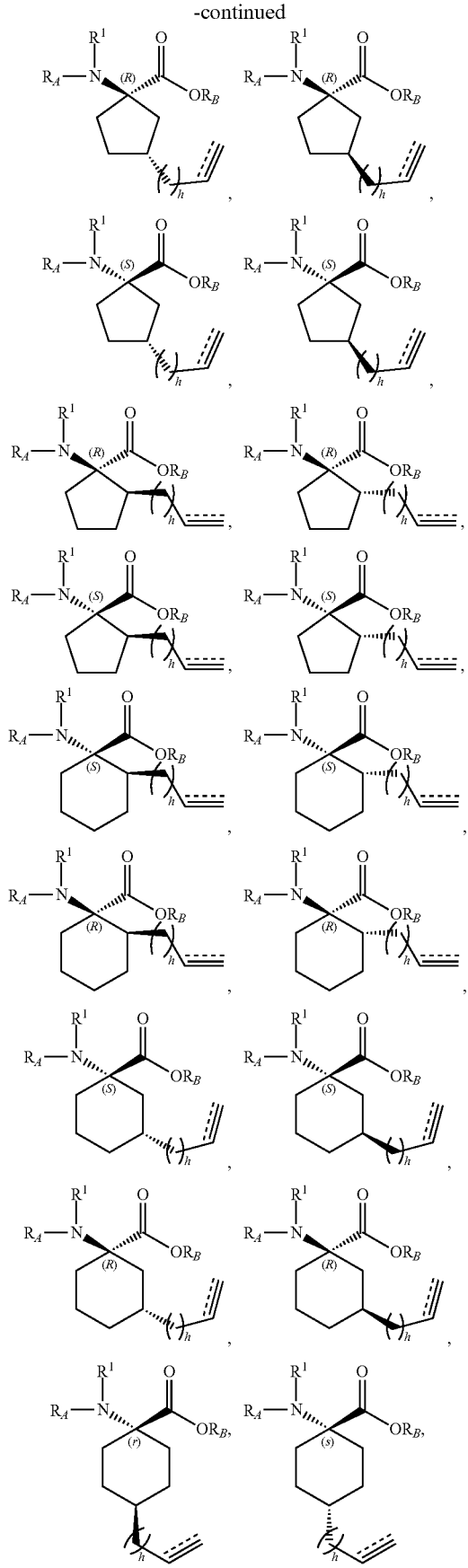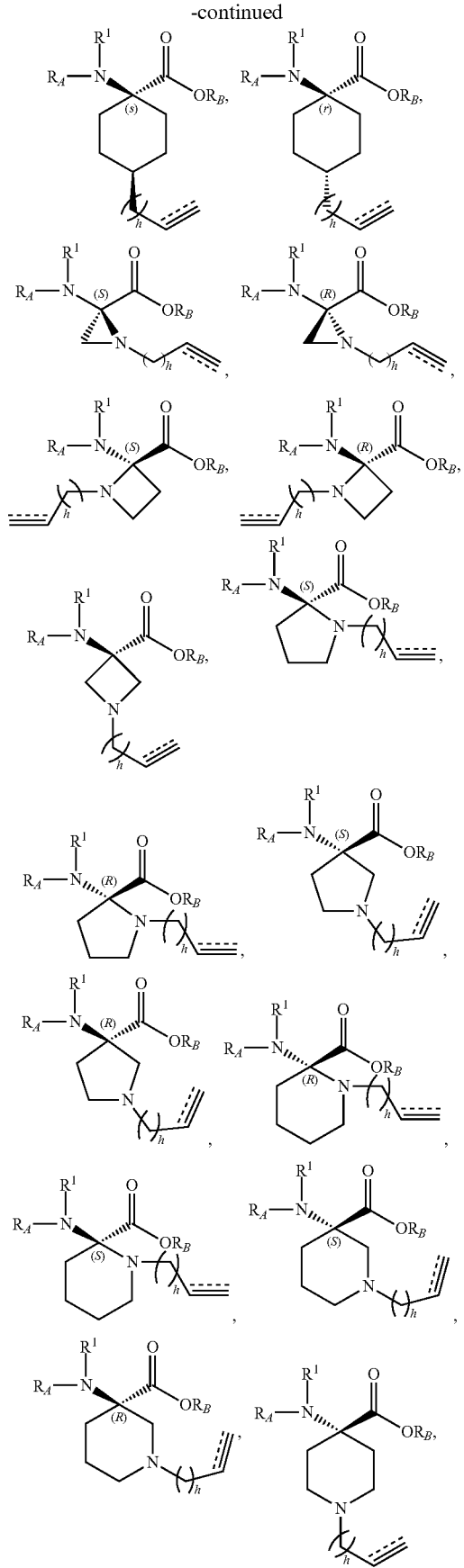

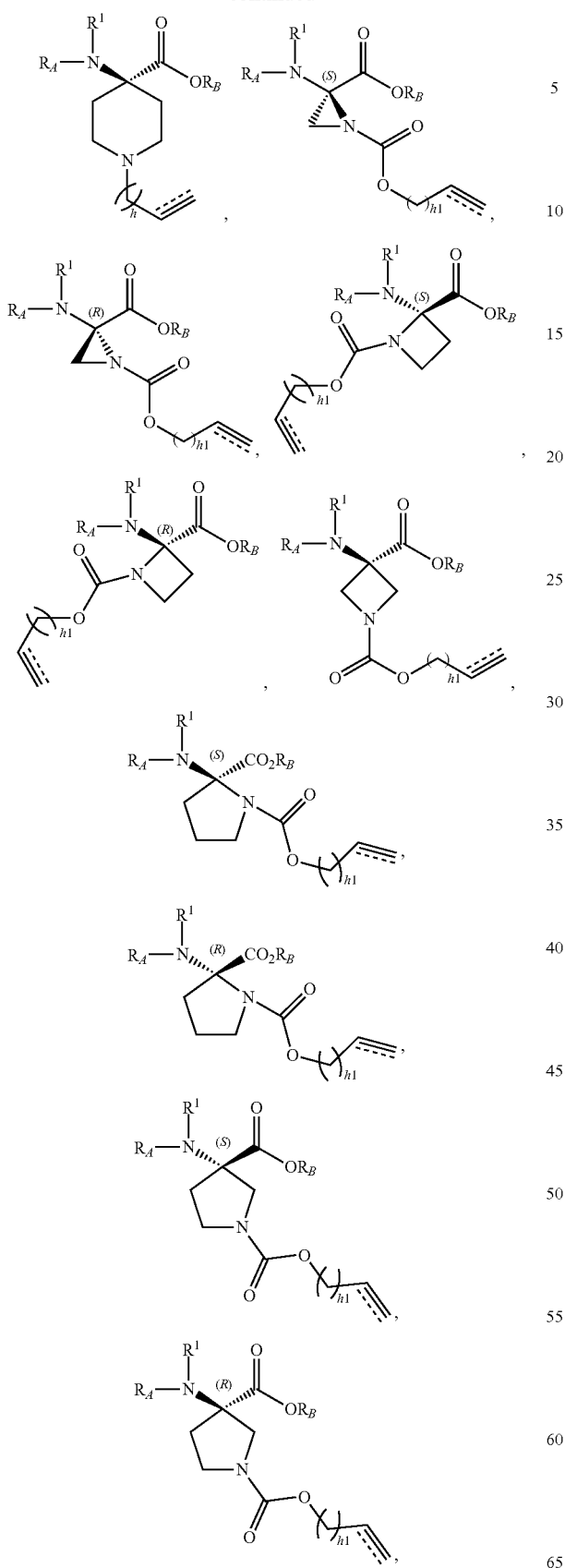
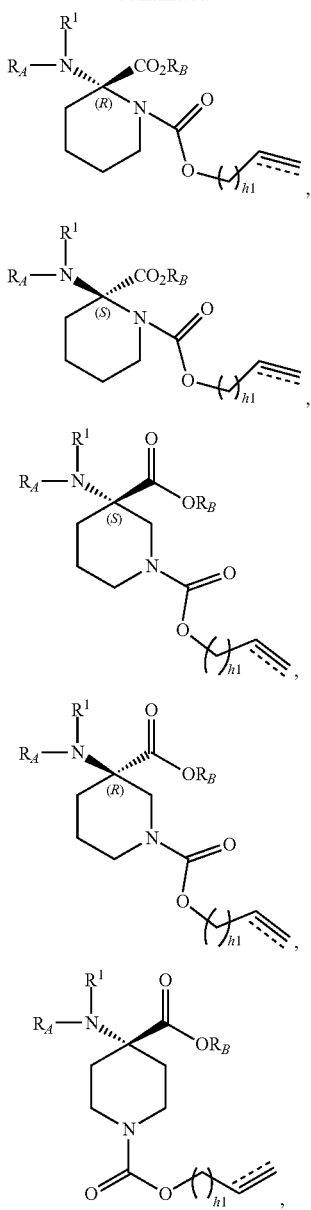
or a salt thereof, wherein h and h1 are as defined herein.
In certain embodiments, the amino acid of Formula (B) is of the formula:
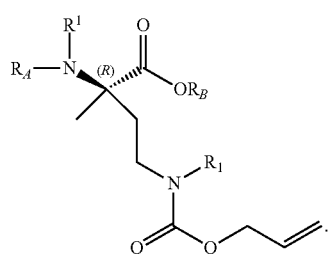
In certain embodiments, the amino acid of Formula (B) is of the formula:

111

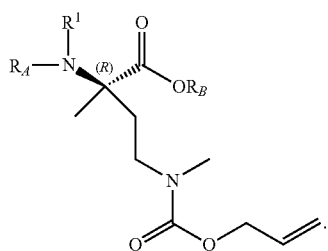

In certain embodiments, the amino acid of Formula (B) is of the formula:

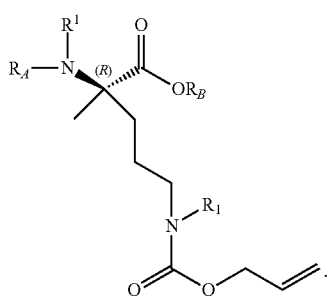

In certain embodiments, the amino acid of Formula (B) is of the formula:

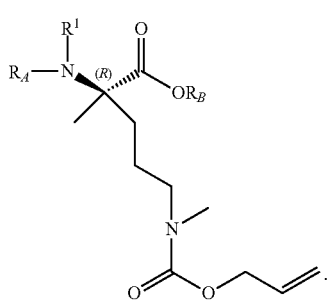

In certain embodiments, the amino acid of Formula (B) is of the formula:

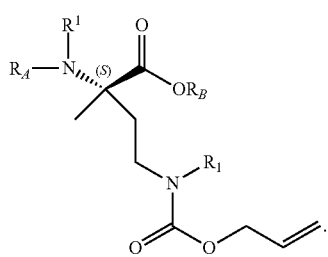

In certain embodiments, the amino acid of Formula (B) is of the formula:

112

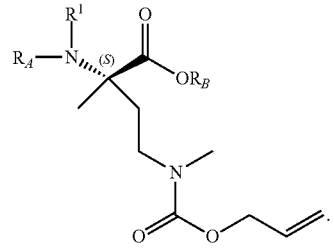

In certain embodiments, the amino acid of Formula (B) is of the formula:

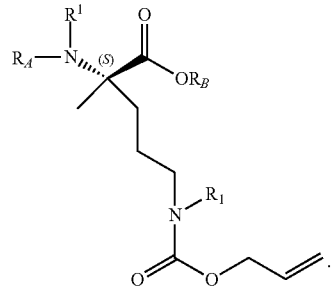

In certain embodiments, the amino acid of Formula (B) is of the formula:

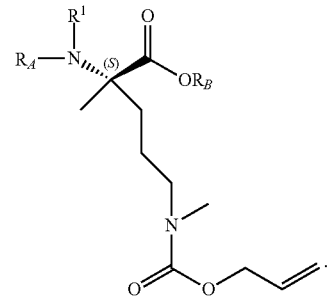

In certain embodiments, the amino acid of Formula (B) is of the formula

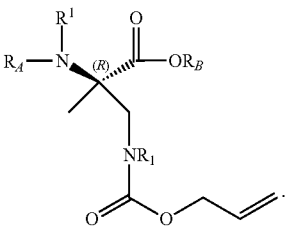

In certain embodiments, the amino acid of Formula (B) is of the formula:

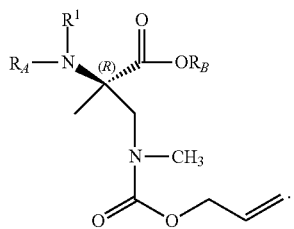

In certain embodiments, the amino acid of Formula (B) is of the formula:

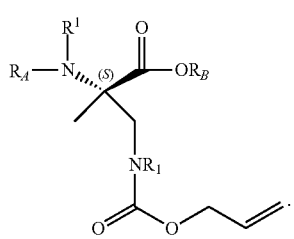

In certain embodiments, the amino acid of Formula (B) is of the formula:

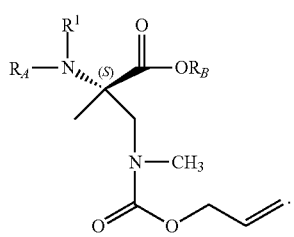

In certain embodiments, the amino acid of Formula (B) is of the formula:

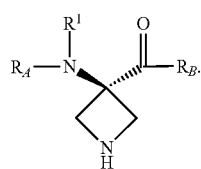

In certain embodiments, the amino acid of Formula (B) is of the formula:

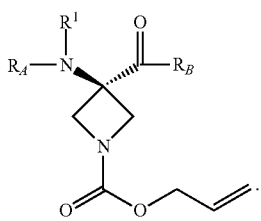

In certain embodiments, the amino acid of Formula (B) is of the formula:

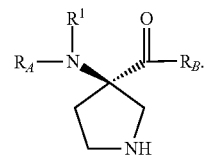

In certain embodiments, the amino acid of Formula (B) is of the formula:

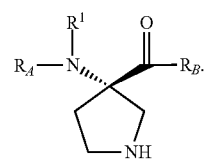

In certain embodiments, the amino acid of Formula (B) is of the formula:

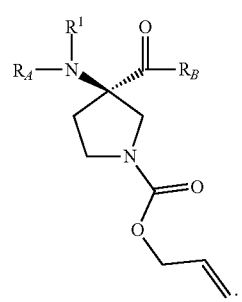

In certain embodiments, the amino acid of Formula (B) is of the formula:

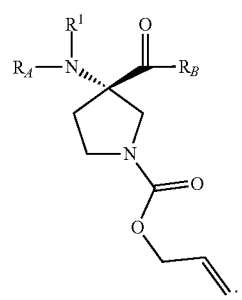

In certain embodiments, the amino acid of Formula (B) is of the formula:

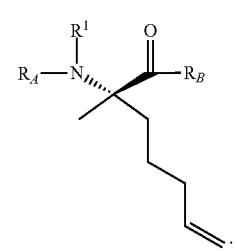

In certain embodiments, the amino acid of Formula (B) is of the formula:

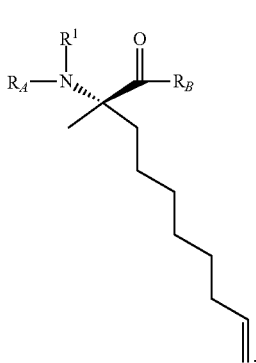

In certain embodiments, the amino acid of Formula (B) is of the formula:

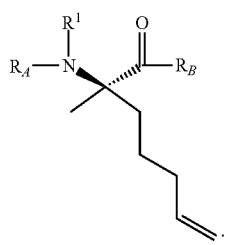

In certain embodiments, the amino acid of Formula (B) is of the formula:

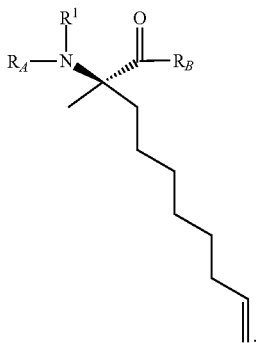

In certain embodiments, Formula (B) is of the formula

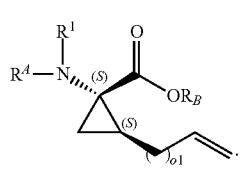

In certain embodiments, Formula (B) is of the formula

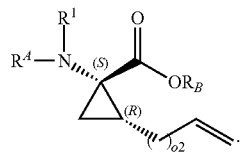

In certain embodiments, Formula (B) is of the formula

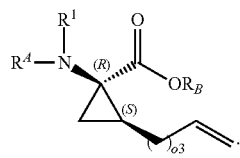

In certain embodiments, Formula (B) is of the formula

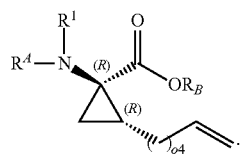

In certain embodiments, the amino acid of Formula (B) is of the formula:

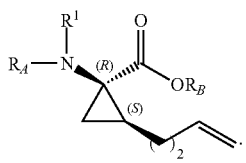

In certain embodiments, the amino acid of Formula (B) is of the formula:

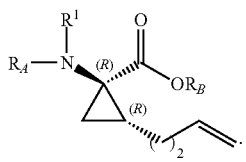

In certain embodiments, the amino acid of Formula (B) is of the formula:

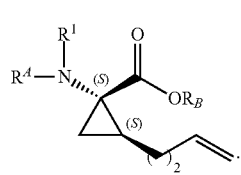

In certain embodiments, the amino acid of Formula (B) is of the formula:

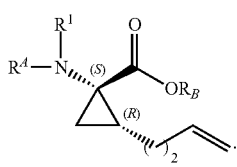

As used herein, each instance of o1, o2, o3, and o4 is independently 0, 1, 2, 3, 4, 5, or 6. In certain embodiments, o1 is 0. In certain embodiments, o1 is 1. In certain embodiments, o1 is 2. In certain embodiments, o1 is 3. In certain embodiments, o1 is 4. In certain embodiments, o1 is 5. In certain embodiments, o1 is 6. As used herein, each instance of o2 is independently 0, 1, 2, 3, 4, 5, or 6. In certain embodiments, o2 is 0. In certain embodiments, o2 is 1. In certain embodiments, o2 is 2. In certain embodiments, o2 is 3. In certain embodiments, o2 is 4. In certain embodiments, o2 is 5. In certain embodiments, o2 is 6. In certain embodiments, o3 is 0. In certain embodiments, o3 is 1. In certain embodiments, o3 is 2. In certain embodiments, o3 is 3. In certain embodiments, o3 is 4. In certain embodiments, o3 is 5. In certain embodiments, o3 is 6. In certain embodiments, o4 is 0. In certain embodiments, o4 is 1. In certain embodiments, o4 is 2. In certain embodiments, o4 is 3. In certain embodiments, o4 is 4. In certain embodiments, o4 is 5. In certain embodiments, o4 is 6.

In certain embodiments, the optional amino acid is of Formula (C)

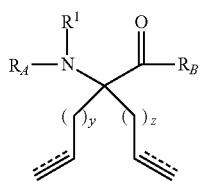

(C-1)

or a salt thereof, wherein $R^1$, $R^A$, $R^B$, y, and z are as defined herein.

In certain embodiments, the optional amino acid of Formula (C) is selected from the group consisting of:

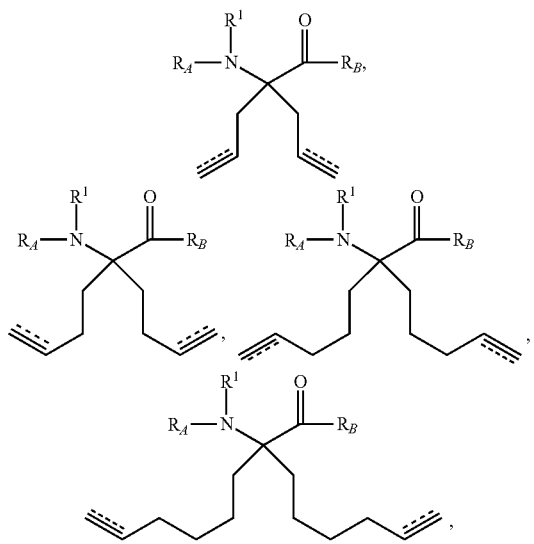

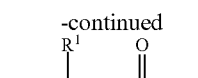

and

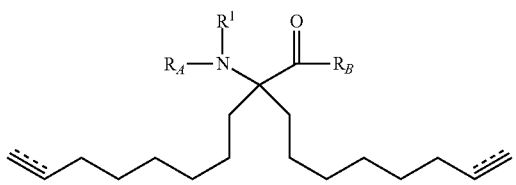

and salts thereof.

In certain embodiments, Formula (A) is at position i and Formula (B) is at position i+3 to form the stapled peptide. In certain embodiments, Formula (A) is at position i and Formula (B) is at position i+4 to form the stapled peptide. In certain embodiments, Formula (A) is at position i and Formula (B) is at position i+5 to form the stapled peptide. In certain embodiments, Formula (A) is at position i and Formula (B) is at position i+6 to form the stapled peptide. In certain embodiments, Formula (A) is at position i and Formula (B) is at position i+7 to form the stapled peptide. In certain embodiments, Formula (A) is at position i and Formula (B) is at position i+8 to form the stapled peptide. In certain embodiments, Formula (A) is at position i and Formula (B) is at position i+9 to form the stapled peptide. In certain embodiments, Formula (A) is at position i and Formula (B) is at position i+10 to form the stapled peptide. In certain embodiments, Formula (A) is at position i and Formula (B) is at position i+11 to form the stapled peptide. In certain embodiments, the amino acid alpha-carbon of Formula (A) having R chirality is at position i. In certain embodiments, the amino acid alpha-carbon of Formula (A) having S chirality is at position i. In certain embodiments, the amino acid alpha-carbon of Formula (B) having R chirality is at position i+3. In certain embodiments, the amino acid alpha-carbon of Formula (B) having S chirality is at position i+3. In certain embodiments, the amino acid alpha-carbon of Formula (B) having R chirality is at position i+4. In certain embodiments, the amino acid alpha-carbon of Formula (B) having S chirality is at position i+4. In certain embodiments, the amino acid alpha-carbon of Formula (B) having R chirality is at position i+5. In certain embodiments, the amino acid alpha-carbon of Formula (B) having S chirality is at position i+5. In certain embodiments, the amino acid alpha-carbon of Formula (B) having R chirality is at position i+6. In certain embodiments, the amino acid alpha-carbon of Formula (B) having S chirality is at position i+6. In certain embodiments, the amino acid alpha-carbon of Formula (B) having R chirality is at position i+7. In certain embodiments, the amino acid alpha-carbon of Formula (B) having S chirality is at position i+7. In certain embodiments, the amino acid alpha-carbon of Formula (B) having R chirality is at position i+8. In certain embodiments, the amino acid alpha-carbon of Formula (B) having S chirality is at position i+8. In certain embodiments, the amino acid alpha-carbon of Formula (B) having R chirality is at position i+9. In certain embodiments, the amino acid alpha-carbon of Formula (B) having S chirality is at position i+9. In certain embodiments, the amino acid alpha-carbon of Formula (B) having R chirality is at position i+10. In certain embodiments, the amino acid alpha-carbon of Formula (B) having S chirality is at position i+10. In certain embodiments, the amino acid alpha-carbon of Formula (B) having R chirality is at position i+11. In certain embodiments, the amino acid alpha-carbon of Formula (B) having S chirality is at position i+11.

As used herein, the phrase "providing at least one additional amino acid" of step (iv) refers to providing at least one natural or unnatural amino acid as defined herein. The above synthetic method may employ any and all known amino acids in order to generate a polypeptide Formula (I). In certain embodiments, the amino acids employable by the above synthetic method are defined and described herein.

In certain embodiments, step (iv) provides at least one structurally different amino acids from (A), (B), and (C). In certain embodiments, step (iv) provides at least two structurally different amino acids. In certain embodiments, step (iv) provides at least three structurally different amino acids. In certain embodiments, step (iv) provides at least four structurally different amino acids. In certain embodiments, step (iv) provides at least five structurally different amino acids. Different amino acids have different propensities for forming different secondary structures. For example, methionine (M), alanine (A), leucine (L), glutamate (E), and lysine (K) all have especially high alpha-helix forming propensities. In contrast, proline (P) and glycine (G) are alpha-helix disruptors. Thus, in certain embodiments, the at least one of the amino acids of step (iv) refers to a group selected from alanine, arginine, asparagine, aspartic acid, cysteine, glutamic acid, glutamine, histidine, isoleucine, leucine, lysine, methionine, phenylalanine, serine, threonine, tryptophan, tyrosine, and valine.

In certain embodiments, the "at least one amino acid" of step (iv) is a dipeptide or a polypeptide. In certain embodiments, step (iv) comprises providing a dipeptide. In certain embodiments, step (iv) comprises providing a polypeptide. In certain embodiments, the polypeptide comprises at least 4 amino acids. In certain embodiments, the polypeptide comprises at least 5 amino acids.

In certain embodiments, the coupling step (v) comprises the use of a coupling reagent. Exemplary coupling reagents include, but are not limited to, benzotriazol-1-yloxy-tris(dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethyllaminopropyl) carbodiimide (EDC), N,N'-carbonyldiimidazole (CDI), 3-(diethoxyphosphoryloxy)-1,2,3-benzotriazin-4(3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), 0-(7-azabenzotriazole-1-yl)-N,N,N',N'-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-yl) uranium tetrafluoroborate (TDBTU), (1-Cyano-2-ethoxy-2-oxoethylidenaminooxy)dimethylamino-morpholino-carbenium hexafluorophosphate (COMU), and O—(N-succinimidyl)-1,1,3,3-tetramethyl uranium tetrafluoroborate (TSTU)).

In certain embodiments, the coupling step (v) comprises a base. Exemplary bases include, but are not limited to, potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N,N-dimethylamino pyridine (DMAP), or triethylamine (NEt$_3$).

In certain embodiments, coupling step (v) is carried out in a medium. A medium is a solvent or a solvent mixture that, in combination with the combined reacting partners and reagents, facilitates the progress of the reaction therebetween. A solvent may solubilize one or more of the reaction components, or, alternatively, the solvent may facilitate the suspension of one or more of the reaction components; see generally, *March's Advanced Organic Chemistry: Reactions*, Mechanisms, and Structure, M. B. Smith and J. March, 5$^{th}$ Edition, John Wiley & Sons, 2001, and *Comprehensive Organic Transformations*, R. C. Larock, 2$^{nd}$ Edition, John Wiley & Sons, 1999, the entire contents of each of which are incorporated herein by reference. solvents for include ethers, halogenated hydrocarbons, aromatic solvents, polar aprotic solvents, or mixtures thereof. In other embodiments, the solvent is diethyl ether, dioxane, tetrahydrofuran (THF), dichloromethane (DCM), dichloroethane (DCE), acetonitrile (ACN), chloroform, toluene, benzene, dimethylformamide (DMF), dimethylacetamide (DMA), dimethylsulfoxide (DMSO), N-methyl pyrrolidinone (NMP), or mixtures thereof.

In certain embodiments, coupling step (v) is conducted at a temperature between about 0° C. and about 100° C., inclusive.

In certain embodiments, the coupling step (v) comprises a coupling reagent, a base, and a medium, and is conducted at temperature of between about 0° C. and about 100° C., inclusive.

In certain embodiments, the method further comprises the step of:

(v) treating the polypeptide of Formula (i) with a ring closing metathesis (RCM) catalyst to provide polypeptide of Formula (I-x):

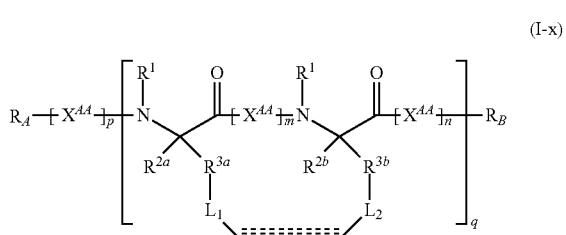

(I-x)

or a salt thereof.

In certain embodiments, the method further comprises the step of:

(vi) treating the polypeptide of Formula (ii) with a ring closing metathesis (RCM) catalyst to provide polypeptide of Formula (VI-x):

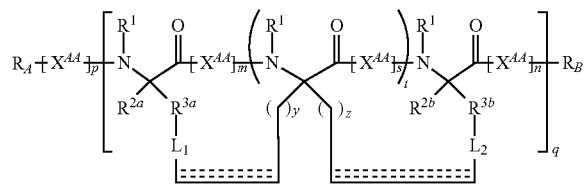

(VI-x)

or a salt thereof.

In certain embodiments, the RCM catalyst is a tungsten (W), molybdenum (Mo), or ruthenium (Ru) catalyst. In certain embodiments, the RCM catalyst is a ruthenuim catalyst. Examples of suitable olefin metathesis catalyst include, but are not limited to, Schrock catalyst, Grubbs Catalyst 1st generation, or benzylidene-bis(tricyclohexylphosphine)dichlororuthenium, Grubbs Catalyst 2nd Generation, or benzylidene[1,3-bis(2,4,6-trimethylphenyl)-2-midazolidinylidene]dichloro-(tricyclohexylphosphine) ruthenium, and Hoveyda-Grubbs Catalyst 2nd Generation, or 1,3-bis-(2,4,6-trimethylphenyl)-2-imidazolidinylidene) dichloro(o-isopropoxyp-phenylmethylene)ruthenium. RCM catalysts employable by the above synthetic method are described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

The metathesis catalyst may be provided in any suitable form that enables it to promote polymerisation. For example, the catalyst may be combined with a suitable carrier material such as a solvent or perhaps a solid and formed into a tablet. It will be appreciated that any such carrier material should be compatible with other components of the curable systems.

Figure 2A:
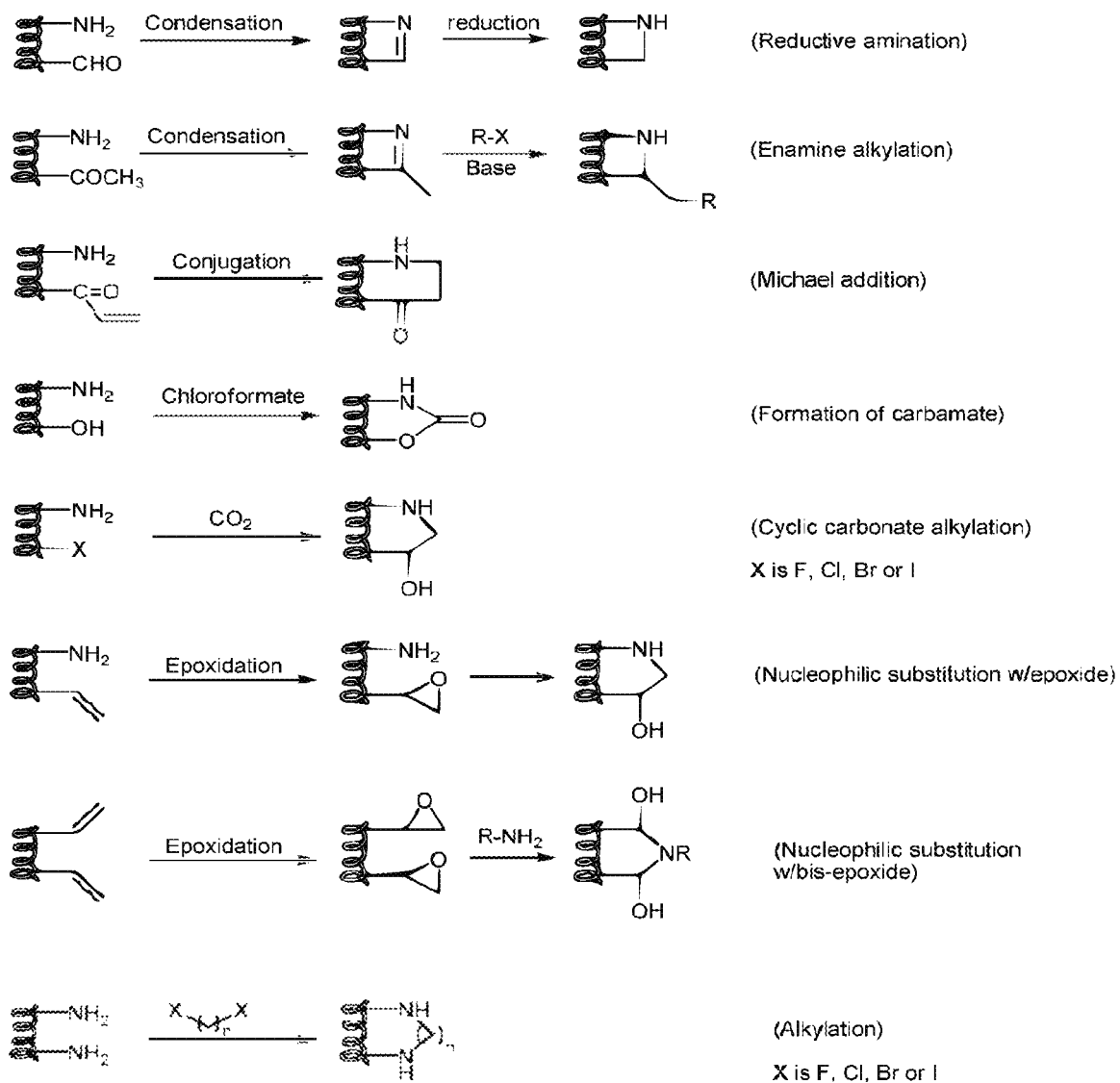
FIGS. 2A and 2B show chemical reactions to form stapled or stitched polypeptides.
Figure 2B:
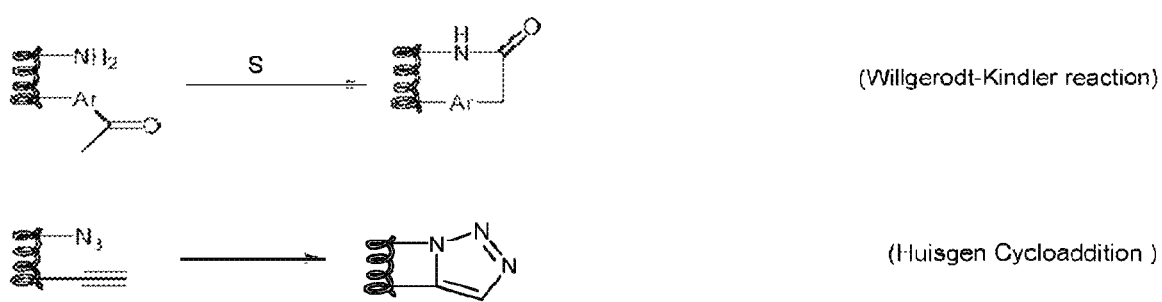

It will also be appreciated, that in addition to RCM catalysts, other reagents capable of promoting carbon-carbon bond or carbon-heteroatom bond formation can also be utilized. For example, other reactions that can be utilized, include, but are not limited to, palladium coupling reactions, transition metal catalyzed cross coupling reactions, pinacol couplings (terminal aldehydes), hydrozirconation (terminal alkynes), nucleophilic addition reactions, and NHK (Nozaki-Hiyama-Kishi (Furstner et al., *J. Am. Chem. Soc.* 1996, 118, 12349)) coupling reactions, reductive amination, Michael addition, cyclic carbonate alkylation (Parrish et al., Perspectives on Alkyl Carbonates in Organic Synthesis, *Tetrahedron*, 2000, 56, 8207-8237), nucleophilic substitution with expoxides, Willgerodt-Kindler reaction, or Huisgen cycloaddition (Mundy et al., Name Reactions and Reagents in Organic Synthesis, 2005, Wiley-Interscience, 2 Ed.). Examples of the carbon-carbon bond or carbon-heteroatom bond formations are shown in FIGS. 2A and 2B. Thus, the appropriate reactive moieties are first incorporated into the desired amino acids, and then the peptide is subjected to reaction disorders to effect the formation of one or more staples.

In certain embodiments, the stapling step generates one stapled product as a preferred product. As used herein a "preferred product" refers to one constitutional isomer present as the major constituent in a mixture of isomers. In certain embodiments, a "preferred product" refers to one constitutional isomer present as a component in at least about 50%, 55%, 60%, 65%, 70%, 75%, 80%, 85%, 90%, 95%, 98%, or 99% of an isomeric mixture.

In certain embodiments, the method further comprises the step of:

(vii) modifying the double bond of the polypeptide of Formula (I-x) to provide a polypeptide of Formula (I-y):

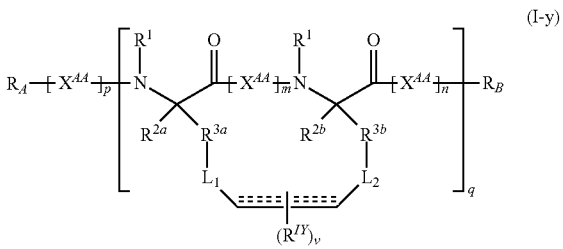

or a salt thereof, wherein $R_A$, $R_B$, $R^1$, $R^{2a}$, $R^{3a}$, $R^{2b}$, $R^{3b}$, $L_1$, $L_2$, $X_{AA}$, p, m, n, and q are as defined above, each instance of $R^{IY}$ is independently hydrogen, halogen, hydroxyl, nitro, alkoxy, —N($R^1$)$_2$, optionally substituted aliphatic, and v is 0, 1, or 2.

In certain embodiments, the method further comprises the step of:

(vii) modifying the double bond of the polypeptide of Formula (VI-x) to provide a polypeptide of Formula (VI-y):

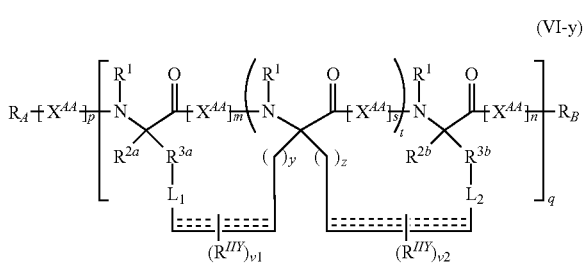

or a salt thereof, wherein $R_A$, $R_B$, $R^1$, $R^{2a}$, $R^{3a}$, $R^{2b}$, $R^{3b}$, $L_1$, $L_2$, $X_{AA}$, p, m, n, and q are as defined in Formula (VI), each instance of $R^{IIY}$ is independently hydrogen, halogen, hydroxyl, nitro, alkoxy, —N($R^1$)$_2$, optionally substituted aliphatic, and each of v1 and v2 is independently 0, 1, or 2.

One of ordinary skill in the art will appreciate that a wide variety of reactions, disorders, and reactive agents may be employed to promote such a transformation, therefore, a wide variety of reactions, disorders, and reactive agents are envisioned; see generally, *March's Advanced Organic Chemistry: Reactions, Mechanisms, and Structure*, M. B. Smith and J. March, 5th Edition, John Wiley & Sons, 2001; *Advance Organic Chemistry, Part B: Reactions and Synthesis*, Carey and Sundberg, 3rd Edition, Plenum Press, New York, 1993; and *Comprehensive Organic Transformations*, R. C. Larock, 2nd Edition, John Wiley & Sons, 1999, the entirety of each of which is hereby incorporated herein by reference. Exemplary reactive agents may be any agent reactive with double bond. In certain embodiments, reactive agents are able to react with a double bond, for example, via hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized staple. As one of ordinary skill in the art will clearly recognize, these above-described transformations will introduce functional groups compatible with the particular stabilized structures and the desired biological interactions. In particularly preferred embodiments, in but one example, the hydrophilicity of stabilized structures may be increased by the introduction of hydroxyl moieties. As one of ordinary skill in the art will realize, these synthetic modifications will be selected to introduce functionalities compatible with the particular stabilized structures and the desired biological interactions.

In certain embodiments, the polypeptide of Formula (I-x) is of the Formula (I-z1):

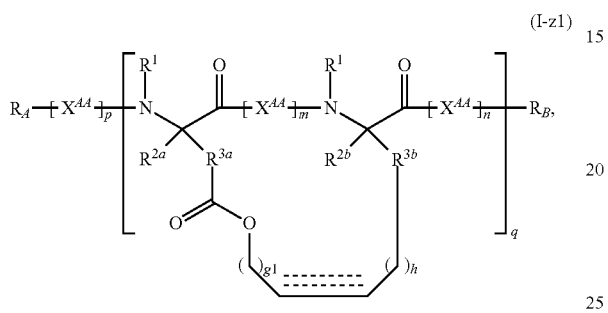

(I-z1)

wherein $R_A$, $R_B$, $R^1$, $R^{2a}$, $R^{3a}$, $R^{2b}$, $R^{3b}$, $L_1$, $L_2$, $X^{AA}$, p, m, n, q, g1, and h are as defined in Formula (I). In certain embodiments, the method does not further comprise the step of extruding —C(=O)O—. In certain embodiments, the method further comprises the step of:

(vii) extruding —C(=O)O— from Formula (I-z1) to provide a polypeptide of Formula (I-z):

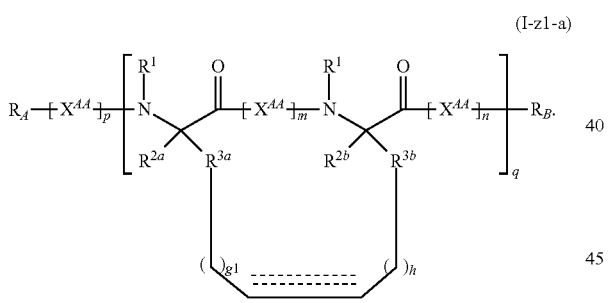

(I-z1-a)

In certain embodiments, the polypeptide of Formula (I-x) is of the Formula (I-z2):

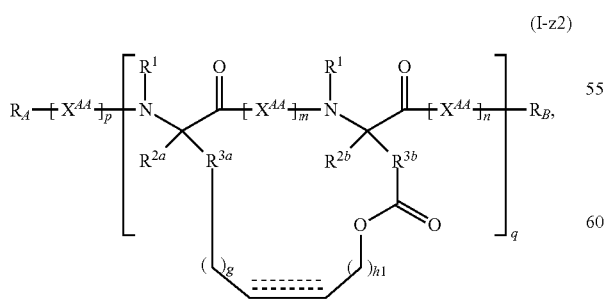

(I-z2)

wherein $R_A$, $R_B$, $R^1$, $R^{2a}$, $R^{3a}$, $R^{2b}$, $R^{3b}$, $L_1$, $L_2$, $X^{AA}$, p, m, n, q, g and h1 are as defined in Formula (I). In certain embodiments, the method does not further comprise the step of extruding —C(=O)O—. In certain embodiments, the method further comprises the step of:

(vii) extruding —C(=O)O— from Formula (I-z2) to provide a polypeptide of Formula (I-z):

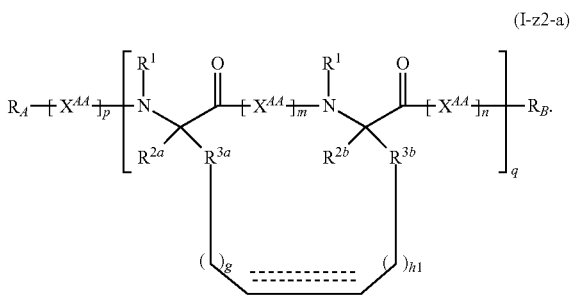

(I-z2-a)

In certain embodiments, the polypeptide of Formula (I-x) is of the Formula (I-z3):

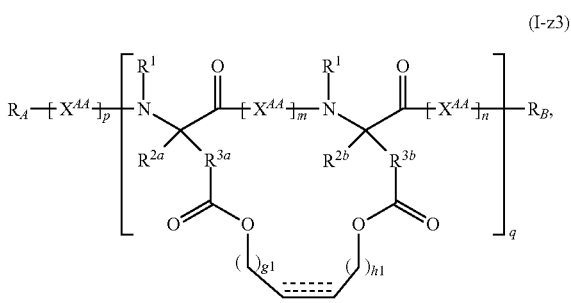

(I-z3)

wherein $R_A$, $R_B$, $R^1$, $R^{2a}$, $R^{3a}$, $R^{2b}$, $R^{3b}$, $L_1$, $L_2$, $X^{AA}$, p, m, n, q, g1 and h1 are as defined in Formula (I). In certain embodiments, the method does not further comprise the step of extruding —C(=O)O—. In certain embodiments, the method further comprises the step of:

(vii) extruding —C(=O)O— from Formula (I-z3) to provide a polypeptide of Formula (I-z1), Formula (I-z2), or Formula (I-z), or a mixture thereof:

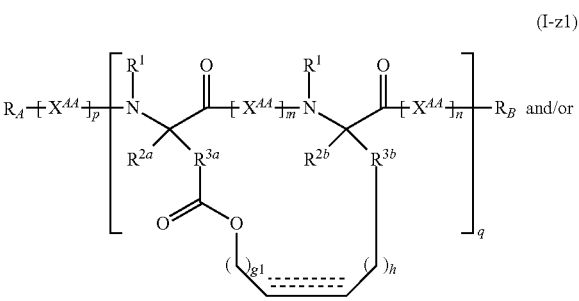

(I-z1)

and/or

-continued

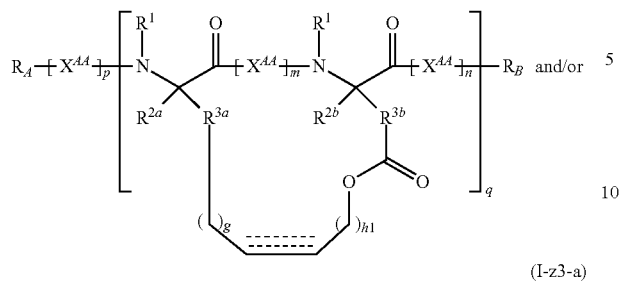
(I-z2)

and/or

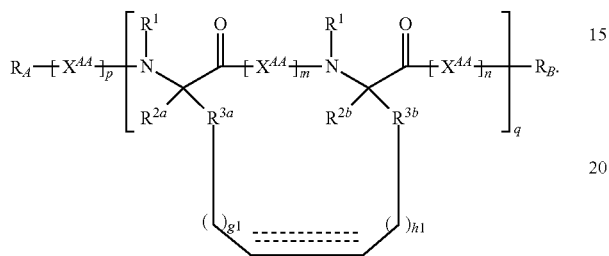
(I-z3-a)

In certain embodiments, the method further comprises the step of:

(vii) modifying the double bond of the polypeptide of Formula (VI-x) to provide a polypeptide of Formula (VI-y):

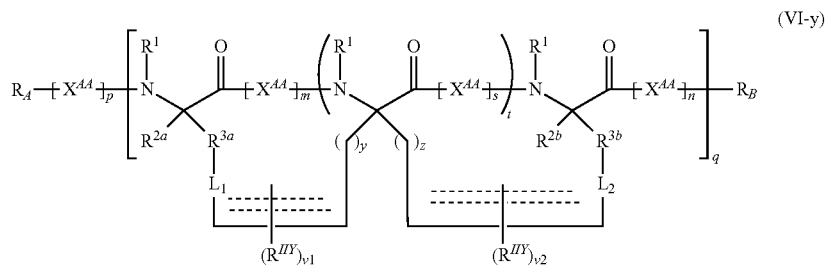
(VI-y)

or a salt thereof, wherein $R_A$, $R_B$, $R^1$, $R^{2a}$, $R^{3a}$, $R^{2b}$, $R^{3b}$, $L_1$, $L_2$, $X^{AA}$, p, m, n, and q are as defined in Formula (VI), each instance of $R^{IIY}$ is independently hydrogen, halogen, hydroxyl, nitro, alkoxy, $-N(R^1)_2$, optionally substituted aliphatic, and each of v1 and v2 is independently 0, 1, or 2.

In certain embodiments, the polypeptide of Formula (VI-x) is of the Formula (VI-z1)

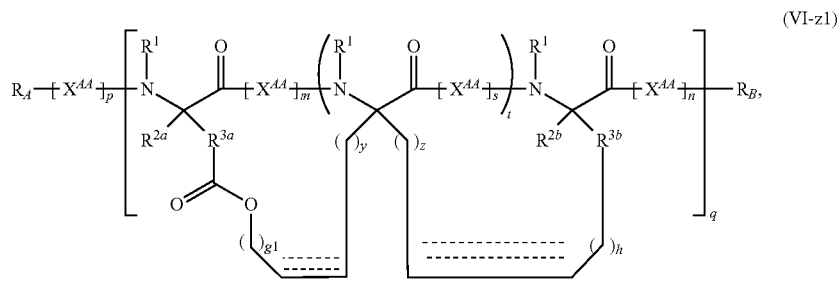
(VI-z1)

wherein $R_A$, $R_B$, $R^1$, $R^{2a}$, $R^{3a}$, $R^{2b}$, $R^{3b}$, $L_1$, $L_2$, $X^{AA}$, p, m, n, q, s, t, g1, and h are as defined in Formula (VI). In certain embodiments, the method does not further comprise the step of extruding $-C(=O)O-$. In certain embodiments, the method further comprises the step of:

(vii) extruding —C(=O)O— from Formula (VI-z1) to provide a polypeptide of Formula (VI-z):

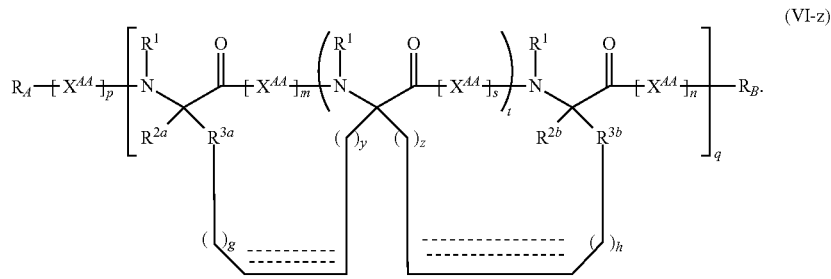

(VI-z)

In certain embodiments, the polypeptide of Formula (VI-x) is of the Formula (VI-z2)

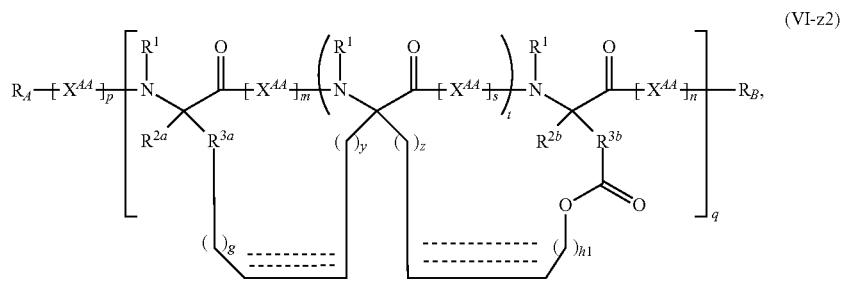

(VI-z2)

wherein $R_A$, $R_B$, $R^1$, $R^{2a}$, $R^{3a}$, $R^{2b}$, $R^{3b}$, $L_1$, $L_2$, $X^{AA}$, p, m, n, q, s, t, g and h1 are as defined in Formula (VI). In certain embodiments, the method does not further comprise the step of extruding —C(=O)O—. In certain embodiments, the method further comprises the step of:

(vii) extruding —C(=O)O— from Formula (VI-z2) to provide a polypeptide of Formula (VI-z):

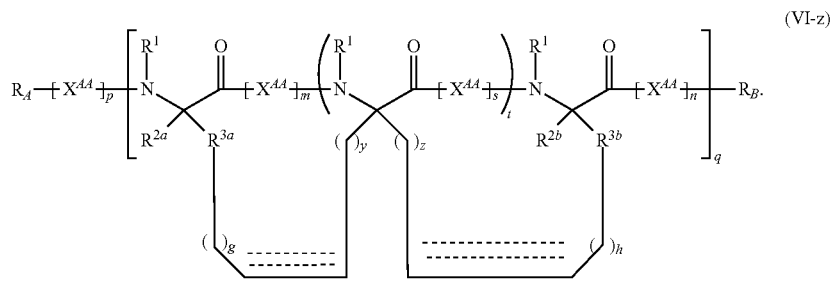

(VI-z)

In certain embodiments, the polypeptide of Formula (VI-x) is of the Formula (VI-z3)

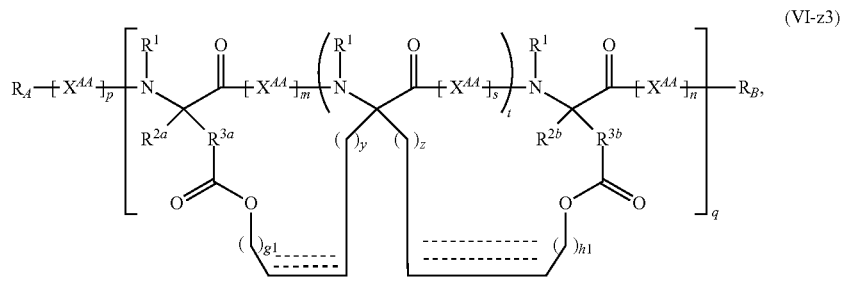

(VI-z3)

wherein $R_A$, $R_B$, $R^1$, $R^{2a}$, $R^{3a}$, $R^{2b}$, $R^{3b}$, $L_1$, $L_2$, $X^{AA}$, p, m, n, q, s, t, g1 and h1 are as defined in Formula (VI). In certain embodiments, the method does not further comprise the step of extruding —C(=O)O—. In certain embodiments, the method further comprises the step of:

(vii) extruding —C(=O)O— from Formula (VI-z3) to provide a polypeptide of Formula (VI-z1), Formula (VI-z2), or Formula (VI-z), or a mixture thereof:

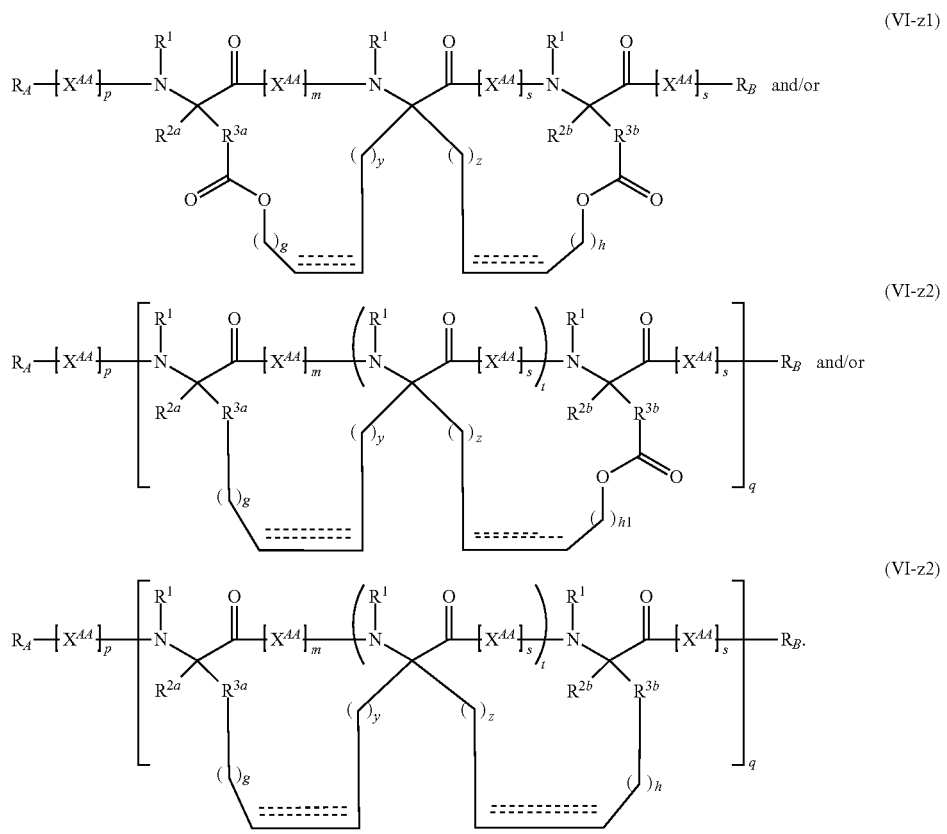

In certain embodiments, the catalyst for extruding —C(=O)O— is a palladium (Pd) catalyst. In certain embodiments, the catalyst for extruding —C(=O)O— is $Pd(PPh_3)_4$. In certain embodiments, the catalyst for extruding —C(=O)O— is a Ruthenium catalyst. In certain embodiments, the catalyst for extruding —C(=O)O— is [Cp*RuCl]$_4$, [Cp*RuCl]4 with bpy, or [Cp*RuCl]$_4$ with TMEDA. In certain embodiments, the catalyst for extruding —C(=O)O— is a transition metal catalyst. In certain embodiments, the catalyst for extruding —C(=O)O— is [Ir(COD)Cl]$_2$ or Ni[P(OEt)$_3$]4. In certain embodiments, the catalyst for extruding —C(=O)O— is a Group VI metal catalyst. In certain embodiments, the catalyst for extruding —C(=O)O— is Mo(CO)$_6$-dppe. (See Chemical Reviews, (2011), 111, 1846-1913; Tet. Lett., 2007, 48(40). 7084-7098; Chemistry Letters, (1984), 1721-1724; Synlett, (2005), 18, 2759-2762).

In certain embodiments, the stapling method can be any one listed in FIGS. 2A and 2B.

In another aspect, in certain embodiments, the above method further comprises activating the inventive polypeptide of Formula (I) or Formula (VI), followed by conjugation with a therapeutically active agent to provide polypeptide of Formula (I) or Formula (VI) conjugated to therapeutically active agent.

Furthermore, in another aspect, in certain embodiments, the above method further comprises treating the polypeptide of Formula (I) or Formula (VI) with a label to provide a polypeptide of Formula (I) or Formula (VI) conjugated to a label.

In another aspect, in certain embodiments, the above method further comprises treating the polypeptide of Formula (I) or Formula (VI) with a diagnostic agent to provide a polypeptide of Formula (I) or Formula (VI) conjugated to a diagnostic agent.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, and electrostatic interactions. An indirect covalent interaction is when two entities are covalently connected, optionally through a linker group.

Conjugation of an agent (e.g., a label, a diagnostic agent, a therapeutically active agent) to the inventive polypeptide may be achieved in a variety of different ways. The agent may be covalently conjugated, directly or indirectly, to the polypeptide at the site of stapling, or to the N-terminus or the C-terminus of the polypeptide chain. Alternatively, the agent may be noncovalently conjugated, directly or indirectly, to the polypeptide at the site of stapling, or to the N-terminus or the C-terminus of the polypeptide chain. Indirect covalent conjugation is by means of one or more covalent bonds. Indirect noncovalent conjugation is by means of one or more noncovalent bonds. Conjugation may also be via a combination of non-covalent and covalent forces/bonds. The agent may also be conjugated through a covalent or non-covalent linking group.

Any bond may be used in the conjugation of a therapeutically active agent, label, and/or diagnostic agent to the inventive polypeptide present invention. Such bonds include amide linkages, ester linkages, disulfide linkages, carbon-carbon bonds, carbamate, carbonate, urea, hydrazide, and the like. In some embodiments, the bond is cleavable under physiological disorders (e.g., enzymatically cleavable, cleavable with a high or low pH, with heat, light, ultrasound, x-ray). However, in some embodiments, the bond is not cleavable.

It will also be appreciated by one of ordinary skill in the art that the synthetic method as described above can also be applied to combinatorial synthesis of inventive polypeptides. Although combinatorial synthesis techniques can be applied in solution, it is more typical that combinatorial techniques are performed on the solid phase using split-and-pool techniques. During the course of the combinatorial synthesis, various parameters can be varied, including, but not limited to placement of amino acids with terminally unsaturated side chains, stereochemistry of amino acids, terminally unsaturated side chain length and functionality, and amino acid residues utilized.

Methods of Use and Treatment

The present invention provides a method of treating a disorder in a subject in need thereof, comprising administering to the subject an effective amount of a polypeptide of Formula (I)-(X), or a salt thereof.

The present invention provides a method of treating a disorder in a subject in need thereof, comprising instructing the subject to take an effective amount of a polypeptide of Formula (I)-(X), or a salt thereof.

The present invention also provides a polypeptide of Formula (I)-(X), or salt thereof, for use in treating a disorder.

As used herein, a "disease" or "disorder" are used interchangeably.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from a disorder which reduces the severity of the disorder or retards or slows the progression of the disorder ("therapeutic treatment"), and also contemplates an action that occurs before a subject begins to suffer from the disorder and which inhibits or reduces the severity of the disorder ("prophylactic treatment").

In general, the "effective amount" of a compound refers to an amount sufficient to elicit the desired biological response, i.e., treating the disorder. As will be appreciated by those of ordinary skill in this art, the effective amount of a compound of the invention may vary depending on such factors as the desired biological endpoint, the pharmacokinetics of the compound, the disorder being treated, the mode of administration, and the age, health, and the subject. An effective amount encompasses therapeutic and prophylactic treatment.

As used herein, and unless otherwise specified, a "therapeutically effective amount" of a compound is an amount sufficient to provide a therapeutic benefit in the treatment of the disorder or to delay or minimize one or more symptoms associated with the disorder. A therapeutically effective amount of a compound means an amount of therapeutic agent, alone or in combination with other therapies, which provides a therapeutic benefit in the treatment of the disorder. The term "therapeutically effective amount" can encompass an amount that improves overall therapy, reduces or avoids symptoms or causes of the disorder, or enhances the therapeutic efficacy of another therapeutic agent.

As used herein, and unless otherwise specified, a "prophylactically effective amount" of a compound is an amount sufficient to prevent the disorder, or one or more symptoms associated with the disorder or prevent its recurrence. A prophylactically effective amount of a compound means an amount of a therapeutic agent, alone or in combination with other agents, which provides a prophylactic benefit in the prevention of the disorder. The term "prophylactically effective amount" can encompass an amount that improves overall prophylaxis or enhances the prophylactic efficacy of another prophylactic agent.

Exemplary disorders include, but are not limited to, proliferative disorders, neurological disorders, immunological disorders, endocrinologic disorders, cardiovascular disorders, hematologic disorders, inflammatory disorders, and disorders characterized by premature or unwanted cell death.

As used herein, a proliferative disorder includes, but is not limited to, cancer, hematopoietic neoplastic disorders, proliferative breast disease, proliferative disorders of the lung, proliferative disorders of the colon, proliferative disorders of the liver, and proliferative disorders of the ovary.

Exemplary cancers include, but are not limited to, carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, and Kaposi's sarcoma.

Exemplary hematopoietic neoplastic disorders include, but are not limited to, disorders involving hyperplastic/neoplastic cells of hematopoietic origin, e.g., arising from myeloid, lymphoid or erythroid lineages, or precursor cells thereof. In certain embodiments, the disorders arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T-cell lymphomas, adult T cell leukemia/lymphoma (ATL), cutaneous T-cell lymphoma (CTCL), large granular lymphocytic leukemia (LGF), Hodgkin's disease, and Reed-Stemberg disease.

Exemplary proliferative breast diseases include, but are not limited to, epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Exemplary proliferative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Exemplary proliferative disorders of the colon include, but are not limited to, non-neoplastic polyps, adenomas, familial syndromes, colorectal carcinogenesis, colorectal carcinoma, and carcinoid tumors.

Exemplary proliferative disorders of the liver include, but are not limited to, nodular hyperplasias, adenomas, and malignant tumors, including primary carcinoma of the liver and metastatic tumors.

Exemplary proliferative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The polypeptides described herein can also be used to treat, prevent or diagnose disorders characterised by overactive cell death or cellular death due to physiologic insult. Some examples of disorders characterized by premature or unwanted cell death, or alternatively unwanted or excessive cellular proliferation, include, but are not limited to hypocellular/hypoplastic, acellular/aplastic, or hypercellular/hyperplastic disorders. Such disorders include but not limited to fanconi anemia, aplastic anemia, thalaessemia, congenital neutropenia, myelodysplasia. The polypeptides of the invention that act to decrease apoptosis can be used to treat disorders associated with an undesirable level of cell death. Thus, the anti-apoptotic peptides of the invention can be used to treat disorders such as those that lead to cell death associated with viral infection, e.g., infection associated with infection with human immunodeficiency virus (HIV).

A wide variety of neurological diseases are characterized by the gradual loss of specific sets of neurons, and the anti-apoptotic peptides can be used in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these disorders does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. The anti-apoptotic peptides of the invention can be used to treat all such disorders associated with undesirable cell death.

Some examples of neurologic disorders that can be treated with the polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, Huntington's Disease, Pick's Disease, Amyotrophic Lateral Schlerosis (ALS), Parkinson's Disease, and Lewy Body Disease.

Some examples of endocrinologic disorders that can be treated with the polypeptides described herein include but are not limited to diabetes, hypothyroidism, hypopituitarism, hypoparathyroidism, hypogonadism, fertility disorders.

Some examples of immunologic disorders that can be treated with the polypeptides described herein include but are not limited to organ transplant rejection, arthritis, lupus, inflammatory bowel disease (IBD), Crohn's disease, asthma, multiple sclerosis, diabetes, graft versus host diseases, auto-immune diseases, psoriasis, rheumatoid arthritis.

Examples of cardiovascular disorders that can be treated or prevented with the polypeptides of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular disorder associated with interventional procedures ("procedural vascular trauma"), such as restenosis following angioplasty, placement of a shunt, stent, synthetic or natural excision grafts, indwelling catheter, valve or other implantable devices.

The inventive polypeptides may serve to treat the above-described disorders, by disrupting native protein-protein, protein-ligand, and/or protein-receptor interactions. For example, many biologically important protein/protein interactions, such as p53/MDM2 and Bcl-X1/Bak, are mediated by one protein donating a helix into a cleft of its helix-accepting partner. The interaction of p53 and MDM2 and mutations in the p53 gene have been identified in virtually half of all reported cancer cases (see, Shair *Chem. & Biol.* 1997, 4, 791, the entire contents of which are incorporated herein by reference). As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic alpha-helix of 2.5 turns that inserts into the MDM2 crevice.

Thus, in certain embodiments, an inventive polypeptide is an alpha helical polypeptide that is capable of binding tightly to a helix acceptor and disrupting native protein/protein interactions. These structures may then be screened using high throughput techniques to identify optimal small molecule peptides. In certain embodiments, an inventive polypeptide is an alpha helical p53 polypeptide capable of binding to the *Xenopus* MDM2 protein. The novel structures that disrupt the MDM2 interaction might be useful for many applications, including, but not limited to, control of soft tissue sarcomas (which overexpresses MDM2 in the presence of wild type p53). These cancers may be held in check with small molecules that could intercept MDM2, thereby preventing suppression of p53. Additionally, small molecules disrupters of MDM2-p53 interactions could be used as adjuvant therapy to help control and modulate the extent of the p53 dependent apoptosis response in conventional chemotherapy.

In addition, the inventive polypeptides may be useful in the area of materials science. For example, molecules such as lipids and other polymeric molecules may be attached to the peptides and thus generate biomaterials.

In addition to the above-mentioned uses, the inventive polypeptides may be used for studies in bioinorganic chemistry or in catalysis, either as a ligand for a transition metal capable of mimicking an important biological environment, or by acting in concert with a particular transition metal catalyst to effect a desired chemical reaction.

The present invention further provides a method of altering a biological pathway in a cell comprising treating the cell with a polypeptide of Formula (I)-(X), or salt thereof. Such a method comprises in vitro or in vivo methods. Such a polypeptide may be useful as a research tool, e.g., for cellular assays.

The present invention provides pharmaceutical compositions comprising a polypeptide of the Formula (I)-(X), or a salt thereof, and a pharmaceutically acceptable excipient. Pharmaceutical compositions comprise compositions for therapeutic use as well as cosmetic compositions. Such compositions may optionally comprise one or more additional therapeutically active agents. In accordance with some embodiments, a method of administering a pharmaceutical composition comprising an inventive composition to a subject in need thereof is provided. In some embodiments, the inventive composition is administered to humans. For the purposes of the present invention, the "active ingredient" generally refers to a polypeptide of the Formula (II), as described herein.

Although the descriptions of pharmaceutical compositions provided herein are principally directed to pharmaceutical compositions for administration to humans, it will be understood by the skilled artisan that such compositions are generally suitable for administration to animals of all sorts. Modification of pharmaceutical compositions for administration to various animals is well understood, and the ordinarily skilled veterinary pharmacologist can design and/or perform such modification with merely ordinary, if any, experimentation.

Pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the invention will vary, depending upon the identity, size, and/or disorder of the subject treated and further depending upon the route by which the composition is to be administered. By way of example, the composition may comprise between 0.1% and 100% (w/w) active ingredient.

As used herein, a pharmaceutically acceptable excipient includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by the United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the Formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of this invention may include ointments, pastes, creams, lotions, gels, powders, solutions, sprays, inhalants and/or patches. Generally, the active component is admixed under sterile disorders with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Alternatively or additionally, conventional syringes may be used in the classical mantoux method of intradermal administration.

Formulations for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Inventive polypeptides provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject will depend upon a variety of factors including the disease, disorder, or disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The polypeptide of Formula (I)-(X), salt thereof, or pharmaceutical composition thereof, may be administered by any route. In some embodiments, the polypeptide of Formula (II), salt thereof, or pharmaceutical composition thereof, are administered by a variety of routes, including oral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), and the disorder of the subject (e.g., whether the subject is able to tolerate oral administration). At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, polypeptide of Formula (II), salt thereof, or pharmaceutical composition thereof, may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. The exact amount of an inventive polypeptide required to achieve an effective amount will vary from subject to subject, depending, for example, on species, age, and general disorder of a subject, severity of the side effects or disorder, identity of the particular compound(s), mode of administration, and the like.

In some embodiments, the present invention encompasses "therapeutic cocktails" comprising inventive polypeptides. In some embodiments, the inventive polypeptide comprises a single species which can bind to multiple targets. In some embodiments, different inventive polypeptides comprise different targeting moiety species, and all of the different targeting moiety species can bind to the same target. In some embodiments, different inventive polypeptides comprise different targeting moiety species, and all of the different targeting moiety species can bind to different targets. In some embodiments, such different targets may be associated with the same cell type. In some embodiments, such different targets may be associated with different cell types.

It will be appreciated that inventive polypeptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

Pharmaceutical compositions of the present invention may be administered either alone or in combination with one or more therapeutically active agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body. It will further be appreciated that therapeutically active agent and the inventive polypeptides utilized in this combination may be administered together in a single composition or administered separately in different compositions.

The particular combination employed in a combination regimen will take into account compatibility of the therapeutically active agent and/or procedures with the inventive polypeptide and/or the desired therapeutic effect to be achieved. It will be appreciated that the combination employed may achieve a desired effect for the same disorder (for example, an inventive polypeptide may be administered concurrently with another therapeutically active agent used to treat the same disorder), and/or they may achieve different effects (e.g., control of any adverse effects).

As used herein, a "therapeutically active agent" refers to any substance used as a medicine for treatment, prevention, delay, reduction or amelioration of a disorder, and refers to a substance that is useful for therapy, including prophylactic and therapeutic treatment. A therapeutically active agent also includes a compound that increases the effect or effectiveness of another compound, for example, by enhancing potency or reducing adverse effects of the compound of Formula (I) or (VI).

In certain embodiments, a therapeutically active agent is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), or inhibitors/intercalators of DNA, RNA, protein-protein interactions, protein-receptor interactions.

In some embodiments, inventive pharmaceutical compositions may be administered in combination with any therapeutically active agent or procedure (e.g., surgery, radiation therapy) that is useful to treat, alleviate, ameliorate, relieve, delay onset of, inhibit progression of, reduce severity of, and/or reduce incidence of one or more symptoms or features of cancer.

Kits

The invention also provides a variety of kits comprising one or more of the polypeptides of the invention. For example, the invention provides a kit comprising an inventive polypeptide and instructions for use. A kit may comprise multiple different polypeptides. A kit may comprise any of a number of additional components or reagents in any combination. All of the various combinations are not set forth explicitly but each combination is included in the scope of the invention.

According to certain embodiments of the invention, a kit may include, for example, (I) one or more inventive polypeptides and, optionally, one or more particular therapeutically active agents to be delivered; (ii) instructions for administration to a subject in need thereof.

Kits typically include instructions which may, for example, comprise protocols and/or describe disorders for production of inventive polypeptides, administration of inventive polypeptides to a subject in need thereof, design of novel inventive polypeptide. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, may be enclosed. An identifier, e.g., a bar code, radio frequency identification (ID) tag, may be present in or on the kit or in or one or more of the vessels or containers included in the kit. An identifier can be used, e.g., to uniquely identify the kit for purposes of quality control, inventory control, tracking, movement between workstations.

In order that the invention described herein may be more fully understood, the following examples are set forth. It should be understood that these examples are for illustrative purposes only and are not to be construed as limiting this invention in any manner.

EXAMPLES

In order that the invention described herein may be more fully understood, the following examples are set forth. It should be understood that these examples are for illustrative purposes only and are not to be construed as limiting this invention in any manner.

Example 1

Preparation of amino acid 1 is shown in Scheme 1:

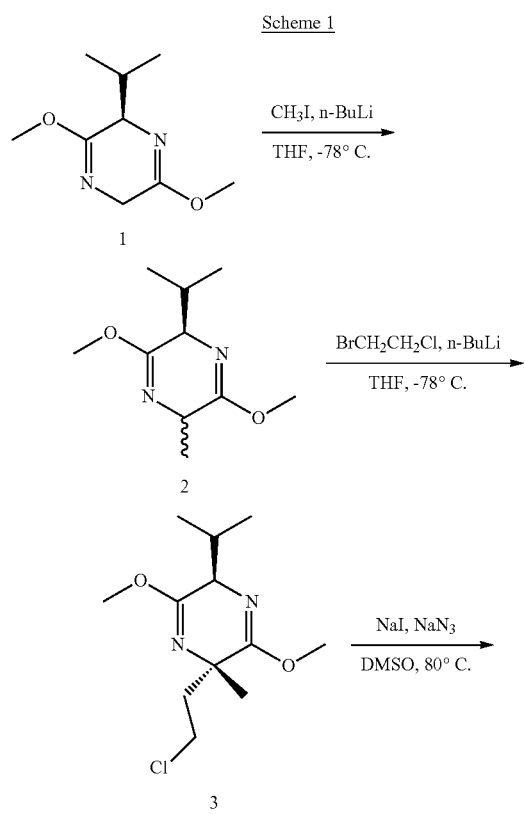

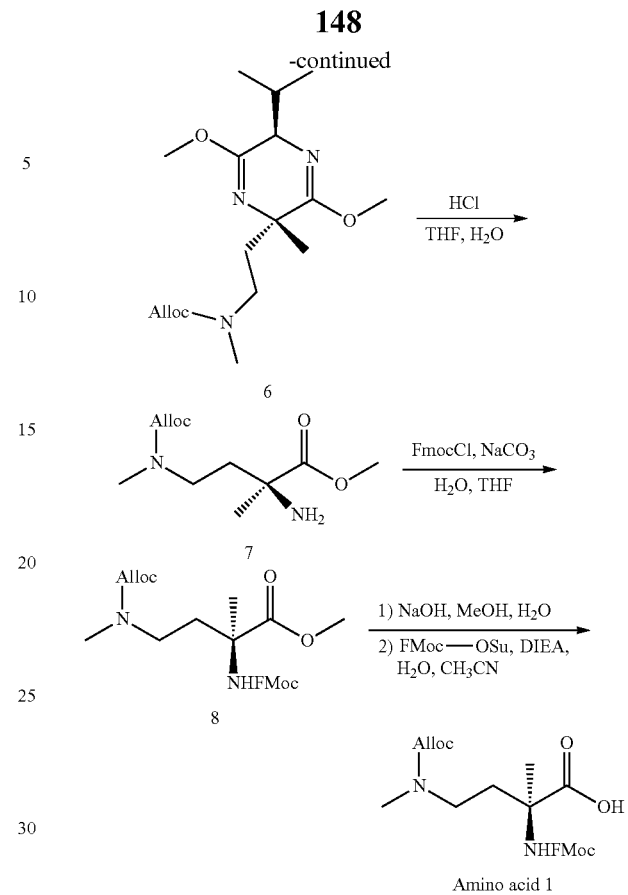

Synthetic Procedures:

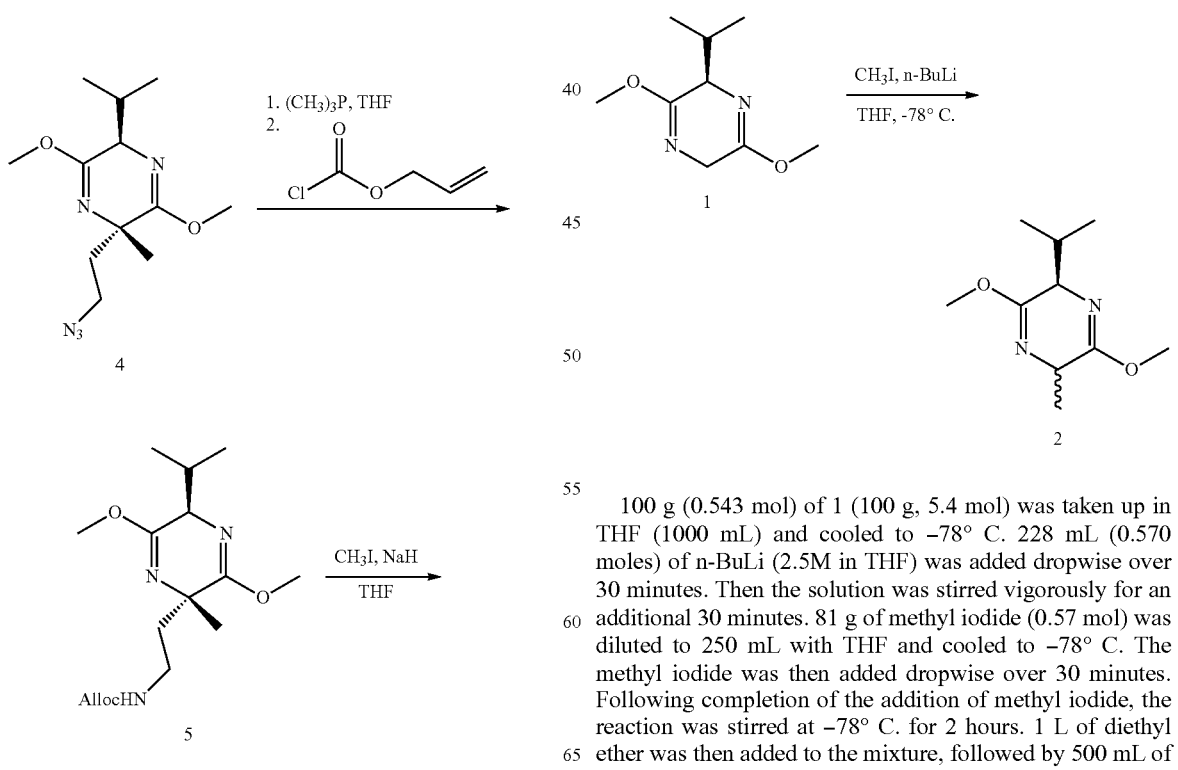

100 g (0.543 mol) of 1 (100 g, 5.4 mol) was taken up in THF (1000 mL) and cooled to −78° C. 228 mL (0.570 moles) of n-BuLi (2.5M in THF) was added dropwise over 30 minutes. Then the solution was stirred vigorously for an additional 30 minutes. 81 g of methyl iodide (0.57 mol) was diluted to 250 mL with THF and cooled to −78° C. The methyl iodide was then added dropwise over 30 minutes. Following completion of the addition of methyl iodide, the reaction was stirred at −78° C. for 2 hours. 1 L of diethyl ether was then added to the mixture, followed by 500 mL of $H_2O$. The reaction was then warmed to room temperature. The aqueous layer was extracted multiple times with diethyl ether and the organic layer were combined, washed with saturated sodium thiosulfate, once with brine, and dried over MgSO₄. The organics were concentrated under vacuum to give residue which was purified by chromatography with gradient of 50:1 to 20:1 petroleum ether: diethyl ether to yield 110 g (80.5%) of 2 (pale yellow oil). ¹H NMR: (400 MHz, CDCl3-d) ppm 0.60-0.72 (m, 3H), 0.94-1.03 (m, 3H), 1.26-1.35 (m, 3H), 2.07-2.30 (m, 1H), 3.53-3.70 (m, 6H), 3.89 (br. s., 2H).

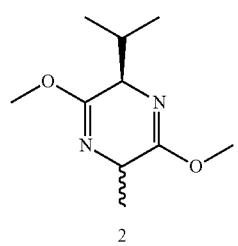

BrCH₂CH₂Cl, n-BuLi
THF, -78° C.

2

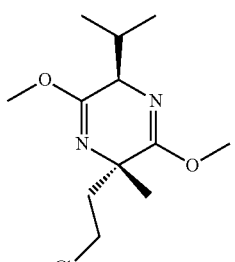

3

40 g (0.202 mol) of 2 was taken up in 400 mL of THF and cooled to −78° C. 85 mL (0.212 mol) of n-BuLi (2.5 M in THF) was added dropwise over 20 minutes. The solution was then stirred vigorously for an additional 40 minutes. 30 g of 1-bromo-2-chloroethane (0.212 moles) was diluted to 200 mL in THF and cooled to −78° C. The 1-bromo-2-chloroethane was then added dropwise over 90 minutes. Following completion of addition of the 1-bromo-2-chloroethane, the reaction was stirred at −78° C. for an additional 90 minutes. 500 mL of diethyl ether were added to the reaction, followed by 500 mL of H₂O. The reaction was then warmed to room temperature. The aqueous layer was extracted with diethyl ether and the combined organics were washed once with H₂O and once with brine then dried over Na₂SO₄. Then the combined organic layer was concentrated under vacuum to give residue which was purified by chromatography (petroleum ether: diethyl ether=50:1) to afford product 3 as pale yellow oil (36 g yield 70%). ¹H NMR: (400 MHz, CDCl3-d) ppm 0.61 (d, J=6.78 Hz, 3H), 1.00 (d, J=6.78 Hz, 3H), 1.23-1.32 (m, 3H), 1.91-2.02 (m, 1H), 2.11-2.32 (m, 2H), 3.13-3.34 (m, 2H), 3.60 (d, J=7.53 Hz, 6H), 3.80-3.95 (m, 1H).

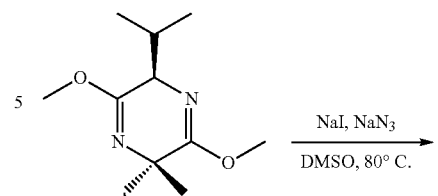

3

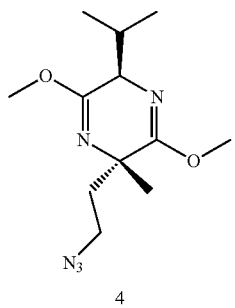

4

To a solution of 3 (20 g, 0.075 mol) in DMSO (300 mL) was added NaI (33 g, 0.226 mol) and NaN₃ (15 g, 226 mmol) at 25° C., then the mixture solution was stirred at 80° C. overnight. Then the solution was cooled and water was added, extracted with diethyl ether (150 ml*3), washed with brine (50 ml), dried over Na₂SO₄ and concentrated under vacuum to afford crude product, used in next step directly.

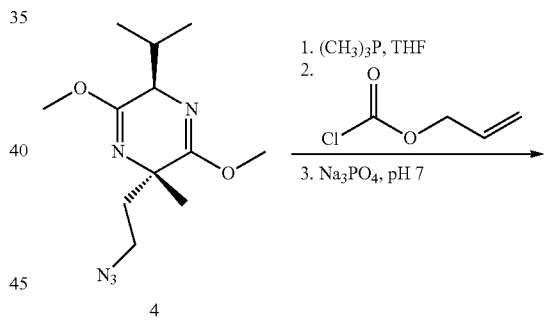

4

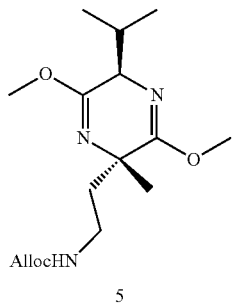

5

19 g (0.0711 mol) of 4 was taken up in 300 mL of THF and stirred at room temperature. 71 mL (0.0711 mol) of (CH₃)₃P (1M in THF) was then added by syringe over a few minutes. After stirring for 45 minutes, 9.2 mL (0.850 mol) of allyl chloroformate was added and the reaction was stirred for an additional 60 minutes at room temperature. 100 mL of 0.4 M K₃PO₄ was then added to convert the phosphonium intermediate to 5. The product was extracted multiple times with DCM, and the combined organics were washed with brine, dried over Na$_2$SO$_4$, and concentrated under vacuum to give residue. The resulting yellow oil was purified by chromatography on silica gel using 3:1 petroleum ether: ethyl acetate to yield 17 g (71.0%, three steps) of 5 as colorless oil. $^1$H NMR: (400 MHz, CDCl3-d) ppm 0.62 (d, J=7.03 Hz, 3H), 1.00 (d, J=6.78 Hz, 3H), 1.26 (s, 3H), 1.68-1.78 (m, 1H), 1.91-2.01 (m, 1H), 2.11-2.23 (m, 1H), 2.96-3.14 (m, 2H), 3.60 (d, J=3.76 Hz, 6H), 3.85-3.92 (m, 1H), 4.46 (br. s., 2H), 5.08-5.20 (m, 2H), 5.77-5.95 (m, 1H).

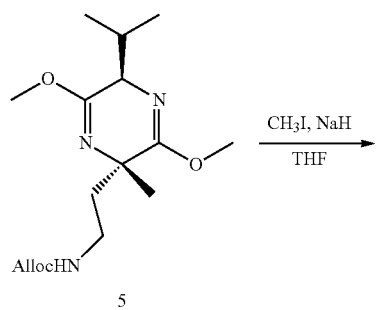

5

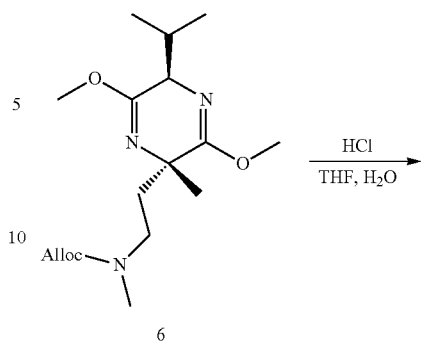

6

To a solution of 6 (6 g, 17.7 mmol) in THF (50 ml) was added HCl/H$_2$O (150 ml, 0.25N) at 18° C. Then the mixture solution was stirred at 18° C. for overnight, then basified with aq. NaOH to pH=8, extracted with DCM, washed with brine, dried over Na$_2$SO$_4$, and concentrated under vacuum to afford residue which was used in next step directly.

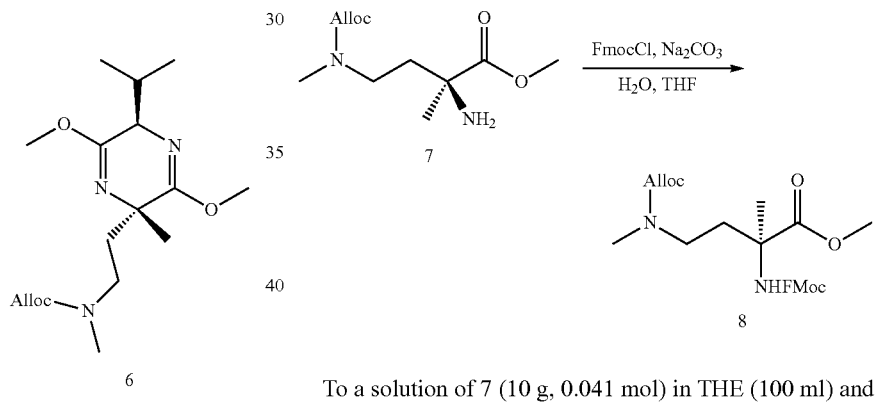

17 g (0.052 mol) of 5 was taken up in 300 mL of THF and stirred at room temperature. 3.12 g (0.078 mol) of NaH (60% dispersion in mineral oil) were added. After the reaction was stirred for 10 minutes, 23 g (0.156 moles) of CH$_3$I was added by syringe over 5 minutes. After stirred for 3 hours, the reaction was quenched by the addition of water, and the product was extracted multiple times with diethyl ether. The combined organics were washed with H$_2$O, saturated sodium thiosulfate, brine, dried over Na$_2$SO$_4$ and concentrated under vacuum to give residue which was purified by chromatography on silica gel (5:1 petroleum ether: ethyl acetate) to yield 13 g (73.1%) of 6 (a slightly yellow oil). $^1$H NMR: (400 MHz, CDCl3-d) ppm 0.64-0.73 (m, 3H), 1.02-1.11 (m, 3H), 1.28-1.38 (m, 3H), 1.68-1.82 (m, 1H), 1.99-2.12 (m, 1H), 2.18-2.39 (m, 1H), 2.76-2.89 (m, 3H), 2.97-3.25 (m, 2H), 3.67 (s, 6H), 3.90-4.04 (m, 1H), 4.46-4.70 (m, 2H), 5.14-5.22 (m, 1H), 5.25-5.36 (m, 1H), 5.81-6.02 (m, 1H).

To a solution of 7 (10 g, 0.041 mol) in THF (100 ml) and H$_2$O (100 ml) was added Na$_2$CO$_3$ (8.7 g, 0.087 mol) and FmocCl (10.3 g, 0.082 mol) at 10° C., then the mixture solution was stirred at 10° C. for 0.5 hour, extracted with ethyl acetate multiple, washed with H$_2$O, brine and concentrated under vacuum to give crude, which was purified by chromatography on silica gel (petroleum ether: ethyl acetate=15:1) to afford product as colorless oil (8.5 g, 45%). 1H NMR: (400 MHz, CDCl3-d) ppm 1.48-1.60 (m, 3H), 2.01-2.20 (m, 1H), 2.23-2.50 (m, 1H), 2.75 (br. s., 3H), 2.96-3.39 (m, 2H), 3.69 (br. s., 3H), 4.04-4.21 (m, 1H), 4.23-4.41 (m, 2H), 4.43-4.55 (m, 2H), 5.04-5.15 (m, 1H), 5.15-5.20 (m, 1H), 5.23 (s, 2H), 5.60-5.99 (m, 2H), 7.21-7.28 (m, 2H), 7.33 (t, J=7.40 Hz, 2H), 7.55 (br. s., 2H), 7.70 (d, J=7.53 Hz, 2H).

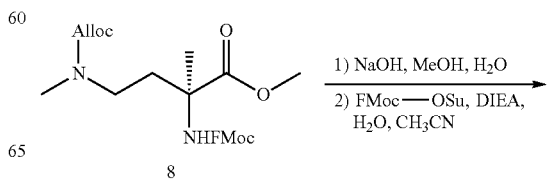

153

-continued

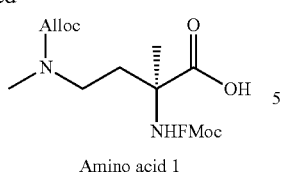

Amino acid 1

To a solution of 8 (8.5 g, 0.0183 mol) in MeOH (80 ml) and H$_2$O (80 ml) was added NaOH (4.38 g, 0.109 mol) at 12° C., and then the mixture was stirred under 12° C. overnight. The mixture solution was acidified with 1N HCl to pH=4, then the solvent was removed under vacuum and dissolved with MeCN (15 ml) and H$_2$O (15 ml), Fmoc-OSu (9.3 g, 0.0275 mol) and DIEA (9.5 g, 0.0732 mol) was added at 12° C., then the mixture solution was stirred at room temperature overnight, extracted with ethyl acetate, washed with 1N HCl, washed with brine and concentrated under vacuum to give crude product, which was purified by chromatography on silica gel (petroleum ether: ethyl acetate=10:1 to 1:1) to afford product as pale solid. The product was separated using SFC to afford final product as pale solid (3.8 g, 44%). $^1$H NMR: WH10057-012-1D1 (400 MHz, DMSO-d$_6$) ppm 1.35 (br. s., 3H), 1.81-1.97 (m, 1H), 1.99-2.20 (m, 1H), 2.79 (d, J=12.05 Hz, 3H), 3.09-3.28 (m, 2H), 4.17-4.33 (m, 3H), 4.41-4.60 (m, 2H), 4.97-5.40 (m, 2H), 5.78-6.08 (m, 1H), 7.35 (d, J=7.53 Hz, 2H), 7.43 (s, 2H), 7.49-7.57 (m, 1H), 7.68-7.77 (m, 2H), 7.90 (d, J=7.53 Hz, 2H), 12.37-12.75 (m, 1H). LCMS: WH10057-012-1B3 (M+1: 232.13). SFC: WH10057-012-1B2_2 ee=100%.

Example 2

Preparation of amino acid 2 is shown in Scheme 2:

Scheme 2

154

-continued

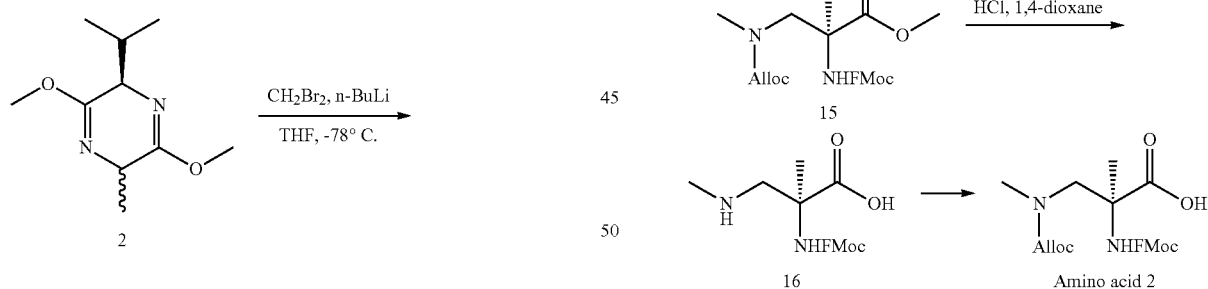

Synthetic Procedures:

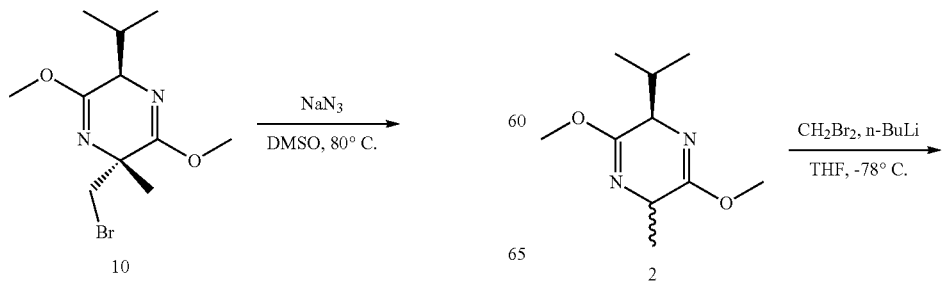

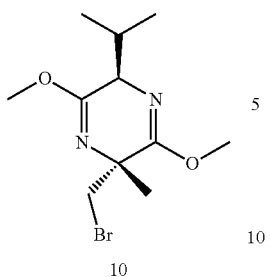

10

78.5 g (396.42 mmol) of synthetic intermediate 2 was taken up in 1.1 L of THF and cooled to −78° C. 436 mL (436 mmol) of n-BuLi (2.5 M in Hexanes) was then added dropwise over 10 minutes, and the reaction was then stirred at −78° C. for an additional 60 minutes. 203 g (1.189 mol) of dibromomethane was taken up in 200 mL of THF and cooled to −78° C. The solution of dibromomethane in THE was then added to the reaction dropwise over 40 minutes. After completion of the addition, the reaction was stirred while allowing it to warm to −20° C. over 3 hours. At the end of this three hours, TLC analysis indicated the reaction was virtually complete and diethyl ether and H$_2$O were added and the reaction was warmed to room temperature. The organics were collected, and the aqueous layer contained no product. The organics were then washed with H$_2$O, brine, dried over MgSO$_4$ and concentrated under reduced pressure. The resulting yellow oil was chromatographed on silica gel to yield 95 g (82.7%) of Compound 10 (slightly yellow oil). $^1$H NMR WH10098-005-1A (400 MHz, CHLOROFORM-d) 0.61 (d, J=6.78 Hz, 3H), 1.02 (d, J=6.78 Hz, 3H), 1.38 (s, 3H), 2.13-2.32 (m, 1H), 3.33 (d, J=9.29 Hz, 1H), 3.63 (d, J=7.03 Hz, 6H), 3.69 (d, J=9.54 Hz, 1H), 3.96 (d, J=3.26 Hz, 1H).

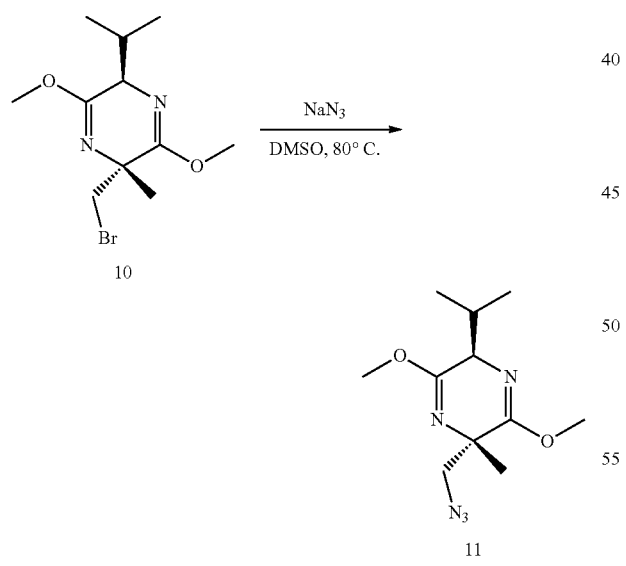

40 g (137 mol) of Compound 10 was taken up in 400 mL of DMSO. 24 g (369 mmol) of NaN$_3$ was added and the reaction was heated to 80° C. and stirred for >24 hours, until TLC analysis (20:1 Hexanes:Ethyl Acetate) confirmed the consumption of Compound 11. After cooling to room temperature, H$_2$O was added to the reaction and the product was then extracted multiple times with DCM. The combined organics were dried over MgSO$_4$ and concentrated under reduced pressure to give oil. The result oil was used directly to the next step. LCMS: WH10098-007-1A (M+1=254.2)

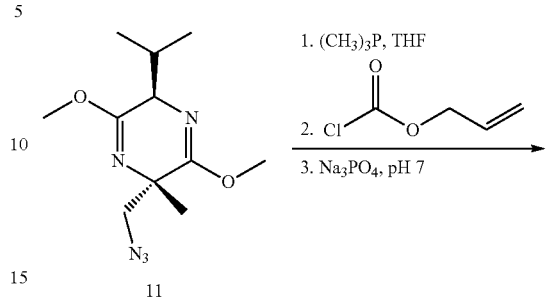

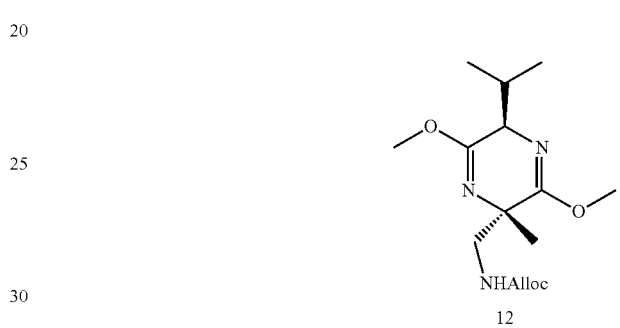

17.3 (68.5 mmol) of compound 11 was taken up in 160 mL of THF and stirred at room temperature. 70 mL (70 mmol) of (CH$_3$)$_3$P (1M in THF) was then added by syringe over a few minutes. After stirring for 45 minutes, 8.8 mL (70 mmol) of allyl chloroformate was added and the reaction was stirred for an additional 60 minutes at room temperature. 600 mL of 0.4 M Na$_3$PO$_4$ (pH7) was then added to convert the phosphonium intermediate to compound 12. The product was extracted multiple times with DCM, and the combined organics were washed with brine, dried over Na$_2$SO$_4$, and concentrated under reduced pressure. The resulting yellow oil was chromatographed on silica gel using 10:1 Hexanes:Ethyl Acetate to yield 13 g (62%) of compound 12 (a colorless oil). $^1$HNMR: (400 MHz, CHLOROFORM-d) 0.71 (d, J=6.78 Hz, 3H), 0.83-0.93 (m, 1H), 1.09 (d, J=6.78 Hz, 3H), 1.33 (s, 3H), 2.26 (dq, J=10.29, 6.78 Hz, 1H), 3.30 (dd, J=12.92, 5.65 Hz, 1H), 3.54 (dd, J=12.92, 6.65 Hz, 1H), 3.68 (d, J=4.27 Hz, 6H), 3.99 (d, J=3.26 Hz, 1H), 4.50-4.64 (m, 2H), 4.82 (br. s., 1H), 5.19-5.38 (m, 2H), 5.92 (ddt, J=16.75, 10.98, 5.46, 5.46 Hz, 1H).

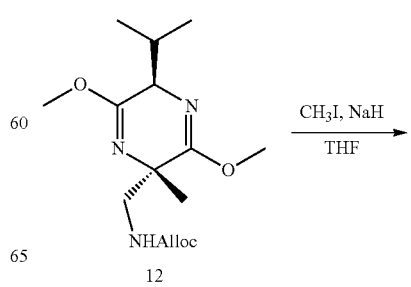

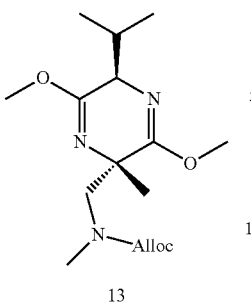

13

13 g (41.8 mmol) of compound 12 was taken up in 105 mL of THF and stirred at room temperature. 2.5 g (62.7 mmol) of NaH (60% dispersion in mineral oil) were added. After the reaction was stirred for 10 minutes, 17.8 g (125.4 mmol) of CH₃I were added by syringe over about 5 minutes. After 1 hour, TLC analysis (5:1 Hexanes:Ethyl Acetate) confirmed the reaction complete and the reaction was quenched by the addition of a saturated solution of KH₂PO₄. H₂O was then added to the solution, and the product was extracted multiple times with DCM. The combined organics were washed with H₂O, saturated sodium thiosulfate, brine, dried over Na₂SO₄ and concentrated under reduced pressure. The resulting yellow oil was chromatographed on silica gel (20:1 Hexanes:Ethyl Acetate) to yield 11.3 g (83.7%) of compound 13 (a slightly yellow oil). ¹HNMR: (400 MHz, CHLOROFORM-d) 0.58 (d, J=6.02 Hz, 3H), 0.99 (d, J=6.78 Hz, 3H), 1.24 (d, J=6.53 Hz, 3H), 1.62 (s, 1H), 2.20 (dtd, J=13.58, 6.70, 6.70, 3.39 Hz, 1H), 2.77 (s, 3H), 3.40-3.54 (m, 2H), 3.55-3.64 (m, 6H), 3.85 (br. s., 1H), 4.47 (br. s., 2H), 5.05-5.33 (m, 2H), 5.84 (d, J=5.02 Hz, 1H).

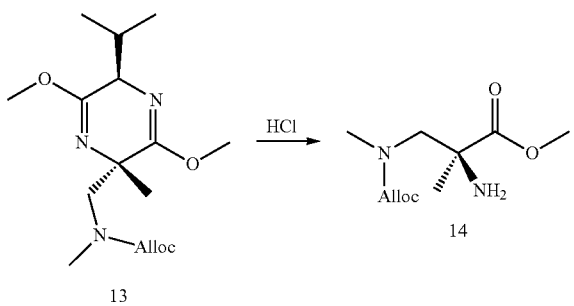

400 ml of 0.25 N HCl was added to the solution of compound 13 (10 g, 30 mmol) in 250 ml of THF and stirring was continued for overnight at 15° C. The excess of HCl and the THF was evaporated in vacuo and the crude compound 14 was obtained as oil which was used for the next step without further purification.

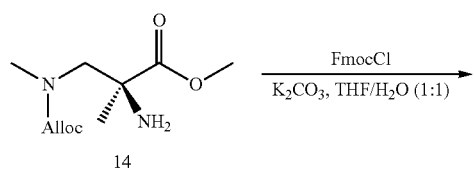

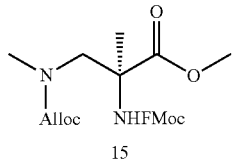

15

A mixture of compound 14 (9 g, crude), FmocCl (13.9 g, 54 mmol, 2 eq.), K₂CO3 (7.45 g, 54 mmol, 2 eq.) in THF (135 ml) and water (135 ml) was stirred at room temperature for 5 h, until TLC analysis (1:1 Hexanes:Ethyl Acetate) confirmed the consumption of compound 15 (9 g, 74%). ¹HNMR: WH10098-011-1A 1H NMR (400 MHz, CHLOROFORM-d) 1.52-1.73 (m, 3H), 2.81 (br. s., 3H), 3.45-3.90 (m, 5H), 4.17 (d, J=6.53 Hz, 1H), 4.20-4.40 (m, 2H), 4.54 (br. s., 2H) 5.05-5.32 (m, 2H), 5.86 (d, J=10.29 Hz, 1H), 7.20-7.27 (m, 2H), 7.33 (t, J=7.40 Hz, 2H), 7.53 (d, J=5.52 Hz, 2H), 7.69 (d, J=7.53 Hz, 2H).

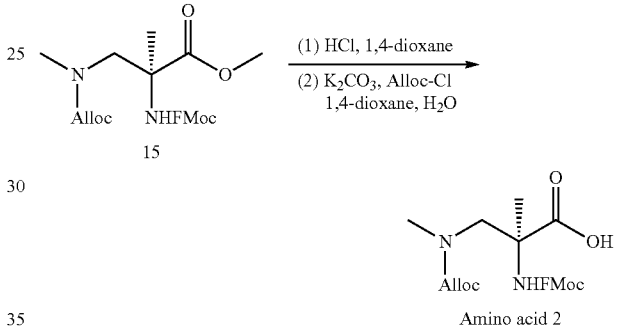

A 6N hydrochloric acid aqueous solution (32 ml) was added to a stirred solution of compound 15 (8 g, 17.6 mmol, 1 eq.) in dioxane (160 ml) at room temperature. And then the mixture was stirred at reflux for 2 d. Only 50% product was found by LC-MS. And about 40% de-Alloc by product was also detected by LC-MS. So the mixture was cooled to room temperature, and acidified with NaOH (1 mol/L) until the pH=8, dioxane was removed under reduce pressure and the aqueous residue was extracted with EtOAc(3*200 ml). The organic extracted were combined, dried over Na₂SO₄, filter and concentrated under reduce pressure to give a mixture of compound 2 (8.1 g). The mixture of amino acid 2 (8.1 g) was dissolved in dioxane (100 ml), H₂O (200 ml). And then K₂CO₃ (12.96 g, 2 eq.), Alloc-Cl (2.835 g, 1.5 eq.) was added. The mixture was stirred at 10° C. for overnight. The reaction was acidified with aqueous HCl (1 mol/L) till pH=7. And the mixture was concentrated under reduced pressure to dryness to provide an oil. The crude product was purified by chromatographed on silica gel using 1:1 Hexanes:Ethyl Acetate to yield 7 g (91%) of amino acid 2 (a colorless oil, ee 80%). The enantiomer was purified by SFC to give the s of amino acid 2 (5 g, ee>99%) as a colorless solid.

¹HNMR: (400 MHz, DMSO-d6) 1.23 (br. s., 3H), 2.64-2.84 (m, 3H), 3.18 (d, J=5.02 Hz, 1H), 3.49-3.69 (m, 1H), 3.86 (d, J=14.05 Hz, 1H), 4.17-4.32 (m, 2H), 4.36-4.59 (m, 3H), 5.09-5.34 (m, 2H), 5.91 (d, J=10.04 Hz, 1H), 7.30-7.36 (m, 2H), 7.38-7.47 (m, 2H), 7.61 (br. s., 1H), 7.66-7.77 (m, 2H), 7.89 (d, J=7.28 Hz, 2H), 12.64 (br. s., 1H). LCMS: WH10098-029-1C (M+1=439.2).

Example 3

Preparation of amino acids 3 and 4 is shown in Scheme 3:

Scheme 3:

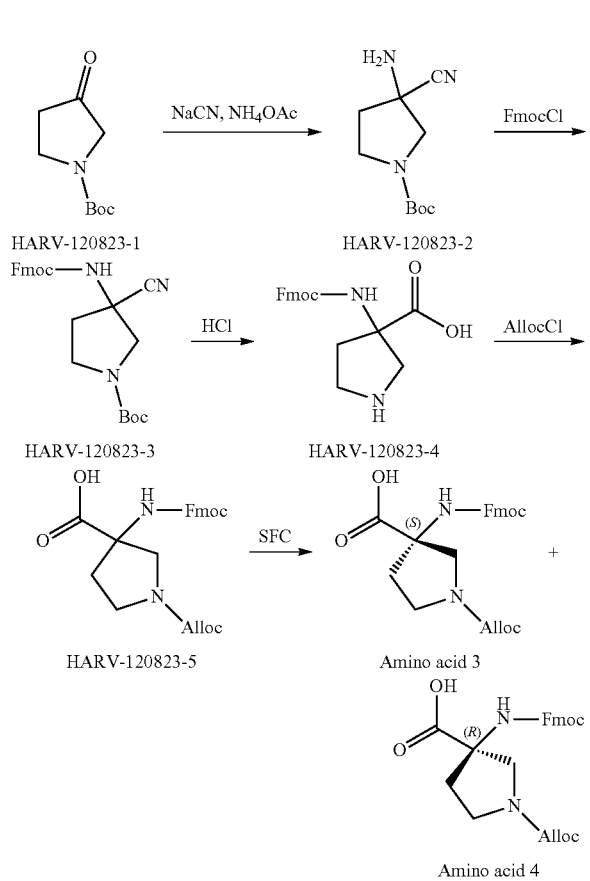

Synthetic Procedure:

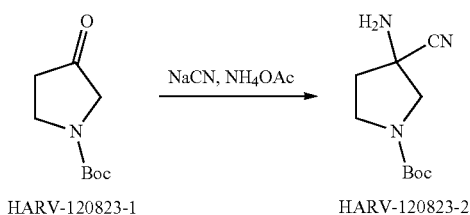

To a solution of HARV-120823-1 (80 g, 0.432 mol) and NH₄OAc (46.61 g, 0.605 mol) in MeOH (1000 mL) was added NaCN (21.71 g, 0.432 mol) at room temperature. After the addition, the mixture was stirred at room temperature overnight. TLC (Petroleum ether/EtOAc=3/1) showed the reaction was complete. The mixture was concentrated and water (300 mL) was added. The mixture was extracted with DCM (3*450 mL). The combined organic layer was washed with brine, dried over Na₂SO₄ and concentrated under reduced pressure to give crude HARV-120823-2. The crude product was dissolved HCl aqueous (<1N) and extracted with DCM. The aqueous layer was added NaHCO₃ to adjust pH=8 and extracted with DCM. The organic layer was dried over Na₂SO₄ and concentrated under reduced pressure to give pure product HARV-120823-2 (85 g, yield: 93%). 1HNMR (CDCl₃, 400 MHz, WH10085-001-1A): δ 3.76-3.73 (m, 1H), 3.61-3.43 (m, 3H), 2.34-2.32 (m, 1H), 1.82 (s, 2H), 1.45 (s, 9H).

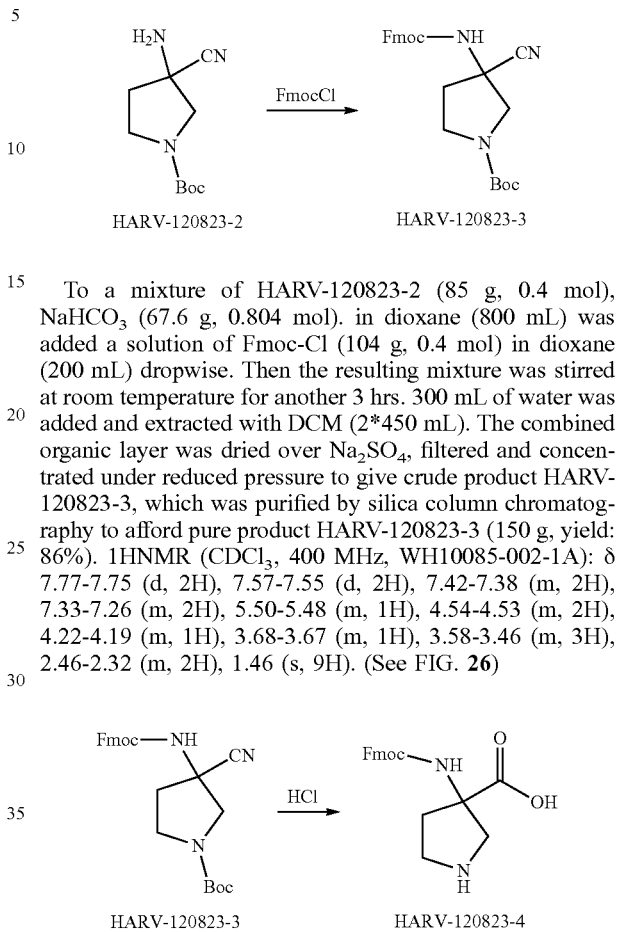

To a mixture of HARV-120823-2 (85 g, 0.4 mol), NaHCO₃ (67.6 g, 0.804 mol). in dioxane (800 mL) was added a solution of Fmoc-Cl (104 g, 0.4 mol) in dioxane (200 mL) dropwise. Then the resulting mixture was stirred at room temperature for another 3 hrs. 300 mL of water was added and extracted with DCM (2*450 mL). The combined organic layer was dried over Na₂SO₄, filtered and concentrated under reduced pressure to give crude product HARV-120823-3, which was purified by silica column chromatography to afford pure product HARV-120823-3 (150 g, yield: 86%). 1HNMR (CDCl₃, 400 MHz, WH10085-002-1A): δ 7.77-7.75 (d, 2H), 7.57-7.55 (d, 2H), 7.42-7.38 (m, 2H), 7.33-7.26 (m, 2H), 5.50-5.48 (m, 1H), 4.54-4.53 (m, 2H), 4.22-4.19 (m, 1H), 3.68-3.67 (m, 1H), 3.58-3.46 (m, 3H), 2.46-2.32 (m, 2H), 1.46 (s, 9H). (See FIG. 26)

A solution of HARV-120823-3 (150 g, 0.346 mol) in concentrated aqueous HCl (1000 mL) was stirred for 20 mins at room temperature. Then the mixture was heated to reflux overnight. The mixture was concentrated under reduced pressure to give 120 g of crude product HARV-120823-4 which was used directly for next step without further purification.

1HNMR (DMSO, 400 MHz, WH10085-005-1A): δ 7.90-7.84 (m, 2H), 7.74-7.65 (m, 2H), 7.44-7.29 (m, 4H), 4.38-4.31 (m, 1H), 4.29-4.22 (m, 2H), 3.74-3.29 (m, 4H), 2.36-2.29 (m, 1H), 2.21-2.13 (m, 1H).

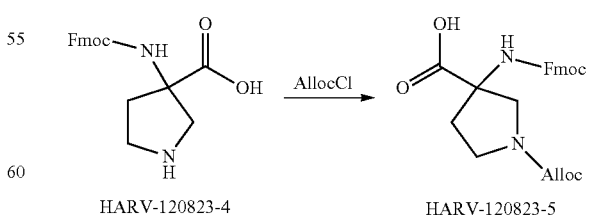

To a solution of HARV-120823-4 (100 g, 0.284 mol) in CH₃CN (200 mL) was added pyridine to adjust pH=7. Then the mixture was stirred for 30 min. Then Alloc-Cl (34.21 g, 0.284 mol) was added drop-wise. After the addition, the resulting mixture was stirred for 1 h. The mixture was concentrated and the residue was dissolved in DCM, washed with HCl solution, separated the organic layer and dried over Na₂SO₄, concentrated to give crude product HARV-120823 which was purified by silica column chromatography to afford the pure product HARV-120823 (80 g, yield: 75%). 1HNMR (CDCl₃, 400 MHz, WH10085-006-1A): δ 7.76-7.74 (d, 2H), 7.57-7.56 (d, 2H), 7.41-7.38 (m, 2H), 7.32-7.29 (m, 2H), 5.93-5.89 (m, 1H), 5.32-5.19 (m, 2H), 4.59 (m, 2H), 4.43 (m, 2H), 4.20-4.18 (m, 1H), 4.00-3.93 (m, 1H), 3.76-3.54 (m, 3H), 2.53-2.27 (m, 2H).

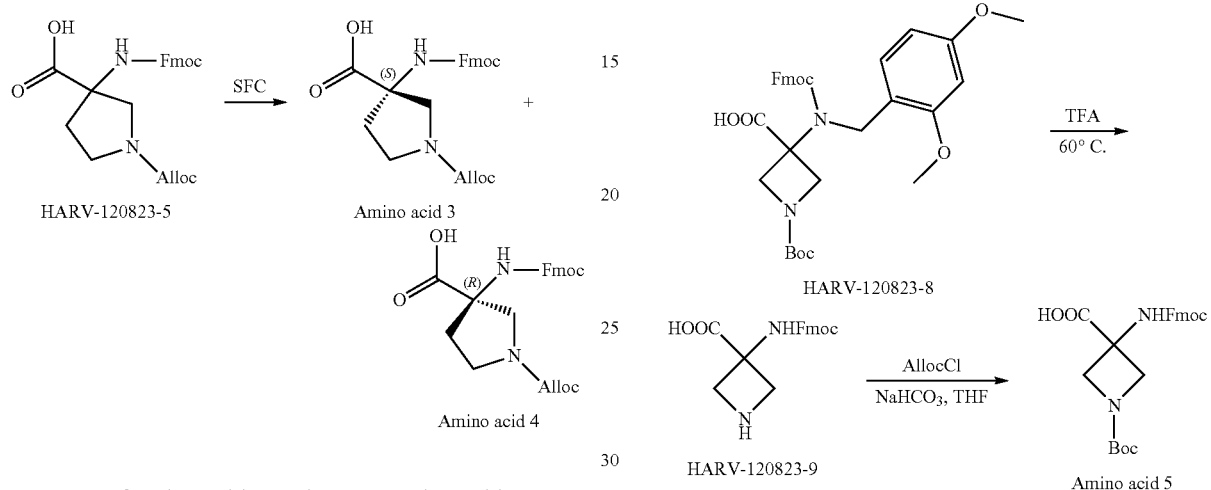

5.06 g of amino acid 3 and 5.07 g amino acid 4. were obtained by Chiral Separation. 1HNMR (DMSO, 400 MHz, WH10085-006-2F): δ 12.91 (brs, 1H); 8.067-8.054 (d, J=5.2 Hz, 1H), 7.90-7.88 (d, 2H), 7.71-7.69 (d, 2H), 7.43-7.39 (m, 2H), 7.35-7.31 (m, 2H), 5.96-5.86 (m, 1H), 5.31-5.15 (m, 2H), 4.53-4.52 (m, 2H), 4.32-4.30 (m, 2H), 4.24-4.21 (m, 1H), 3.83-3.63 (m, 1H), 3.61-3.51 (m, 3H), 2.23-2.17 (m, 2H).

Example 4

Preparation of amino acid 5 is shown in Scheme 3:

Scheme 4

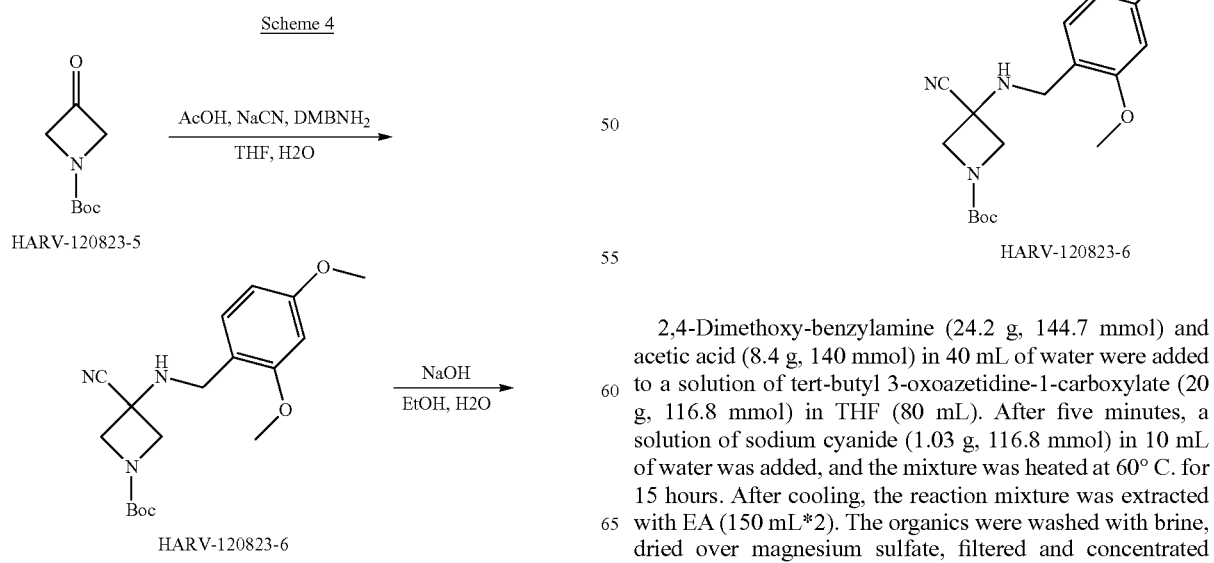

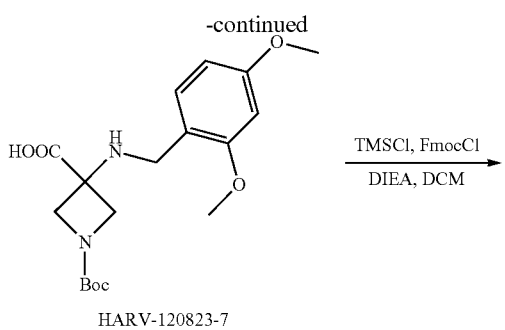

Synthetic Procedure:

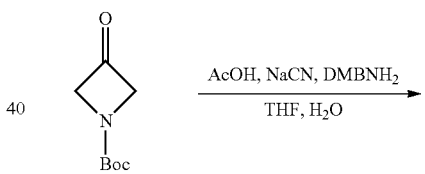

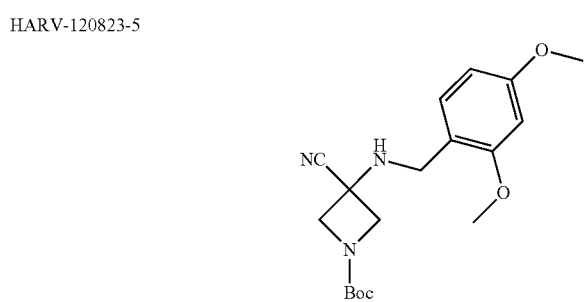

2,4-Dimethoxy-benzylamine (24.2 g, 144.7 mmol) and acetic acid (8.4 g, 140 mmol) in 40 mL of water were added to a solution of tert-butyl 3-oxoazetidine-1-carboxylate (20 g, 116.8 mmol) in THF (80 mL). After five minutes, a solution of sodium cyanide (1.03 g, 116.8 mmol) in 10 mL of water was added, and the mixture was heated at 60° C. for 15 hours. After cooling, the reaction mixture was extracted with EA (150 mL*2). The organics were washed with brine, dried over magnesium sulfate, filtered and concentrated under reduced pressure. The resulting residue was purified on a silica gel column using PE/EA=20/1~5/1 to give 35 g product as a pale yellow oil (yield 86.24%).

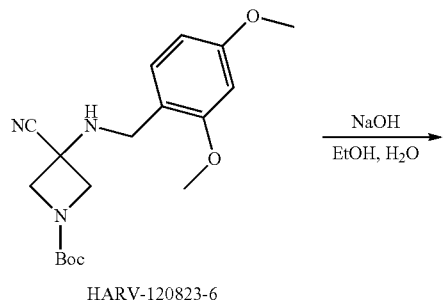
HARV-120823-6

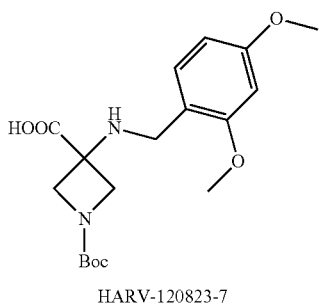
HARV-120823-7

To a solution of 3-cyano-3-(2,4-dimethoxy-benzylamino)-azetidine-1-carboxylic acid tert-butyl ester (35 g, 100 mmol) in ethanol (400 mL) was added NaOH (12.09 g, 300 mmol). The mixture was stirred at room temperature for 16 hours. Then an aqueous solution of NaOH (200 mL, 5 M) was added, the mixture was stirred at 90° C. for 2 h. LCMS showed starting material was consumed. After cooling to room temperature, the residue was neutralized to pH-6 with acetic acid. The precipitate was filtered, washed with water and dried in vacuo to give 30 g product (yield 81.27%). $^1$HNMR (400 MHz, DMSO-d6, WH10085-004-1A) δ 7.22 (d, J=8.4 Hz, 1H), 6.54 (s, 1H), 6.49 (d, J=8.0 Hz, 1H), 4.12-4.08 (m, 2H), 3.78-3.75 (m, 8H), 3.67 (s, 2H), 1.38 (s, 9H).

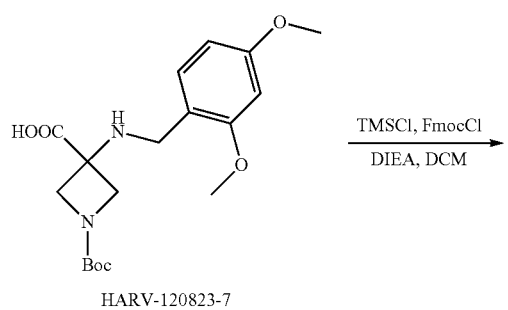
HARV-120823-7

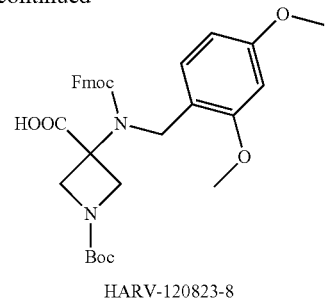
HARV-120823-8

To a solution of 3-(2,4-Dimethoxy-benzylamino)-azetidine-1,3-dicarboxylic acid mono-tert-butyl ester (21 g, 57.31 mmol) in DCM (200 mL) was added TMSCl (6.23 g, 57.31 mmol), FmocCl (14.83 g, 57.31 mmol) and DIEA (14.81 g, 114.63 mmol). The mixture was stirred at room temperature for 30 minutes, TLC and LCMS showed the starting material was consumed. Then water was added and the mixture was extracted with DCM (3×150 mL). The combined organic layers were washed with sat. NaHCO$_3$ and brine, dried over MgSO4 and concentrated to give the residue, which was used directly for the next step.

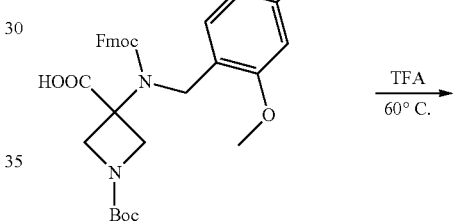
HARV-120823-8

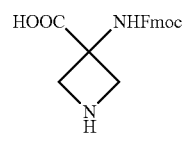
HARV-120823-9

3-[(2,4-Dimethoxy-benzyl)-(9H-fluoren-9-ylmethoxycarbonyl)-amino]-azetidine-1,3-dicarboxylic acid mono-tert-butyl ester (30 g, 51 mmol) in CF$_3$COOH (200 mL) was stirred at 60° C. for 16 hours. LCMS showed the starting material was consumed. After cooling to room temperature, the mixture was concentrated to give residue used directly for the next step.

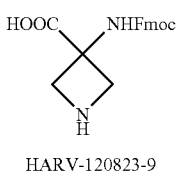
HARV-120823-9

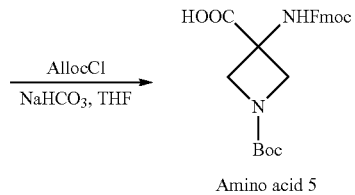
Amino acid 5

To a solution of 3-(9H-Fluoren-9-ylmethoxycarbonylamino)-azetidine-3-carboxylic acid (30 g, 88.66 mmol) in THF (200 mL) were added sat. NaHCO$_3$ (40 mL) and Alloc-Cl (11 g, 88.7 mmol). The mixture was stirred at room temperature for 30 minutes, TLC and LCMS showed the starting material was consumed. Then water was added and the mixture was extracted with DCM (3×150 mL). The combined organic layers were washed with sat. $NaHCO_3$, brine, dried over $MgSO_4$ and concentrated. The residue was purified by silica gel column (DCM:MeOH=100:1~5:1) to give 6.5 g product. (yield 30.2% for 3 steps). $^1$HNMR (400 MHz, DMSO-d6): 7.89 (d, J=7.6 Hz, 2H), 7.68 (d, J=7.2 Hz, 2H), 7.43-7.32 (m, 4H), 5.93-5.86 (m, 1H), 5.27 (d, J=17.2 Hz, 1H), 5.16 (d, J=14.4 Hz, 1H), 4.48 (d, J=5.2 Hz, 2H), 4.33 (d, J=6.4 Hz, 2H), 4.24 (t, J=6.4 Hz, 1H), 4.12-4.00 (m, 4H). MS: m/z 445.2 [M+Na]$^+$.

Example 5

Preparation of Stapled Peptides

Solid-Phase Peptide Synthesis: Peptides were prepared using Fmoc chemistry on one of the following resins: Rink Amide MBHA, Rink Amide MBHA Low Loading, PAL-NovaSyn TG, NovaPEG Rink Amide resin, or NovaPEG Rink Amide Low Loading Resin. The dry resin was typically swelled in dichloromethane and then N-methyl-2-pyrrolidone (NMP) before use. Fmoc protecting groups were removed using 25% (v/v) piperidine in NMP (4×5 min). Natural amino acids were typically coupled for 60 minutes using 4 equivalents of Fmoc-protected amino acid, 4 equivalents of (1-Cyano-2-ethoxy-2-oxoethylidenaminooxy)dimethylamino-morpholino-carbenium hexafluorophosphate (COMU) as the coupling reagent, and 8 equivalents of N,N-diisopropylethylamine (DIPEA) as the base. Non-natural amino acids (e.g. $S_5$, $Pyr_R$ et al. such as those shown in FIG. 10) were typically coupled for 120 minutes using 3 equivalents of Fmoc-protected amino acid, 3 equivalents of (1-Cyano-2-ethoxy-2-oxoethylidenaminooxy)dimethyl-amino-morpholino-carbenium hexafluorophosphate (COMU) as the coupling reagent, and 6 equivalents of N,N-diisopropylethylamine (DIPEA) as the base. NMP was used to wash the resin (5×1 min) in between each coupling and deprotection step.

N-terminal Acetylation: Peptides used for Circular Dichroism Spectroscopy (CD) were prepared with either free N-termini or acetylated N-termini. To acetylate the N-terminus on the solid phase, the N-terminal Fmoc was deprotected and the resin subsequently washed with NMP. Acetylation was typically carried out by treating the resin-bound peptide for 1-2 hours with a solution of 20 equivalents of acetic anhydride and 40 equivalents of DIPEA in NMP. After completion of the reaction, the resin was typically washed with NMP (5×1 min), DCM (3×1 min), and dried with methanol.

N-terminal labeling with Fluorescein Isothiocyanate Isomer I (FITC): Prior to labeling with FITC on the solid phase, Fmoc-p-alanine was coupled to the N-terminus of the peptides using procedures described above for natural amino acids. After subsequent deprotection of the N-terminal Fmoc, the resin-bound peptide was treated with a solution of 7 equivalents of FITC and 14 equivalents of DIPEA in NMP for 4 hours. After completion of the reaction, the resin was typically washed with NMP (5×1 min), DCM (3×1 min), and dried with methanol.

N-terminal labeling with 5-carboxyfluorescein (FAM): Prior to labeling with FAM on the solid phase, Fmoc-p-alanine was coupled to the N-terminus of the peptides using procedures described above for natural amino acids. After subsequent deprotection of the N-terminal Fmoc, the resin-bound peptide was typically treated with a solution in NMP of 8 equivalents of FAM, 8 equivalents of N,N-diisopropylcarbodiimide (DIC) and 8 equivalents of HOBT $H_2O$ for 2 hours. After the coupling reaction, the resin was washed with NMP (5×1 min) followed by 25% piperidine in NMP (3×10 min, or until the solution was no longer colored). After the final wash with 25% piperidine in NMP, the resin was typically washed with NMP (5×1 min), DCM (3×1 min), and dried with methanol.

Ring-Closing Metathesis: Ring-closing metathesis was performed on the solid phase on peptides that contained either an N-terminal acetyl cap or an N-terminal Fmoc using the following general procedure. The resin was swelled in dry 1,2-dichloroethane (DCE) for at least 20 minutes. The resin-bound peptide was then treated for 2 hours with 25 mole % (relative to the initial loading of the resin) of Grubbs $1^{st}$ Generation metathesis catalyst (Benzylidene-bis(tricyclohexylphosphine)dichlororuthenium, Bis(tricyclohexylphosphine)benzylidine ruthenium(IV) dichloride) dissolved to a concentration of approximately 8-10 mg/mL in DCE. Generally, 2 or 3 treatments with catalyst were used to achieve complete conversion to the hydrocarbon-stapled or alloc-stapled product. In between each treatment, excess catalyst was removed by washing with DCE (3×1 min). After the final treatment with catalyst, the resin was typically washed multiple times with DCE, multiple times with DCM, and dried with methanol.

Palladium-catalyzed $CO_2$ Extrusion: Resin containing alloc-stapled peptides prepared by ring closing metathesis using the above procedures was swelled in dry dichloromethane (DCM) for at least 20 minutes. The resin was then treated for 15-30 minutes with 20-40 mole % (relative to the moles of carbamates present in the staple, calculated relative to the initial loading of the resin) of $Pd(PPh_3)_4$ dissolved in dry DCM to a final concentration of approximately 5-10 mM. Typically, 2 treatments were performed to ensure complete reaction of the alloc-stapled starting material. In between each treatment, the resin was washed with dry DCM (3×1 min).

Peptide Cleavage/Deprotection and Purification: The side-chain protecting groups were removed and the peptides cleaved from the resin simultaneously using the following procedure. Dry resin was treated with a solution of trifluoroacetic acid:triisopropylsilane:water (95:2.5:2.5) for 3 hours. After completion of the incubation, the volume of the solution was reduced by evaporation under a stream of $N_{2(g)}$ and the resulting residue was treated with cold diethyl ether. The precipitated peptide was pelleted by centrifugation, the supernatant decanted, and the pellet air-dried. The crude peptides were typically dissolved in a 1:1 solution of acetonitrile:water and then purified by reverse phase HPLC using acetonitrile containing 0.1% (v/v) trifluoroacetic acid and water containing 0.1% (v/v) trifluoroacetic acid as the components of the mobile phase. The purity of the HPLC fractions was assessed by LC/MS, and clean fractions were pooled and concentrated by speedvac. The peptides were then lyophilized to dryness.

Liquid chromatography-mass spectrometry (LC/MS): The purified Alloc-stapled and amino-stapled peptides were analyzed by reverse-phase LC/MS using an Agilent 1260 series instrument and a Zorbax SB-C18 column. The mobile phase consisted of a gradient of acetonitrile and water, both containing 0.1% (v/v) trifluoroacetic acid.

Table 9 provides the electrospray mass spectral data (either under positive-ion or negative-ion mode) from LC/MS for the exemplary peptides.

TABLE 9

| Stapled peptide | m/z (positive ion or negative ion mode indicated) | Stapled peptide structure |
|---|---|---|
| Ac-SAH-p53-8 Pyr$_R$/S$_8$ amino-stapled | 2122.2 (M + H⁺) | |
| Ac-SAH-p53-8 R$_8$/Pyr$_S$ amino-stapled | 2122.2 (M + H⁺) | |

TABLE 9-continued

| Stapled peptide | m/z (positive ion or negative ion mode indicated) | Stapled peptide structure |
|---|---|---|
| Ac-SAH-p53-4 R$_8$/Pyr$_{15}$ amino-stapled | 2082.1 (M + H$^+$) | |
| Ac-SAH-p53-4 Pyr$_R$/S$_8$ amino-stapled | 2082.1 (M + H$^+$) | |

TABLE 9-continued
| Stapled peptide | m/z (positive-ion or negative-ion mode indicated) | Stapled peptide structure |
|---|---|---|
| FAM-b-ala-SAH-p53-8 Pyr$_R$/S$_8$ Amino-Stapled | 2509.2 (M + H$^+$) | 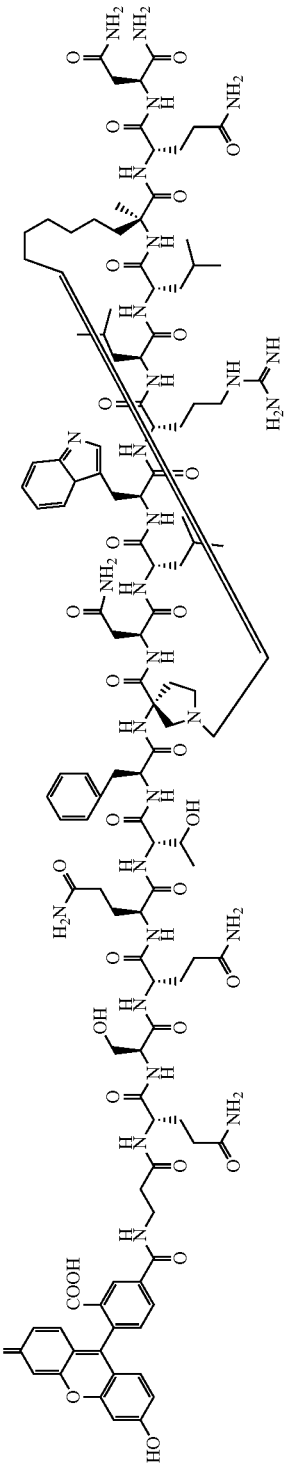 |
| FAM-b-ala-SAH-p53-8 R$_8$/Pyr$_S$ Amino-Stapled | 2509.2 (M + H$^+$) | 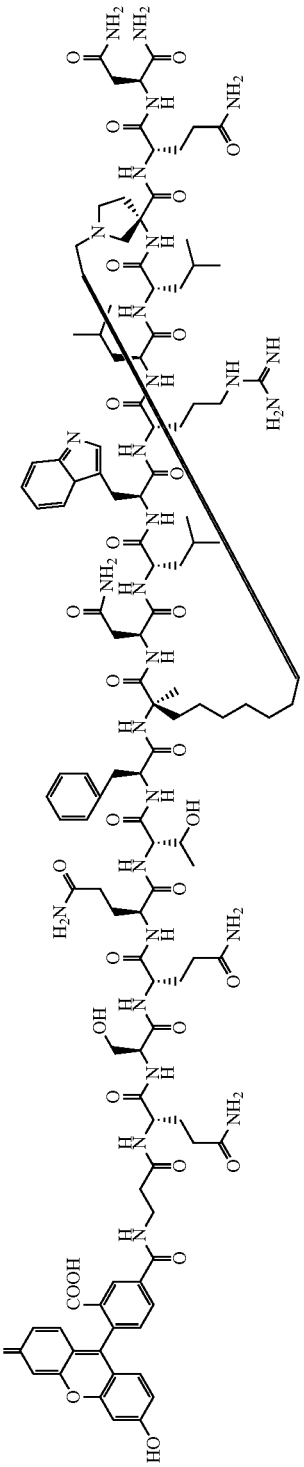 |

TABLE 9-continued
| Stapled peptide | m/z (positive ion or negative ion mode indicated) | Stapled peptide structure |
|---|---|---|
| FAM-b-ala-SAH-p53-4 Pyr$_R$/S$_8$ Amino-Stapled | 2469.2 (M + H$^+$) | 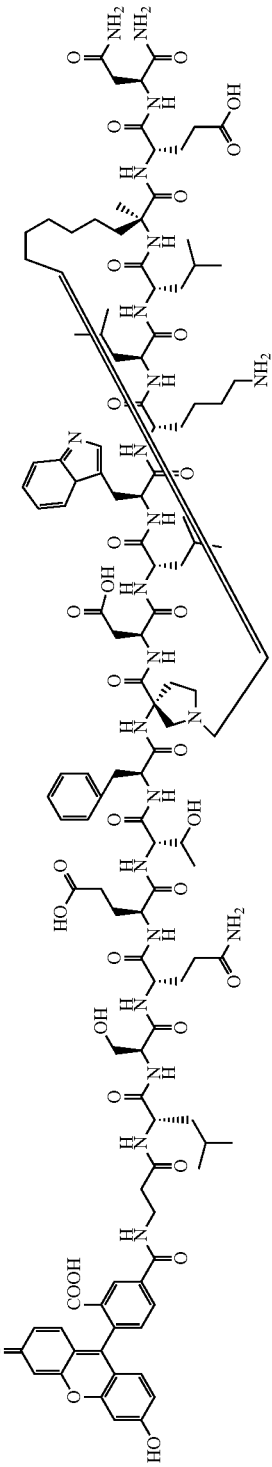 |
| FAM-b-ala-SAH-p53-4 R$_8$/Pyr$_S$ Amino-Stapled | 2469.2 (M + H$^+$) | 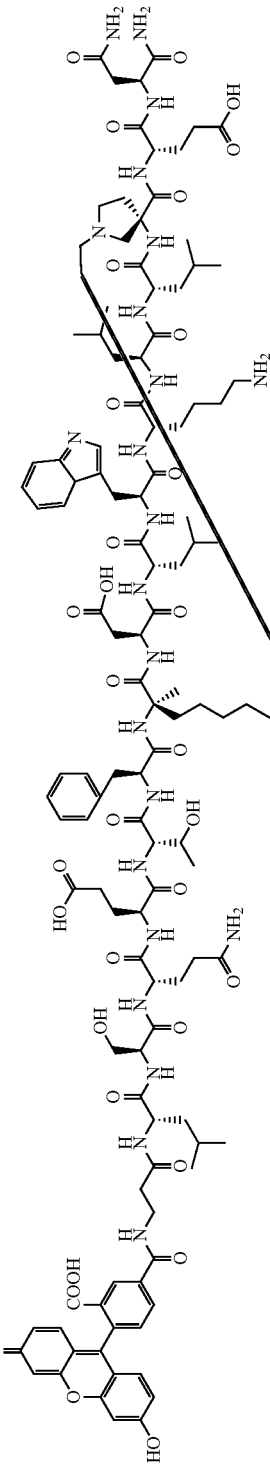 |

TABLE 9-continued
| Stapled peptide | m/z (positive ion or negative ion mode indicated) | Stapled peptide structure |
|---|---|---|
| Ac-b-ala-PM2 Pyr$_R$/S$_8$ Amino-Stapled | 1544.8 (M − H$^+$) | 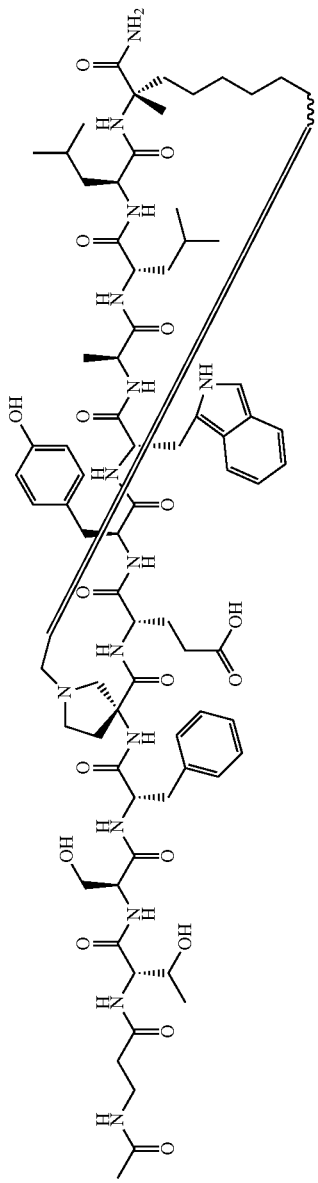 |
| Ac-b-ala-PM2 R$_8$/Pyr$_5$ Amino-Stapled | 1544.8 (M − H$^+$) | 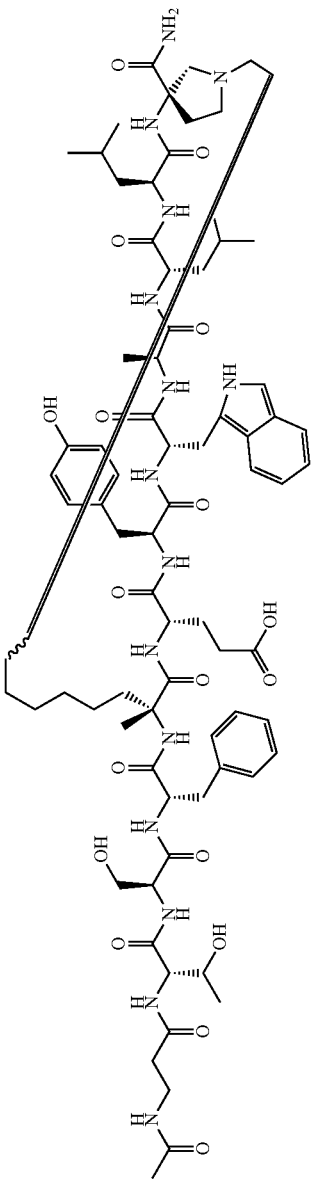 |

TABLE 9-continued

| Stapled peptide | m/z (positive ion or negative ion mode indicated) | Stapled peptide structure |
|---|---|---|
| Ac-b-ala-PM2 R$_8$/S$_G$N Amino-Stapled | 1546.8 (M − H$^+$) | |
| FAM-b-ala-PM2 Pyr$_R$/S$_8$ Amino-Stapled | 1860.9 (M − H$^+$) | |

TABLE 9-continued
| Stapled peptide | m/z (positive ion or negative ion mode indicated) | Stapled peptide structure |
|---|---|---|
| FAM-b-ala-PM2 R$_8$/Pyr$_5$ Amino-Stapled | 1860.9 (M − H$^+$) | 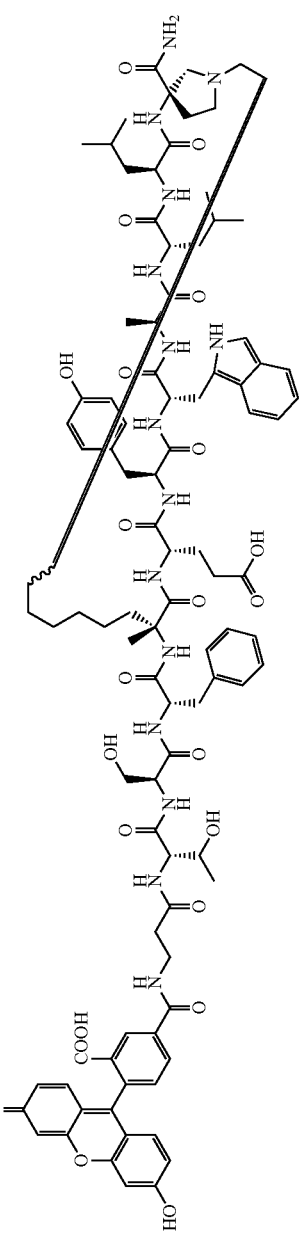 |
| FAM-b-ala-PM2 R$_8$/S$_G$N Amino-Stapled | 1862.9 (M − H$^+$) | 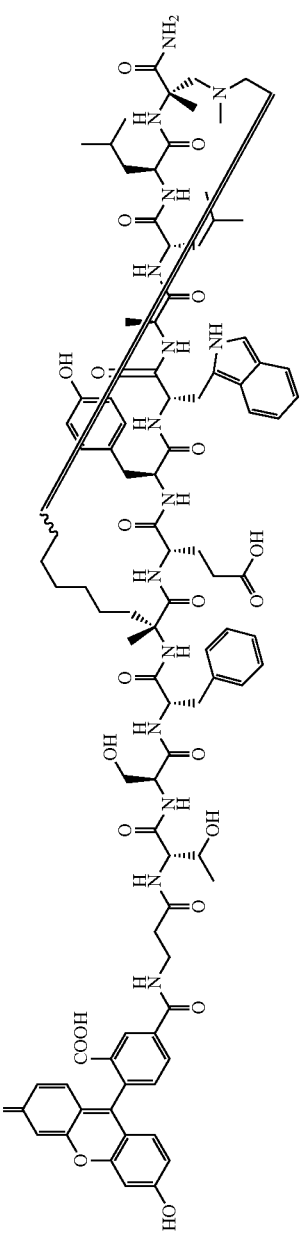 |

TABLE 9-continued

| Stapled peptide | m/z (positive ion or negative ion mode indicated) | Stapled peptide structure |
|---|---|---|
| Ac-PM2 Pyr$_R$/S$_8$ Alloc-stapled | 1517.8 (M − H$^+$) | |
| Ac-PM2 Pyr$_R$/Pyr$_S$ Alloc-Stapled Isomer A | 1532.7 (M − H$^+$) | |

TABLE 9-continued

| Stapled peptide | m/z (positive ion or negative ion mode indicated) | Stapled peptide structure |
|---|---|---|
| Ac-PM2 Pyr$_R$/Pyr$_S$ Alloc-Stapled Isomer B | 1532.7 (M − H$^+$) | |

Example 6

Characterization of Stapled Peptides

Figure 11A:
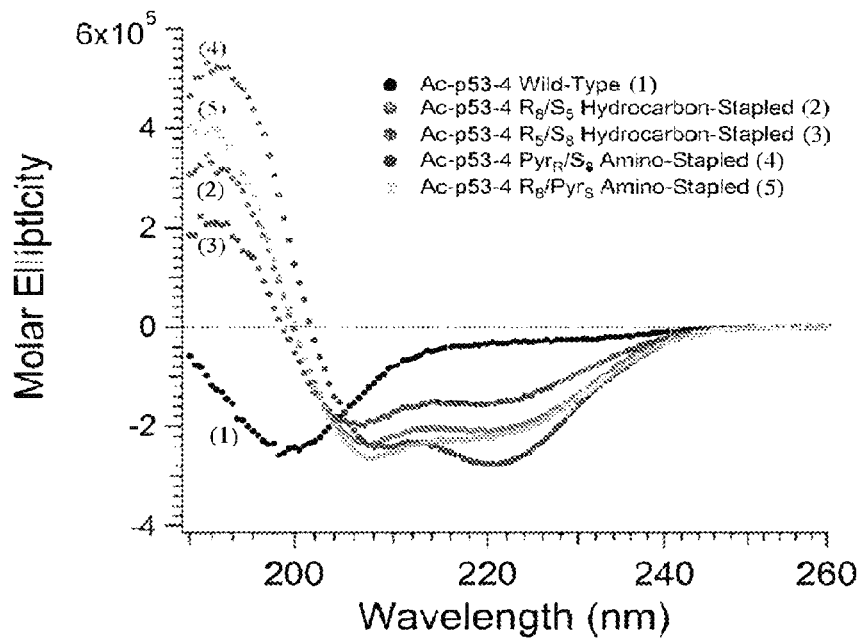
Figure 11B:
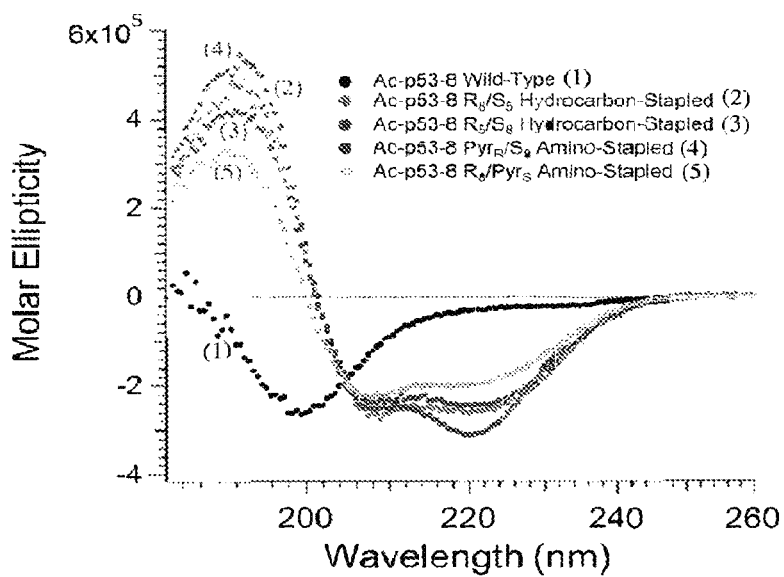
Figure 11C:
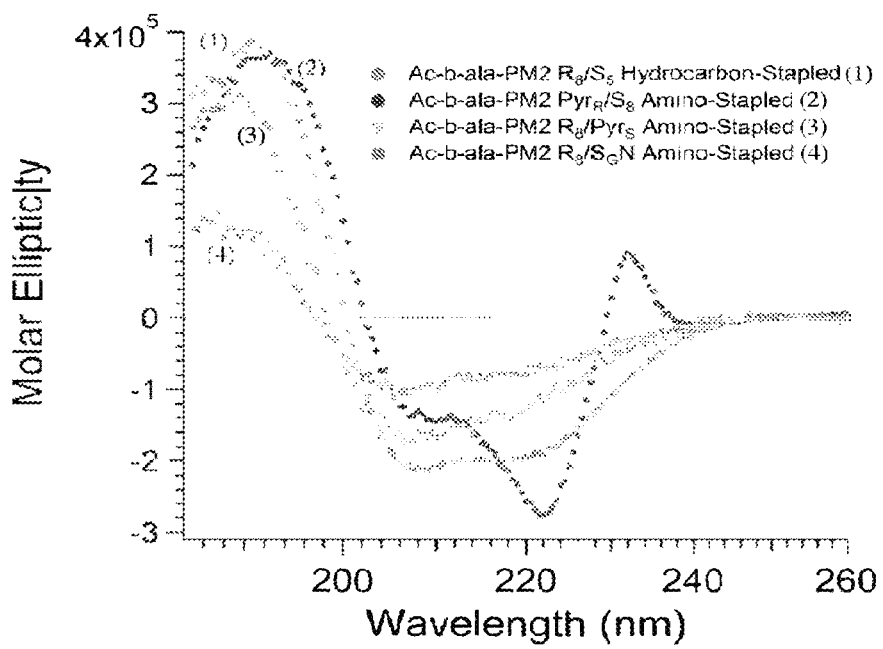
Figure 11D:
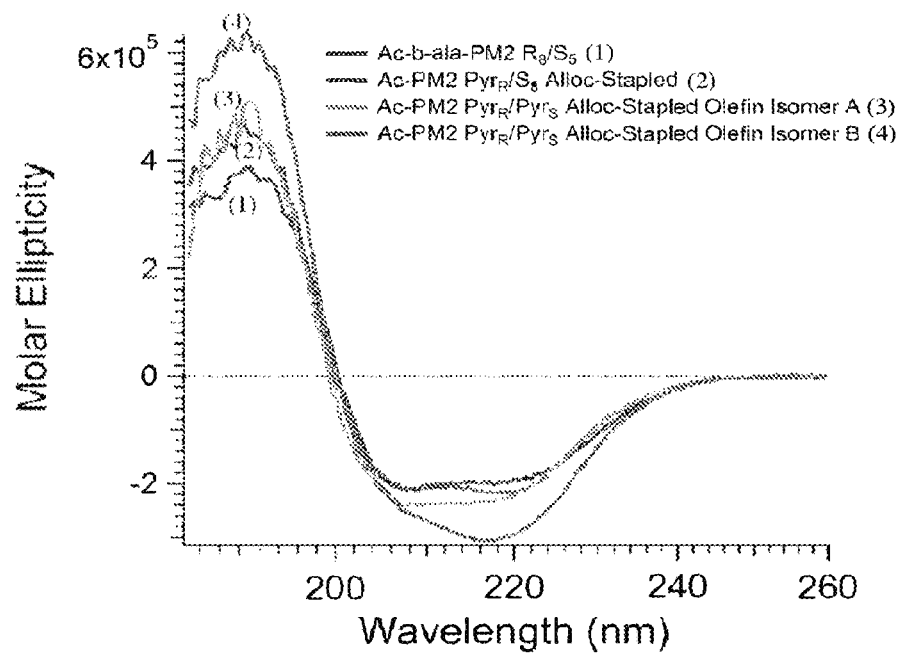
Figure 12A:
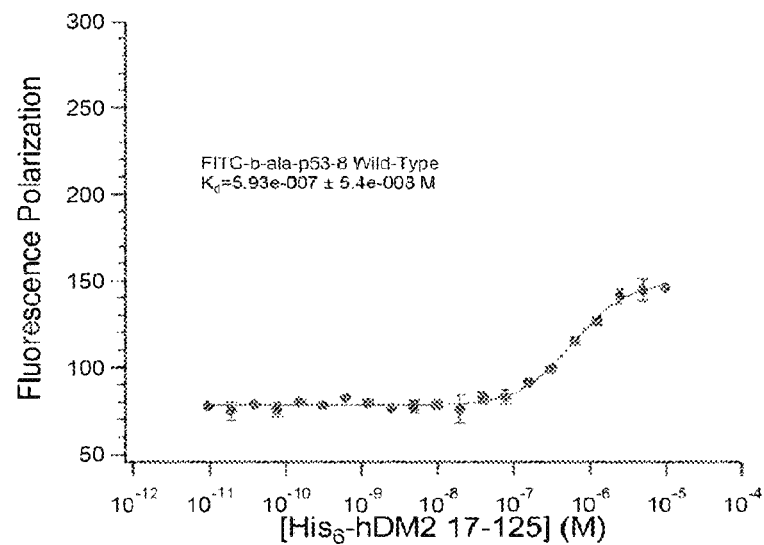
Figure 12B:
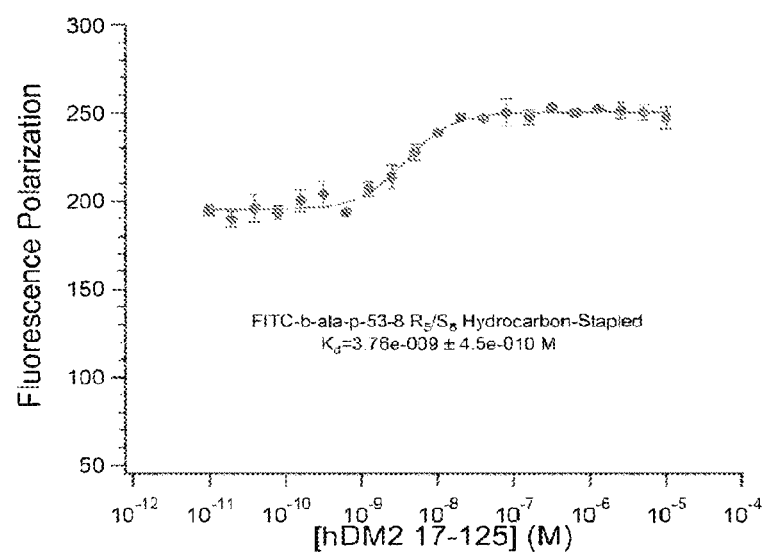
Figure 12C:
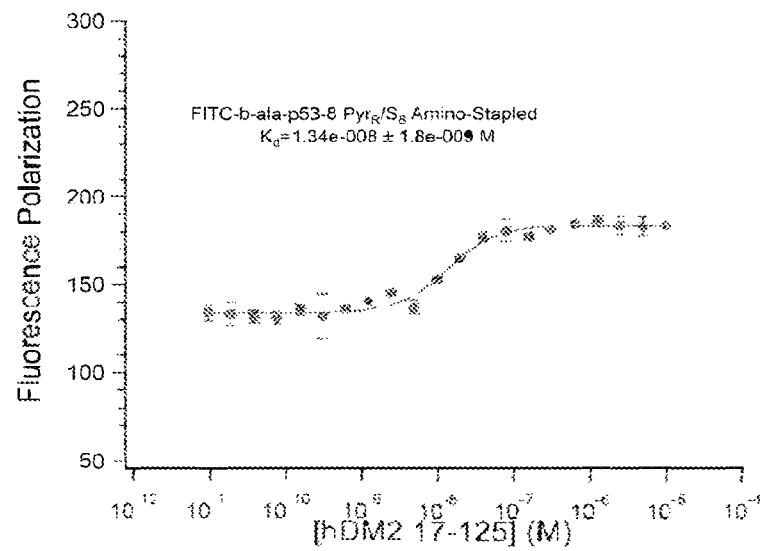
Figure 12D:
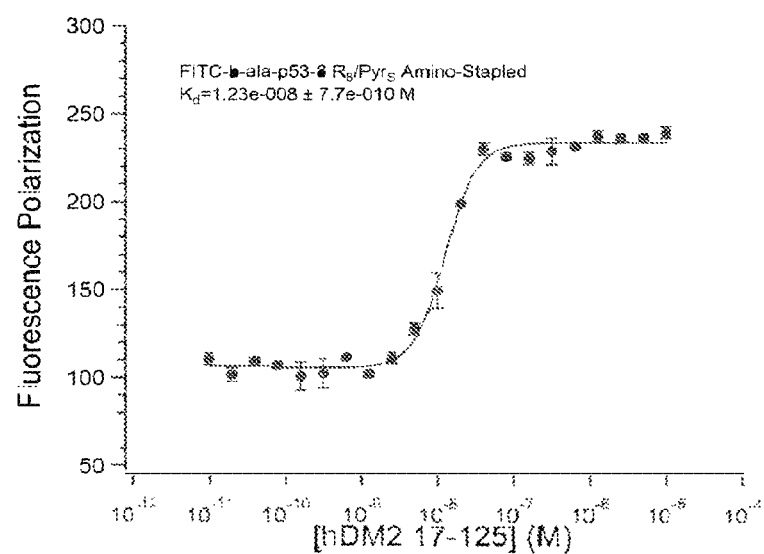
Figure 12E:
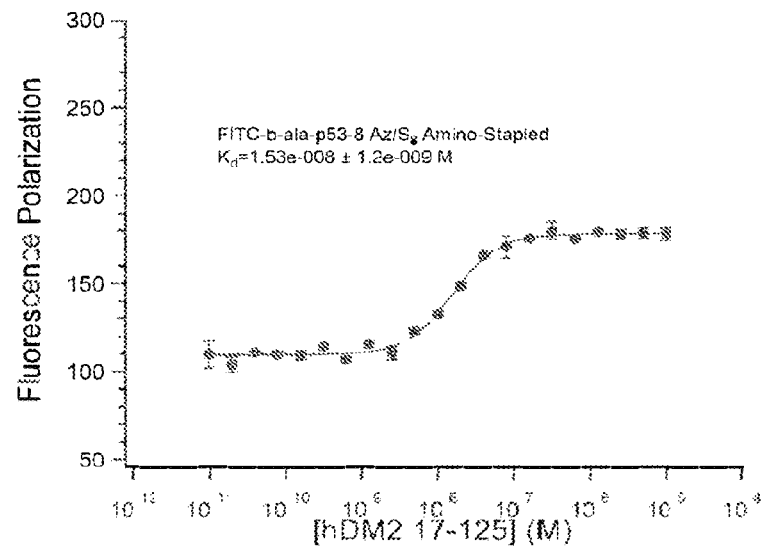
Figure 12F:
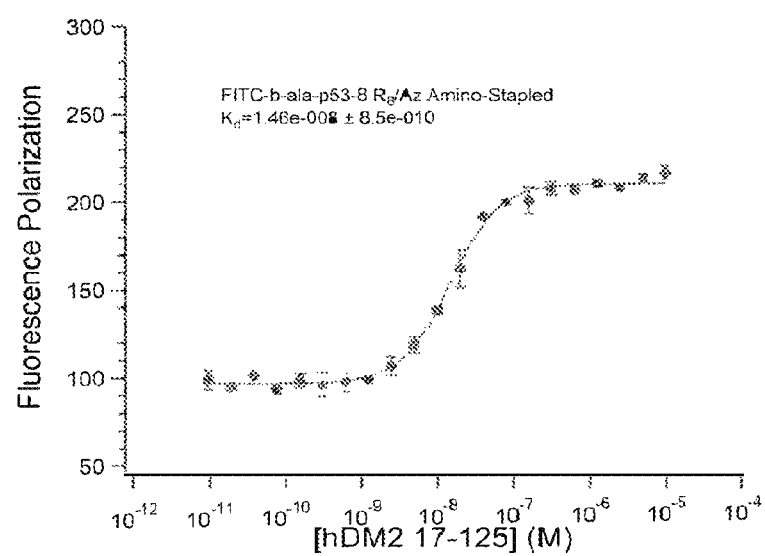
Figure 12G:
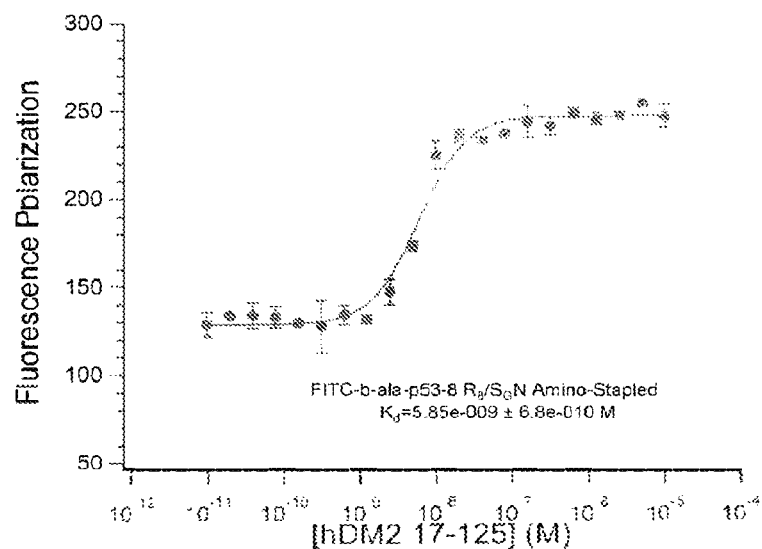
Figure 12H:
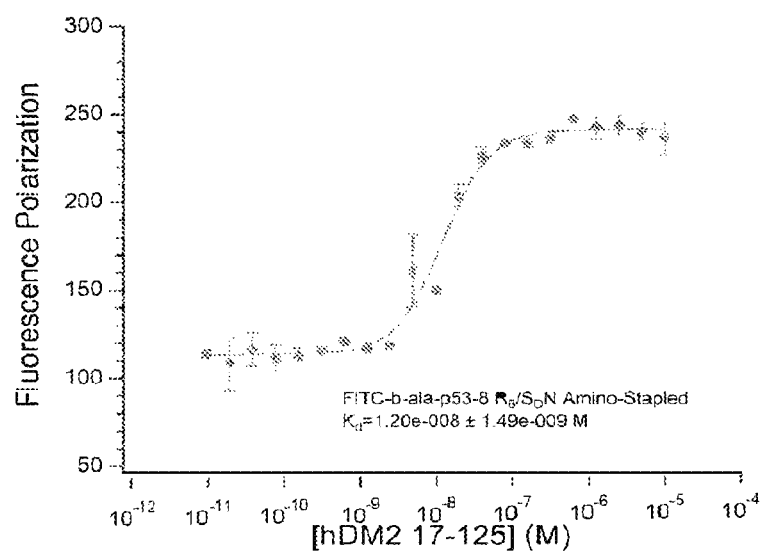
Figure 12I:
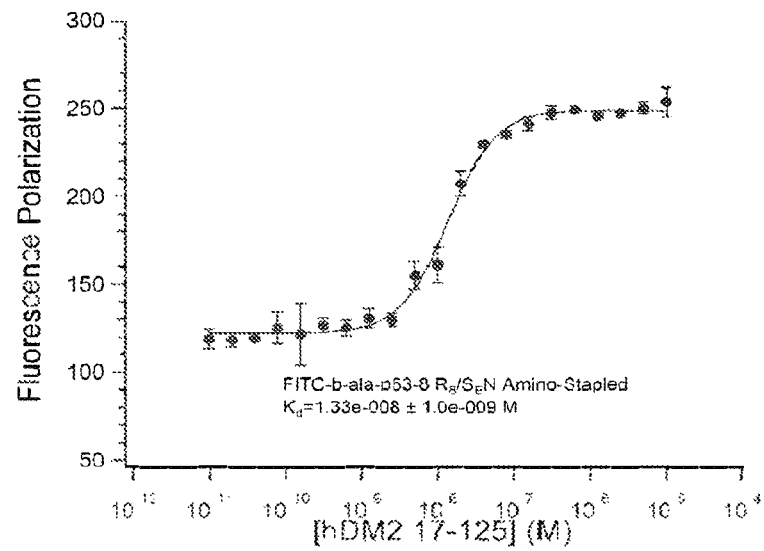
Figure 12J:
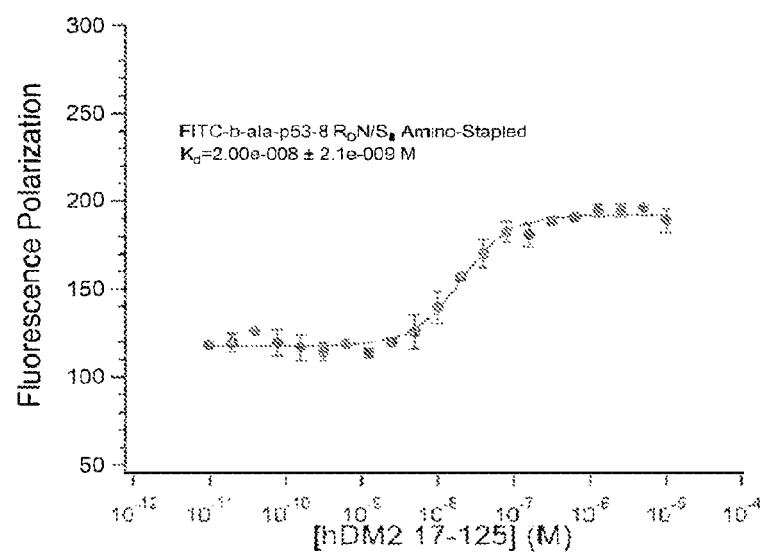
Figure 12K:
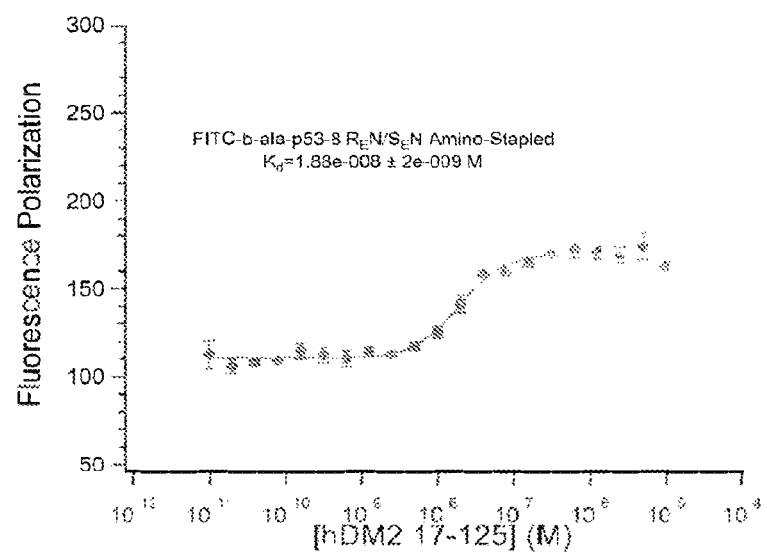

Circular Dichroism (CD) Spectroscopy: CD spectra (FIGS. 11A-11D) were obtained using unlabeled peptides in 10 mM sodium phosphate pH 7.0 buffer. The raw data has been converted to the concentration-independent unit of molar ellipticity. α-Helices typically show dual minima at approximately 208 nm and 222 nm and a maximum at approximately 192 nm. In FIG. 11D, two distinct LC/MS peaks with the same mass were found for the Ac-PM2 $Pyr_R/Pyr_S$ Alloc-Stapled peptide. These likely correspond to the E and Z isomers of the olefin in the staple. Both peptides are a-helical, although one isomer shows a slightly higher a-helical character.

Fluorescence Polarization (FP) Binding Assay Data: The p53-4, p53-8 and PM2 peptide sequences are all known to bind to the p53 recruitment pocket of the E3 ubiquitin ligase HDM2. For these binding experiments, a hexahistidine-tagged version of HDM2 (residues 17-125) was expressed in E. coli and purified to >90% purity. Standard fluorescence polarization assays were used to examine the binding of FITC-labeled peptides to this HDM2 construct. Assays were performed at room temperature and the buffer used was 50 mM TRIS pH8.0, 140 mM NaCl, 5 mM β-mercaptoethanol. Error bars shown in FIGS. 12A-12K are the standard deviation of duplicate experiments. The dissociation constant ($K_d$) indicated on each plot was found by fitting the data with the Hill equation.

Cell Penetration by Confocal Microscopy: HeLa cells grown in DMEM/10% FBS with Pen/Strep were treated with 10 µM FITC-labeled peptide at 37° C. for 3.5 hours then washed and fixed with paraformaldehyde. The intracellular accumulation of the labeled peptides (FIGS. 13A-13C) was then imaged using a 20× objective on an Olympus FV300 Confocal Fluorescence Microscope.

Cell Penetration by Flow Cytometry: Jurkat cells grown in RPMI-1640/10% FBS with Pen/Strep were treated with 5 µM FITC-labeled peptide at 37° C. for 4 hours then washed multiple times and suspended in PBS containing propidium iodide. The intracellular accumulation of the labeled peptides was then analyzed by flow cytometry. Dead cells, which were positive for propidium iodide, were removed from analysis. Samples were performed in duplicate. The mean cellular fluorescence is shown in FIG. 14A.

HeLa cells grown in EMEM/10% FBS with Pen/Strep were treated with 5 µM FAM-labeled peptide at 37° C. for 4 hours then washed multiple times and suspended in PBS containing propidium iodide. The intracellular accumulation of the labeled peptides was then analyzed by flow cytometry. Dead cells, which were positive for propidium iodide, were removed from analysis. Samples were performed in duplicate or triplicate. The mean cellular fluorescence is shown in FIG. 14B.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. An amino acid of Formula (D):

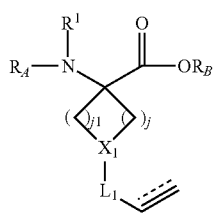

or a pharmaceutically acceptable salt thereof, wherein:

- $R^1$ is hydrogen; substituted or unsubstituted $C_{1-6}$ alkyl; or an amino protecting group;
- $L_1$ is substituted or unsubstituted $C_{1-10}$ alkylene, or —C(=O)OR$^6$—;
- $R_A$ is hydrogen or an amino protecting group;
- $R_B$ is hydrogen;
- $X_1$ is N;
- $R^6$ is $C_{1-6}$ alkylene; and
- each of j and j1 is independently an integer between 1 and 10, inclusive, wherein when one of j and j1 is 2, the other is 1, or an integer between 3 and 10, inclusive.

2. The amino acid of claim 1, wherein the amino acid is selected from the group consisting of:

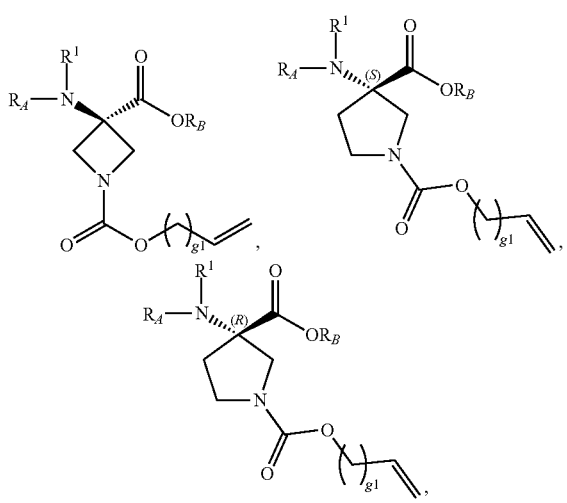

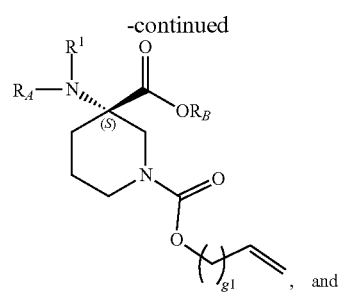

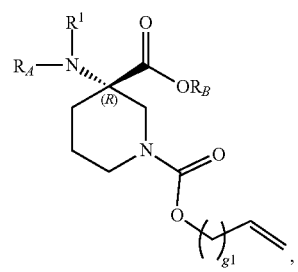

or a salt thereof, wherein g1 is one to six.

3. The amino acid of claim 1, wherein $R^1$ is an amino protecting group.

4. The amino acid of claim 1, wherein $R^1$ is substituted or unsubstituted $C_{1-6}$ alkyl.

5. The amino acid of claim 1, wherein $R^1$ is hydrogen.

6. The amino acid of claim 4, wherein $R_A$ is an amino protecting group.

7. The amino acid of claim 1, wherein ======== represents a double bond.

8. The amino acid of claim 1, wherein ======== represents a triple bond.

9. The amino acid of claim 1, wherein $R^1$ is an amino protecting group and $R_A$ is hydrogen.

10. The amino acid of claim 9, wherein the amino acid protecting group is Fmoc.

11. The amino acid of claim 9, wherein ======== represents a double bond.

12. The amino acid of claim 10, wherein ======== represents a double bond.

13. An amino acid of Formula (D):

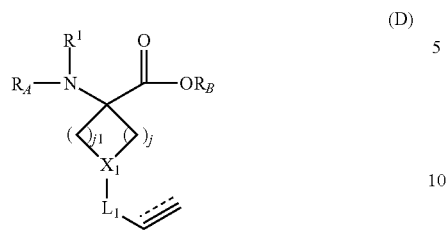

or a pharmaceutically acceptable salt thereof,
wherein:
  $R^1$ is an amino protecting group;
  $L_1$ is a substituted or unsubstituted $C_{1-10}$ alkylene, or —C(=O)OR$^6$—;
  $R_A$ is cyclic or acyclic, branched or unbranched, substituted or unsubstituted aliphatic;
cyclic or acyclic, branched or unbranched, substituted or unsubstituted heteroaliphatic; or
substituted or unsubstituted heteroaryl;
  $R_B$ is hydrogen;
  $X_1$ is N;
  $R^6$ is $C_{1-6}$ alkylene; and
  each of j and j1 is independently an integer between 1 and 10, inclusive.

14. The amino acid of claim 13, wherein ═══ represents a double bond.

\* \* \* \* \*